(12) United States Patent
Bolotina

(10) Patent No.: US 11,360,102 B2
(45) Date of Patent: Jun. 14, 2022

(54) BIOMARKERS FOR THE EARLY DETECTION OF PARKINSON'S DISEASE

(71) Applicant: BOSTON MEDICAL CENTER CORPORATION, Boston, MA (US)

(72) Inventor: Victoria Bolotina, North Andover, MA (US)

(73) Assignee: BOSTON MEDICAL CENTER CORPORATION, Boston, MA (US)

(*) Notice: Subject to any disclaimer, the term of this patent is extended or adjusted under 35 U.S.C. 154(b) by 0 days.

(21) Appl. No.: 15/760,783

(22) PCT Filed: Sep. 23, 2016

(86) PCT No.: PCT/US2016/053330
§ 371 (c)(1),
(2) Date: Mar. 16, 2018

(87) PCT Pub. No.: WO2017/053718
PCT Pub. Date: Mar. 30, 2017

(65) Prior Publication Data
US 2019/0049466 A1     Feb. 14, 2019

Related U.S. Application Data

(60) Provisional application No. 62/232,199, filed on Sep. 24, 2015, provisional application No. 62/222,619, filed on Sep. 23, 2015.

(51) Int. Cl.
*G01N 33/68* (2006.01)
*C12Q 1/6883* (2018.01)
*G01N 33/53* (2006.01)

(52) U.S. Cl.
CPC ....... *G01N 33/6896* (2013.01); *C12Q 1/6883* (2013.01); *G01N 33/5308* (2013.01); *C12Q 2600/156* (2013.01); *C12Q 2600/158* (2013.01); *G01N 2800/2835* (2013.01); *G01N 2800/60* (2013.01); *G01N 2800/70* (2013.01)

(58) Field of Classification Search
CPC ....... G01N 33/6896; G01N 2800/2835; G01N 2800/70; C12Q 1/6883
See application file for complete search history.

(56) References Cited

U.S. PATENT DOCUMENTS

2009/0099259 A1   4/2009   Jouni et al.
2011/0067123 A1   3/2011   Andersen et al.
2015/0104806 A1   4/2015   Alessi et al.

*Primary Examiner* — Olga N Chernyshev
(74) *Attorney, Agent, or Firm* — Nixon Peabody LLP; Ronald I. Eisenstein; Nicole D. Kling

(57) ABSTRACT

Disclosed are biomarkers for Parkinson's disease (PD), including idiopathic PD (idPD). The present invention relates generally to assays, kits, compositions, solid supports and methods that measure a decrease in the expression or function of PLA2g6(L) variant of PLA2g6 (PARK 14) gene in a sample from the subject, including non-neuronal cells as a biomarker for preclinical (prodromal) or early stage Parkinson's disease (PD) and idiopathic PD (idPD), as well as assays, kits, compositions and methods that can detect the functional consequences of decreased expression of PLA2g6(L), including decreased store operated Ca2+ entry (SOCE), deficit of Ca2+ in endoplasmic reticulum stores, and autophagic dysfunction in the cells obtained from the subjects in preclinical (prodromal) and early stage PD diagnosis and for monitoring Parkinson's Disease progression.

4 Claims, 55 Drawing Sheets

Specification includes a Sequence Listing.

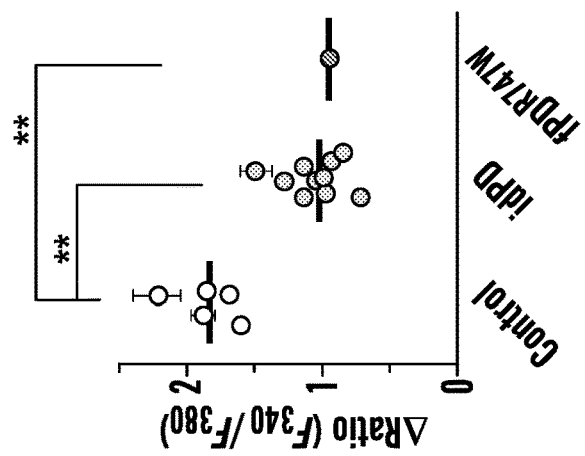

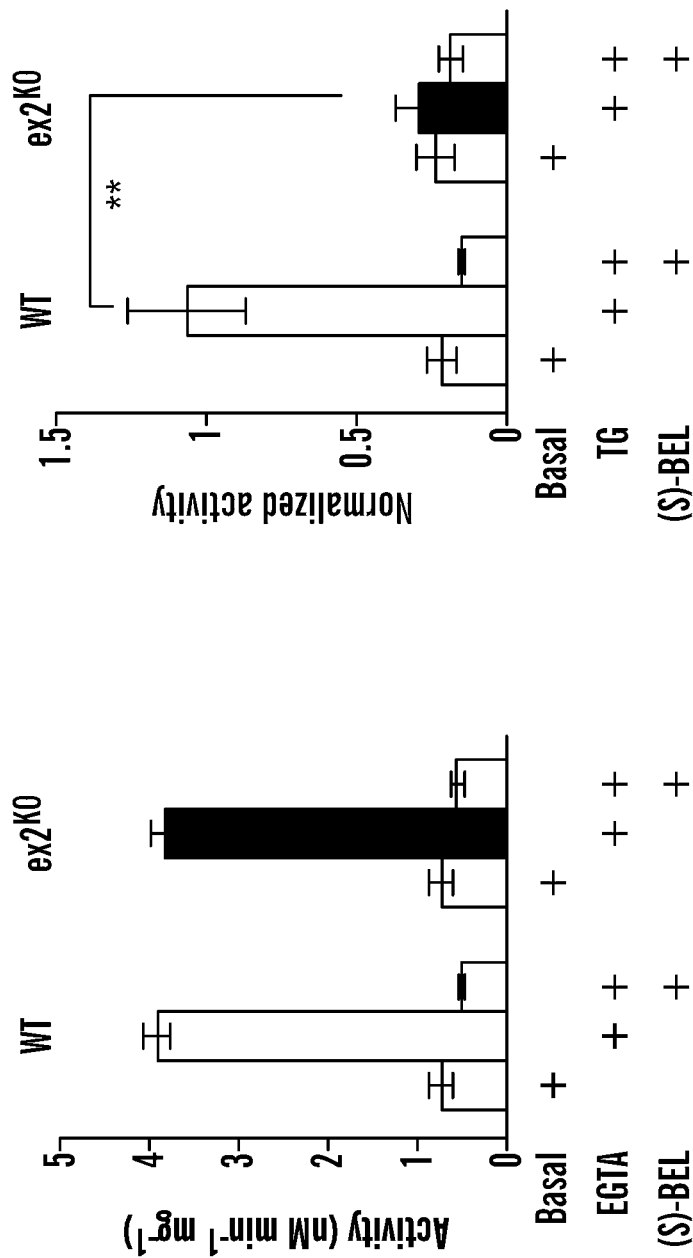

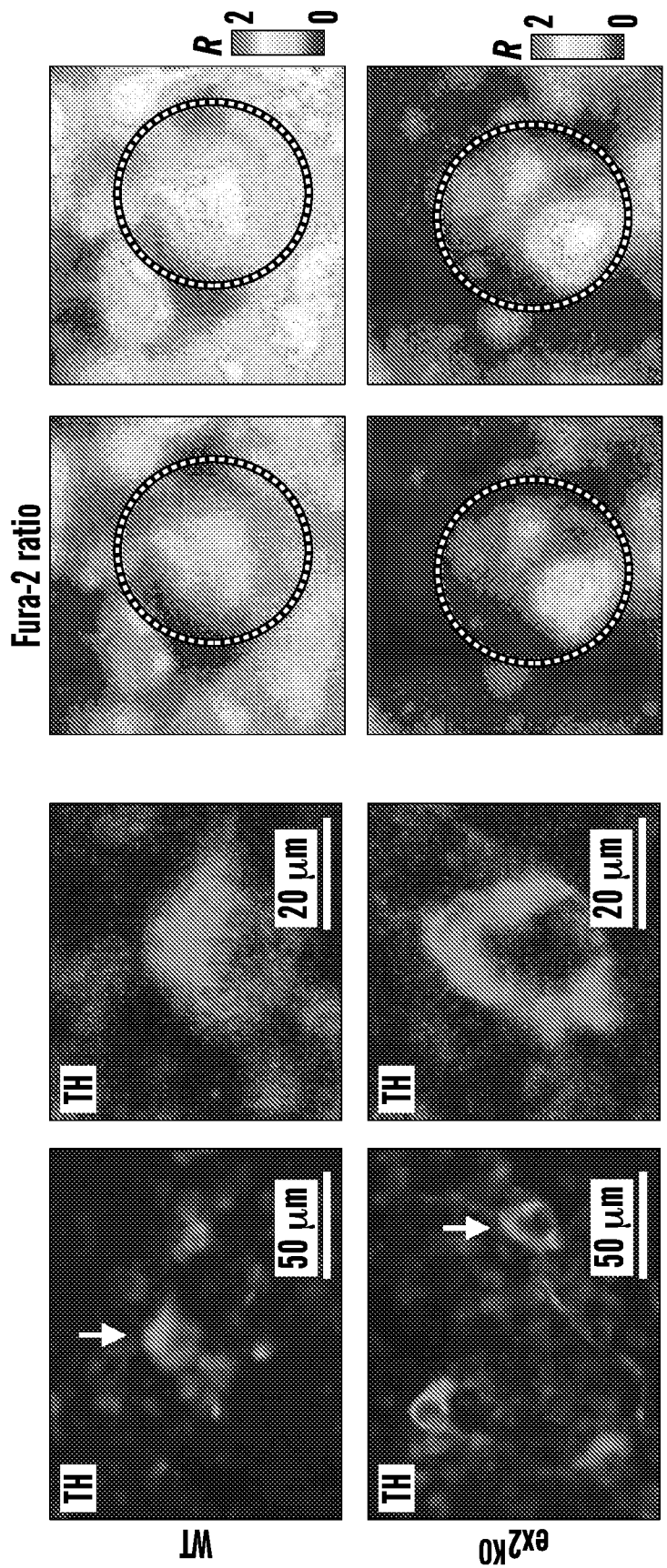

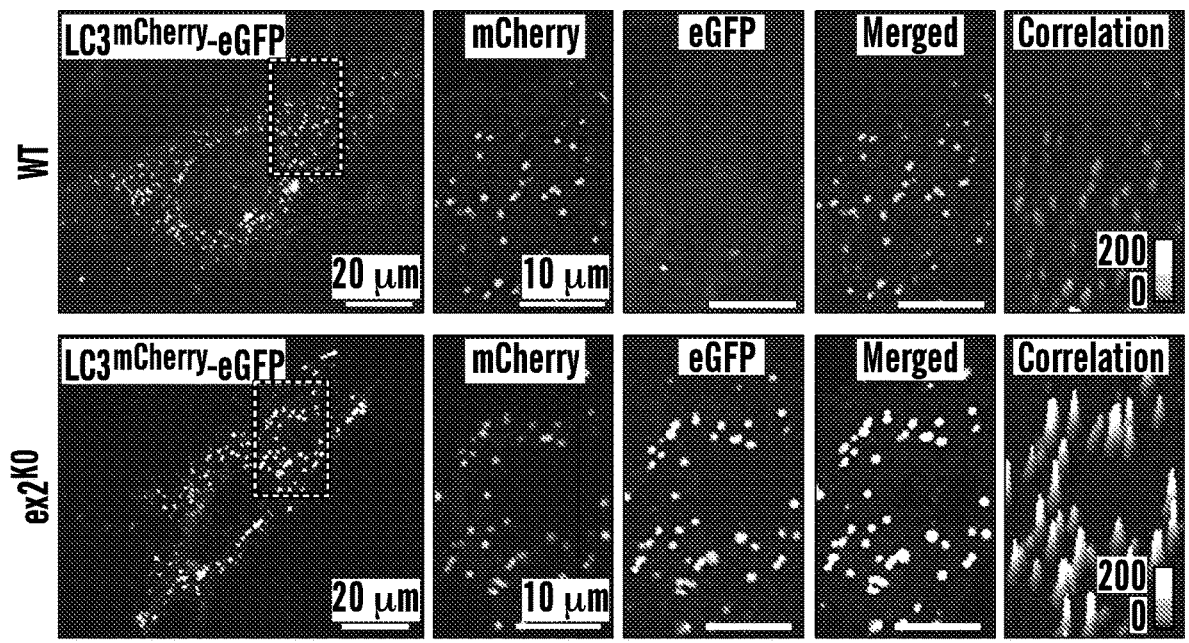
*FIG. 5D*
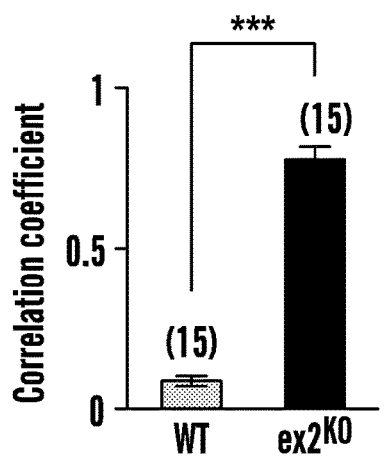 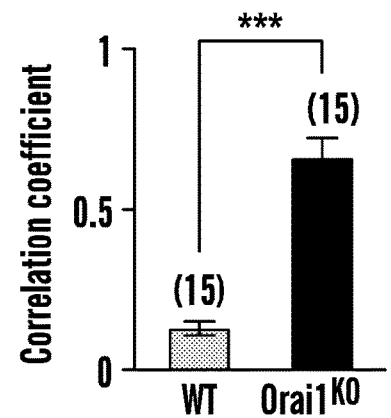
*FIG. 5E*    *FIG. 5F*

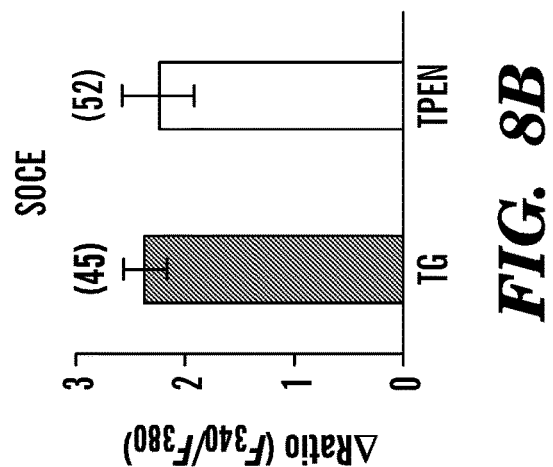
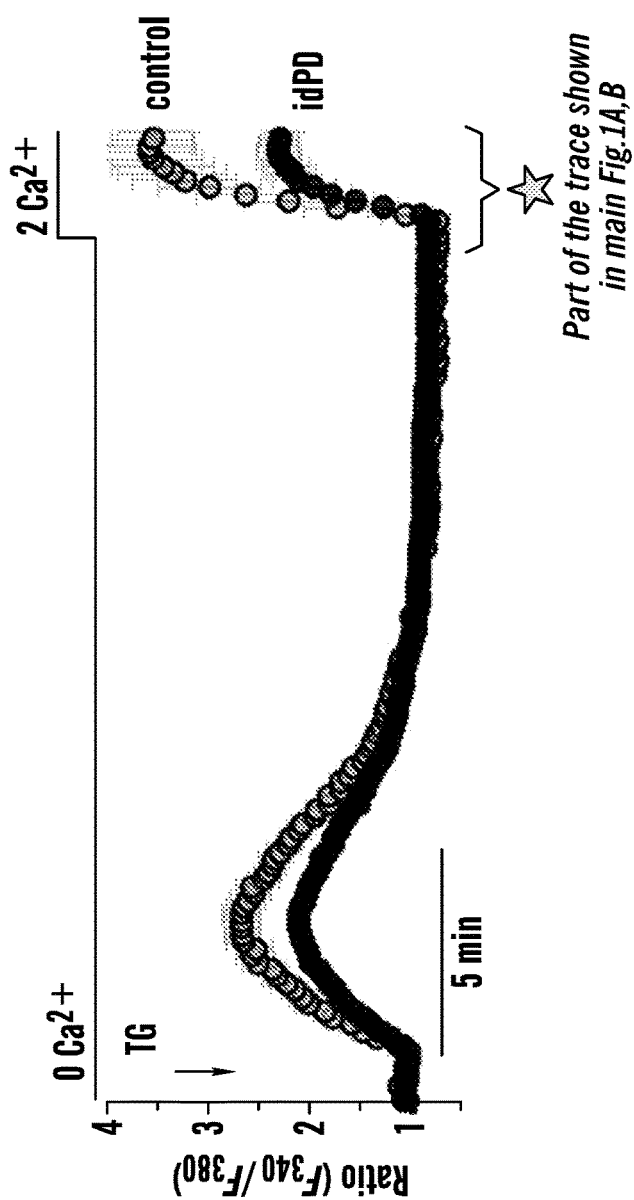
FIG. 8A
FIG. 8B

| Name | Transcript ID | bp | Protein | Biotype |
|---|---|---|---|---|
| PLA2G6-001 | ENST00000332509.7 | 3271 | 806aa | Protein coding |
| PLA2G6-201 | ENST00000335539.7 | 3060 | 752aa | Protein coding |
| PLA2G6-002 | ENST00000402064.5 | 3011 | 752aa | Protein coding |
| PLA2G6-019 | ENST00000452794.5 | 781 | 124aa | Protein coding |
| PLA2G6-016 | ENST00000427114.5 | 688 | 229aa | Protein coding |
| PLA2G6-015 | ENST00000498338.1 | 675 | 120aa | Protein coding |
| PLA2G6-014 | ENST00000430886.5 | 656 | 166aa | Protein coding |
| PLA2G6-003 | ENST00000435484.5 | 612 | 99aa | Protein coding |
| PLA2G6-027 | ENST00000594306.1 | 595 | 50aa | Protein coding |
| PLA2G6-017 | ENST00000452542.5 | 591 | 197aa | Protein coding |
| PLA2G6-010 | ENST00000447598.6 | 567 | 99aa | Protein coding |
| PLA2G6-012 | ENST00000436218.5 | 552 | 151aa | Protein coding |
| PLA2G6-005 | ENST00000417303.6 | 501 | 99aa | Protein coding |
| PLA2G6-018 | ENST00000427453.5 | 499 | 157aa | Protein coding |
| PLA2G6-007 | ENST00000455341.2 | 364 | 79aa | Protein coding |
| PLA2G6-023 | ENST00000448094.5 | 1147 | 226aa | Nonsense mediated decay |
| PLA2G6-026 | ENST00000454670.1 | 741 | 168aa | Nonsense mediated decay |
| PLA2G6-021 | ENST00000490473.1 | 601 | No protein | Processed transcript |
| PLA2G6-009 | ENST00000479641.5 | 571 | No protein | Processed transcript |
| PLA2G6-004 | ENST00000420435.5 | 539 | No protein | Processed transcript |
| PLA2G6-011 | ENST00000445591.5 | 534 | No protein | Processed transcript |
| PLA2G6-008 | ENST00000452972.1 | 524 | No protein | Processed transcript |
| PLA2G6-006 | ENST00000426674.1 | 471 | No protein | Processed transcript |
| PLA2G6-024 | ENST00000496409.1 | 859 | No protein | Retained intron |
| PLA2G6-025 | ENST00000463287.1 | 786 | No protein | Retained intron |
| PLA2G6-022 | ENST00000491986.1 | 753 | No protein | Retained intron |
| PLA2G6-013 | ENST00000471636.5 | 569 | No protein | Retained intron |
| PLA2G6-020 | ENST00000480154.1 | 323 | No protein | Retained intron |

*FIG. 11A*

| CCDS | UniProt | RefSeq | Flags |
|---|---|---|---|
| CCDS13967 | O60733 | NM_003560 NP_003551 | TSL:1GENCODE basicAPPRIS P1 |
| CCDS33645 | O60733 | NM_001004426 NP_001004426 | TSL:5GENCODE basic |
| CCDS33645 | O60733 | NM_001199562 NP_001186491 | TSL:1GENCODE basic |
| - | H0Y4M7 | - | CDS 5' incompleteTSL:4 |
| - | H0Y6T3 | - | CDS 5' and 3' incompleteTSL:3 |
| - | M0R1Q9 | - | CDS 3' incompleteTSL:4 |
| - | B0QYE9 | - | CDS 3' incompleteTSL:5 |
| - | F2Z3G2 | - | TSL:4GENCODE basic |
| - | M0R3D9 | - | CDS 3' incompleteTSL:4 |
| - | H0Y7G5 | - | CDS 5' and 3' incompleteTSL:5 |
| - | F2Z3G2 | - | TSL:5GENCODE basic |
| - | F8WEN3 | - | TSL:4GENCODE basic |
| - | F2Z3G2 | - | TSL:4GENCODE basic |
| - | H0Y6W2 | - | CDS 5' incompleteTSL:4 |
| - | F8WEQ9 | - | CDS 3' incompleteTSL:2 |
| - | E7EX67 | - | TSL:5 |
| - | H7C3P5 | - | CDS 5' incompleteTSL:3 |
| - | - | - | TSL:4 |
| - | - | - | TSL:4 |
| - | - | - | TSL:4 |
| - | - | - | TSL:4 |
| - | - | - | TSL:4 |
| - | - | - | TSL:4 |
| - | - | - | TSL:3 |
| - | - | - | TSL:2 |
| - | - | - | TSL:2 |
| - | - | - | TSL:4 |
| - | - | - | TSL:3 |

*FIG. 11A (cont.)*

Sequence comparison of SEQ ID NO: 2 (PLA2g6(L)) v. SEQ ID NO: 4 (PLA2g6(S))

```
SEQ NO: 2    MQFFGRLVNTFSGVTNLFSNPFRVKEVAVADYTSSDRVREEGQLILFQNTPNRTWDCVLV    60
             MQFFGRLVNTFSGVTNLFSNPFRVKEVAVADYTSSDRVREEGQLILFQNTPNRTWDCVLV
SEQ NO: 4    MQFFGRLVNTFSGVTNLFSNPFRVKEVAVADYTSSDRVREEGQLILFQNTPNRTWDCVLV    60

SEQ NO: 2    NPRNSQSGFRLFQLELEADALVNFHQYSSQLLPFYESSPQVLHTEVLQHLTDLIRNHPSW   120
             NPRNSQSGFRLFQLELEADALVNFHQYSSQLLPFYESSPQVLHTEVLQHLTDLIRNHPSW
SEQ NO: 4    NPRNSQSGFRLFQLELEADALVNFHQYSSQLLPFYESSPQVLHTEVLQHLTDLIRNHPSW   120

SEQ NO: 2    SVAHLAVELGIRECFHHSRIISCANCAENEEGCTPLHLACRKGDEILVELVQYCHTQMD    180
             SVAHLAVELGIRECFHHSRIISCANCAENEEGCTPLHLACRKGDEILVELVQYCHTQMD
SEQ NO: 4    SVAHLAVELGIRECFHHSRIISCANCAENEEGCTPLHLACRKGDEILVELVQYCHTQMD    180

SEQ NO: 2    VTDYKGETVFHYAVQGDNSQVLQLLGRNAVAGLNQVNNQGLTPLHLACQLGKQEMVRVLL   240
             VTDYKGETVFHYAVQGDNSQVLQLLGRNAVAGLNQVNNQGLTPLHLACQLGKQEMVRVLL
SEQ NO: 4    VTDYKGETVFHYAVQGDNSQVLQLLGRNAVAGLNQVNNQGLTPLHLACQLGKQEMVRVLL   240

SEQ NO: 2    LCNARCNIMGPNGYPIHSAMKFSQKGCAEMIISMDSSQIHSKDPRYGASPLHWAKNAEMA   300
             LCNARCNIMGPNGYPIHSAMKFSQKGCAEMIISMDSSQIHSKDPRYGASPLHWAKNAEMA
SEQ NO: 4    LCNARCNIMGPNGYPIHSAMKFSQKGCAEMIISMDSSQIHSKDPRYGASPLHWAKNAEMA   300

SEQ NO: 2    RMLLKRGCNVNSTSSAGNTALHVAVMRNRFDCAIVLLTHGANADARGEHGNTPLHLAMSK   360
             RMLLKRGCNVNSTSSAGNTALHVAVMRNRFDCAIVLLTHGANADARGEHGNTPLHLAMSK
SEQ NO: 4    RMLLKRGCNVNSTSSAGNTALHVAVMRNRFDCAIVLLTHGANADARGEHGNTPLHLAMSK   360

SEQ NO: 2    DNVEMIKALIVFGAEVDTPNDFGETPTFLASKIGRLV TRKAILTLLRTVGAEYCFPPIHG  420
             DNVEMIKALIVFGAEVDTPNDFGETPTFLASKIGR +
SEQ NO: 4    DNVEMIKALIVFGAEVDTPNDFGETPTFLASKIGRQL-----------------------  397
```

FIG. 11B

```
SEQ NO: 2    VPAEQGSAAPHHPFSLERAQPPPISLNNLELQDLMHISRARKPAFILGSMRDEKRTHDHL    480
                          + RA+ P                              AFILGSMRDEKRTHDHL
SEQ NO: 4    ----------QDLMHISRARKP--------------------AFILGSMRDEKRTHDHL    426

SEQ NO: 2    LCLDGGGVKGLIIIQLLIAIEKASGVATKDLFDWVAGTSTGGILALAILHSKSMAYMRGM    540
             LCLDGGGVKGLIIIQLLIAIEKASGVATKDLFDWVAGTSTGGILALAILHSKSMAYMRGM
SEQ NO: 4    LCLDGGGVKGLIIIQLLIAIEKASGVATKDLFDWVAGTSTGGILALAILHSKSMAYMRGM    486

SEQ NO: 2    YFRMKDEVFRGSRPYESGPLEEFLKREFGEHTKMTDVRKPKVMLTGTLSDRQPAELHLFR    600
             YFRMKDEVFRGSRPYESGPLEEFLKREFGEHTKMTDVRKPKVMLTGTLSDRQPAELHLFR
SEQ NO: 4    YFRMKDEVFRGSRPYESGPLEEFLKREFGEHTKMTDVRKPKVMLTGTLSDRQPAELHLFR    546

SEQ NO: 2    NYDAPETVREPRFNQNVNLRPPAQPSDQLVWRAARSSGAAPTYFRPNGRFLDGGLLANNP    660
             NYDAPETVREPRFNQNVNLRPPAQPSDQLVWRAARSSGAAPTYFRPNGRFLDGGLLANNP
SEQ NO: 4    NYDAPETVREPRFNQNVNLRPPAQPSDQLVWRAARSSGAAPTYFRPNGRFLDGGLLANNP    606

SEQ NO: 2    TLDAMTEIHEYNQDLIRKGQANKVKKLSIVVSLGTGRSPQVPVTCVDVFRPSNPWELAKT    720
             TLDAMTEIHEYNQDLIRKGQANKVKKLSIVVSLGTGRSPQVPVTCVDVFRPSNPWELAKT
SEQ NO: 4    TLDAMTEIHEYNQDLIRKGQANKVKKLSIVVSLGTGRSPQVPVTCVDVFRPSNPWELAKT    666

SEQ NO: 2    VFGAKELGKMVVDCCTDPDGRAVDRARAWCEMVGIQYFRLNPQLGTDIMLDEVSDTVLVN    780
             VFGAKELGKMVVDCCTDPDGRAVDRARAWCEMVGIQYFRLNPQLGTDIMLDEVSDTVLVN
SEQ NO: 4    VFGAKELGKMVVDCCTDPDGRAVDRARAWCEMVGIQYFRLNPQLGTDIMLDEVSDTVLVN    726

SEQ NO: 2    ALWETEVYIYEHREEFQKLIHLLLSP    806
             ALWETEVYIYEHREEFQKLI LLLSP
SEQ NO: 4    ALWETEVYIYEHREEFQKLIQLLLSP
```

*FIG. 11B (cont.)*

TIRF image of endogenous PLA2g6(L) at the bottom of MEF cell

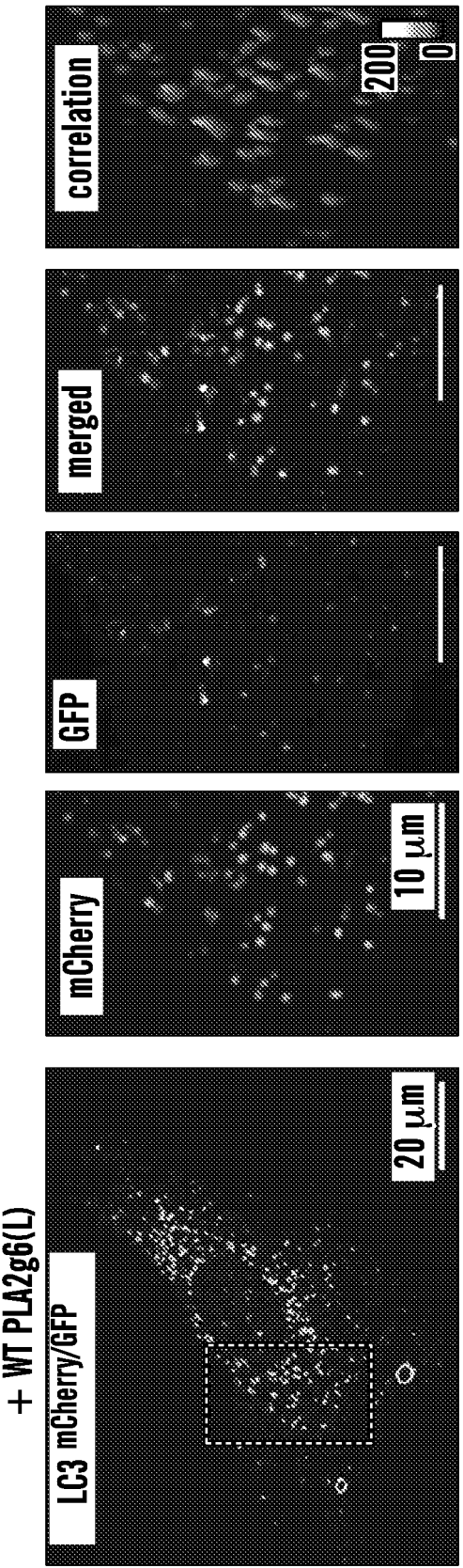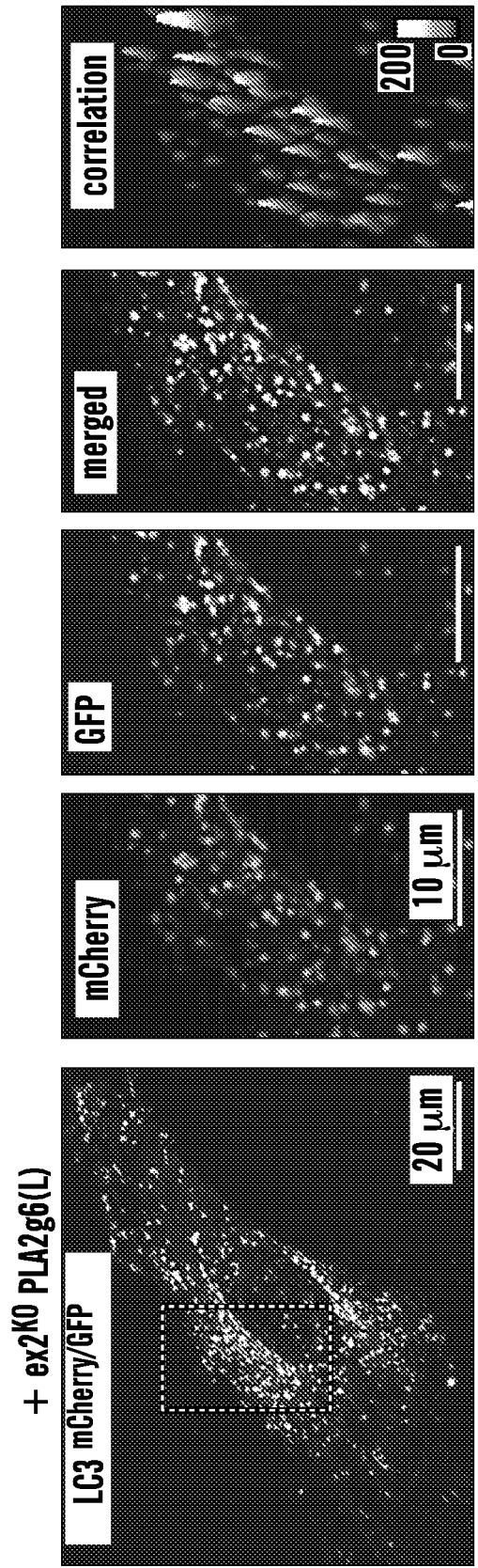
FIG. 25A

BIOMARKERS FOR THE EARLY DETECTION OF PARKINSON'S DISEASE

CROSS REFERENCE TO RELATED APPLICATIONS

This application is a 371 National Phase Entry of International Patent Application No. PCT/US16/53330 filed on Sep. 23, 2016 which claims benefit under 35 U.S.C. 119(e) of U.S. Provisional Patent Application Ser. No. 62/222,619 filed on Sep. 23, 2015 and U.S. Provisional Patent Application Ser. No. 62/232,199, filed on Sep. 24, 2015, the contents of which are incorporated herein by reference in their entirety.

SEQUENCE LISTING

The sequence listing of the present application has been submitted electronically via EFS-Web as an ASCII formatted sequence listing with a file name "701586-085822-PCT_SL", creation date of Mar. 15, 2018 and a size of 36,135 bytes. The sequence listing submitted via EFS-Web is part of the specification and is herein incorporated by reference in its entirety.

FIELD OF THE INVENTION

Disclosed are biomarkers for Parkinson's disease (PD), including idiopathic PD (idPD). The present invention relates generally to assays, kits, compositions, and methods using expression or function of PLA2g6(L) variant of PLA2g6 (PARK14) gene as a biomarker for preclinical (prodromal) or early stage Parkinson's disease (PD) and idiopathic PD (idPD). Also disclosed are assays, kits, compositions and methods assessing functional consequences of decreased expression of PLA2g6(L), including decreased store-operated $Ca^{2+}$ entry (SOCE), deficit of $Ca2+$ in endoplasmic reticulum stores, and autophagic dysfunction in the cells obtained from the subjects for diagnosis of preclinical (prodromal) and early clinical stage PD and for monitoring Parkinson's Disease progression.

BACKGROUND OF THE INVENTION

Neurodegenerative diseases affect millions of people, greatly reducing their quality of life and, in many cases, causing death. Parkinson's disease affects more than half a million Americans each year. Parkinson's disease is characterized by debilitating motor dysfunctions, including slowness of movement (bradykinesia), tremor at rest, rigidity of the extremities and neck, stooped posture, minimal facial expressions, problems swallowing (dysphagia), and a paucity of associated movements (e.g., arm swinging). Some patients also experience dementia.

Parkinson's disease is a movement disorder of increasing occurrence in aging populations. Parkinson's disease (PD) is a neurodegenerative disease that afflicts approximately 4-6 million people worldwide. In the United States, approximately one to two hundred people per 100,000 have PD. The prevalence of PD increases in the older population, with approximately 4% of people over the age of 80 suffering from this disease (Davie (2008) Brit Med Bull 86(1) p. 109), although 10% of patients are under 40 years of age (Kumari (2009) FEBS J. 276(22) p. 6455).

The vast majority of Parkinson's Disease (PD) cases (about 85%) are idiopathic, occurring upon aging with no distinct triggers or clear underlying mechanisms. Currently, there are no established markers or routine screening approaches/procedures for prediction or detection of human PD in early preclinical stages in aging population or for early detection of iPD. Idiopathic PD (iPD) is a neurodegenerative disease that stems from accelerated loss of DA neurons in SNc, which progress silently (without clear clinical manifestations) for many years prior to onset of the clear symptoms of PD-associated motor dysfunction. iPD is age-dependant and usually has a gradual onset between the ages of 50 and 70, progressing slowly until death 10 to 20 years later. Typically, iPD is not diagnosed until only 30-40% of DA neurons remain in SNc. It would be highly desirable to be able to identify a subject with a predisposition to iPD, or a subject that has iPD without any clinical symptoms, and therefore be able to administer a suitable PD treatment to prevent further decline in SNc neurons before the onset of the PD symptoms.

The most desirable approach to prevent or stop the development of PD is early detection of PD, even before symptoms develops (e.g., in an asymptomatic PD patient), which will allow to start preventive treatment before the loss of DA neurons crosses the critical threshold (60-70% loss) and before the onset of the symptoms. However, currently there are no established markers or routine screening approaches/procedures for detection of human PD in early preclinical stages in aging population.

Genetic mutations in specific genes (PARKs) are thought to be the primary risk factors for familial Parkinson's disease (fPD), which comprises about 15% of all PD cases. Several PARKs have been linked to autophagic dysfunction, mitochondrial dysfunction, α-synuclein aggregation and other cellular defects, which are now viewed as hallmarks of human PD[1-4].

SUMMARY OF THE INVENTION

The present invention relates to biomarkers and methods of use, and screening tactics for early detection of idiopathic Parkinson's disease in aging humans. The present invention is based, in part, on the discovery that impairment of the PLA2g6 (PARK14)-dependent $Ca^{2+}$ signaling can trigger age-dependent PD, and can be detected in the cells from idiopathic PD (idPD) patients. Furthermore, the inventor has discovered that the PLA2g6(L) variant of PLA2g6 is critical for PLA2g6 (PARK14)-dependent $Ca^{2+}$ signaling, and that loss of expression or impairment of the function of PLA2g6 (L) variant causes increased vulnerability of dopaminergic (DA) neurons and their premature age-dependent death leading to Parkinson's Disease (PD).

Herein, the inventors herein assessed PLA2g6 (PARK14) function, as well as the function of the store-operated $Ca^{2+}$ signaling in human age-dependent PD. The inventors herein demonstrate that impairment of the store-dependent $Ca^{2+}$ signaling function of PLA2g6 (PARK14) can identify a subject with, or likely to develop idiopathic PD. Although PLA2g6 (PARK14), and multiple mutations in PLA2g6 (PARK14) have been linked to familial PD, its association with idPD have been unknown, and have not been used as a biomarker for any stage (preclinical, early, or late) of PD in aging humans.

Herein, analysis of the cells (primary skin fibroblasts) from idiopathic PD (idPD) patients revealed a significant loss of PLA2g6(L) expression and function leading to deficiency in store-operated PLA2g6(L)-dependent Ca2+ signaling, which the inventors mimicked in a new B6.Cg-Pla2g6ΔEx2-VB (PLA2g6 ex2KO) mouse model. Here, the inventors demonstrate that genetic or molecular impairment of PLA2g6(L)-dependent Ca2+ signaling is a trigger for: (i) autophagic dysfunction, (ii) progressive loss of dopaminergic (DA) neurons in substantia nigra pars compacta (SNc) and (iii) age-dependent L-DOPA-sensitive motor dysfunction. Therefore, the inventors have discovered a sequence of pathological events that can trigger and/or contribute to idPD, and have been able to mimic this pathology in a novel genetic mouse model.

Accordingly, using a wide array of genetic, molecular, cellular, imaging, behavior and other approaches for in vivo and in vitro studies in human cells and new mouse model, the inventors discovered a decrease in expression and/or function of PARK14/PLA2g6(L) as major source for cellular vulnerability that is associated with premature death of DA neurons and age-dependent PD.

More specifically, the inventors herein have discovered significant defects in PARK14/PLA2g6(L) expression and function, which lead to significant defects in functional responses to specific tests (i.e., distinct signatures of defects) in the cells of patients with idiopathic PD (which account for approximately 85% of all PD patients). In particular, the inventors discovered that a decrease in PLA2g6(L) expression and/or function result in impaired specific cellular functions that are directly associated with human PD. Importantly, such defects in PLA2g6(L) function and/or expression leads to deficiency in specific cellular responses, such as a deficit in endogenous Store-operated Ca2+ Entry (SOCE) and resulting depletion of Ca2+ stores, and that such disruption can occur not only in dopaminergic (DA) neurons, but also in non-neuronal cell samples (e.g., skin fibroblasts, blood cells and others) from aged humans, and they mirror those occurring in dopaminergic neurons (DA) in the substantia nigra pars compacta (SNc), which can trigger, or accelerate premature age-dependent death of DA neurons and development of PD.

Herein, the inventors have demonstrated that detecting a decrease in PLA2g6(L) expression and/or impairment of its $Ca^{2+}$ signaling function in the cells obtained from human subjects, e.g., blood or skin cells can be used as biomarker to identify a subject at risk of developing age-dependent PD, and is a particularly useful biomarker for identifying asymptomatic subjects that are in prodromal, or very early stage of idiopathic PD.

More specifically, using human samples of primary skin fibroblasts (hPSF) from a group of 10 idPD patients (and 5 control donors), the inventors demonstrate a very significant and highly reproducible decrease in PLA2g6(L) expression levels (see FIG. 1F and FIG. 1G), and significant impairment of cellular responses to experimentally-induced depletion of intracellular ER Ca2+ stores, including deficit in endogenous Store-operated Ca2+ Entry (SOCE) (see FIGS. 1A and 1C), depletion of Ca2+ stores (see FIG. 1E), and autophagic dysfunction (FIG. 7B).

Accordingly, the present invention provides methods, assays and kits to identify subjects that have a decreased expression of PLA2g6(L), or decreased PLA2g6(L) function leading to an increase in cellular vulnerability, which identifies the subject as being predisposed to accelerated loss of DA neurons in SNc and development of PD, as well as subjects who already have preclinical stages of PD with significant loss of DA neurons that have not yet reached a threshold for its clinical manifestation (e.g., pre- or asymptomatic PD subjects).

In some embodiments, methods, kits and assays for secondary tests on the cells from the subjects (e.g., subjects tested positive in the initial screen) could be used to confirm the presence and severity of cellular defect(s) associated with impaired PLA2g6 function. In some embodiments, subjects identified with deficiency in PLA2g6 expression or decreased PLA2g6 function can be treated with an appropriate therapy for the treatment of Parkinson's disease, and in some embodiments, with exogenous PLA2g6(L) nucleic acid (e.g., mRNA or modified RNA encoding PLA2g6(L) protein), or PLA2g6(L) protein or other PLA2g6(L) agonist.

The present invention relates to a diagnostic and/or prognostic tool, a screening tool, as well as methods and processes for early detection of a subject likely to develop idiopathic Parkinson's disease (PD). In some embodiments, the present invention relates to methods to identify a subject with early stage idiopathic PD (iPD) by detecting any one or more of the following; (i) a detection of relative expression of PLA2g6 (L) and PLA2g6 (S) variants of PLA2g6 (e.g., specifically, a reduction in PLA2g6(L)/PLA2g6(S) or PLA2g6(L)/total PLA2g6 ratio), (ii) a detection of a cleavage of the N terminus of PLA2g6 (i.e., detection of the presence of products of such cleavage), (iii) a reduced or decreased mRNA and/or protein expression of PLA2g6 (either the L (PLA2g6L) or the S (PLA2g6S) splice variants), or (iv) cleavage of the N-terminus of the PLA2g6 protein (e.g., a deletion of at least 50, or at least 100, or at least 150, or at least 178 N-terminal amino acids of PLA2g6 protein). In particular, the inventors demonstrate that a cryptic $ATG_2$ in Exon 4 initiated translation and resulted in a PLA2g6 protein that lacks the first 178 N-terminal amino acids, which while it retained PARK14 catalytic activity, resulted in a loss of $Ca^{2+}$ store-dependent activation of PLA2g6. In some embodiments, a subject identified with iPD according to (i) to (iv) above can be treated for PD, for example, administration of a treatment for PD known by one of ordinary skill in the art, or in some instances, administration of an antibody, such as PRX002, against the protein alpha-synuclein, or an anti-alpha-synuclein antibody vaccine such as disclosed in US application 2005/0196818 or 2013/0108546, or in some embodiments, by administering exogenous PLA2g6(L) nucleic acid (e.g., mRNA or modified RNA encoding PLA2g6(L) protein), or PLA2g6(L) protein or other PLA2g6(L) agonist.

In one embodiment of the aspect, a secondary diagnostic step can be performed. For example, if a level of PLA2g6(L) in the sample, e.g., blood sample, is found to indicate that the subject has iPD or is at risk of developing iPD or PD, then an additional method of confirming the diagnosis can be performed to confirm that the subject has, or is likely to get iPD or PD, as well as to further assess the extent of PLA2g6(L) dysfunction and SOCE dysregulation. Any of a variety of additional diagnostic steps can be used, such as ultrasound, PET scanning, MRI, or any other imaging techniques, biopsy, clinical examination, ductogram, or any other method. Additionally, the non-neuronal sample can also be assayed for any of SOCE, Ca2+ store deficiency and/or autophagy function according to the methods as disclosed herein.

Accordingly, in some embodiments, the methods, compositions and kits as disclosed herein measure SOCE (endogenous Store-Operated $Ca^{2+}$ Entry) and/or $Ca^{2+}$ store levels in live cells (e.g., blood and/or skin cells) obtained from the subject, and a lower SOCE and/or $Ca^{2+}$ store level measured as compared to a threshold level indicates that the subject has or is at risk of developing PD, including iPD. In some embodiments, the methods, compositions and kits as disclosed herein measure $Ca^{2+}$ store levels in live cells (e.g., blood cells such as platelets or other, skin and fibroblast cells etc.) obtained from the subject, and a depletion of $Ca^{2+}$ stores as compared to a threshold level of Ca$^{2+}$ stores indicates that the subject has or is at risk of developing PD, including iPD.

In some embodiments, the methods, compositions and kits as disclosed herein measure autophagic function of the cells (e.g., blood and/or skin cells) obtained from the subject, and an autophagic dysfunction measured as compared to a threshold level of autophagic function indicates that the subject has or is at risk of developing PD, including iPD.

Furthermore, the inventors have demonstrated specific set of biomarkers associated with human idPD, approaches for their effective interrogation, and informative readouts were identified, which are deemed to be suitable for early detection of idiopathic PD in humans.

The advantages described below will be realized and attained by means of the elements and combinations particularly pointed out in the appended claims. It is to be understood that both the foregoing general description and the following detailed description are exemplary and explanatory only and are not restrictive.

One aspect disclosed herein relates to an assay for detecting Parkinson's disease (PD) in a subject, or detecting a subject at risk of developing PD, the assay comprising; (a) performing quantitative RT-PCR on a sample obtained from the subject to measure the expression levels of (i) PLA2g6 (L), any one or more of PLA2g6(S), total PLA2g6, and/or a normalizing control gene; and (b) calculating the ratios of any one or more of:
  i. PLA2g6(L) to the normalizing control gene
  ii. PLA2g6(L) to PLA2g6(S)
  iii. PLA2g6(L) to total PLA2g6

In some embodiments, the assay further comprises a step of detecting PD in the subject where there is a statistically significant decrease in the expression of PLA2g6(L) identified by decrease in any one of the ratios (i), (ii) or (iii), or a statistically significant decrease in the level of PLA2g6(L) as compared to a reference PLA2g6(L) level.

Another aspect disclosed herein relates to an assay for detecting Parkinson's disease (PD) in a subject, or detecting a subject at risk of developing PD, the assay comprising; (a) contacting a sample obtained from the subject with an antibody that specifically binds to PLA2g6(L) (i.e., anti-PLA2g6(L) antibody), and at least one of; (i) a pan specific anti-PLA2g6 antibody that binds to PLA2g6(L) and PLA2g6(S) proteins, (ii) an anti-PLA2g6(S) antibody, (iii) an anti-normalizing protein antibody, (b) detecting and quantification of binding between the anti-PLA2g6(L) antibody and PLA2g6(L) protein, and detecting and quantification at least one of: the binding between the anti-PLA2g6 antibody and the PLA2g6(L) and PLA2g6(S) proteins, the binding between anti-PLA2g6(S) antibody and PLA2g6(S) protein, and the binding between anti-normalizing protein antibody and normalizing protein; and (c) calculating the ratios of any one or more of:
  i. the amount of PLA2g6(L) protein to PLA2g6(S) protein
  ii. the amount of PLA2g6(L) protein to total PLA2g6 protein
  iii. the amount of PLA2g6(L) protein to normalizing protein Another aspect disclosed herein relates to a method for identifying a human subject having, or at risk of, developing Parkinson's Disease (PD) comprising:
  a. contacting a sample obtained from the subject with primer pairs that specifically amplify the mRNA encoding PLA2g6(L), PLA2g6(S), total PLA2g6 and/or a normalizing control gene;
  b. performing quantitative RT-PCR to produce amplified nucleic acids encoding PLA2g6(L), PLA2g6(S), total PLA2g6 and/or the normalizing control gene;
  c. detecting the presence of the amplified nucleic acids encoding PLA2g6(L), PLA2g6(S), total PLA2g6 and/or the normalizing control gene;
  d. calculating the ratios of any one or more of:
    iv. PLA2g6(L) to the normalizing control gene
    v. PLA2g6(L) to PLA2g6(S)
    vi. PLA2g6(L) to total PLA2g6

In some embodiments, the assay further comprises detecting PD in the subject where there is a statistically significant decrease in the level of PLA2g6(L) protein revealed by changes in any one of the ratios (i), (ii) or (iii), or a statistically significant decrease in the level of PLA2g6(L) protein as compared to a reference PLA2g6(L) protein level.

Another aspect disclosed herein relates to a method for identifying a human subject having, or at risk of, developing Parkinson's Disease (PD) comprising:
  a. contacting a sample obtained from the subject with a pan specific anti-PLA2g6 antibody and an antibody that specifically binds to PLA2g6(L) (anti-PLA2g6(L) antibody), and
  b. detecting binding between the anti-PLA2g6 antibody and the total PLA2g6 protein, and detecting the binding between the anti-PLA2g6(L) antibody and PLA2g6(L) protein.
  c. quantification of the changes in the amount of PLA2g6 (L) protein by changes in the ratios of any one or more of:
    vii. PLA2g6(L) to the normalizing protein
    viii. PLA2g6(L) to PLA2g6(S)
    ix. PLA2g6(L) to total PLA2g6.

In some embodiments, the method further comprising diagnosing the subject as having or at risk of developing Parkinson's Disease (PD) when any of the (i) to (iii) ratio level of PLA2g6(L) protein is detected to be significantly lower by at least one standard deviation σ (sigma) than a reference standard.

Another aspect disclosed herein relates to a method for identifying a human subject having, or at risk of, developing Parkinson's Disease (PD) comprising, such as idiopathic Parkinson's disease comprising: (i) contacting a sample obtained from the subject with an antibody that specifically binds to PLA2g6(L) (anti-PLA2g6(L) antibody) and does not specifically bind to PLA2g6(S), (ii) detecting binding between PLA2g6(L) protein and the anti-PLA2g6(L) antibody; (iii) diagnosing the subject as having or at risk of developing Parkinson's Disease (PD) when the protein level of PLA2g6(L) in the sample obtained from the subject is detected to be significantly decreased by at least 1, or 2, or 3, or 4 standard deviation σ (sigma) as compared to a reference control level for PLA2g6(L) protein.

In some embodiments, the assays and methods as disclosed herein, further comprise a second assay to measure Ca$^{2+}$ levels, by measuring any one of: (i) Store operated Ca$^{2+}$ Entry (SOCE) in response to experimental (artificial) depletion of Ca2+ in stores in a sample comprising live cells from the subject, and detecting a decrease in SOCE response, by at least 1, or 2, or 3, or 4 standard deviation σ (sigma) in the cells obtained as compared to a reference standard; and/or (ii) measuring ER Ca$^{2+}$ store levels in a sample comprising live cells from the subject, and detecting a decrease in ER Ca$^{2+}$ store levels, by at least 1, or 2, or 3, or 4 standard deviation σ (sigma) in the cells obtained as compared to a reference standard, and/or autophagy function in a sample comprising live cells from the subject, and detecting a decrease in autophagy function, by at least 1, or 2, or 3, or 4 standard deviation σ (sigma) in the cells obtained as compared to a reference standard.

In some embodiments, the statistically significant decrease is a decrease of at least one, or at least 2 or at least 3 standard deviation σ (sigma) as compared to a reference standard level from healthy individuals known not to have PD.

In some embodiments, the sample for use in the assays, methods and kits as disclosed herein is selected from the group of: whole blood, plasma, specific blood cells, skin fibroblasts, CSF or any non-neuronal cells collected from the subject, and in some embodiments, the blood sample is a total plasma sample or a platelet rich plasma (PRP) sample.

In some embodiment, an anti-PLA2g6(L) antibody for use in the assays, methods and kits as disclosed herein binds to an epitope at least partially encoded by exon 8b of PLA2g6(L), but is spliced out in PLA2g6(S), for example, an anti-PLA2g6(L) antibody can binds to an epitope at least partially located in any one of SEQ ID NO: 16, SEQ ID NO: 17 or SEQ ID NO:18.

In some embodiment, a reference PLA2g6(L) mRNA or protein level, or a reference standard for use in the assays, methods and kits as disclosed herein is the level of PLA2g6 (L) mRNA or protein in at least one healthy individual known not to have PD, or the level of PLA2g6(L) mRNA or protein measured from a sample obtained from the same subject from at least one earlier timepoint or earlier age.

In some embodiment, the assays, methods and kits as disclosed herein can be used to identify a subject with Parkinson's Disease (PD), for example, idiopathic PD (iPD).

Another aspect of the disclosure relates to a kit comprising: a set of primers and probes specific for PLA2g6(L) mRNA; and at least one of: a set of primers and probes specific for PLA2g6(S) mRNA, a set of primers and probes specific for a total PLA2g6 mRNA, a set of primers and probes for normalization control mRNA.

Another aspect of the disclosure relates to a kit comprising: an anti-PLA2g6(L) antibody; and at least one of: a pan-specific PLA2g6 antibody that binds to PLA2g6(L) and PLA2g6(S), an anti-PLA2g6(S) antibody, an anti-normalizing protein antibody.

Another aspect of the disclosure relates a method for identifying a human subject having, or at risk of, developing Parkinson's Disease (PD) comprising: (i) measuring Store operated Ca$^{2+}$ Entry (SOCE) in response to experimental (artificial) depletion of Ca in the stores in a sample comprising live cells from the subject, (ii) detecting a decrease in SOCE response, by at least 1, or 2, or 3, or 4 standard deviation σ (sigma) in the cells obtained as compared to a reference standard.

Another aspect of the disclosure relates to a method for identifying a human subject having, or at risk of, developing Parkinson's Disease (PD) comprising: measuring ER Ca$^{2+}$ store levels in a sample comprising live cells from the subject, detecting a decrease in ER Ca$^{2+}$ store levels, by at least 1, or 2, or 3, or 4 standard deviation σ (sigma) in the cells obtained as compared to a reference standard.

Another aspect of the disclosure relates to a method for identifying a human subject having, or at risk of, developing Parkinson's Disease (PD) comprising: measuring autophagy function in a sample comprising live cells from the subject, and detecting a decrease in autophagy function, by at least 1, or 2, or 3, or 4 standard deviation σ (sigma) in the cells obtained as compared to a reference standard.

Another aspect of the disclosure relates to a method for treating idiopathic Parkinson's Disease (iPD) comprising identifying a subject as having or at risk of PD, including idiopathic Parkinson's Disease (iPD) according to any of the methods, assays and kits of any of the paragraphs above, and administering preventive or restorative therapy to delay, or reverse progression of the disease. In some embodiments, The method of an effective therapy for PD is administering an agonist of PLA2g6(L) or a nucleic acid encoding human PLA2g6(L) or a functional fragment thereof.

BRIEF DESCRIPTION OF THE DRAWINGS

The accompanying drawings, which are incorporated in and constitute a part of this specification, illustrate embodiments of the invention and, together with the description, serve to explain the objects, advantages, and principles of the invention.

FIGS. 1A-1G show that deficiency in PARK14 and store-operated Ca$^{2+}$ signaling in human primary skin fibroblasts from patients with idiopathic PD (idPD) and with familial PLA2g6$^{R747W}$ mutation (fPD$^{R747W}$). FIGS. 1A and 1B show representative traces show store-operated Ca$^{2+}$ entry (SOCE) upon Ca$^{2+}$ addition in thapsigargin pretreated (TG, 5 µM for 20 min) fibroblasts from control, idPD patients (shown in FIG. 1A), and fPD$^{R747W}$ patient (shown in FIG. 1B): each trace show Ca$^{2+}$ influx (average ΔRatio (F$_{340}$/F$_{380}$)±SD) in a group of 10-20 individual cells measured simultaneously; full traces are shown in FIG. 8A. FIG. 1C is a comparative analysis of SOCE in fibroblasts from control idPD and fPD$^{R747W}$ patients. Data for each patient show the average±SE from at least 3 independent experiments, with up to 120 cells analyzed for each patient (see FIG. 8C for details). FIG. 1D shows the catalytic PLA2g6 activity in homogenates of fibroblasts from control, idPD and fPD$^{R747W}$ patients: summary results show average activity (±SEM) from 3 repetitions under basal conditions, after activation in the presence of 10 mM EGTA, and after inhibition with 25 µM of (S)-BEL (see FIG. 9A for details). FIG. 1E shows that activation of PLA2g6 by TG-induced depletion of Ca$^{2+}$ stores in intact fibroblasts from control, idPD, and fPD$^{R747W}$ patients: summary results show average activity (±SEM) from 3 repetitions under basal conditions, after activation by TG (5 µM for 10 minutes), and after inhibition with (S)-BEL (see FIG. 9B for details). FIG. 1F shows the relative expression of Orai1, STIM1, TRPC1, PLA2g6(L) and PLA2g6(S) in fibroblasts from control and idPD patients: summary results of qRT-PCR analysis normalized to GAPDH for each sample, with group averages shown by the horizontal line (see FIG. 10 for details). (p<0.01), *(p<0.001). FIG. 1G shows the relative expression of PLA2g6(L) and PLA2g6(S) in platelets from idPD patients. The qRT-PCR results of PLA2g6(L) and PLA2g6(S) expression is normalized to GAPDH for each sample.

FIGS. 2A-2G shows that new PARK14 (PLA2g6) ex2$^{KO}$ mouse model mimics idPD-associated deficiency in store-operated PLA2g6(L)-dependent Ca$^{2+}$ signaling. FIG. 2A is a schematic illustration of Pla2g6 (PARK14) gene with exons and ATG sites; below, corresponding full length [(L) or PLA2g6(L)] variant of wild type (WT) PLA2g6 protein, and N terminal truncated protein in ex2$^{KO}$ mouse in which exon 2 was genetically deleted (see FIGS. 12-16). FIG. 2B shows the catalytic activity of PLA2g6 in homogenates of mouse embryonic fibroblasts (MEFs) from WT and ex2$^{KO}$ mice: summary results show average activity (±SE) from 3 repetitions under basal conditions, after activation in the presence of 10 mM EGTA, and after inhibition with 25 µM (S)-BEL. FIG. 2C shows that activation of PLA2g6 by TG-induced depletion of $Ca^{2+}$ stores in intact MEFs from WT and $ex2^{KO}$ mice: summary results show average activity (±SE from 3 repetitions) under basal conditions, after activation by TG (5 µM for 10 minutes), and after inhibition with (S)-BEL. FIG. 2D shows that Impairment of TG-induced SOCE in the $ex2^{KO}$ MEFs: representative traces show $Ca^{2+}$ response to TG (5 µM) application in the absence of extracellular $Ca^{2+}$, followed by SOCE upon $Ca^{2+}$ addition in WT and $ex2^{KO}$ cells. Each trace shows $Ca^{2+}$ responses (average±SD) in a group of 10-20 individual cells measured simultaneously. FIG. 2E shows summary data show the differences in the peak SOCE in the WT and $ex2^{KO}$ cells: average±SE from 3-6 independent experiments per each condition. FIG. 2F shows representative traces (average±SD) show ionomycin (IM, 1 µM)-induced $Ca^{2+}$ release from intracellular stores (in the presence of extracellular EGTA) in WT and $ex2^{KO}$ MEFs. FIG. 2G shows summary data from experiments like in (f) show peak $Ca^{2+}$ release (average±SE) from 3-6 independent experiments. The numbers of cells summarized for each condition is specified above the bars; *(p<0.05), (p<0.01), *(p<0.001).

FIGS. 3A-3F shows Store-operated $Ca^{2+}$ signaling in iPSC-derived DA neurons from WT and $ex2^{KO}$ mice. FIG. 3A shows representative images of iPSC-derived A9 midbrain DA neurons positive for tyrosine hydroxylase (TH+) from WT and PLA2g6 $ex2^{KO}$ mice. FIG. 3B shows images that demonstrate $Ca^{2+}$ changes due to SOCE in specific DA neurons outlined by dotted circles and shown by an arrow in (FIG. 3A): images show Fura-2 Ratio ($F_{340}/F_{380}$) in individual TH+ neuron before (left) and after (right) $Ca^{2+}$ addition to TG-pretreated cells, as shown in (FIG. 3C). FIG. 3C shows TG-induced SOCE (average±SD) in individual iPSC-derived DA (TH+) neurons from WT and $ex2^{KO}$ mice: traces show $Ca^{2+}$ changes in response to TG (5 µM) application in the absence of extracellular $Ca^{2+}$, followed by SOCE upon $Ca^{2+}$ addition. FIG. 3D shows summary data comparing the peak SOCE (average±SE) in DA (TH+) neurons from WT and FIG. 3E shows summary data from $ex2^{KO}$ mice, IM (100 nM)-induced $Ca^{2+}$ release (average±SD) from intracellular stores in DA (TH+) neurons from WT and $ex2^{KO}$ mice. FIG. 3F shows summary data from experiments like in (FIG. 3F), and show peak $Ca^{2+}$ release (average±SE). The data represent the results from 3 independent experiments. The numbers of cells analyzed for each condition is specified above the bars; *(p<0.05), **(p<0.01).

FIG. 4A shows the progressive motor dysfunction in ageing $ex2^{KO}$, but not WT mice (see methods for details); human age equivalent is shown below; insert illustrates unstable gait of representative 18-month old $ex2^{KO}$ animal; numbers above each point represent the number of animals per each age group. FIG. 4B shows analysis of PAS staining shows significant increase in the number of PAS(+) degenerative neurons in SNc, but not hippocampus or M1/M2 motor cortex of the 16-month old $ex2^{KO}$ mice (average±SE from 3 pairs of age-matched animals). FIG. 3C shows example of immunostaining of TH+ positive (brown) neurons in SNc in the brain from WT and $ex2^{KO}$ littermates (16-month old); the bar is 500 µm. FIG. 4D shows summary data (average±SE) show progressive age-dependent reduction in the number of TH+ neurons in $ex2^{KO}$ mice; the results of the blinded stereological analysis of SN area of the brain in the groups of age-matched WT and $ex2^{KO}$ animals (for more details see FIG. 19). FIGS. 4E-4I show results of behavioral studies of the age-matched groups of the WT and $ex2^{KO}$ mice show: FIG. 4E shows progressive age-dependent increase in the number of missteps in the balance beam test; FIG. 4F shows age and dose-dependent improvement of motor performance by L-DOPA in $ex2^{KO}$ mice; relative change in the number of missteps in balance beam test made 1 h after L-DOPA (5, 10 or 25 µM) administration versus control in the 12 (n=12), 16 (n=8) and 20 (n=8) month old animals; FIG. 4G shows significant increase in time required for 16-month old $ex2^{KO}$ mice to re-orient on the top of the pole; FIG. 4H shows significantly reduced rotarod performance of the 16-18-month old $ex2^{KO}$ mice; FIG. 4I shows no difference in the grip strength of the 16-18-month old WT and $ex2^{KO}$ mice. All data are mean±SE; numbers above each bar represent the number of animals tested per each group; (p<0.01), *(p<0.001).

FIGS. 5A-5F show autophagic dysfunction in $ex2^{KO}$ mice. FIG. 5A shows co-localization of tyrosine hydroxylase (TH) and PLA2g6(L) (observed in green) in DA neurons in SNc of $ex2^{KO}$ mice (see FIG. 20 for details). Nuclei are stained with DAPI (blue). Image on the right shows magnified part of the image on the left (identified by dotted rectangle). FIG. 5B are representative images show LC3 aggregation in TH+ neurons of the $ex2^{KO}$, but not WT brain: results of co-immunostaining for TH (red), LC3 (green) and DAPI (blue) in SNc area of the brain from 16-month old $ex2^{KO}$ and WT littermates (see FIG. 21 for details). FIG. 5C are representative Western Blot and summary data (average±SE) show significant increase in LC3-II/actin ratio in tissue samples from the $ex2^{KO}$ mice (n=3). Images have been cropped for presentation. Full size images are shown in FIG. 27. FIG. 5D are representative images of $LC3^{mCherry/eGFP}$ (tandem mCherry/eGFP (green)-tagged LC3) in live MEF cells from the WT and $ex2^{KO}$ mice. Composite image of the whole cell is shown on the left, and magnified mCherry, eGFP and merged images on the right show the part of the cell identified by dotted rectangle. Far right image shows correlation map for red and green signals (see FIG. 22 and Methods for details). FIG. 5E shows summary data show increase in the correlation coefficient (in experiments like in (FIG. 5D)) in the cells from $ex2^{KO}$ mice, compared with WT cells; bars show average (±SE) from 3 independent experiments. FIG. 5F shows summary data (like in FIG. 5E), and show significant increase in the correlation coefficient in the cells from $Orai1^{KO}$ mice (for more details see FIG. 23). *(p<0.05), ***(p<0.001).

FIGS. 6A-6G show results from rescue experiments in live $ex2^{KO}$ MEF cells transfected with WT PLA2g6(L), or its PD-associated F72L mutant, or A80T mutant that does not have association with human PD. FIGS. 6H-6N show the dominant-negative effects of PLA2g6(L) deficiency in live WT MEF cells transfected with empty vector (control), or PLA2g6(L) $ex2^{KO}$, or one of two human PD-associated PLA2g6(L) mutants (F72L or R747W). FIGS. 6A-6B, and FIGS. 6K-6L show SOCE upon $Ca^{2+}$ addition to TPEN pretreated cells (400 µM for 3 min); FIGS. 6C-6D and FIGS. 6M-6N show ionomycin (IM, 1 µM)-induced intracellular $Ca^{2+}$ store release; FIGS. 6E-6G, and FIGS. 6H-6J show autophagic flow visualized by $LC3^{mCherry/eGFP}$ fluorescence (as in FIG. 4D-4E) in live MEF cells. Representative $Ca^{2+}$ traces show average±SD from 10-20 cells recorded simultaneously. All summary data (bars) show average±SE from 3-6 independent experiments per each condition; the number of cells for each condition is specified above the bars; *(p<0.05), (p<0.01),* (p<0.001). (For more details see FIG. 24 and FIG. 25).

FIG. 7A shows representative images and correlation maps of $LC3^{mCherry/eGFP}$ in live primary human skin fibroblasts from control, idiopathic (idPD) and familial (fPD) $PLA2g6^{R747W}$ mutant patients. FIG. 7B shows summary data (average±SE) from experiments like in (a) show significant impairment of autophagy in idPD (n=10) and $fPD^{R747W}$ (n=1) versus control (n=5) patients, which is evident from the higher correlation coefficient for $LC3^{mCherry/eGFP}$ (see FIG. 26 for details); (p<0.01). FIGS. 7C-7D show results of the rescue experiments in live fibroblasts from idPD patient, with FIG. 7C showing SOCE (like in experiments in FIG. 1A) and FIG. 7D showing the correlation coefficient (like in experiments in FIG. 6A-6B) 48 hours after cells transfection with either PLA2g6(L), or empty vector as a control. Summary data show average±SE from the numbers of cells specified above the bars. (p<0.01). FIG. 7E is a schematic illustration of a previously unknown sequence of pathological events that can be initiated by idiopathic or genetic deficiency in store-operated activation of PLA2g6 (PARK14), which can lead to SOCE impairment, depletion of intracellular $Ca^{2+}$ stores, and autophagic dysfunction, which results in progressive loss of DA neurons in SNc and age-dependent Parkinson's disease.

FIGS. 8A-8C show store-operated $Ca^{2+}$ entry (SOCE) in primary skin fibroblasts (hPSF) from human donors. FIG. 8A shows representative trace showing changes in cytosolic $Ca^{2+}$ following thapsigargin (TG, 5 μM) application in the absence of extracellular $Ca^{2+}$ (initial $Ca^{2+}$ rise due to passive $Ca^{2+}$ leak from ER stores), followed by SOCE (second $Ca^{2+}$ rise due to $Ca^{2+}$ influx into the cells upon extracellular $Ca^{2+}$ addition). The average Fura2 Ratio ($F_{340}/F_{380}$)±SD from a group of 10-20 individual cells measured simultaneously. The area marked by star identifies the part of the experiment that is chosen for representative traces that illustrate SOCE in the FIG. 1A-1B. FIG. 8B shows store-operated $Ca^{2+}$ entry (SOCE) in hPSF can be triggered by either TG-induced inhibition of SERCA (that allows passive $Ca^{2+}$ leak from the stores), OR by TPEN-induced buffering of free $Ca^{2+}$ in ER stores. FIG. 8C shows comparative analysis of SOCE in primary skin fibroblasts from 5 control donors, 10 patients with idiopathic PD (idPD), and a patient with familial PD caused by R747W mutation in PLA2g6. Data for each patient show the average±SE from at least 3 independent experiments, with up to 120 cells analyzed for each patient; **p<0.01.

FIG. 9A shows summary data show catalytic PLA2g6 activity in homogenates of hPSF from each individual donor: summary results for each patient show average activity (±SEM) from 3 repetitions under basal conditions, after PLA2g6 was fully activated by 10 mM EGTA-induced displacement of inhibitory CaM, and after PLA2g6 inhibition with 25 μM of (S)-BEL. FIG. 9B shows summary data show activation of PLA2g6 by TG-induced depletion of $Ca^{2+}$ stores in intact hPSF from individual control and idPD patients: summary data for each patient show average activity (±SEM) from 3 repetitions in basal conditions, after activation by TG (5 μM for 10 minutes), and after inhibition with (S)-BEL, normalized to catalytic activity for each patient. ***p<0.001.

FIG. 10A shows the results of the quantitative Real Time PCR (qRT-PCR) analysis of expression levels of Orai1, STIM1, TRPC1, and FIG. 10B shows the results of the quantitative Real Time PCR (qRT-PCR) analysis of expression levels of two major splice variants of Pla2g6 gene: full length PLA2g6(L) and shorter PLA2g6(S) in which exon 8b is spliced out. Each data point is average±SE (n=2) normalized to the level of GAPDH expression in corresponding sample from each patient.

FIGS. 11A-11B shows different PLA2g6A gene splice variants. FIG. 11A is a table listing the different PLA2g6A gene splice variants, with PLA2G6-001 encoding the PLA2g6(L) variant, and PLA2G6-201 and PLA2G6-002 encoding the PLA2g6(S) variant. FIG. 11B is a sequence comparison of SEQ ID NO: 2 corresponding to PLA2g6(L) protein as compared to SEQ ID NO: 4 corresponding to PLA2g6(S). The highlighted and underlined region in SEQ ID NO: 2 (i.e., TRKAILTLLRTVGAEYCFPPIHGV-PAEQGSAAPHHPFSLERAQPPPISLNNLELQDLMHIS-RARKP (SEQ ID NO: 16) can be used as a target area for binding of an antibody that specifically binds to PLA2g6(L) as compared to PLA2g6(S) protein. In particular, an antibody specific to the PLA2g6(L) protein can bind to an epitope located in any one or both of the sequences TRKAILTLLRTVGAEYCFPPIHGVPAEQGSAAP (SEQ ID NO: 17) or PISLNNLELQDLMHISRARKP (SEQ ID NO: 18).

FIG. 14A is a schematic representation of WT Pla2g6 locus with positions of four sets of primers used for PCR-based genotyping (sets 1 and 2) of the colony, or for confirmation of the lack of Pla2g6 exon 2 in transcripts from mouse brains (set 3 and 4). FIG. 14B and FIG. 14C show representative results of tail DNA genotyping for 9 animals from the colony using PCR primer sets 1 and 2. Expected length of PCR products for primer set 1 are 4028 (WT) and 2900 bp (ex2 KO allele), and for set 2 only WT allele (857 bp product) can be detected. Taken together, PCR with both sets of primers allowed for unambiguous determination of the Pla2g6 locus genotype for each animal within the colony. FIG. 14D and FIG. 14E show total RNA isolated from brains of two representative pairs of WT and exon 2 KO animals was reverse-transcribed and used as a template for PCR with primer sets 3 and 4. Expected length of PCR products for primer set 3 are 736 (WT) and 486 bp (ex2 KO allele), and for set 4 only WT allele (644 bp product) can be detected. As expected, for both animals previously genotyped as Exon 2 KO (using primer sets 1 and 2), transcripts coding for PLA2g6 are present in the brain, but are missing exon 2. Additionally, the product amplified with the primer set 3 from brains of $ex2^{KO}$ mice was cloned and sequenced, and both the expected cDNA sequence and the lack of Exon 2 were confirmed (data not shown).

FIG. 17A show representative Western blot that shows that recombinant $^{myc}$PLA2g6(S)$^{his}$ and $^{myc}$PLA2g6(L)$^{his}$ protein can be detected with Myc antibody, while only $^{myc}$PLA2g6(L)$^{his}$ protein can be recognized by custom-made PIN antibody that specifically targets PIN domain (encoded by exon 8b), which is present in (L), but spliced out in (S) variant of PLA2g6. Images have been cropped for presentation. Full size images are presented in FIG. 27. FIG. 17B shows a Western blot that shows that not only recombinant $^{myc}$(L)$^{his}$, but also endogenous PLA2g6(L) protein from WT mouse can be specifically recognized by PIN antibody. Blot on the bottom shows the same membrane stained for β-actin. Please, notice that recombinant protein contains myc and his tags on its N and C termini, respectively, which slightly increase its MW in comparison with equivalent endogenous protein in WT mice. Images have been cropped for presentation. Full size images are presented in FIG. 27. FIG. 17C shows representative TIRF image of MEF cell stained with mPIN ab. TIRF image (the bottom of the cell) shows that PIN ab recognizes endogenous PLA2g6(L) at plasma membrane.

FIG. 18A shows representative traces show $Ca^{2+}$ influx in WT and $ex2^{KO}$ cells pretreated with TPEN (400 μM for 5 min). The average Ratio $(F_{340}/F_{380})$±SD is recorded from a group of 10-20 individual cells measured simultaneously. TPEN-induced buffering of $Ca^{2+}$ in ER stores is known to mimic TG-induced depletion of ER, and both treatments activate similar SOCE (as shown in FIG. 1B). FIG. 18B show summary data from experiments show the peak TPEN-induced SOCE in the WT and $ex2^{KO}$ cells in control conditions, and after PLA2g6 inhibition with S-BEL (50 μM for 20 min): average±SE from 3-6 independent experiments per each condition. ***p<0.001

FIG. 19A shows immunostaining for tyrosine hydroxylase (TH, brown) of VTA area. FIG. 19B shows TH (brown) and Niss1 (blue) staining in the SNc area, showing significant loss of DA neurons in SNc area of $ex2^{KO}$ mice FIG. 20A shows representative immunostaining for tyrosine hydroxylase (TH from Calbiochem, brown) in brain slices and corresponding (enlarged) nigrostriatal area of the brain of 16-month old WT and $ex2^{KO}$ littermates. FIG. 20B shows results of blinded stereological analysis of the total numbers of TH+ neurons in SN (both sides) of WT and $ex2^{KO}$ mice (data for littermate pairs are connected with lines). FIG. 20C shows the summary data for WT and $ex2^{KO}$ mice show relative differences in the numbers of TH+ neurons in $ex2^{KO}$ animals normalized to their WT littermates. (p<0.01), *(p<0.001).

FIG. 21A shows immunostaining of substantia nigra par compacta (SNpc) area shows localization of tyrosine hydroxylase (TH) with PLA2g6(L) (custom-made αPIN, green); nuclei stained with DAPI; FIG. 21B shows enlarged images of the corresponding areas identified in (FIG. 21A). FIG. 21C shows negative control showing the results of staining with secondary Alexa594 and Alexa488 antibodies (both from Molecular Probes) in the absence of primary antibodies.

FIG. 22A shows representative images (the whole cells are shown on the left, and enlarged part of the cells are shown on the right) and correlation maps of tandem mCherry/eGFP tagged LC3 in live MEF cells. Experiments were done 48 hours after transfection. Thapsigargin treatment was 10 nM for 24 hours before the experiment. FIG. 22B shows the summary results of comparative analysis of the correlation coefficient of mCherry and eGFP. FIG. 22C shows the size of mCherry particles; the data show average±SE; summary data from a total of 15 cells per condition (5 cells from each of 3 independent experiments), *($p<0.05$), ***($p<0.001$).

FIG. 23A show representative traces (left) and summary data (right) show significant impairment of TPEN-induced SOCE in MEFs from Orai1$^{KO}$ mice compared to WT control (1 day in culture). Traces show the average SOCE (±SD) from a group of 10-20 individual cells measured simultaneously. Summary data show average (±SE) from 3 independent experiments; the numbers of the cells analyzed in shown above the bars. FIG. 23B shows that there is a progressive increase in TPEN-induced Ca$^{2+}$ entry following prolonged culture of MEFs from Orai1$^{KO}$ mice demonstrate the ability of MEFs to compensate for genetic Orai1 (and SOCE) deficiency. SOCE was assessed in MEFs (P2) from WT and Orai1$^{KO}$ mice after 1, 2 and 4 days in culture. FIG. 23C shows representative traces (left) and summary data (right) show significant loss of ionomycin (IM)-induced Ca$^{2+}$ release from the stores in MEFs from Orai1$^{KO}$ mice (1 day in culture). Traces show the average SOCE (±SD) from a group of 10-20 individual cells measured simultaneously. Summary data show average (±SE) from 3 independent experiments; the numbers of the cells analyzed are shown above the bars. FIG. 23D shows a progressive increase in IM-induced Ca$^{2+}$ release following prolonged culture of MEFs from Orai1$^{KO}$ mice demonstrate the ability of MEFs to compensate for Orai1 deficiency, and to restore their ER stores. FIG. 23E shows representative images (left) and summary data for correlation coefficient (right) of tandem mCherry (red)/eGFP(green) tagged LC3 in live MEF cells from Orai1$^{KO}$ mice. Experiments similar to those described in main FIG. 4$d,f$. The data show average±SE; summary data from a total of 15 cells per condition (5 cells from each of 3 independent experiments). $p<0.01$*($p<0.001$).

FIG. 24A shows representative images (the whole cells are shown on the left, and enlarged part of the cells are shown on the right) and correlation maps of tandem mCherry/eGFP tagged LC3 in live MEF cells from ex2$^{KO}$ mice. The cells where transfected with LC3$^{mCherry/eGFP}$ together with either WT PLA2g6(L) (images on the top), or its human PD-associated F72L mutant (images on the bottom). Experiments were done 48 hours after transfection. FIG. 24B shows the summary results of comparative analysis of the correlation coefficient of mCherry and eGFP, and FIG. 24C shows the size of mCherry particles; the data show average±SE; summary data from a total of 15 cells per condition (5 cells from each of 3 independent experiments), ***($p<0.001$).

FIGS. 25A-25C shows the dominant-negative effect of ex2$^{KO}$ PLA2g6(L) on LC3$^{mCherry/eGFP}$ autophagic flow in WT MEFs. FIG. 25A show representative images (the whole cells are shown on the left, and enlarged part of the cells are shown on the right) and used to calculate correlation maps of tandem mCherry (red)/eGFP(green) tagged LC3 in live MEF cells from WT mice which are shown in FIG. 25B. The cells where transfected with LC3$^{mCherry/eGFP}$ together with either WT PLA2g6(L) (images on the top), or ex2$^{KO}$ (N-terminus truncated) PLA2g6(L) that mimics PLA2g6 protein found in ex2$^{KO}$ mice (images on the bottom). Experiments were done 48 hours after transfection. FIG. 25B shows the summary results of comparative analysis of the correlation coefficient of mCherry and eGFP, and FIG. 25C shows the size of mCherry particles; the data show average±SE; summary data from a total of 15 cells per condition (5 cells from each of 3 independent experiments), ***($p<0.001$).

FIG. 26A shows representative images (the whole cells are shown on the left, and enlarged part of the cells are shown on the right), which are used to calculate correlation maps of tandem mCherry (red)/eGFP(green) tagged LC3 in live hPSF from control, idPD and familial PD (PLA2g6$^{R747}$ mutant) patients. Experiments were done 48 hours after transfection. FIG. 26B shows the summary results of comparative analysis of correlation coefficient of mCherry and eGFP in hPSF from individual patients. FIG. 26C shows a summary of correlation coefficients for three groups of patients: the data show average (±SE) in 15 cells for each patient, **($p<0.01$).

DETAILED DESCRIPTION OF THE INVENTION

Figure 1E:
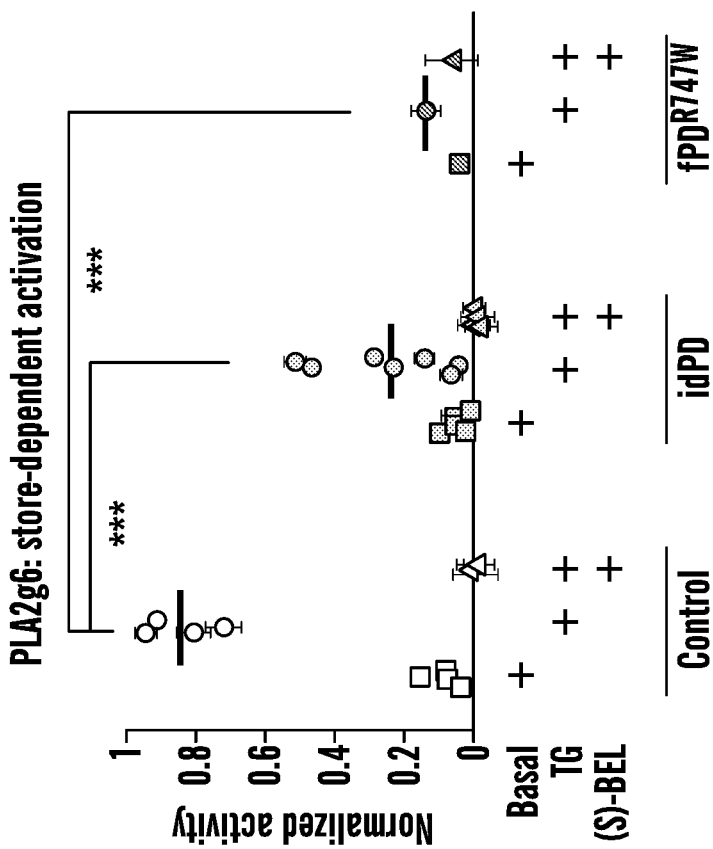
Figure 1D:
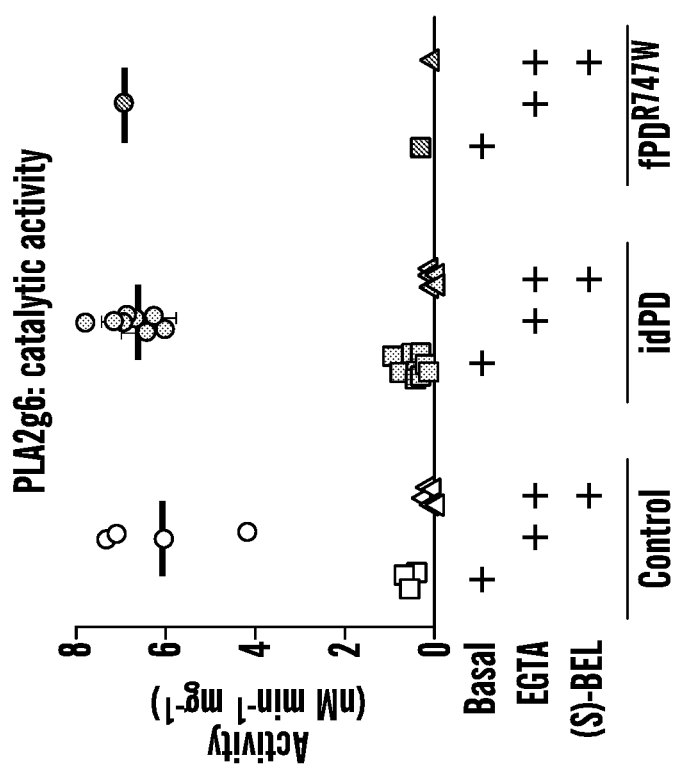

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

The disclosure herein refers to PD biomarkers and methods, compositions and kits for detection of pre-clinical stages of human PD, or iPD in easy collectible cell samples obtained from the subject, e.g., from skin cells, neuronal cells and non-neuronal cell samples (e.g., skin fibroblasts, blood cells and others). More specifically, a decrease in PLA2g6(L) expression and/or function serves as a useful biomarker to identify a subject at risk of developing age-dependent PD, or having iPD in prodromal (preclinical) or early clinical stages.

Herein, the inventors have surprisingly discovered that a decreased mRNA or protein expression of PLA2g6(L) leads to a decrease in SOCE, and resulting deficit in Ca2+ stores in cell samples (e.g., blood cells such as platelets, skin fibroblasts and other cells) from aged humans. Surprisingly, the decreased mRNA or protein expression of PLA2g6(L), decrease in SOCE and deficits in Ca2+ER stores and autophagic dysfunction in non-neuronal cells were found to mirror those occurring in Dopaminergic neurons in substantia nigra pars compacta, which can lead to premature age-dependent death of DA neurons and development of PD.

Accordingly, the disclosure herein refers compositions assays, methods and kits to measure any one or a combination of the following in any cell samples from the subjects (including non-neuronal cells):

i) mRNA and/or protein expression level of PLA2g6(L), for example, a detection of relative expression of PLA2g6 (L) and PLA2g6 (S) variants, e.g., a reduction in PLA2g6 (L):PLA2g6(S) ratio or a reduction of PLA2g6(L):total PLA2g6 ratio, as compared to a tissue and/or aged matched reference level (e.g., reference standard), where a significantly lower PLA2g6(L) mRNA and/or protein expression level as compared to the reference standard level indicates that the subject has or is at risk of developing PD, including iPD.

(ii) detection of a cleavage product of the N terminus of PLA2g6 (i.e., detection of the presence of products of such cleavage, e.g., detection of a deletion of at least 50, or at least 100, or at least 150, or at least 178 N-terminal amino acids of PLA2g6 protein. In particular, the inventors demonstrate that a cryptic $ATG_2$ in Exon 4 initiated translation and resulted in a PLA2g6 protein that lacks the first 178 N-terminal amino acids, which while it retained PARK14 catalytic activity, resulted in a loss of $Ca^{2+}$ store-dependent activation of PLA2g6, and leads to the loss of DA neurons and PD-like motor dysfunction in PLA2g6ex2KO mouse model.

(iii) measure SOCE (endogenous Store-Operated $Ca^{2+}$ Entry) and/or $Ca^{2+}$ store levels in live cells (e.g., blood and/or skin cells, as well as other non-neuronal cells) obtained from the subject, where a lower SOCE and/or $Ca^{2+}$ store level measured as compared to a reference threshold level indicates that the subject has or is at risk of developing PD, including iPD, and/or (iv) measure autophagic function of the cells (e.g., blood and/or skin cells) obtained from the subject, and an autophagic dysfunction measured as compared to a threshold level of autophagic function indicates that the subject has or is at risk of developing PD, including iPD.

Currently, there are no established markers or routine screening approaches/procedures for prediction or detection of human PD in early preclinical stages in aging population or for early detection of iPD. Idiopathic PD (iPD) is a neurodegenerative disease that stems from accelerated loss of DA neurons in SNc, which progress silently (without clear clinical manifestations) for many years prior to onset of the clear symptoms of PD-associated motor dysfunction. Typically, iPD is not diagnosed until only 30-40% of DA neurons remain in SNc. It would be highly desirable to be able to identify a subject with a predisposition to iPD, or a subject that has iPD without any clinical symptoms, and therefore be able to administer a suitable PD treatment to prevent further decline in SNc neurons before the onset of the PD symptoms.

Accordingly, the disclosure herein is advantageous in that the assays, kits, compositions and methods as disclosed herein can be used as regular non-invasive screening (e.g., using a blood or skin cell sample obtained from the subject) at annual or bi-annual screening of subjects at any age from age 30 onwards, to identify if the subject at risk of developing PD. Accordingly, advantages of the present invention are numerous in the fact that the biomarkers as disclosed herein can be used to identify a subject with a predisposition to iPD, or a subject that has iPD without any clinical symptoms, and therefore be able to administer a suitable PD treatment to prevent further decline in SNc neurons before the onset of the PD symptoms. Additionally, the assays, kits, compositions and methods as disclosed herein can be used to monitor progression of iPD in a subject over time (e.g., a subject can be monitored about every 2, or about every 3, or about every 6 months, or yearly etc.), as well as be useful in clinical trials to test for effective treatments for iPD and PD.

The inventors have discovered distinct and significant defects in PARK14/PLA2g6(L) expression and functional responses to specific in vitro tests in the cells of patients with idiopathic PD. The inventors have demonstrated that such defects impair specific cellular functions that increase DA neurons vulnerability to cellular stress induced by aging or other pathological insults, which are directly associated with human PD.

Accordingly, the present invention relates to testing biological samples obtained from the subject, e.g., samples of cells from simple blood test, or from skin biopsy, to identify subjects that carry such defects and identify the subjects as predisposed to an accelerated loss of DA neurons in SNc and development of PD, as well as identify subjects who already have preclinical stages of PD (with significant loss of DA neurons that have not yet reached a threshold for its clinical manifestation). Secondary tests on the live cells from the subjects tested positive in the initial screen could be used to confirm the presence and severity of cellular defect(s) associated with impaired PLA2g6 function which can be used as reporters of the severity and/or progression of the Parkinson's disease in the subject.

In some embodiments, the present invention relates to a method for early detection of Parkinson's disease in a subject and administering a treatment for Parkinson disease to the subject, the method comprising: performing at least one of the following assays:

(i) measuring mRNA levels and/or protein levels of PLA2g6 variants, i.e., the ratio of PLA2g6(L)/PLA2g6 (S) variants, or PLA2g6(L)/total PLA2g6 protein in non-neuronal cells obtained from the subject, comparing the level of the mRNA and/or protein expression level for PLA2g6(L) and PLA2(S) in the non-neuronal sample to a reference level, and classifying the subject as having early stage Parkinson's disease based on the comparison to the reference level, wherein (i) a decrease in the level of mRNA and/or level of protein expression of PLA2g6 relative to the reference level indicates the subject has Parkinson's disease and/or defects in the PARK14/PLA2g6(L) expression and (ii) lack of a decrease in the level of mRNA and/or level of protein expression of PLA2g6 relative to the reference level indicates the subject does not have Parkinson's disease. In some embodiments, a subject identified to have PD according to the assays and methods disclosed herein can be administered a treatment appropriate for subjects with Parkinson's disease. Those subject not identified to have PD, or at risk of developing PD are not administered a PD treatment, but can continue to be routinely screened using the assays, methods and kits disclosed herein; or (ii) measuring SOCE (endogenous Store-Operated $Ca^{2+}$ Entry) in live cells (e.g., blood and/or skin cells) obtained from the subject, comparing the SOCE in the sample to a reference level, and classifying the subject as having early stage Parkinson's disease based on the comparison of the SOCE to the reference level wherein a decrease in the SOCE relative to the reference level indicates the subject has Parkinson's disease and/or defects in the PARK14/PLA2g6(L) expression and lack of a decrease in the SOCE relative to the reference level indicates the subject does not have Parkinson's disease, and administering a treatment appropriate for subjects with Parkinson's disease to the subject having Parkinson's disease and not administering a treatment to a subject not identified to have Parkinson's disease, and routinely screening the subject not identified with PD with one or more of the methods and assays described herein.

(iii) measuring $Ca^{2+}$ store levels in non-neuronal cells (e.g., blood and/or skin cells) obtained from the subject, comparing the $Ca^{2+}$ store levels in the non-neuronal sample to a reference level, and classifying the subject as having early stage Parkinson's disease based on the comparison to the reference level wherein a decrease in the $Ca^{2+}$ store levels relative to the reference level indicates the subject has Parkinson's disease and/or defects in the PARK14/PLA2g6(L) expression or function, and lack of a decrease in the $Ca^{2+}$ store levels relative to the reference level indicates the subject does not have Parkinson's disease, and administering a treatment appropriate for subjects with Parkinson's disease to the subject having Parkinson's disease and not administering a treatment to a subject not identified to have Parkinson's disease, or routinely screening the subject not identified with PD with one or more of the methods and assays described herein, or (iv) measuring depletion of $Ca^{2+}$ store levels in non-neuronal cells (e.g., blood and/or skin cells) obtained from the subject, comparing the depletion of the $Ca^{2+}$ store levels in the non-neuronal sample to a reference level, and classifying the subject as having early stage Parkinson's disease based on the comparison to the reference level wherein a depletion of the $Ca^{2+}$ store levels relative to the reference level indicates the subject has Parkinson's disease and/or defects in the PARK14/PLA2g6(L) expression or function, and lack of depleted $Ca^{2+}$ store levels relative to the reference level indicates the subject does not have Parkinson's disease, and administering a treatment appropriate for subjects with Parkinson's disease to the subject having Parkinson's disease and not administering a treatment to a subject not identified to have Parkinson's disease, and routinely screening the subject not identified with PD with one or more of the methods and assays described herein, or (v) measure autophagic function of the cell samples (e.g., blood and/or skin cells) obtained from the subject, comparing the autophagic function in the non-neuronal sample to a reference level, and classifying the subject as having early stage Parkinson's disease based on the comparison to the reference level wherein a decrease autophagic function and/or an increase in autophagic dysfunction relative to the reference level indicates the subject has Parkinson's disease and/or defects in the PARK14/PLA2g6(L) function, and lack of a decrease autophagic function and/or lack of autophagic dysfunction relative to the reference level indicates the subject does not have Parkinson's disease, and administering a treatment appropriate for subjects with Parkinson's disease to the subject having Parkinson's disease and not administering a treatment to a subject not identified to have Parkinson's disease, and routinely screening the subject not identified with PD with one or more of the methods and assays described herein, or (vi) detecting cleavage of the N-terminus of the PLA2g6 protein (e.g., a deletion of at least 50, or at least 100, or at least 150, or at least 178 N-terminal amino acids of PLA2g6 protein); comparing the N-terminus of the PLA2g6 protein in the non-neuronal sample to a reference level, and classifying the subject as having early stage Parkinson's disease based on the comparison to the reference level wherein a deletion of at least 50-aa, or at least 100-aa or at least 150-aa, or at least the 178-N-terminal amino acids of the PLA2g6 protein relative to the reference level indicates the subject has Parkinson's disease and/or defects in the PARK14/PLA2g6(L) expression or function, and lack of a deletion of at least 50-aa, or at least 100-aa or at least 150-aa, or at least the 178-N-terminal amino acids of the PLA2g6 protein relative to the reference level indicates the subject does not have Parkinson's disease, and administering a treatment appropriate for subjects with Parkinson's disease to the subject having Parkinson's disease and not administering a treatment to a subject not identified to have Parkinson's disease, and routinely screening the subject not identified with PD with one or more of the methods and assays described herein.

Definitions

The term "PLA2g6" as used herein is known by synonyms "phospholipase A2, group VI (cytosolic, calcium-independent)", iPLA2, iPLA2beta, NBIA2, "neurodegeneration with brain iron accumulation 2", PARK14, PNPLA9, GVI; PLA2; INAD1; NBIA2A; NBIA2B; PNPLA9; CaI-PLA2; IPLA2-VIA. The human PLA2g6 gene is found on 22q13.1. There are three different splice variants of the PLA2g6 gene (Genebank numbers: (PLG2G6-001 is NM_003560 (806aa), PLG2G6-201 is NM_001004426 (752aa) and PLG2G6-002 is NM_001199562 (752aa).

The term "idiopathic" refers to a disease or disorder arising spontaneously or from an obscure or unknown cause. The phrase "idiopathic Parkinson's disease" or iPD, refers to Parkinson's disease that does not involve mutations in any known PD-associated (PARKs) genes, and refers to a Parkinson's disease developing spontaneously where the cause for the condition is unknown.

The term "biomarker" as used herein is meant any assayable characteristic or composition that can be used to identify a condition (e.g., PD or iPD or lack thereof) or the status of a condition in a subject or sample. A biomarker can, in some examples disclosed herein, be a gene whose expression characteristics can be used to identify a condition or status of a condition in a subject or sample. In other examples, a biomarker can be a gene product.

By "gene product" is meant a transcript, nucleic acid, or protein. Thus, disclosed herein are biomarkers whose presence, absence, or relative amount can be used to identify a condition or status of a condition in a subject or sample. In one particular example, a biomarker can be a gene product whose presence or absence in a subject is characteristic of a subject having or not having a particular neurodegenerative disease, having a particular risk for developing a neurodegenerative disease, or being at a particular stage of disease. In still another example, a biomarker can be a gene product whose increase or decrease indicates a particular neurodegenerative disease, a particular risk for developing a neurodegenerative disease, or a particular stage of disease. In another example, a biomarker can be a group of various gene products, the presence or absence of which is indicative of a subject having or not having a particular neurodegenerative disease, having a particular risk for developing a neurodegenerative disease, or being at a particular stage of disease. In a further example, a biomarker can be a group of gene products whose pattern of increasing and decreasing expression characterizes a particular neurodegenerative disease or lack thereof. Still further, a biomarker can be a gene product or group of gene products whose pattern of expression is characteristic of the presence or absence of a neurodegenerative disease, or a particular prognosis or outcome of a disease. As used herein, a biomarker can be a surrogate for other clinical tests. Biomarkers identified herein can be measured to determine levels, expression, activity, or to detect variants. As used throughout when detecting levels of expression or activity are discussed, it is understood that this could reflect variants of a given biomarker. Variants include amino acid or nucleic acid variants or post translationally modified variants.

Throughout, whenever a protein is discussed, the nucleic acid (e.g., transcript) is also disclosed, unless explicitly stated to the contrary or as would be understood by one of ordinary skill in the art based on the context. Similarly, whenever a nucleic acid is discussed, the protein is also disclosed. In discussions of gene products herein, proteins, nucleic acids, and transcripts collectively, unless explicitly stated to the contrary or as would be understood by one of ordinary skill in the art based on the context.

As used herein, a "subject" refers to a mammal, preferably a human. The term "individual", "subject", and "patient" are used interchangeably herein, and refer to an animal, for example a mammal, such as a human. The term "mammal" is intended to encompass a singular "mammal" and plural "mammals," and includes, but is not limited: to humans, non-human primates such as apes, monkeys, orang-utans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and bears.

A "subject in need" of treatment for a particular condition can be a subject having that condition, diagnosed as having that condition, or at risk of developing that condition.

As used herein, the term "biomarker" refers to a polypeptide expressed endogenously in an individual or found or sequestered in a non-neuronal biological sample from an individual.

As used herein "a" or "standard deviation" refers to a measure of the amount of variation or dispersion from the average in a population.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed. It is also understood that throughout the application data is provided in a number of different formats and that this data represents endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15.

The term "optional" or "optionally" as used herein means that the subsequently described event or circumstance may or may not occur, and that the description includes instances where said event or circumstance occurs and instances where it does not.

The term "probes" as used herein are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

The term "primers" as used herein are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art which do not interfere with the enzymatic manipulation. ESO-EteftSIiSM^bs," "elevates," or "raises" refer to levels above control or reference levels. The terms can also include the appearance or occurrence of an event (e.g., a level above a control or reference level that is zero). The terms "decreases," "reduces," or "lowers" refer to levels below control or reference levels. These terms can also include the absence or ablation of an event (e.g., a level of zero when a control or reference level is not zero).

As used herein, the terms "subject" and "patient" are used interchangeably and mean an individual. Thus, "subject" or "patient" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" or "patient" can also include a mammal, such as a primate. In one particular aspect, a "subject" or "patient" can be a human.

As used herein, "sample" refers to any biological non-neuronal material obtained from a subject or patient. In one aspect, a sample can comprise blood, cerebrospinal fluid ("CSF"), or urine. In some embodiments, the biological sample is a blood sample. In other aspects, a sample can comprise whole blood, plasma, leukocytes enriched from blood samples, and cultured cells (e.g., leukocytes from a subject). A sample can also include a biopsy or tissue sample including neural tissue. In still other aspects, a sample can comprise whole cells and/or a lysate of the cells. Examples of cells include, but are not limited to, leukocytes such as neutrophils, monocytes, basophils, lymphocytes, eosinophils, or any combination thereof. In another particular aspect, a sample can comprise a leukocyte or substantially pure population of leukocytes or a lysate thereof. The term "sample" also includes untreated or pretreated (or pre-processed) blood samples. In some embodiments, a sample can comprise one or more cells from the subject. In some embodiments, a sample is taken from a human subject, and in alternative embodiments the sample is taken from any mammal, such as rodents, animal models of diseases, commercial animals, companion animals, dogs, cats, sheep, cattle, and pigs, etc. The sample can be pretreated as necessary for storage or preservation, by dilution in an appropriate buffer solution or concentrated, if desired. Any of a number of standard aqueous buffer solutions, employing one of a variety of buffers, such as phosphate, Tris, or the like, at physiological pH can be used. The sample can in certain circumstances be stored for use prior to use in the assays as disclosed herein. Such storage can be at +4° C. or frozen, for example at −20° C. or −80° C.

The term "substantially pure" with respect to a population of leukocytes or lysates thereof is intended to refer to a sample that contains less than about 1%, less than about 5%, less than about 7%, less than about 10%, less than about 12%, less than about 15%, less than about 20%, less than about 25%, or less than about 30% of cells other than leukocytes, based on the total number of cells in the sample. In a specific example, a sample can comprise lymphocytes, a substantially pure population of lymphocytes, or a lysate of a substantially pure population of lymphocytes. Optionally, the leukocytes can be enriched for a selected type. For example, the leukocyte population can be enriched for lymphocytes and used in the methods described herein. Enrichment can be accomplished using cell sorting techniques like FACS.

The term "blood sample" or "blood" as used herein include, but are not limited to, whole blood, serum or plasma. In some embodiments, the whole blood sample is further processed into serum or plasma samples. The term also includes a mixture of the above-mentioned samples.

As used herein the term "agent" refers to a protein-binding agent that specifically binds to a target protein or target mRNA (e.g., PLA2g6(L) or PLA2g6(S)) and permits detection and/or quantification of levels, concentrations, expression levels, or activity of the total protein in the non-neuronal sample, such, as for example, a blood sample, a normalizing protein (e.g., actin or GAPDH), or PLA2g6 (L) or PLA2g6(S) in the sample, e.g., blood sample. Such protein-binding agents include, but are not limited to, small molecules, antibodies, antibody fragments (e.g., antigen-binding fragments of antibodies), recombinant antibodies, chimeric antibodies, tribodies, midibodies, protein-binding agents, small molecules, recombinant protein, peptides, aptamers, avimers and protein-binding derivatives or fragments thereof. As used herein, the phrase "agent specific for PLA2g6(L) polypeptide" refers to a protein-binding agent that permits detection and/or quantification of levels, concentrations, or expression levels for the PLA2g6(L) polypeptide. Such agents include, but are not limited to, antibodies, recombinant antibodies, chimeric antibodies, tribodies, midibodies, protein-binding agents, small molecules, recombinant protein, peptides, aptamers, avimers and protein-binding derivatives or fragments thereof. As defined herein, an agent upon binding to a PLA2g6(L) polypeptide, normalizing protein, or total protein forms an "agent-biomarker complex," (e.g., agent-PLA2g6(L) complex), "agent-normalizing protein complex," or "agent-total protein complex." As used herein, the term "reporter molecule information" refers to data derived from a signal indicating binding of an agent to or complex formation with the PLA2g6(L) polypeptide biomarker in the blood sample, i.e., formation of an agent-PLA2g6(L) complex," "agent-normalizing protein complex," or "agent-total protein complex." A signal can comprise e.g., light, fluorescence, colorimetric or other detectable signal that indicates agent binding to an acute kidney injury biomarker, a normalizing protein, or total protein.

The terms "protein-binding molecule" refers to an agent or protein which specifically binds to an protein, such as an a protein-binding molecule which specifically binds a PLA2g6 biomarker protein, e.g., to a PLA2g6(L) polypeptide. Protein-binding molecules are well known in the art, and include antibodies, protein-binding peptide and the like. The region on the protein which binds to the protein-binding molecule is referred to as the epitope, and the protein which is bound to the protein-binding molecule is often referred to in the art as an antigen. In some embodiments, a protein-binding molecule which specifically binds to PLA2g6(L) binds to an epitope at least partially encoded by exon 8b of PLA2g6 gene.

As used herein, the term "antibody" refers to immunoglobulin molecules and immunologically active portions of immunoglobulin molecules, i.e., molecules that contain an antigen binding site that specifically bind an antigen. The terms also refers to antibodies comprised of two immunoglobulin heavy chains and two immunoglobulin light chains as well as a variety of forms besides antibodies; including, for example, Fv, Fab, and F(ab)'2 as well as bifunctional hybrid antibodies (e.g., Lanzavecchia et al., Eur. J. Immunol. 17, 105 (1987)) and single chains (e.g., Huston et al., Proc. Natl. Acad. Sci. U.S.A., 85, 5879-5883 (1988) and Bird et al., Science 242, 423-426 (1988), which are incorporated herein by reference). (See, generally, Hood et al., Immunology, Benjamin, N.Y., 2ND ed. (1984), Harlow and Lane, Antibodies. A Laboratory Manual, Cold Spring Harbor Laboratory (1988) and Hunkapiller and Hood, Nature, 323, 15-16 (1986), which are incorporated herein by reference). In some embodiments, antibody reagents, e.g. antibodies, monoclonal and chimeric antibodies useful in the methods as disclosed herein can be manufactured using well-known methods, e. g., as described in Howard and Kaser "Marking and Using Antibodies: A Practical Handbook" CRC Press (2006); which is incorporated by reference herein in its entirety. Antibody fragments or antigen-binding antibody fragments includes any protein or peptide containing molecule that comprises at least a portion of an immunoglobulin molecule, and include, but are not limited to a complementarily determining region (CDR) of a heavy or light chain or a ligand binding portion thereof, a heavy chain or light chain variable region, a heavy chain or light chain constant region, a framework (FR) region, or any portion thereof, or at least one portion of a binding protein, any of which can be incorporated into an antibody of the present invention. The antibodies can be polyclonal or monoclonal and can be isolated from any suitable biological source, e.g., murine, rat, sheep and canine. Additional sources are identified infra. The term "antibody" is further intended to encompass digestion fragments, specified portions, derivatives and variants thereof, including antibody mimetics or comprising portions of antibodies that mimic the; structure and/or function of an antibody or specified fragment or portion thereof, including single chain antibodies and fragments thereof. Examples of binding fragments encompassed within the term "antigen binding portion" of an antibody include a Fab fragment, a monovalent fragment consisting of the VL, VH, CL and CH, domains; a F(ab') 2 fragment, a bivalent fragment comprising two Fab fragments linked by a disulfide bridge at the hinge region; a Ed fragment consisting of the VH and CH, domains; a Fv fragment consisting of the VL and VH domains of a single arm of an antibody, a dAb fragment (Ward et al. (1989) Nature 341:544-546), which consists of a VH domain; and an isolated complementarily determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)). Bird et al. (1988) Science 242:423-426 and Huston et al. (1988) Proc. Natl. Acad. Sci. USA 85:5879-5883. Single chain antibodies are also intended to be encompassed within the term "fragment of an antibody." Any of the above-noted antibody fragments are obtained using conventional techniques known to those of skill in the art, and the fragments are screened for binding specificity and neutralization activity in the same manner as are intact antibodies.

The terms "antigen-binding fragment" or "antigen-binding domain", which are used interchangeably herein to refer to one or more fragments of a full length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546; which is incorporated by reference herein in its entirety), which consists of a VH or VL domain; and (vi) an isolated complementarity determining region (CDR) that retains specific antigen-binding functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., U.S. Pat. Nos. 5,260,203, 4,946,778, and 4,881,175; Bird et al. (1988) Science 242:423-426; and Huston et al. (1988) Proc. Natl. Acad. Sci. USA 85:5879-5883. Antibody fragments can be obtained using any appropriate technique including conventional techniques known to those of skill in the art. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition, irrespective of how the antibody was generated.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. The phrase can also refer to continuous or discontinuous epitopes in which the primary sequence (i.e., the amino acid sequence) is not similar but nonetheless the epitopes are still recognized by the same antibody.

The term "antibody variant" is intended to include antibodies produced in a species other than a mouse. It also includes antibodies containing post translational modifications to the linear polypeptide sequence of the antibody or fragment. It further encompasses fully human antibodies. The term "antibody derivative" is intended to encompass molecules that bind an epitope as defined above and which are modifications or derivatives of a native monoclonal antibody of this invention. Derivatives include, but are not limited to, for example, bispecific, multispecific, heterospecific, trispecific, tetraspecific, multispecific antibodies, diabodies, chimeric, recombinant and humanized.

The term "human antibody" as used herein, is intended to include antibodies having variable and constant regions derived from human germline immunoglobulin sequences. The human antibodies of the present invention can include amino acid residues not encoded by human germline immunoglobulin sequences (e.g., mutations introduced by random or site-specific mutagenesis in vitro or by somatic mutation in viva). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e.g., CDR, framework, CL, CH domains (e.g., CH1, CH2, CH3), hinge, (Via, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain); genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody can be at least about 95%, or even at least about 96%, or least about 97%, or least about 98%, or least about 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody can display no more than 5, or even no more than 4, 3, 2, or 1 amino acid difference from the amino acid sequence encoded by the germline immunoglobulin gene.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human monoclonal antibody" refers to antibodies displaying a single binding specificity which have variable and constant regions derived from human germline immunoglobulin sequences. The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the antibody, e.g., from a transfectoma, antibodies isolated from a recombinant, combinatorial human antibody library, and antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in viva somatic mutagenesis) and thus the amino acid sequences of the VH and VL regions of the recombinant antibodies are sequences that, while derived from and related to human germline VH and VL sequences, can not naturally exist within the human antibody germline repertoire in vivo. As used herein, "isotype" refers to the antibody class (e.g., IgM or IgG1) that is encoded by heavy chain constant region genes.

An "antigen-binding site" or "binding portion" refers to the part of an immunoglobulin molecule that participates in antigen binding. The antigen-binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complementarity determining regions" or "CDRs" and are characterized, for example by Kabat et al. Sequences of proteins of immunological interest, 4th ed. U.S. Dept. Health and Human Services, Public Health Services, Bethesda, Md. (1987).

As used herein, the term "specific binding" refers to a chemical interaction between two molecules, compounds, cells and/or particles wherein the first entity (e.g., antibody or antigen-binding fragment) binds to the second, target entity (e.g., PLA2g6(L) polypeptide) with greater specificity and affinity than it binds to a third entity which is a non-target, e.g., PLA2g6(S). In some embodiments, specific binding can refer to an affinity of the first entity for the second target entity which is at least 10 times, at least 50 times, at least 100 times, at least 500 times, at least 1000 times or greater than the affinity for the third non-target entity. In particular, the terms "specifically binds," "specific binding affinity" (or simply "specific affinity"), and "specifically recognize," and other related terms when used to refer to binding between a protein and an antibody, refers to a binding reaction that is determinative of the presence of the protein in the presence of a heterogeneous population of proteins and other biologics. Thus, under designated conditions, a specified antibody binds preferentially to a particular protein (e.g., PLA2g6(L)) and does not bind in a significant amount to other proteins, including PLA2g6(S) present in the sample. An antibody that specifically binds to a protein has an association constant of at least $10^3 M^{-1}$ or $10^4 M^{-1}$, sometimes $10^{5M}-1$ or $10^6 M^{-1}$, in other instances $10^6 M^{-1}$ or $10^{10} M^{-1}$, preferably $10^8 M^{-1}$ to $10^9 M^{-1}$, and more preferably, about $10^{10} M^{-1}$ to $10^{11} M^{-1}$ or higher. Protein-binding molecules with affinities greater than 108M-1 are useful in the methods of the present invention. A variety of immunoassay formats can be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

An "array" broadly refers to an arrangement of agents (e.g., proteins, antibodies, replicable genetic packages) in positionally distinct locations on a substrate. In some instances the agents on the array are spatially encoded such that the identity of an agent can be determined from its location on the array. A "microarray" generally refers to an array in which detection requires the use of microscopic detection to detect complexes formed with agents on the substrate. A "location" on an array refers to a localized area on the array surface that includes agents, each defined so that it can be distinguished from adjacent locations (e.g., being positioned on the overall array, or having some detectable characteristic, that allows the location to be distinguished from other locations). Typically, each location includes a single type of agent but this is not required. The location can have any convenient shape (e.g., circular, rectangular, elliptical or wedge-shaped). The size or area of a location can vary significantly. In some instances, the area of a location is greater than 1 cm2, such as 2 cm2, including any area within this range. More typically, the area of the location is less than 1 cm2, in other instances less than 1 mm2, in still other instances less than 0.5 mm2, in yet still other instances less than 10,000 mm2, or less than 100 mm2.

A "label" refers to an agent that can be detected by using physical, chemical, optical, electromagnetic and/or other methods. Examples of detectable labels that can be utilized include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates.

As used herein, the terms "treat," "treatment," "treating," or "amelioration" refer to therapeutic treatments, wherein the object is to reverse, alleviate, ameliorate, inhibit, slow down or stop the progression or severity of a condition associated with decrease in levels or decreased function of PLA2g6(L), including parkinson's disease and/or iPD. The term "treating" is not intended to cure PD or iPD. The term "treating" includes reducing or alleviating at least one adverse effect or symptom of a PD or iPD. Treatment is generally "effective" if one or more symptoms or clinical markers are reduced. Alternatively, treatment is "effective" if the progression of PD or iPD is reduced or halted. That is, "treatment" includes not just the improvement of symptoms or markers of iPD (e.g., an increase in PLA2g6(L) or an increase in functioning of Store-operated Ca2+ Entry (SOCE), but also a cessation of, or at least slowing of, progress or worsening of symptoms of iPD or PD compared to what would be expected in the absence of treatment. Beneficial or desired clinical results include, but are not limited to, alleviation of one or more symptom(s), diminishment of extent of disease, stabilized (i.e., not worsening)

state of disease, delay or slowing of disease progression, amelioration or palliation of the disease state, remission (whether partial or total), and/or decreased mortality, whether detectable or undetectable. For example, treatment is considered effective if the extent or at least one symptom of PD and/or iPD is reduced, or the progression of PD or iPD is halted. In another example, treatment is considered effective if any symptom associated with iPD is reduced, e.g, any one or more of bradykinesia, tremor at rest, rigidity of the extremities and neck, stooped posture, minimal facial expressions, problems swallowing (dysphagia), and a paucity of associated movements (e.g., arm swinging) is reduced. The term "treatment" of a disease also includes providing relief from the symptoms or side-effects of the disease (including palliative treatment).

As used herein, the term "treating" with respect to treatment of PD and iPD includes reducing or alleviating at least one adverse effect or symptom of a condition, disease or disorder associated with PD oe iPD As used herein, the term treating is used to refer to the reduction of a symptom and/or a biochemical marker of P or iPD by at least 10%, or alternatively, and increase in PLA2g6(L) by at least 10%. As a non-limiting example, a treatment can be measured by measuring an increase in PLA2g6(L) protein levels in the blood as disclosed herein, for example an increase in blood PLA2g6(L) protein levels and/or function (e.g., Store-operated Ca2+ Entry (SOCE)) by at least 10% as compared to the blood PLA2g6(L) protein levels measured in a blood sample obtained from the subject at an earlier timepoint. In some embodiments, the terms "treat" and "treatment" is administration of an appropriate therapy to the subject identified with iPD for a beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total). "Treatment" can also mean prolonging survival as compared to expected survival if not receiving treatment.

The term "effective amount" as used herein refers to the amount of therapeutic agent or pharmaceutical composition to increase PLA2g6(L) or stop at least one symptom or marker of the disease or disorder. For example, an effective amount using the methods as disclosed herein would be considered as the amount sufficient to reduce a symptom or marker of the disease or disorder or cancer by at least 10%. An effective amount as used herein would also include an amount sufficient to prevent or delay the development of a symptom of the disease, alter the course of PD or iPD (for example but not limited to, slowing the progression of a symptom of the disease), or reverse a symptom of the disease.

As used herein, the term "pharmaceutical composition" refers to the one or more active agents in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject, e.g. parenteral, intravenous, intralesional, or intratumoral. Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection. The administration can be systemic or local.

As used herein the term "comprising" or "comprises" is used in reference to compositions, methods, and respective component(s) thereof, that are essential to the invention, yet open to the inclusion of unspecified elements, whether essential or not. The term "comprises" means "includes." The abbreviation, "e.g." is derived from the Latin exempli gratia, and is used herein to indicate a non-limiting example. Thus, the abbreviation "e.g." is synonymous with the term "for example." As used herein the term "consisting essentially of" refers to those elements required for a given embodiment. The term permits the presence of elements that do not materially affect the basic and novel or functional characteristic(s) of that embodiment of the invention. The term "consisting of" refers to compositions, methods, and respective components thereof as described herein, which are exclusive of any element not recited in that description of the embodiment.

The term "statistically significant" or "significantly" refers to statistical significance and generally means a two standard deviation (2SD) difference.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±1% of the value being referred to. For example, about 100 means from 99 to 101.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

PLA2g6 (PARK14)

PLA2g6 is a multifaceted enzyme that is best known for its catalytic function, which was linked to phospholipid remodeling in cells (for review see Ref.[12]). The loss of the catalytic activity of PLA2g6 has been reported to be associated with infantile neuroaxonal dystrophy (INAD) and results in early death in humans, and in mouse models[13-19]. In contrast to INAD mutations, PD-associated mutations in PLA2g6 were reported not to affect its catalytic activity[20]. The inventors previously discovered[21;22-26] and others confirmed[27-31] that PLA2g6 plays an important role in activation of endogenous store-operated Ca$^{2+}$ entry (SOCE). Notably, besides Orai1 (store-operated plasma membrane Ca$^{2+}$ channel) and STIM1 (Ca$^{2+}$ sensor in endoplasmic reticulum (ER)), PLA2g6 was identified in an RNAi screen as one of the essential components of endogenous SOCE (supplemental material in[32]). It is well established that SOCE is activated upon depletion of ER Ca$^{2+}$ stores (for review see[33-35]), and is crucial for their timely refilling in a wide variety of cell types. However, the role of store-operated Ca$^{2+}$ signaling in dopaminergic (DA) neurons and PD remains largely unknown.

PLA2g6 protein is an A2 phospholipase, a class of enzyme that catalyzes the release of fatty acids from phospholipids. The encoded protein may play a role in phospholipid remodelling, arachidonic acid release, leukotriene and prostaglandin synthesis, fas-mediated apoptosis, and transmembrane ion flux in glucose-stimulated B-cells. Several transcript variants encoding multiple isoforms have been described, but the full-length nature of only three of them have been determined to date.

The PLA2G6 gene is conserved in human, chimpanzee, Rhesus monkey, dog, cow, mouse, rat, chicken, zebrafish, fruit fly, mosquito, C. elegans, and frog. 191 organisms have orthologs with human gene PLA2G6. The human PLA2g6 gene is found on chromosome 22q13.1 and identified by Gene ID No: 8398, with the genomic sequence identified by RefSeq ID No: NG_007094.2. There are a total of 28 splice variants of the human PLA2g6 gene, the first three are of interest herein, and are: PLG2G6-001 (NM_003560.2) which is 806aa in length and is referred to as PLA2g(L) variant, PLG2G6-201 (NM_001004426), which is 752aa and PLG2G6-002 (NM_001199562) which is 752aa, the latter two encoding the PLA2g6(S) variant. For completeness, but not being limited to theory, other human PLA2g6 gene splice variants are shown in the Table of FIG. 11A.

The three variants of PLA2g6 gene that are the subject of the present disclosure are outlined below:

Variant 1 of the PLA2g6 gene encodes isoform a, also referred to PLA2g6(L) and the mRNA is assigned Accession number AF064594.1, herein referred to as SEQ ID NO: 1. The mRNA is also referred to as NM_003560.2. The PLA2g6(L) protein corresponds to the amino acid sequence of Genbank No. AAC97486.1, herein referred to as SEQ ID NO: 2.

Variant 2 of the PLA2g6 gene encodes isoform b, also referred to as PLA2g6(S) form, and corresponding to mRNA sequence Accession number NM_001004426.1 (referred to herein as SEQ ID NO: 3), and is also referred to as 85/88 kDa calcium-independent phospholipase A2 isoform b, which lacks an in-frame exon (exon 8b) compared to PLA2g6(L) (i.e., variant 1 or a). The resulting isoform (b) protein corresponds to amino acid sequence of NP_001004426.1, referred to as SEQ ID NO: 4 herein, and has the same N- and C-termini but lacks an internal segment compared to isoform a. Variants 2 and 3 of the PLA2g6 gene both encode the same isoform (b) (PLA2g6(S) variant). Isoform b (PLA2g6(S)) is found in the cytoplasm while isoform a (PLA2g6(L)) is membrane-bound.

Variant 3 of the PLA2g6 gene also encodes isoform b, also referred to as PLA2g6(S) form, and corresponding to mRNA sequence Accession number NM 001199562.1 (referred to herein as SEQ ID NO: 5), and differs in the 5' UTR and lacks an in-frame exon (exon 8b) as compared to variant 1. The resulting isoform (b) protein from the variant 3 gene corresponds to amino acid sequence of NP 001186491.1, referred to as SEQ ID NO: 6 herein, and has the same N- and C-termini but lacks an internal segment compared to isoform a. The resulting isoform (b) has the same N- and C-termini but lacks an internal segment compared to isoform a (PLA2g6(L)). Variants 2 and 3 of the PLA2g6 gene both encode the same isoform (b) (PLA2g6(S) variant). Isoform b (PLA2g6(S)) is found in the cytoplasm while isoform a (PLA2g6(L)) is membrane-bound.

In the human mRNA of NM_001004426.1 encoding the PLA2g6(S) protein, there is a second ATG at residue 626 in the NP_001004426.1. La Cognata et al., (Splicing: Splicing: is there an alternative contribution to Parkinson's disease? 2015, Volume 16, Issue 4, pp 245-263, Neurogenetics, which is incorporated herein in its entirety by reference). As disclosed herein, the inventors surprisingly discovered that the expression of the PLA2g6(L) variant, which is a specific plasma membrane-associated splice variant of PLA2g6[39], is significantly reduced in idPD patients (see FIG. 1F and FIG. 10B). The inventors demonstrate that the expression of the PLA2g6(S) splice variant, which lacks exon 8b and encodes a cytosolic enzyme that was shown to be involved in lipid remodeling[12], is expressed at the same levels as in control donors.

The cDNA for human PLA2g6(L) variant (Ref.[83,84]) is Genbank #AF064594.1, and comprises nucleotides of SEQ ID NO: 1 as follows:

(SEQ ID NO: 1)
CTGGGGGTCCGTTCCCCAACTTCCTCGGCGCTCCGGACTCCCAAGTCTCCGCCGGACCCTCCTTTGGATA

TTCCTCGTGTCTCCGATTCTGAGAGAGGGGGAAGACGGTGGGGCCTCCCCACCTGCCCCGCAGAAGATGC

AGTTCTTTGGCCGCCTGGTCAATACCTTCAGTGGCGTCACCAACTTGTTCTCTAACCCATTCCGGGTGAA

-continued

```
GGAGGTGGCTGTGGCCGACTACACCTCGAGTGACCGAGTTCGGGAGGAAGGGCAGCTGATTCTGTTCCAG

AACACTCCCAACCGCACCTGGGACTGCGTCCTGGTCAACCCCAGGAACTCACAGAGTGGATTCCGACTCT

TCCAGCTGGAGTTGGAGGCTGACGCCCTAGTGAATTTCCATCAGTATTCTTCCCAGCTGCTACCCTTCTA

TGAGAGCTCCCCTCAGGTCCTGCACACTGAGGTCCTGCAGCACCTGACCGACCTCATCCGTAACCACCCC

AGCTGGTCAGTGGCCCACCTGGCTGTGGAGCTAGGGATCCGCGAGTGCTTCCATCACAGCCGTATCATCA

GCTGTGCCAATTGCGCGGAGAACGAGGAGGGCTGCACACCCCTGCACCTGGCCTGCCGCAAGGGTGATGG

GGAGATCCTGGTGGAGCTGGTGCAGTACTGCCACACTCAGATGGATGTCACCGACTACAAGGGAGAGACC

GTCTTCCATTATGCTGTCCAGGGTGACAATTCTCAGGTGCTGCAGCTCCTTGGAAGGAACGCAGTGGCTG

GCCTGAACCAGGTGAATAACCAAGGGCTGACCCCGCTGCACCTGGCCTGCCAGCTGGGGAAGCAGGAGAT

GGTCCGCGTGCTGCTGCTGTGCAATGCTCGGTGCAACATCATGGGCCCCAACGGCTACCCCATCCACTCG

GCCATGAAGTTCTCTCAGAAGGGGTGTGCGGAGATGATCATCAGCATGGACAGCAGCCAGATCCACAGCA

AAGACCCCGTTACGGAGCCAGCCCCCTCCACTGGGCCAAGAACGCAGAGATGGCCCGCATGCTGCTGAA

ACGGGGCTGCAACGTGAACAGCACCAGCTCCGCGGGGAACACGGCCCTGCACGTGGCGGTGATGCGCAAC

CGCTTCGACTGTGCCATAGTGCTGCTGACCCACGGGGCCAACGCGGATGCCCGCGGAGAGCACGGCAACA

CCCCGCTGCACCTGGCCATGTCGAAAGACAACGTGGAGATGATCAAGGCCCTCATCGTGTTCGGAGCAGA

AGTGGACACCCCGAATGACTTTGGGGAGACTCCTACATTCCTAGCCTCCAAAATCGGCAGACTTGTCACC

AGGAAGGCGATCTTGACTCTGCTGAGAACCGTGGGGGCCGAATACTGCTTCCCACCCATCCACGGGGTCC

CCGCGGAGCAGGGCTCTGCAGCGCCACATCATCCCTTCTCCCTGGAAAGAGCTCAGCCCCCACCGATCAG

CCTAAACAACCTAGAACTACAGGATCTCATGCACATCTCACGGGCCCGGAAGCCAGCGTTCATCCTGGGC

TCCATGAGGGACGAGAAGCGGACCCACGACCACCTGCTGTGCCTGGATGGAGGAGGAGTGAAAGGCCTCA

TCATCATCCAGCTCCTCATCGCCATCGAGAAGGCCTCGGGTGTGGCCACCAAGGACCTGTTTGACTGGGT

GGCGGGCACCAGCACTGGAGGCATCCTGGCCCTGGCCATTCTGCACAGTAAGTCCATGGCCTACATGCGC

GGCATGTACTTTCGCATGAAGGATGAGGTGTTCCGGGGCTCCAGGCCCTACGAGTCGGGGCCCCTGGAGG

AGTTCCTGAAGCGGGAGTTTGGGGAGCACACCAAGATGACGGACGTCAGGAAACCCAAGGTGATGCTGAC

AGGGACACTGTCTGACCGGCAGCCGGCTGAACTCCACCTCTTCCGGAACTACGATGCTCCAGAAACTGTC

CGGGAGCCTCGTTTCAACCAGAACGTTAACCTCAGGCCTCCAGCTCAGCCCTCAGACCAGCTGGTGTGGC

GGGCGGCCCGAAGCAGCGGGGCAGCTCCTACTTACTTCCGACCCAATGGGCGCTTCCTGGACGGTGGGCT

GCTGGCCAACAACCCCACGCTGGATGCCATGACCGAGATCCATGAGTACAATCAGGACCTGATCCGCAAG

GGTCAGGCCAACAAGGTGAAGAAACTCTCCATCGTTGTCTCCCTGGGGACAGGGAGGTCCCCACAAGTGC

CTGTGACCTGTGTGGATGTCTTCCGTCCCAGCAACCCCTGGGAGCTGGCCAAGACTGTTTTTGGGGCCAA

GGAACTGGGCAAGATGGTGGTGGACTGTTGCACGGATCCAGACGGGCGGGCTGTGGACCGGGCACGGGCC

TGGTGCGAGATGGTCGGCATCCAGTACTTCAGATTGAACCCCCAGCTGGGGACGGACATCATGCTGGATG

AGGTCAGTGACACAGTGCTGGTCAACGCCCTCTGGGAGACCGAGGTCTACATCTATGAGCACCGCGAGGA

GTTCCAGAAGCTCATCCACCTGCTGCTCTCACCCTGAGGGTCCCCAGCCTCTCACCGGCCCCAGCTGACC

TCGTCCATTCAGCCCCTGCCAGGCCAAGCCCAGCCACTGCCCTCCCGGGCAGATCTGGGCCCAGGCACCT

CTGAGTCCATAGACCAGGCCTGGGAGAATGCCAAGCTGCCTGCCCGAGGCTGGTCCTGAAGGCCTGTCTC

CCACTAACCCCCCCTTCCATCACTTTCTGTCATGCCAGGNTGGGAAAGTCTAGAGCCCCCTTTGGCCCCT

TTCCCTGACTGTCAAGGACAACTGACTCCCCCATCAGCTCAAACATTAAGGGTACCCGGGCACAACCGTA

CCCGTGCCCCCAGCCCCAGCCTACCCTGAGGGCCTGCCGGGCTGCCTTTGCCCCAGCCCCCAGCAAGGGC

ATTCCCAGGCTTCCTGGTGGGTGCAGCCCAATCCCTCTGCCCTCTGCTCCGTTCCCTGGGGGCTGGGACT
```

```
                                            -continued
AAAGAAATGGGTGTCCCCCACCCCATCAGCTGGGAAAGCCCAGGCCGCAGGAGTGGGATGCCCGTTGGAC

TTTGCCCCTCACACTGGCCCAGCCCCTCACACTGCCCCACCCCGAGAACCCTCAGCTCTCAAAGGTCACT

CCTGGGAGTTTCTTCTTCCCAATGGAAGTGGCTTAAGAGCCAAAACTGAAATAAATCATTTGGATTCAAG

TTCAAAAAAAAAAAAAAAAA
```

SEQ ID NO: 2 encodes PLA2g6(L) protein, Accession No: AAC97486.1, which is as follows:

```
                                                    (SEQ ID NO: 2)
MQFFGRLVNTFSGVTNLFSNPFRVKEVAVADYTSSDRVREEGQLILFQN

TPNRTWDCVLVNPRNSQSGFRLFQLELEADALVNFHQYSSQLLPFYESS

PQVLHTEVLQHLTDLIRNHPSWSVAHLAVELGIRECFHHSRIISCANCA

ENEEGCTPLHLACRKGDGEILVELVQYCHTQMDVTDYKGETVFHYAVQG

DNSQVLQLLGRNAVAGLNQVNNQGLTPLHLACQLGKQEMVRVLLLCNAR

CNIMGPNGYPIHSAMKFSQKGCAEMIISMDSSQIHSKDPRYGASPLHWA

KNAEMARMLLKRGCNVNSTSSAGNTALHVAVMRNRFDCAIVLLTHGANA

DARGEHGNTPLHLAMSKDNVEMIKALIVFGAEVDTPNDFGETPTFLSKI

GRLVTRKAILTLLRTVGAEYCFPPIHGVPAEQGSAAPHHPFSLERAQPP

PISLNNLELQDLMHISRARKPAFILGSMRDEKRTHDHLLCLDGGGVKGL

IIIQLLIAIEKASGVATKDLFDWVAGTSTGGILALAILHSKSMAYMRGM

YFRMKDEVFRGSRPYESGPLEEFLKREFGEHTKMTDVRKPKVMLTGTLS

DRQPAELHLFRNYDAPETVREPRFNQNVNLRPPAQPSDQLVWRAARSSG

AAPTYFRPNGRFLDGGLLANNPTLDAMTEIHEYNQDLIRKGQANKVKKL

SIVVSLGTGRSPQVPVTCVDVFRPSNPWELAKTVFGAKELGKMVVDCCT

DPDGRAVDRARAWCEMVGIQYFRLNPQLGTDIMLDEVSDTVLVNALWET

EVYIYEHREEFQKLIHLLLSP
```

In some embodiments, a subject identified to have a deletion of a portion of the N-terminus of at least 50 amino acids according to the methods as disclosed herein, or any subject with a PLA2g6 splice variant selected from the group of: of PLG2G6-014 (6), PLG2G6-026 (9), PLG2G6-015 (10), PLG2G6-010 (11), PLG2G6-023 (12), PLG2G6-027 (14), PLG2G6-012 (16), PLG2G6-019 (17), PLG2G6-016 (21), PLG2G6-015 (22), PLG2G6-018 (23), PLG2G6-003 (24), PLG2G6-017 (25) or PLG2G6-007 (26) (based on Enemble names) can be detected and treated with an appropriate PD treatment, and/or exogenous PLA2g6 protein or mRNA (e.g., a modified mRNA encoding the PLA2g6 protein) according to the methods as disclosed herein.

Parkinson's Disease

Parkinson's disease is a movement disorder of increasing occurrence in aging populations. Parkinson's disease is a progressive disorder which can begin with mild limb stiffness and infrequent tremors and progress over a period of ten or more years to frequent tremors and memory impairment, to uncontrollable tremors and dementia. Symptoms include pronounced tremor of the extremities, bradykinesia, rigidity and postural change. A perceived pathophysiological cause of Parkinson's disease is progressive destruction of dopamine producing cells in the basal ganglia which comprise the pars compartum of the substantia nigra, a basal nuclei located in the brain stem. Loss of dopamineric neurons results in a relative excess of acetylcholine. Jellinger, K. A., Post Mortem Studies in Parkinson's Disease—Is It Possible to Detect Brain Areas For Specific Symptoms?, J Neural Transm 56 (Supp); 1-29:1999.

There is currently no non-invasive test for early diagnosis of PD. In normal situations, a patient is typically diagnosed with PD has having one or more symptoms or hallmark physical behaviors, including: bradykinesia, rigidity and rest tremor. Often these physical symptoms are asymmetric. Within the brain, PD is characterized by a progressive and profound loss of neuromelanin-containing dopaminergic neurons in the substantia nigra pars compacta with the presence of eosinophillic, intracytoplasmic and proteinaceous inclusions termed Lewy bodies in the surviving neurons (Davie, ibid and Kumari, ibid). By the time of death, a patient will have lost 50-70% of its SNc neurons as compared to an individual without PD.

Lewy bodies are α-synuclein reactive inclusions that are made up of made of several neurofilament proteins combined with proteolytic enzymes. Lewy bodies are found in PD, and a variant of dementia called Dementia with Lewy Bodies, but are not observed in any other neurological diseases.

It appears to have many factors can play a role in disease onset and/or progression of PD. In particular, genes including α-synuclein (PARK1/PARK4, SCNA), parkin (PARK 2), PARK 3, ubiquitin carboxy-terminal hydrolyase L1 (PARK5) etc.) as well as environmental factors such as exposure to heavy metals and certain pesticides are believed to contribute to PD.

Additionally, familial PD can be associated with genetic mutations, such as in the leucine rich repeat kinase 2 gene (LRRK2, also known as PARK8) has been identified to be involved in both familial and sporatic forms of PD. In fact, studies suggest that LRRK2 mutations may be responsible for between 5 and 13% of familial PD, and from 1 to 5% of sporadic PD. Gene duplications of α-synuclein, which lead to increased gene expression, causes rare cases of autosomal dominant PD. The function of the α-synuclein gene (SNCA) in a wild type setting is still unclear, but it appears that it plays a role in the regulation of autophagy (Winslow and Rubensztein (2010, online publication) Autophagy 7:4, p 1-3). It appears that overexpression of the protein inhibits the secretory pathway by a loss of function of the Rab1a protein which is involved in autophagasome formation at a very early stage of the autophagy process. This in turn may lead to the cellular pathologies observed in PD: abnormal protein aggregation, mitochondrial abnormalities, increased levels of reactive oxygen species and increased sensitivity to cell death (Winslow and Rubensztein ibid). In addition to increased gene dosage of the wild type SCNA gene, three mutations have been found which are also associated with PD. The three mutations, A53T, A30P, and E46K are all localized in the N-terminal domain of the protein, and appear to exacerbate toxic fibril formation (Perkevi et al (2009) The Anatomical Record 292 (12): 1893). However, cellular and transgenic animal models expressing such mutants only partially recapitulate PD pathology. See, Dawson et al. (2010) Neuron 66(5):646-61. Individuals with PD caused by .alpha.-synuclein mutation have similar clinical and pathological features of their PD as patients with idiopathic PD, however the onset of symptoms occurs significantly than typically seen with other PD patients (Pankratz and Foroud (2004) Am Soc Exp Neu Ther 1:235-242).

While mutations in the PARK14 gene (PLA2g6 gene) have been identified in familial PD, their mutations are not present in iPD. (Lu et al., PLA2G6 mutations in PARK14-linked young-onset parkinsonism and sporadic Parkinson's disease. Am J Med Genet Part B 159B:183-191).

Assays:

As disclosed herein, the inventors surprisingly discovered that the expression of PLA2g6(L) (a specific plasma membrane-associated splice variant of PLA2g6[39]) is significantly reduced in idPD patients (FIG. 1F and FIG. 10B), while expression of the PLA2g6(S) splice variant (which lacks exon 8b and encodes a cytosolic enzyme that was shown to be involved in lipid remodeling[12]) is the same, as in control donors.

In some embodiments, disclosed herein are assays, methods, composition and kits allow for any one or more of: (i) measurement of mRNA levels for the total and specific (L) and (S) variants of PLA2g6, and analysis of the ratios of (L)/(S) and (L)/total mRNA, and/or (ii) analysis of (L) protein expression, e.g., using our own custom-made PIN antibody that specifically recognizes (L) variant; and/or (iii) detection of the cleavage products.

More specifically, assays, methods, kits and compositions disclosed herein can be used to detect one or more of the following (i) the relative expression of PLA2g6 (L) and PLA2g6 (S) variants of PLA2g6 (e.g., specifically, a reduction in PLA2g6(L):PLA2g6(S) or PLA2g6(L):total PLA2g6 ratio), and/or (ii) cleavage of the N terminus of PLA2g6 (i.e., detection of the presence of products of such cleavage), and/or (iii) a reduced or decreased mRNA and/or protein expression of PLA2g6 (either the L (PLA2g6L) or the S (PLA2g6S) splice variants).

In some embodiments, the disclosure herein refers compositions assays, methods and kits to measure any one or a combination of the following in cells, including non-neuronal cells:

(i) mRNA and/or protein expression level of PLA2g6(L), for example, a detection of relative expression of PLA2g6 (L) and PLA2g6 (S) variants, e.g., a reduction in PLA2g6 (L):PLA2g6(S) ratio or a reduction of PLA2g6(L):total PLA2g6 ratio, as compared to a tissue and/or aged matched reference level, where a significantly lower PLA2g6(L) mRNA and/or protein expression level as compared to the reference threshold level indicates that the subject has or is at risk of developing PD, including iPD, (ii) detection of a cleavage product of the N terminus of PLA2g6 (i.e., detection of the presence of products of such cleavage, e.g., detection of a deletion of at least 50, or at least 100, or at least 150, or at least 178 N-terminal amino acids of PLA2g6 protein. In particular, the inventors demonstrate that a cryptic $ATG_2$ in Exon 4 initiated translation and resulted in a PLA2g6 protein that lacks the first 178 N-terminal amino acids, which while it retained PARK14 catalytic activity, resulted in a loss of $Ca^{2+}$ store-dependent activation of PLA2g6.

In some embodiments, a subject identified with PD according to (i) to (ii) above can be treated for PD or iPD, for example, administration of a treatment for PD known by one of ordinary skill in the art, or in some instances, by administering a PLA2g6(L) agonist or protein thereof. In some embodiments, the PLA2g6(L) agonist is a PLA2g6(L) protein or a nucleic acid, such as a modified RNA or mRNA encoding PLA2g6(L) protein, or a functional fragment thereof.

Measurement of levels of PLA2g6 expression (either mRNA and/or protein) in non-neuronal cells can be performed by one of ordinary skill in the art, e.g., using a modified PLA2 assay kit containing S-BEL (a chiral specific substrate that discriminates PLA2g6 from other PLAs), western blotting, QRT-PCR, antibody detection methods and the like. In some embodiments, the levels are detected on a high-throughput manner, e.g., ELISA methods, and, for example, in a dip-stick like format, where a decreased level of PLA2g6 protein below a threshold level is easily and quickly detected. In all embodiments, the threshold level of PLA2g6 protein or mRNA is from a healthy or control non-neuronal cell of the same type (e.g, blood, skin).

Decreased Levels of PLA2g6(L) mRNA or PLA2g6(L) Protein as Compared to a Reference Standard for PLA2g6 (L) mRNA or Protein Level.

In one aspect, the invention provides a method for diagnosing a subject at risk of developing PD or having, at risk of developing iPD by measuring PLA2g6(L) mRNA in a non-neuronal sample, e.g., blood sample, obtained from the subject. In some embodiments, the methods and assays and kits as disclosed herein measure the amount of the PLA2g6 (L) mRNA (e.g., SEQ ID NO: 1) in the blood obtained in the subject. In some embodiments, the measured PLA2g6(L) mRNA (e.g., SEQ ID NO: 1) in the blood obtained in the subject is compared to a reference PLA2g6(L) mRNA level, e.g., the PLA2g6(L) mRNA level of an age- and tissue-matched sample from a healthy, normal subject. In some embodiments, where the level of PLA2g6(L) mRNA in the non-neuronal sample from the subject is at, or lower than 50% as compared to the reference PLA2g6(L) mRNA level of an age- and tissue-matched sample from a healthy, normal subject, the subject is identified as being at risk of developing PD or iPD during their lifetime, and sometimes within the next 2-10 years of performing the assay. In another embodiment, where the level of PLA2g6(L) mRNA in the non-neuronal sample obtained from the subject is decreased by a statistically significant amount by at least one standard deviation $\sigma$ (sigma), or preferably at least two standard deviation $\sigma$ (sigma) as compared to the reference PLA2g6 (L) mRNA level of an age- and tissue-matched sample from a healthy, normal subject, the subject is identified as having iPD or is at risk of developing PD or iPD during their lifetime, and sometimes within the next 2-10 years of performing the assay Accordingly, where a subject is identified as being at risk of developing iPD or PD, the subject can be administered an appropriate treatment for PD. In some embodiments, a decrease relatative to the PLA2g6(L) reference mRNA or protein level indicates the subject has iPD or is at risk of iPD or PD is a level which is at least 1 standard deviation ($\sigma$) lower than a PLA2g6(L) mRNA or protein reference level, e.g., $1\sigma$, $2\sigma$, $3\sigma$, or $4\sigma$ or lower than the reference level.

In some embodiments, if the measured PLA2g6(L) mRNA in the non-neuronal sample, e.g., blood sample obtained in the subject is significantly lower as compared to a reference PLA2g6(L) mRNA level, the subject is identified as being at risk of developing PD, or has or is at risk of developing iPD. In some embodiments, if the measured PLA2g6(L) mRNA in the non-neuronal sample, such as e.g., blood sample is at least about 50% lower, or at least about 60% lower, or at least about 60% lower, or at least about 70% lower, or at least about 80% lower, or at least about 90% lower, or at least about 2-fold lower, or at least about 2-fold lower, or at least about 3-fold lower, or at least 4-fold lower as compared to a reference PLA2g6(L) mRNA level, the subject is identified as being at risk of developing PD, or has or is at risk of developing iPD. In some embodiments, where the level of PLA2g6(L) mRNA in the non-neuronal sample from the subject is at, or lower than 50% as compared to the reference PLA2g6(L) mRNA level of an age- and tissue-matched sample from a healthy, normal subject, the subject is administered an appropriate treatment for PD.

In some embodiments, a decreased level a measured PLA2g6(L) mRNA in the sample, e.g., blood sample that is at least 0.5-fold, or at least 0.6-fold, or at least 0.7-fold, or at least 0.8-fold, or at least 0.9-fold, or at least 1-fold, or at least 1.2-fold, or at least 1.4-fold, or at least 1.6-fold, or at least 1.8-fold, or at least 2-fold, or at least 2.2-fold, or at least 2.4-fold, or at least 2.6-fold, or at least 2.8-fold, or at least 3-fold, or between 3.0 and 3.5-fold, or between 3.5 and 4-fold, or at least 4-fold, or more lower than a reference level for PLA2g6(L) mRNA indicates the subject has iPD, or is at risk of getting iPD as they increase in age.

One can use any method to measure the expression level of SEQ ID NO: 1 in a sample, e.g., using QRT-PCR, for example using Taqman problems. Suitable Taqman probes for measuring PLA2g6(L) mRNA level are Hs00899715_m1. Typically, the level of PLA2g6(L) mRNA is normalized to a housekeeping gene, such as, e.g., actin or GAPDH. Suitable Taqman problems for GAPDH include, for example, 4333764F.

In another aspect, the disclosure provides a method for diagnosing a subject at risk of developing PD or having, at risk of developing iPD by measuring PLA2g6(L) protein in a non-neuronal sample, e.g., blood sample, obtained from the subject. In some embodiments, the methods and assays and kits as disclosed herein measure the amount of the PLA2g6(L) protein (e.g., SEQ ID NO: 2) in the blood obtained in the subject. In some embodiments, the measured PLA2g6(L) protein (e.g., SEQ ID NO: 2) in the blood obtained in the subject is compared to a reference PLA2g6 (L) protein level, e.g., the PLA2g6(L) protein level of an age- and tissue-matched sample from a healthy, normal subject. In some embodiments, where the level of PLA2g6 (L) protein (e.g., SEQ ID NO: 2) in the non-neuronal sample from the subject is at, or lower than 50% as compared to the reference PLA2g6(L) protein level of an age- and tissue-matched sample from a healthy, normal subject, the subject is identified as being at risk of developing PD or iPD during their lifetime, and sometimes within the next 2-10 years of performing the assay. In another embodiment, where the level of PLA2g6(L) protein (e.g., SEQ ID NO: 2) in the non-neuronal sample obtained from the subject is decreased by a statistically significant amount by at least one standard deviation σ (sigma), or preferably at least two standard deviation σ (sigma) as compared to the reference PLA2g6 (L) protein level of an age- and tissue-matched sample from a healthy, normal subject, the subject is identified as having iPD or is at risk of developing PD or iPD during their lifetime, and sometimes within the next 2-10 years of performing the assay. Accordingly, where a subject is identified as being at risk of developing iPD or PD, the subject can be administered an appropriate treatment for PD.

In some embodiments, if the measured PLA2g6(L) protein (e.g., SEQ ID NO: 2) in the non-neuronal sample, e.g., blood sample obtained in the subject is significantly lower as compared to a reference PLA2g6(L) protein level, the subject is identified as being at risk of developing PD, or has or is at risk of developing iPD. In some embodiments, if the measured PLA2g6(L) protein in the non-neuronal sample, such as e.g., blood sample is at least about 50% lower, or at least about 60% lower, or at least about 60% lower, or at least about 70% lower, or at least about 80% lower, or at least about 90% lower, or at least about 2-fold lower, or at least about 2-fold lower, or at least about 3-fold lower, or at least 4-fold lower as compared to a reference PLA2g6(L) protein (e.g., SEQ ID NO: 2) level, the subject is identified as being at risk of developing PD, or has or is at risk of developing iPD. In some embodiments, where the level of PLA2g6(L) protein in the non-neuronal sample from the subject is at, or lower than 50% as compared to the reference PLA2g6(L) protein level of an age- and tissue-matched sample from a healthy, normal subject, the subject is administered an appropriate treatment for PD.

In some embodiments, a decreased level a measured PLA2g6(L) protein (e.g., SEQ ID NO: 2) in the non-neuronal sample, e.g., blood sample that is at least 0.5-fold, or at least 0.6-fold, or at least 0.7-fold, or at least 0.8-fold, or at least 0.9-fold, or at least 1-fold, or at least 1.2-fold, or at least 1.4-fold, or at least 1.6-fold, or at least 1.8-fold, or at least 2-fold, or at least 2.2-fold, or at least 2.4-fold, or at least 2.6-fold, or at least 2.8-fold, or at least 3-fold, or between 3.0 and 3.5-fold, or between 3.5 and 4-fold, or at least 4-fold, or more lower than a reference level for PLA2g6(L) protein (e.g., SEQ ID NO: 2) indicates the subject has iPD, or is at risk of getting iPD as they increase in age.

One can use any method to measure the protein expression of SEQ ID NO: 2 for measuring PLA2g6(L). In some embodiments, an antibody, e.g., antibody specific to the PLA2g6(L) isoform is used. In some embodiments, the antibody is a polyclonal or monoclonal antibody, or antigen binding fragment thereof, which binds to an epitope at least partially encoded by exon 8b of the PLA2g6 gene, which is absent in PLA2g6(S) protein.

Ratios of PLA2g6(L) mRNA/PLA2g6(S) mRNA

In some embodiments, the level of mRNA of PLA2g6(L) of SEQ ID NO: 1 is compared to the level of PLA2g6 (S) mRNA, e.g., the level of PLA2g6 (S) mRNA in the same non-neuronal sample obtained from the subject, or a reference PLA2g6(S) mRNA level, e.g., the PLA2g6(S) mRNA level of an age- and tissue-matched sample from a healthy, normal subject. Accordingly, in some embodiments, where the level of PLA2g6(L) mRNA of SEQ ID NO: 1 in the non-neuronal sample from the subject is at, or lower than 50% as compared to the reference PLA2g6(S) mRNA level of an age- and tissue-matched sample from a healthy, normal subject, or of the level of PLA2g6(S) mRNA of SEQ ID NO: 3 and/or SEQ ID NO: 5 in the same non-neuronal sample, the subject is identified as being at risk of developing PD or iPD during their lifetime, and sometimes within the next 2-10 years of performing the assay. In another embodiment, where the level of PLA2g6(L) mRNA in the non-neuronal sample obtained from the subject is decreased by a statistically significant amount by at least one standard deviation σ (sigma), or preferably at least two standard deviation a (sigma) as compared to either a reference PLA2g6(S) mRNA level of an age- and tissue-matched sample from a healthy, normal subject, or the level of PLA2g6(S) mRNA of SEQ ID NO: 3 and/or SEQ ID NO: 5 in the same non-neuronal sample, the subject is identified as having iPD or is at risk of developing PD or iPD during their lifetime. Accordingly, where a subject is identified as being at risk of developing iPD or PD, the subject can be administered an appropriate treatment for PD.

In some embodiments, if the measured PLA2g6(L) mRNA of SEQ ID NO: 1 in the non-neuronal sample, e.g., blood sample obtained in the subject is significantly lower as compared to a reference PLA2g6(S) mRNA level or the level of PLA2g6(S) mRNA of SEQ ID NO: 3 and/or SEQ ID NO: 5 in the same non-neuronal sample, the subject is identified as being at risk of developing PD, or has or is at risk of developing iPD. In some embodiments, if the measured PLA2g6(L) mRNA of SEQ ID NO: 1 in the non-neuronal sample, such as e.g., blood sample is at least about 50% lower, or at least about 60% lower, or at least about 60% lower, or at least about 70% lower, or at least about 80% lower, or at least about 90% lower, or at least about 2-fold lower, or at least about 2-fold lower, or at least about 3-fold lower, or at least 4-fold lower as compared to a reference PLA2g6(S) mRNA level or the level of PLA2g6 (S) mRNA of SEQ ID NO: 3 and/or SEQ ID NO: 5 in the same non-neuronal sample, the subject is identified as being at risk of developing PD, or has or is at risk of developing iPD. In some embodiments, where the level of PLA2g6(L) mRNA in the non-neuronal sample from the subject is at, or lower than 50% as compared to the reference PLA2g6(L) mRNA level of an age- and tissue-matched sample from a healthy, normal subject, the subject is administered an appropriate treatment for PD.

In some embodiments, a decreased level a measured PLA2g6(L) mRNA in the non-neuronal sample, e.g., blood sample that is at least 0.5-fold, or at least 0.6-fold, or at least 0.7-fold, or at least 0.8-fold, or at least 0.9-fold, or at least 1-fold, or at least 1.2-fold, or at least 1.4-fold, or at least 1.6-fold, or at least 1.8-fold, or at least 2-fold, or at least 2.2-fold, or at least 2.4-fold, or at least 2.6-fold, or at least 2.8-fold, or at least 3-fold, or between 3.0 and 3.5-fold, or between 3.5 and 4-fold, or at least 4-fold, or more lower than compared to a reference PLA2g6(S) mRNA level or the level of PLA2g6(S) mRNA of SEQ ID NO: 3 and/or SEQ ID NO: 5 in the same non-neuronal sample indicates the subject has iPD, or is at risk of getting iPD as they increase in age.

One can use any method to measure the expression level of SEQ ID NO: 3 or SEQ ID NO: 5 in a sample, e.g., using QRT-PCR, for example using Taqman problems. Suitable Taqman probes for measuring PLA2g6(S) mRNA level are Hs00895670 ml. Typically, the level of PLA2g6(S) mRNA is normalized to a housekeeping gene, such as, e.g., actin or GAPDH. Suitable Taqman problems for GAPDH include, for example, 4333764F.

Another aspect disclosed herein is comparing the protein level of PLA2g6(L) of SEQ ID NO: 2 to the total level of PLA2g6 (S) protein of SEQ ID NO: 4 and/or SEQ ID NO: 6. In some embodiments, the level of PLA2g6(L) protein is compared to the total PLA2g6 (S) protein (of SEQ ID NO: 4 and/or SEQ ID NO: 6) in the same non-neuronal sample obtained from the subject, or a reference PLA2g6(S) protein level, e.g., the PLA2g6(S) protein level of an age- and tissue-matched sample from a healthy, normal subject. Accordingly, in some embodiments, where the level of PLA2g6(L) protein of SEQ ID NO: 2 in the non-neuronal sample from the subject is at, or lower than 50% as compared to the reference PLA2g6(S) protein level of an age- and tissue-matched sample from a healthy, normal subject, or of the level of PLA2g6(S) protein of SEQ ID NO: 4 and/or SEQ ID NO: 6 in the same non-neuronal sample, the subject is identified as being at risk of developing PD or iPD during their lifetime, and sometimes within the next 2-10 years of performing the assay. In another embodiment, where the level of PLA2g6(L) protein in the non-neuronal sample obtained from the subject is decreased by a statistically significant amount by at least one standard deviation σ (sigma), or preferably at least two standard deviation σ (sigma) as compared to either a reference total PLA2g6(S) protein level of an age- and tissue-matched sample from a healthy, normal subject, or the total level of PLA2g6(S) protein of SEQ ID NO: 4 and/or SEQ ID NO: 6 in the same non-neuronal sample, the subject is identified as having iPD or is at risk of developing PD or iPD during their lifetime. Accordingly, where a subject is identified as being at risk of developing iPD or PD, the subject can be administered an appropriate treatment for PD.

In some embodiments, a measured PLA2g6(L) protein level of SEQ ID NO: 2 in the non-neuronal sample, e.g., blood sample obtained in the subject that is significantly lower as compared to either a reference total PLA2g6(S) protein level, and/or the total level of PLA2g6(S) protein of SEQ ID NO: 4 and/or SEQ ID NO: 6 in the same non-neuronal sample, the subject is identified as being at risk of developing PD, or has or is at risk of developing iPD. In some embodiments, if the measured PLA2g6(L) protein in the non-neuronal sample, such as e.g., a blood sample, is at least about 50% lower, or at least about 60% lower, or at least about 60% lower, or at least about 70% lower, or at least about 80% lower, or at least about 90% lower, or at least about 2-fold lower, or at least about 2-fold lower, or at least about 3-fold lower, or at least 4-fold lower as compared to a reference PLA2g6(S) protein level or the total level of PLA2g6(S) protein of SEQ ID NO: 4 and/or SEQ ID NO: 6 in the same non-neuronal sample, the subject is identified as being at risk of developing PD, or has or is at risk of developing iPD. In some embodiments, where the level of PLA2g6(L) protein in the non-neuronal sample from the subject is at, or lower than 50% as compared to the reference PLA2g6(L) protein level of an age- and tissue-matched sample from a healthy, normal subject, the subject is administered an appropriate treatment for PD.

In some embodiments, a decreased level a measured PLA2g6(L) protein in the non-neuronal sample, e.g., blood sample that is at least 0.5-fold, or at least 0.6-fold, or at least 0.7-fold, or at least 0.8-fold, or at least 0.9-fold, or at least 1-fold, or at least 1.2-fold, or at least 1.4-fold, or at least 1.6-fold, or at least 1.8-fold, or at least 2-fold, or at least 2.2-fold, or at least 2.4-fold, or at least 2.6-fold, or at least 2.8-fold, or at least 3-fold, or between 3.0 and 3.5-fold, or between 3.5 and 4-fold, or at least 4-fold on a log scale, or lower than 4-fold on a log scale a compared to a reference total PLA2g6(S) protein level, or the total level of PLA2g6 (S) protein of SEQ ID NO: 4 and/or SEQ ID NO: 6 in the same non-neuronal sample indicates the subject has iPD, or is at risk of getting iPD as they increase in age.

Ratios of PLA2g6(L)/Total PLA2g6 mRNA Levels ((L) and (S) mRNAs)

In some embodiments, the level of mRNA of PLA2g6(L) of SEQ ID NO: 1 is compared to the level of total PLA2g6 mRNA, e.g., the level of PLA2g6(L) and PLA2g6(S) mRNA in the same non-neuronal sample obtained from the subject, or a reference PLA2g6(L) and PLA2g6(S) mRNA level, e.g., the total PLA2g6(L) and PLA2g6(S) mRNA levels of an age- and tissue-matched sample from a healthy, normal subject. Accordingly, in some embodiments, where the level of PLA2g6(L) mRNA of SEQ ID NO: 1 in the non-neuronal sample from the subject is $\frac{1}{3}^{rd}$, or less than $\frac{1}{3}^{rd}$ of the total PLA2g6 mRNA reference level (i.e., the total mRNA levels of SEQ ID NO: 1, SEQ ID NO: 3 and SEQ ID NO: 5) of an age- and tissue-matched sample from a healthy, normal subject, or the total PLA2g6 mRNA level of SEQ ID NO: 1, and SEQ ID NO: 3 and SEQ ID NO: 5 in the same non-neuronal sample, the subject is identified as being at risk of developing PD or iPD during their lifetime, and sometimes within the next 2-10 years of performing the assay. In another embodiment, where the level of PLA2g6(L) mRNA in the non-neuronal sample obtained from the subject is decreased by a statistically significant amount by at least one standard deviation σ (sigma), or preferably at least two standard deviation σ (sigma) as compared to either the total PLA2g6 mRNA reference level (i.e., the total mRNA levels of SEQ ID NO: 1, SEQ ID NO: 3 and SEQ ID NO: 5 of an age- and tissue-matched sample from a healthy, normal subject), or the total PLA2g6 mRNA level of SEQ ID NO: 1, and SEQ ID NO: 3 and SEQ ID NO: 5 in the same non-neuronal sample, the subject is identified as having iPD or is at risk of developing PD or iPD during their lifetime. Accordingly, where a subject is identified as being at risk of developing iPD or PD, the subject can be administered an appropriate treatment for PD.

In some embodiments, if the measured PLA2g6(L) mRNA of SEQ ID NO: 1 in the non-neuronal sample, e.g., blood sample obtained in the subject is significantly lower as compared the reference total PLA2g6 mRNA level (i.e., mRNA levels of SEQ ID NO: 1, and SEQ ID NO: 3 and SEQ ID NO: 5) of an age- and tissue-matched sample from a healthy, normal subject, or the level of total PLA2g6 mRNA of SEQ ID NO: 1, and SEQ ID NO: 3 and SEQ ID NO: 5 in the same non-neuronal sample, the subject is identified as being at risk of developing PD, or has or is at risk of developing iPD. In some embodiments, if the measured PLA2g6(L) mRNA of SEQ ID NO: 1 in the non-neuronal sample, such as e.g., blood sample is at least about 30% lower, or at least about 40% lower, or at least about 50% or at least about 60% lower, or at least about 70% lower, or at least about 80% lower, or at least about 90% lower, or at least about 2-fold lower, or at least about 2-fold lower, or at least about 3-fold lower, or at least 4-fold lower as compared to the reference total PLA2g6 mRNA level (i.e., mRNA levels of SEQ ID NO: 1, and SEQ ID NO: 3 and SEQ ID NO: 5) of an age- and tissue-matched sample from a healthy, normal subject, or the level of total PLA2g6 mRNA of SEQ ID NO: 1, and SEQ ID NO: 3 and SEQ ID NO: 5 in the same non-neuronal sample, the subject is identified as being at risk of developing PD, or has or is at risk of developing iPD. Stated another way, if the measured PLA2g6(L) mRNA of SEQ ID NO: 1 in the non-neuronal sample, such as e.g., blood sample obtained from the subject is equal or less than $\frac{1}{3}^{rd}$ (33%), or less than 30%, or less than 29%, or less than 28%, or less than 27%, or less than 26%, or less than 25%, or less than 24%, or less than 23%, or less than 22%, or less than 21%, or less than 20%, or less than 19%, or less than 18%, or less than 17%, or less than 16%, or less than 15%, or less than 14%, or less than 13%, or less than 12%, or less than 11%, or less than 10%, as compared to the reference total PLA2g6 mRNA level (i.e., total mRNA levels of SEQ ID NO: 1, and SEQ ID NO: 3 and SEQ ID NO: 5 in an age- and tissue-matched sample from a healthy, normal subject), or the level of total PLA2g6 mRNA of SEQ ID NO: 1, SEQ ID NO: 3 and SEQ ID NO: 5 in the same non-neuronal sample, the subject is identified as being at risk of developing PD, or has or is at risk of developing iPD.

In some embodiments, where the level of PLA2g6(L) mRNA in the non-neuronal sample from the subject is $\frac{1}{3}^{rd}$ or less than $\frac{1}{3}^{rd}$ as compared to the reference total PLA2g6 mRNA level (i.e., total mRNA levels of SEQ ID NO: 1, SEQ ID NO: 3 and SEQ ID NO: 5 of an age- and tissue-matched sample from a healthy, normal subject), or the level of total PLA2g6 mRNA of SEQ ID NO: 1, and SEQ ID NO: 3 and SEQ ID NO: 5 level in the same non-neuronal sample, the subject is administered an appropriate treatment for PD.

In some embodiments, the protein level of PLA2g6(L) of SEQ ID NO: 2 is compared to the level of total PLA2g6 protein, i.e., the total level of PLA2g6(L) and PLA2g6(S) protein combined in the same non-neuronal sample obtained from the subject, or a reference PLA2g6(L) and PLA2g6(S) protein level, e.g., the total PLA2g6(L) and PLA2g6(S) protein levels of an age- and tissue-matched sample from a healthy, normal subject. Accordingly, in some embodiments, where the protein level of PLA2g6(L) of SEQ ID NO: 2 in the non-neuronal sample from the subject is $\frac{1}{3}^{rd}$, or less than $\frac{1}{3}^{rd}$ of the total PLA2g6 protein reference level (i.e., the total protein levels of SEQ ID NO: 2, SEQ ID NO: 4 and SEQ ID NO: 6) of an age- and tissue-matched sample from a healthy, normal subject, or the total PLA2g6 protein level of SEQ ID NO: 2, and SEQ ID NO: 4 and SEQ ID NO: 6 in the same non-neuronal sample, the subject is identified as being at risk of developing PD or iPD during their lifetime, and sometimes within the next 2-10 years of performing the assay. In another embodiment, where the level of PLA2g6(L) protein in the non-neuronal sample obtained from the subject is decreased by a statistically significant amount by at least one standard deviation σ (sigma), or preferably at least two standard deviation σ (sigma) as compared to either the total PLA2g6 protein reference level (i.e., the total protein levels of SEQ ID NO: 2, SEQ ID NO: 4 and SEQ ID NO: 6 of an age- and tissue-matched sample from a healthy, normal subject), or the total PLA2g6 protein level of SEQ ID NO: 2, and SEQ ID NO: 4 and SEQ ID NO: 6 in the same non-neuronal sample, the subject is identified as having iPD or is at risk of developing PD or iPD during their lifetime. Accordingly, where a subject is identified as being at risk of developing iPD or PD, the subject can be administered an appropriate treatment for PD.

In some embodiments, if the measured PLA2g6(L) protein level of SEQ ID NO: 2 in the non-neuronal sample, e.g., blood sample obtained in the subject is significantly lower as compared the reference total PLA2g6 protein level (i.e., protein levels of SEQ ID NO: 2, and SEQ ID NO: 4 and SEQ ID NO: 6) of an age- and tissue-matched sample from a healthy, normal subject, or the level of total PLA2g6 protein of SEQ ID NO: 2, and SEQ ID NO: 4 and SEQ ID NO: 6 in the same non-neuronal sample, the subject is identified as being at risk of developing PD, or has or is at risk of developing iPD. In some embodiments, if the measured PLA2g6(L) protein of SEQ ID NO: 2 in the non-neuronal sample, such as e.g., blood sample is at least about 30% lower, or at least about 40% lower, or at least about 50% or at least about 60% lower, or at least about 70% lower, or at least about 80% lower, or at least about 90% lower, or at least about 2-fold lower, or at least about 2-fold lower, or at least about 3-fold lower, or at least 4-fold lower as compared to the reference total PLA2g6 protein level (i.e., protein levels of SEQ ID NO: 2, and SEQ ID NO: 4 and SEQ ID NO: 6) of an age- and tissue-matched sample from a healthy, normal subject, or the level of total PLA2g6 protein of SEQ ID NO: 2, and SEQ ID NO: 4 and SEQ ID NO: 6 in the same non-neuronal sample, the subject is identified as being at risk of developing PD, or has or is at risk of developing iPD. Stated another way, if the measured PLA2g6(L) protein level of SEQ ID NO: 2 in the non-neuronal sample, such as e.g., blood sample obtained from the subject is equal or less than $\frac{1}{3}^{rd}$ (33%), or less than 30%, or less than 29%, or less than 28%, or less than 27%, or less than 26%, or less than 25%, or less than 24%, or less than 23%, or less than 22%, or less than 21%, or less than 20%, or less than 19%, or less than 18%, or less than 17%, or less than 16%, or less than 15%, or less than 14%, or less than 13%, or less than 12%, or less than 11%, or less than 10%, as compared to the reference total PLA2g6 protein level (i.e., total mRNA levels of SEQ ID NO: 2, and SEQ ID NO: 4 and SEQ ID NO: 6 in an age- and tissue-matched sample from a healthy, normal subject), or the level of total PLA2g6 protein of SEQ ID NO: 2, and SEQ ID NO: 4 and SEQ ID NO: 6 in the same non-neuronal sample, the subject is identified as being at risk of developing PD, or has or is at risk of developing iPD.

In some embodiments, where the level of PLA2g6(L) protein in the non-neuronal sample from the subject is $\frac{1}{3}^{rd}$ or less than $\frac{1}{3}^{rd}$ as compared to the reference total PLA2g6 protein level (i.e., total protein levels of SEQ ID NO: 2, and SEQ ID NO: 4 and SEQ ID NO: 6 of an age- and tissue-matched sample from a healthy, normal subject), or the level of total PLA2g6 protein of SEQ ID NO: 2, and SEQ ID NO: 4 and SEQ ID NO: 6 level in the same non-neuronal sample, the subject is administered an appropriate treatment for PD.

In some embodiments as disclosed herein, the level of PLA2g6(L) and PLA2g6(S) proteins measured in a non-neuronal sample, e.g., blood sample obtained from the subject can be used to determine stage or progression of iPD in a subject and can be used to determine the appropriate treatment regimen, e.g., an a more aggressive treatment for subject identified with significantly low PLA2g6(L) mRNA or protein as compared to reference levels PLA2g6(L) levels, or PLA2g6(S) levels.

In another embodiment, the method comprises contacting a non-neuronal sample, such as, but not limited to a blood sample, obtained from a subject in need thereof with at least one agent or protein-binding agent that specifically binds to PLA2g6(L) polypeptide, e.g., binds to an epitope at least partially encoded by exon 8b of PLA2g6(L) or binds to an epitope at least partially located in any of SEQ ID NO: 16, SEQ ID NO: 17 or SEQ ID NO: 18 disclosed herein. In some embodiment, the method further comprises also contacting the non-neuronal sample, e.g., blood sample obtained from a subject in need thereof with at least one agent specific for a normalizing protein or housekeeping gene, such as creatinine, actin or GAPDH, where the agents specific for PLA2g6(L) and the normalizing protein are used in an assay to determine the level or concentration of the PLA2g6(L) mRNA or polypeptide and the level or concentration of the normalizing protein; and diagnosing a subject with iPD, or a risk of developing PD or iPD based on the level or concentration of the PLA2g6(L) mRNA or polypeptide. In some embodiments, the method further comprises determining a therapeutic treatment for the subject.

In one embodiment, the concentration or level of mRNA or protein of PLA2g6(L) in the non-neuronal sample obtained from the subject is compared with a reference concentration or level of mRNA or protein for PLA2g6(L) (e.g., the concentration or level of PLA2g6(L) mRNA or protein from a healthy individual or plurality of healthy individuals, or a subject or plurality of subjects who are confirmed not to PD or iPD), and where there is a >0.5 fold decrease (e.g., a greater than 50% decrease) in the concentration or level of the PLA2g6(L) mRNA or protein in the non-neuronal sample obtained from the subject as compared to a reference mRNA or protein PLA2g6(L) level indicates the subject has iPD or at risk of developing iPD or PD. In one embodiment, the concentration of the mRNA or protein of PLA2g6(L) is compared with the concentration of the normalizing protein (e.g., creatinine and/or albumin and/or actin, and/or GAPDH as the normalizing protein), where at least a 50% decrease in the PLA2g6(L) mRNA or protein levels as compared to the normalizing protein is indicative of the subject having iPD or at risk of developing iPD or PD.

In other embodiments, the level or concentration of the PLA2g6(L) mRNA and/or protein is measured by measuring the activity of the PLA2g6(L) protein, or by measuring SOCE or measuring $Ca^{2+}$ stores, as well as other methods commonly known to persons of ordinary skill in the art.

Reference Standard Levels

In some embodiments, the reference level of PLA2g6(L) mRNA or protein is obtained from an individual subject or plurality of subjects that do not have PD or iPD.

In one embodiment of the aspect, a secondary diagnostic step can be performed. For example, if a level of PLA2g6(L) in the sample, e.g., blood sample, is found to indicate that the subject has iPD or is at risk of developing iPD or PD, then an additional method of confirming the diagnosis can be performed to confirm that the subject has, or is likely to get iPD or PD, as well as to further assess the extent of PLA2g6(L) dysfunction and SOCE dysregulation. Any of a variety of additional diagnostic steps can be used, such as ultrasound, PET scanning, MRI, or any other imaging techniques, biopsy, clinical examination, ductogram, or any other method. Additionally, the non-neuronal sample can also be assayed for any of SOCE, Ca2+ store deficiency and/or autophagy function according to the methods as disclosed herein.

The present invention further provides for methods of prognostic evaluation of a patient suspected of having, or having, iPD. The method comprises measuring the level of PLA2g6(L) mRNA or protein levels in a non-neuronal sample obtained from a patient and comparing the observed level with a range of PLA2g6(L) mRNA or protein levels normally found in non-neuronal samples (of the same cell type, e.g., whole blood, plasma, serum etc.) of healthy individuals, or comparing the level of PLA2g6(L) mRNA or protein with either PLA2g6(S) mRNA or protein levels in the same subject, or with the total PLA2g6 (PLA2g6(L)/(S)) mRNA or protein levels in the same non-neuronal sample obtained from the subject. A low level for example, a PLA2g6(L) statistically significant level by at least two or more standard deviation a (sigma) corresponds to a poor prognosis, while a lower level of PLA2g6 mRNA or protein by a statistically significant level of one standard deviation σ (sigma) indicates that the risk of getting iPD, or the iPD progression and/or PLA2g6(L) dysfunction is less severe and corresponds to a better prognosis.

Measuring levels or concentrations of PLA2g6(L) polypeptide, and optionally PLA3g6(S) protein can be measured by any means known to those skilled in the art. See., e.g., U.S. patent application Ser. No. 11/829,323, including ELISA, multiplex bead, mass spectrometry, and PCR assays. The antibodies for use in the present invention can be obtained from a commercial source, or prepared by well-known methods.

Figure 17A:
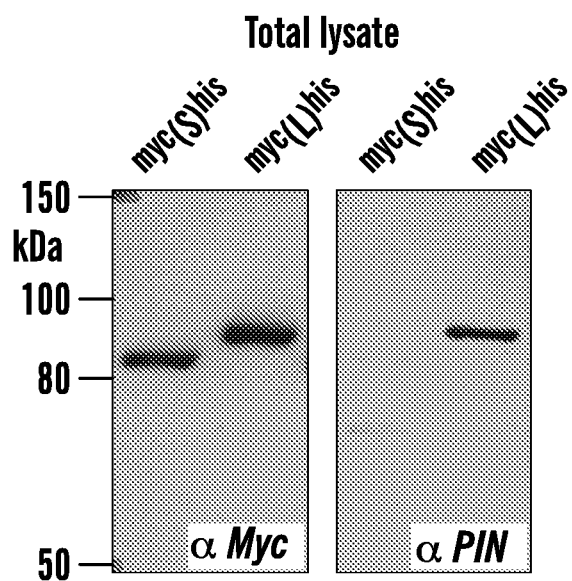
FIGS. 17A-17C show data to validate the custom mPIN ab that specifically recognizes (L), but not (S) variant of PLA2g6.
Figure 17B:
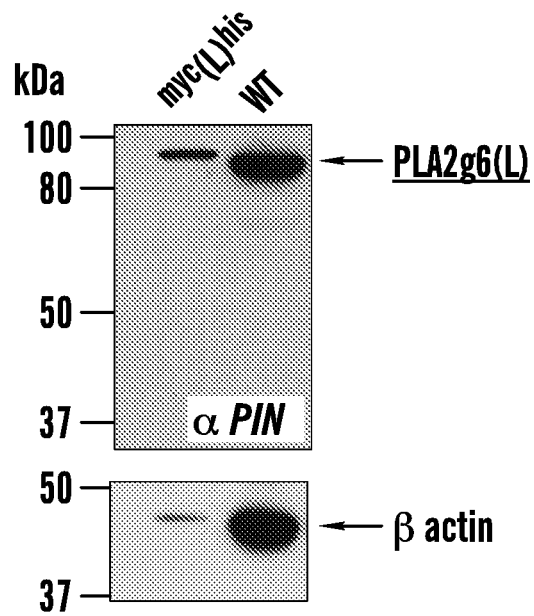
Figure 17C:
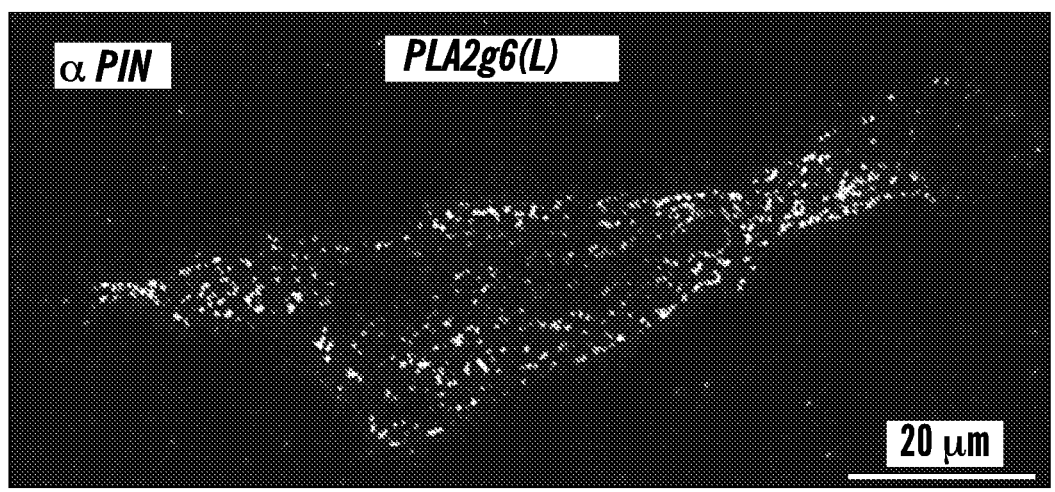

In some embodiments, a suitable antibody that specifically binds to PLA2g6(L) protein is a PIN antibody, that specifically targets an epitope that is located in at least part of the PIN domain, which is encoded by exon 8b that is present only in (L) splice variant of PLA2g6. Specificity of the anti-PIN antibody is shown in FIG. 17. In some embodiments, an anti-PLAg6(L) antibody specifically binds to an epitope at least partially encoded by exon 8b of PLA2g6(L) or binds to an epitope at least partially located in any of SEQ ID NO: 16, SEQ ID NO: 17 or SEQ ID NO: 18 disclosed herein.

The terms "decreased concentration", "decrease in the level", "lower level", or "lower concentration" of a PLA2g6 (L) mRNA or protein level refers to a level or concentration of PLA2g6(L) mRNA or protein biomarker that is statistically significant or significantly below the level or concentration of that biomarker found in a control or reference sample, in a sample from the same subject at a different timepoint, or relative to a reference concentration or level. As used herein, the phrase "lower level" or "decrease in the level" can be for example a 50% decrease or lower, e.g., 60%, 70% 80% or more than 80% decrease. For purposes of comparison, the test sample and control sample are from the same sample type, that is, obtained from the same biological source (e.g., plasma, serum or whole blood).

As used herein, the term "normalizing protein" or "normalizing factor" refers to a protein against which the amounts of a biomarker of interest are normalized to, to permit comparison of amounts of the protein of interest in different biological samples. In some embodiments, the normalizing protein is PLA2g6(S) mRNA or protein, or alternatively, can be housekeeping gene, such as creatinine, albumin or GAPDH. In some embodiments, the different biological samples are from different subjects. In other embodiments, the different biological samples are from the same subject, but after different timepoints. Generally, a normalizing protein is constitutively expressed and is not differentially regulated between at least two physiological states or conditions from which samples will be analyzed, e.g., given disease and non-disease states. Thus, for example, a normalizing protein does not vary substantially (i.e., <15%, preferably <10%, <7%, <5%, <4%, <3%, <2%, <1% or less) in the presence and absence of iPD. In one embodiment, a normalizing protein is selected based on the degree of correlation (e.g., lowest amount of scatter or lowest standard deviation among replicates) of the protein measured over a series of sample dilutions, compared to the predicted relationship of the dilution series (e.g., predicted by linear regression). In this embodiment, a normalizing protein is selected that has the highest degree of correlation (e.g., as compared to another protein in a protein sample subjected to the same measurement) for measured protein levels assessed over the dilution series. The term "highest degree of correlation" refers to a standard deviation for protein measurements (e.g., replicate measurements) over a dilution series of less than 2 compared to the predicted relationship over the dilution series; preferably the standard deviation is less than 1.5, less than 1, less than 0.5, less than 0.1, less than 0.01, less than 0.001 or more, including a standard deviation of zero (e.g., measured and predicted values are the same). In some embodiments, the normalizing protein is the product of a "housekeeping gene". As referred to herein, the term "housekeeping gene" refers to a gene encoding a protein that is constitutively expressed, and is necessary for basic maintenance and essential cellular functions. A housekeeping gene generally is not expressed in a cell- or tissue-dependent manner, most often being expressed by all cells in a given organism. Some examples of normalizing proteins encoded by housekeeping genes include e.g., actin, tubulin, GAPDH, among others. In one embodiment, a housekeeping gene product is used as a normalizing protein.

Measuring Levels of PLA2g6(L) and PLA2g6(S) mRNA Expression

Methods to measure gene expression products of PLA2g6 (L) of SEQ ID NO: 1 and PLA2g6(S) of SEQ ID NO: 3 and 5 described herein are well known to a skilled artisan. Such methods to measure gene expression products, e.g., protein level, include ELISA (enzyme linked immunosorbent assay), western blot, and immunoprecipitation, immunofluorescence using detection reagents such as an antibody or protein binding agents. Alternatively, a peptide can be detected in a subject by introducing into a subject a labeled anti-peptide antibody and other types of detection agent. For example, the antibody can be labeled with a radioactive marker whose presence and location in the subject is detected by standard imaging techniques.

In certain embodiments, the gene expression products as described herein can be instead determined by determining the level of messenger RNA (mRNA) expression of PLA2g6 (L) of SEQ ID NO: 1 and optionally, PLA2g6(S) of SEQ ID NO: 3 and 5 as described herein. Such molecules can be isolated, derived, or amplified from a biological sample, such as a whole blood or plasma, e.g., platelet rich plasma. Detection of mRNA expression is known by persons skilled in the art, and comprise, for example but not limited to, PCR procedures, RT-PCR, Northern blot analysis, differential gene expression, RNA protection assay, microarray analysis, hybridization methods etc. In some embodiments, the level of the mRNAs can be measured using quantitative RT-PCR.

In general, the PCR procedure describes a method of gene amplification which is comprised of (i) sequence-specific hybridization of primers to specific genes or sequences within a nucleic acid sample or library, (ii) subsequent amplification involving multiple rounds of annealing, elongation, and denaturation using a thermostable DNA polymerase, and (iii) screening the PCR products for a band of the correct size. The primers used are oligonucleotides of sufficient length and appropriate sequence to provide initiation of polymerization, i.e. each primer is specifically designed to be complementary to a strand of the genomic locus to be amplified. In an alternative embodiment, mRNA level of gene expression products described herein can be determined by reverse-transcription (RT) PCR and by quantitative RT-PCR (QRT-PCR) or real-time PCR methods. Methods of RT-PCR and QRT-PCR are well known in the art.

The nucleic acid sequences of the genes described herein have been assigned NCBI accession numbers for different species such as human, mouse and rat. In particular, the NCBI accession numbers for the nuclei acid sequences of the human genes are included herein. Accordingly, a skilled artisan can design an appropriate primer based on the known sequence for determining the mRNA level of the respective gene.

Nucleic acid and ribonucleic acid (RNA) molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Roiff, A et al. PCR: Clinical Diagnostics and Research, Springer (1994)).

PCR Procedures:

In general, the PCR procedure describes a method of gene amplification which is comprised of (i) sequence-specific hybridization of primers to specific genes within a nucleic acid sample or library, (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified.

In an alternative embodiment, mRNA level of gene expression products described herein can be determined by reverse-transcription (RT) PCR and by quantitative RT-PCR (QRT-PCR) or real-time PCR methods. Methods of RT-PCR and QRT-PCR are well known in the art.

In some embodiments, one or more of the reagents (e.g., an antibody reagent and/or nucleic acid probe) described herein can comprise a detectable label and/or comprise the ability to generate a detectable signal (e.g., by catalyzing reaction converting a compound to a detectable product). Detectable labels can comprise, for example, a light-absorbing dye, a fluorescent dye, or a radioactive label. Detectable labels, methods of detecting them, and methods of incorporating them into reagents (e.g., antibodies and nucleic acid probes) are well known in the art.

In some embodiments, detectable labels can include labels that can be detected by spectroscopic, photochemical, biochemical, immunochemical, electromagnetic, radiochemical, or chemical means, such as fluorescence, chemifluorescence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). The detectable label can be linked by covalent or non-covalent means to the reagent. Alternatively, a detectable label can be linked such as by directly labeling a molecule that achieves binding to the reagent via a ligand-receptor binding pair arrangement or other such specific recognition molecules. Detectable labels can include, but are not limited to radioisotopes, bioluminescent compounds, chromophores, antibodies, chemiluminescent compounds, fluorescent compounds, metal chelates, and enzymes.

In other embodiments, the detection reagent is label with a fluorescent compound. When the fluorescently labeled antibody is exposed to light of the proper wavelength, its presence can then be detected due to fluorescence. In some embodiments, a detectable label can be a fluorescent dye molecule, or fluorophore including, but not limited to fluorescein, phycoerythrin, phycocyanin, o-phthaldehyde, fluorescamine, Cy3™, Cy5™, allophycocyanine, Texas Red, peridenin chlorophyll, cyanine, tandem conjugates such as phycoerythrin-Cy5™, green fluorescent protein, rhodamine, fluorescein isothiocyanate (FITC) and Oregon Green™, rhodamine and derivatives (e.g., Texas red and tetrarhodamine isothiocyanate (TRITC)), biotin, phycoerythrin, AMCA, CyDyes™, 6-carboxyfluorescein (commonly known by the abbreviations FAM and F), 6-carboxy-2',4', 7',4,7-hexachlorofluorescein (HEX), 6-carboxy-4',5'-dichloro-2',7'-dimethoxyfluorescein (JOE or J), N,N,N',N'-tetramethyl-6carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g., Cy3, Cy5 and Cy7 dyes; coumarins, e.g. umbelliferone; benzimide dyes, e.g., Hoechst 33258; phenanthridine dyes, e.g., Texas Red; ethidium dyes; acridine dyes; carbazole dyes; phenoxazine dyes; porphyrin dyes; polymethine dyes, e.g., cyanine dyes such as Cy3, Cy5, etc.; BODIPY dyes and quinoline dyes. In some embodiments, a detectable label can be a radiolabel including, but not limited to $^{3}H$, $^{125}I$, $^{35}S$, $^{14}C$, $^{32}P$, and $^{33}P$. In some embodiments, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use to detectably label an antibody reagent include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase. In some embodiments, a detectable label is a chemiluminescent label, including, but not limited to lucigenin, luminol, luciferin, isoluminol, theromatic acridinium ester, imidazole, acridinium salt and oxalate ester. In some embodiments, a detectable label can be a spectral colorimetric label including, but not limited to colloidal gold or colored glass or plastic (e.g., polystyrene, polypropylene, and latex) beads.

In some embodiments, detection reagents can also be labeled with a detectable tag, such as c-Myc, HA, VSV-G, HSV, FLAG, V5, HIS, or biotin. A reagent can also be detectably labeled using fluorescence emitting metals such as $^{152}Eu$, or others of the lanthanide series. These metals can be attached to the reagent using such metal chelating groups as diethylenetriaminepentaacetic acid (DTPA) or ethylenediaminetetraacetic acid (EDTA).

In some embodiments, the amplicons amplified during PCR can be 300 bp or less, e.g., 300 bp or less, 200 bp or less, 150 bp or less, 100 bp or less, 75 bp or less, 70 bp or less, 65 bp or less, 60 bp or less, 55 bp or less, or 50 bp or less. In some embodiments, the amplicons amplified during PCR can be 50-80 bp. In some embodiments, the amplicons amplified during PCR can be 100 bp or less.

In some embodiments, the PCR reaction can be a duplex PCR reaction, e.g., the level of two target nucleic acids can be measured simultaneously in the same reaction mixture. In some embodiments, the PCR reaction can be a multiplex PCR reaction, e.g., the level of two or more target nucleic acids can be measured simultaneously in the same reaction mixture.

In some embodiments of any of the aspects described herein, the level of expression products of more than one gene can be determined simultaneously (e.g., a multiplex assay) or in parallel. In some embodiments, the level of expression products of no more than 200 other genes is determined. In some embodiments, the level of expression products of no more than 100 other genes is determined. In some embodiments, the level of expression products of no more than 20 other genes is determined. In some embodiments, the expression level of no more than 10 other genes is determined.

In some embodiments of the various aspects described herein, the assay or method further comprises measuring the level of one or more marker genes selected from the group consisting of PLA2g6(L) (SEQ ID NO: 1) and PLA2g6(S) (SEQ ID NO: 3 and/or SEQ ID NO: 5). A decrease in the expression of PLA2g6(L) (e.g., the mRNA level) relative to a reference mRNA PLA2g6(L) level, or PLA2g6(S) mRNA level indicates the subject has iPD, or is at risk of developing PD or iPD as they age. The sequences of gene expression products of the foregoing genes are known, see, e.g., the NCBI entries for the given Ref Seq numbers, and one of skill in the art can readily design primer to detect and/or measure expression product levels. In some embodiments, the level of the expression product can be normalized, e.g., to GAPDH or alternatively to PLA2g6(S).

Internal Controls:

In some embodiments, an internal control can be added to the PCR amplification reaction prior to the measuring step(s), e.g., a known amount of the internal control can be added. As used herein, "internal control" refers to a nucleic acid molecule which is not present in the sample in situ and the detection of which can control for variance in the PCR reaction, e.g., varying efficiencies or failed reactions as opposed to variances in the actual level of PLA2g6(L). In some embodiments, the level PLA2g6(L) can be normalized relative to the measured level (or to the ratio of detected vs. originally added) internal control. In some embodiments, this normalization is performed before calculating a ratio of PLA2g6(L):GAPDH, or to PLA2g6(L):PLA2g6(S). Those of ordinary skill in the art are aware of methods of normalization.

The internal control can be, e.g., a DNA or a RNA, e.g., a mRNA. In some embodiments, the internal control can be added prior to a reverse transcriptase reaction. In some embodiments, the internal control can be after a reverse transcriptase reaction.

In some embodiments, the level of the internal control can be detected during PCR, e.g., in a duplex PCR reaction with PLA2g6(L), PLA2g6(S) and GAPDH or other normalizing transcript. In some embodiments, the level of the internal control can be measured simultaneously with the measurement of the gene markers (e.g., PLA2g6(L) and optionally PLA2g6(S)) mRNA levels.

In some embodiments, the internal control comprises a nucleic acid sequence which is not found in the sample, e.g., a nucleic acid sequence (e.g., an RNA) not found in non-neuronal cells. In some embodiments, the internal control can be a synthetic nucleic acid sequence. In some embodiments, the internal control can be a non-human nucleic acid sequence. In some embodiments, the internal control can be a non-mammalian nucleic acid sequence. In some embodiments, the internal control can be a luciferase nucleic acid.

Primers and probes can be readily designed using the exemplary sequences provided herein, e.g., based on SEQ ID NO: 1, 3 and 5, and by shortening or lengthening the primers or probes, or selecting alternative sequences from the mRNA to which primers and/or probes can hybridize.

In some embodiments, the PCR reactions described above herein can additionally be performed with known quantities of PLA2g6(L) and/or PLA2g6(S) nucleic acids, e.g., multiple PCR reactions can be performed with multiple known quantities of PLA2g6(L) and/or PLA2g6(S) nucleic acids, and a standard curve can be generated and/or calculated. The use of such standard curves, e.g., to correct for reaction efficiencies and accurately calculate the original amount of a target present in a sample is known in the art.

Measuring Protein Levels of PLA2g6(L) and PLA2g6(S) in a Sample

The invention provides, in part, a variety of assay formats that can be used to determine the concentration or level of PLA2g6(L) mRNA or protein, and one or more of PLA2g6(S) mRNA or protein or a normalizing mRNA or protein levels. Examples of assay formats for measuring protein levels include known techniques such as Western blot analysis, radioimmunoassay (hereinafter referred to as "RIA"), Immunoradiometric assay (IRMA), chemiluminescent immunoassays, such as enzyme-linked immunosorbent assay (hereinafter referred to as "ELISA"), multiplex bead assays, a fluorescence antibody method, passive haemagglutination, mass spectrometry (such as MALDI/TOF (time-of-flight), SELDI/TOF), liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, and tandem mass spectrometry HPLC. Some of the immunoassays can be easily automated by the use of appropriate instruments such as the IMx™ (Abbott, Irving, Tex.) for a fluorescent immunoassay and Ciba Corning ACS 180™ (Ciba Corning, Medfield, Mass.) for a chemiluminescent immunoassay.

In some embodiments, an agent which specifically binds to PLA2g6(L) protein is an antibody or antibody fragment (e.g., an antigen-binding Ab fragment), or a protein-binding molecule which specifically binds an expression product of PLA2g6(L) mRNA. In some embodiments, an agent which specifically binds to PLA2g6(L) protein is an antibody or antibody fragment (e.g., an antigen-binding Ab fragment), or a protein-binding molecule which a PLA2g6(L) polypeptide.

In some embodiments, an agent which specifically binds to PLA2g6(L) is an antibody or antibody fragment (e.g., an antigen-binding Ab fragment), or a protein-binding molecule which can specifically bind the PIN domain. In some embodiment, an anti-PLA2g6(L) antibody binds to an epitope located in any one or more of SEQ ID NO: 16, SEQ ID NO: 17 or SEQ ID NO: 18. In some embodiments, an agent which specifically binds to PLA2g6(L) is an antibody or antibody fragment (e.g., an antigen-binding Ab fragment), or a protein-binding molecule can bind glycosylated or partially glycosylated PLA2g6(L) polypeptide. In some embodiments, an agent which specifically binds to PLA2g6(L) is an antibody or antibody fragment (e.g., an antigen-binding Ab fragment), or a protein-binding molecule can bind unglycosylated PLA2g6(L) polypeptide. In some embodiments, an agent which specifically binds to PLA2g6(L) is an antibody or antibody fragment (e.g., an antigen-binding Ab fragment), or a protein-binding molecule can bind to glycosylated, or partially glycosylated, or unglycosylated ectodomain of PLA2g6(L) polypeptide, e.g., to glycosylated, or partially glycosylated, or unglycosylated protein or fragment of SEQ ID NO: 2.

In some embodiments, an agent which specifically binds to PLA2g6(L) is small or large organic or inorganic molecule. As used herein, the term "small molecule" refers to natural or synthetic molecules having a molecular weight less than about 10,000 grams per mole, organic or inorganic compounds having a molecular weight less than about 5,000 grams per mole, than about 1,000 grams per mole, or less than about 500 grams per mole.

In some embodiments, an agent which specifically binds to PLA2g6(L) is an antibody or antibody fragment (e.g., an antigen-binding Ab fragment), or a protein-binding molecule. Suitable antibodies include, but are not limited to, polyclonal, monoclonal, chimeric, humanized, recombinant, single chain, $F_{ab}$, $F_{ab'}$, $F_{sc}$, $R_v$, and $F_{(ab')2}$ fragments, and an $F_{ab}$ expression library. In some embodiments, neutralizing antibodies can be used an agent which specifically binds to PLA2g6(L). Antibodies are readily raised in animals such as rabbits or mice by immunization with the antigen. Immunized mice are particularly useful for providing sources of B cells for the manufacture of hybridomas, which in turn are cultured to produce large quantities of monoclonal antibodies. In general, an antibody molecule obtained from humans can be classified in one of the immunoglobulin classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

Antibodies provide high binding avidity and unique specificity to a wide range of target antigens and haptens. Monoclonal antibodies useful in the practice of the methods disclosed herein include whole antibody and fragments thereof and are generated in accordance with conventional techniques, such as hybridoma synthesis, recombinant DNA techniques and protein synthesis.

The PIN domain of the PLA2g6(L) polypeptide, or a portion or fragment thereof, can serve as an antigen, and additionally can be used as an immunogen to generate antibodies that immunospecifically bind the antigen, using standard techniques for polyclonal and monoclonal antibody preparation. Preferably, the antigenic peptide comprises at least 10 amino acid residues, or at least 15 amino acid residues, or at least 20 amino acid residues, or at least 30 amino acid residues. In some embodiments, an agent which specifically binds to PLA2g6(L) is an antibody or antibody fragment (e.g., an antigen-binding Ab fragment), or a protein-binding molecule binds to an epitope within, overlapping, or in close proximity to the amino acid sequence encoded by exon 8b in PLA2g6(L). In some embodiments, an anti-PLA2g6(L) antibody specifically binds to an epitope at least partially encoded by exon 8b of PLA2g6(L) or binds to an epitope at least partially located in any of SEQ ID NO: 16, SEQ ID NO: 17 or SEQ ID NO: 18 disclosed herein.

Useful monoclonal antibodies and fragments can be derived from any species (including humans) or can be formed as chimeric proteins which employ sequences from more than one species. Human monoclonal antibodies or "humanized" murine antibody are also used in accordance with the present invention. For example, murine monoclonal antibody can be "humanized" by genetically recombining the nucleotide sequence encoding the murine Fv region (i.e., containing the antigen binding sites) or the complementarily determining regions thereof with the nucleotide sequence encoding a human constant domain region and an Fc region. Humanized targeting moieties are recognized to decrease the immunoreactivity of the antibody or polypeptide in the host recipient, permitting an increase in the half-life and a reduction the possibly of adverse immune reactions in a manner similar to that disclosed in European Patent Application No. 0,411,893 A2. The murine monoclonal antibodies should preferably be employed in humanized form. Antigen binding activity is determined by the sequences and conformation of the amino acids of the six complementarily determining regions (CDRs) that are located (three each) on the light and heavy chains of the variable portion (Fv) of the antibody. The 25-kDa single-chain Fv (scFv) molecule, composed of a variable region (VL) of the light chain and a variable region (VH) of the heavy chain joined via a short peptide spacer sequence, is the smallest antibody fragment developed to date. Techniques have been developed to display scFv molecules on the surface of filamentous phage that contain the gene for the scFv. scFv molecules with a broad range of antigenic-specificities can be present in a single large pool of scFv-phage library. Some examples of high affinity monoclonal antibodies and chimeric derivatives thereof, useful in the methods of the present invention, are described in the European Patent Application EP 186,833; PCT Patent Application WO 92/16553; and U.S. Pat. No. 6,090,923.

Chimeric antibodies are immunoglobin molecules characterized by two or more segments or portions derived from different animal species. Generally, the variable region of the chimeric antibody is derived from a non-human mammalian antibody, such as murine monoclonal antibody, and the immunoglobin constant region is derived from a human immunoglobin molecule. Preferably, both regions and the combination have low immunogenicity as routinely determined.

An agent which specifically binds to PLA2g6(L) protein, e.g., an antibody or antibody fragment (e.g., an antigen-binding Ab fragment), or a protein-binding molecule which specifically binds an expression product of PLA2g6(L).

RIA and ELISA provide the benefit of detection sensitivity, rapidity, accuracy, possible automation of procedures, and the like, for the determination of the concentration or level of PLA2g6(L)polypeptide biomarker (Modern Rheumatology 13: 22-26 (2003)), Ohkuni et al., (International Congress Series 1289: 71-74 (2006)), and Mitchell et al., (Mol Microbiol. 5: 1883-8 (1991)). Radioimmunoassay (Kashyap, M. L. et al., J. Clin. Invest., 60:171-180 (1977)) is a technique in which detection antibody can be used after labeling with a radioactive isotope such as 125I. Antibody arrays or protein chips can also be employed, see for example U.S. Pat. Application Nos: 20030013208A1; 20020155493A1; 20030017515 and U.S. Pat. Nos. 6,329,209; 6,365,418, which are herein incorporated by reference in their entirety.

The most common enzyme immunoassay is the "Enzyme-Linked Immunosorbent Assay (ELISA). There are different forms of ELISA which are well known to those skilled in the art, e.g. standard ELISA, competitive ELISA, and sandwich ELISA. The standard techniques for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. 1984, J. Clin. Chem. Clin. Biochem., 22:895-904. ELISA is a technique for detecting and measuring the concentration of an antigen, such as an acute kidney injury biomarker, using a labeled (e.g. enzyme linked) form of the antibody. In a "sandwich ELISA", an antibody is linked to a solid phase (i.e. a microtiter plate) and exposed to a biological sample containing antigen (e.g. an acute kidney injury biomarker). The solid phase is then washed to remove unbound antigen. A labeled antibody (e.g. enzyme linked) is then bound to the plate bound-antigen (if present) forming an antibody-antigen-antibody sandwich. Examples of enzymes that can be linked to the antibody are alkaline phosphatase, horseradish peroxidase, luciferase, urease, and B-galactosidase. The enzyme linked antibody reacts with a substrate to generate a colored reaction product that can be measured. In a "competitive ELISA", a specific concentration of an antibody specific for PLA2g6(L) polypeptide is incubated with a sample. The PLA2g6(L)-antibody mixture is then contacted with a solid phase (e.g. a microtiter plate) that is coated with PLA2g6(L) protein biomarker. The more PLA2g6(L) biomarker present in the sample, the less free antibody that will be available to bind to the solid phase. A labeled (e.g., enzyme linked) secondary antibody is then added to the solid phase to determine the amount of primary antibody bound to the solid phase.

In some embodiments, the concentration of PLA2g6(L) biomarkers, and or PLA2g6(S) and/or a normalizing protein can be determined simultaneously, in a multiplex fashion, by ELISA (enzyme-linked immunosorbent assay). The non-neuronal sample, e.g., blood sample can be, for example, one of a plurality of blood samples obtained at one of the various timepoints from a subject in need.

In some embodiments, the sample is a human blood sample from a subject, to be tested for determining the concentration of PLA2g6(L) mRNA and/or protein according to the methods described herein. In some embodiments, the sample is a platelet rich plasma (PRP). In some embodiments, the sample is a non-neuronal sample. In some embodiments, the sample is a neuronal sample, e.g., CSF, spinal tap sample and the like. In some embodiments, the sample, e.g., blood sample (e.g., plasma, serum, platelet rich plasma (PRP) etc.) from the individual may further be serially diluted, according to the needs of the assay, and as known to one of ordinary skill in the art. In some embodiments, one or more of a plurality of antibodies or antigen-binding fragments specific for PLA2g6(L) being assayed in a sample is contacted with the sample to bind PLA2g6(L) protein present in the sample, thus forming a PLA2g6(L)-antibody complex or PLA2g6(L)-antigen-binding fragment complex. In some embodiments, each antibody or antigen-binding fragment specific for PLA2g6(L) or PLA2g6(S) or a normalizing protein is labeled with a different label. In some embodiments, each different label is a fluorescent label. In all such embodiments, each different label has a unique emission spectra, such that each antibody can be detected individually. The levels or concentrations of PLA2g6(L) and/or PLA2g6(S) and/or normalizing protein can then be determined by calculating changes in the emission spectrum, wherein the relative intensity of signal from each of the fluorescent labels correlates with the number of antibodies against the particular biomarker being assayed. For example, a well that displays a more intense signal of the label on the antibody against PLA2g6(L) will have a greater concentration of PLA2g6(L) than a well with a weak signal for that particular label. The wells can be normalized to a well comprising all of the necessary ELISA reagents with the exception of the sample. A series of standards having known concentrations of each of the various biomarkers being assayed permits actual quantification of the concentration of each of the biomarkers in the sample.

In some aspects, the concentration or level of PLA2g6(L) can be determined alone, or in combination with other biomarkers (i.e., PLA2g6(S)) simultaneously, in a multiplex fashion, using a multiplex bead assay. For example, in one embodiment, beads of different sizes or colors (emission spectra) are used for multiplexed immunoassays to determine the concentration of PLA2g6(L) and optionally, PLA2g6(S) biomarkers. In some embodiments of this aspect, a plurality of beads of different sizes are coated with different antibodies, wherein each bead of a specific size is conjugated to an antibody specific for a single biomarker (e.g., a bead of one size is conjugated to an antibody for PLA2g6(L) and beads of different sizes are conjugated to different antibodies specific to PLA2g6(S) and/or antibodies specific to normalizing proteins. Accordingly, each bead can be differentiated by its unique light scatter characteristics. A non-neuronal sample, e.g., blood sample, such as a plasma or serum sample, to be assayed for the presence of PLA2g6 (L) protein and optionally PLA2g6(S), and optionally at least one other biomarker is then contacted with a plurality of beads of different sizes, forming a bead-biomarker conjugate, and the concentrations of PLA2g6(L) and PLA2g6 (S) and the other biomarker or normalizing protein can then be ascertained by, for example, performing flow cytometric analyses on the bead bound-sample. In some embodiments, one of the other biomarkers assessed in a multiplex bead assay is a normalizing protein to detect the level of protein in the blood sample. In some embodiments, a biomarker assessed with PLA2g6(L) biomarker is PLA2g6(S) or GAPDH, or actin or other suitable normalizing proteins.

In some embodiments of this aspect, such bead-based technology can be employed wherein bead populations are identified by one type of fluorescence, while the biomarker-dependent signal is generated by detection reagents carrying a second type of fluorescent signal, thus creating a bead set specific for PLA2g6(L) and one or more other biomarkers (e.g., PLA2g6(S) or normalizing proteins). In preferred embodiments, the distinguishable bead populations are prepared by staining the beads with two or more fluorescent dyes at various ratios. Each bead having a specific ratio of the two or more fluorescent dyes is conjugated to an antibody specific for one of a plurality of biomarkers, thus assigning each bead a unique fluorescent signature. The immunoassay signal is generated by detection reagents, coupled to a third type of fluorescent dye. A sample to be assayed for the presence of PLA2g6(L) and optionally PLA2g6(S), and/or least one other biomarker or normalizing protein, is then contacted with the plurality of beads with unique fluorescent signatures and biomarker specificity, forming a bead-biomarker conjugate for PLA2g6(L) or PLA2g6(S) or other biomarker present in the sample. The concentrations of PLA2g6(L) and each of other proteins or biomarkers can be ascertained by flow cytometric analyses on the bead bound-sample. For example, in some embodiments, beads are dyed with fluorochromes having different fluorescence intensities. In some embodiments, the beads are 7.5 µm in diameter. In some embodiments, the fluorescent dye incorporated in the beads fluoresces strongly at 650 nm upon excitation with an argon laser. Each bead population of a given fluorescence intensity represents a discrete population for constructing an immunoassay for a single biomarker. Each bead population having a given fluorescence intensity upon excitation is covalently coupled with an antibody directed against a specific biomarker, e.g., an antibody directed against PLA2g6(L). These antibody-bound bead populations, each of which are unique in their fluorescence emission intensity, serve as capture beads for PLA2g6(L) and optionally, PLA2g6(S), as well as optionally normalizing proteins in the non-neuronal sample obtained from the subject.

Accordingly, as defined herein a "capture bead" is a bead having a unique fluorescence emission intensity conjugated to an antibody specific for a biomarker, e.g., PLA2g6(L). When these capture beads specific for different biomarkers are used as a mixture, the levels of individual biomarkers, such as PLA2g6(L) and PLA2g6(S), and/or GAPDH or other normalizing protein, can be simultaneously measured within a given non-neuronal sample, e.g., blood sample. In some embodiments, detection is further mediated by the binding of a specific detection antibody, for example, an antibody that detects any bead-biomarker complex present in a sample, that is directly conjugated with phycoerythrin (PE), to each of the corresponding capture bead-biomarker complexes present in the sample, thus providing a second fluorescent signal for each capture bead. The fluorescent signal is proportional to the concentration of the biomarker in the sample. Separately established calibration curves can be used to determine the concentration of each biomarker in the test sample, using dedicated analysis software, such as CBA software. The data collected using a flow cytometer include information about the physical and spectral parameters of the beads, such as size and the fluorescence emission characteristics of each bead population. These fluorescence emission characteristics include the fluorescent emission of the dyed beads, and the potential fluorescent emissions of the detection fluorochrome (for example, phycoerythrin). When samples are analyzed using a flow cytometer in conjunction with a typical data acquisition and analysis package (for e.g., BD CellQuest™ software), a list-mode data file is saved using a flow cytometry standard file format, FCS. The data stored in the FCS files can be reanalyzed to determine the median fluorescence intensities (MFI) of the various bead populations, defined by their unique physical and spectral characteristics, to then compare reference samples with unknowns. The level of the biomarkers, e.g., PLA2g6(L) and optionally PLA2g6(S) being assayed within the individual non-neuronal sample, e.g., blood samples can then be calculated from calibration curves generated by serial dilutions of standard analyte solutions of known concentration. An automated or semiautomated analysis method can be used for rapid reanalysis of the data stored in each FCS file. For example, BD CBA Software is written in the Microsoft® Excel Visual Basic for Applications (VBA) programming language. The CBA Software can recognize FCS 2.0 and 3.0 format data files and automates the identification of CBA bead populations and the determination of detector fluorochrome MFI values for each bead population within the data file for a single sample. Using this data analysis function of the CBA Software for multiple standard files, the MFI values for standards are then determined and plotted. From the plotted standard curve and complex mathematical interpolation, values for unknown samples can be rapidly determined in comparison to known standards using the software.

Other techniques can be used to detect levels of PLA2g6 (L) protein and/or PLA2g6(S) protein in the non-neuronal sample are encompassed for use in the practice the methods described herein, according to a practitioner's preference, and based upon the present disclosure. The suitability of a given method for measuring PLA2g6(L) levels will depend on the ability of that method or assay to distinguish between PLA2g6(L) and PLA2g6(S), as well as other proteins in the non-neuronal sample, e.g., blood sample. Thus, an immunoassay can distinguish on the basis of selective binding to PLA2g6(L) and not to PLA2g6(S) or another agent or protein in the non-neuronal sample, e.g., blood sample. Spectrometric approaches can be applied when a given agent will have a distinct spectrum or profile in the assay relative to others. One such technique is Western blotting (Towbin et at., Proc. Nat. Acad. Sci. 76:4350 (1979)), wherein a suitably treated sample is run on an SDS-PAGE gel before being transferred to a solid support, such as a nitrocellulose filter. Detectably labeled antibodies that specifically bind to PLA2g6(L) can then be used to detect PLA2g6(L) levels or concentrations, where the intensity of the signal from the detectable label corresponds to the amount of PLA2g6(L) protein present. Levels can be quantitated, for example by densitometry.

The prognostic methods of the invention also are useful for determining a proper course of treatment for a patient identified to have iPD or at risk of developing PD or iPD. A course of treatment refers to the therapeutic measures taken for a patient after diagnosis of being at risk of developing PD.

In one embodiment, methods to detect the PLA2g6(L) proteins and fragments and functional variants thereof as disclosed herein include ELISA (enzyme linked immunosorbent assay), western blot, immunoprecipitation, immunofluorescence using detection reagents such as an antibody or protein binding molecules or protein-binding agents. Alternatively, a PLA2g6(L) protein biomarker can be detected in a subject by introducing into a subject a labeled anti-PLA2g6(L) biomarker antibody and other types of detection agent. For example, the antibody can be labeled with a radioactive marker whose presence and location in the subject is detected by standard imaging techniques, particularly useful are methods that detect a PLA2g6(L) protein or fragment thereof expressed in a subject or in a biological sample.

Methods to detect level the PLA2g6(L) polypeptide in a non-neuronal sample, e.g., blood sample are well known to persons skilled in the art, and are encompassed for use in this invention. Commercially available antibodies and/or ELISA kits for detection of the expression of the PLA2g6(L) polypeptide in a sample are also useful in the methods of this invention. Some examples of such protein-binding molecules useful to detect the PLA2g6(L) polypeptide, and optionally PLA2g6(S) are commercially available, and include, but are not limited to, commercially available antibodies from Cell Signalling Technologies (MA, USA), which can be found at world wide web site: "cell signal-dot-com". In some embodiments, antibodies from other antibody companies, such as for example, Abnova corporation, Anogen, Alpco Diagnostics, Ray Biotech, alphagenix, autogen, R&D Systems, Pepro Tech EC Ltd, cytolab, Bender MedSystems GmbH, Biovision Research Products, EBD biosciences, Chemicon, Axxora Platform, Promo Cell Distrubuters, Cell Science, Santa Cruz Biotechnology, Sigma etc. can be used. In alternative embodiments, antibodies directed against the PLA2g6(L) polypeptide and/or its PIN domain can also be used in disease diagnostics and prognostics.

In another embodiment, immunohistochemistry ("IHC") and immunocytochemistry ("ICC") techniques can be used. IHC is the application of immunochemistry to tissue sections, whereas ICC is the application of immunochemistry to cells or tissue imprints after they have undergone specific cytological preparations such as, for example, liquid-based preparations. Immunochemistry is a family of techniques based on the use of an antibody, wherein the antibodies are used to specifically target molecules inside or on the surface of cells. The antibody typically contains a marker that will undergo a biochemical reaction, and thereby experience a change color, upon encountering the targeted molecules. In some instances, signal amplification can be integrated into the particular protocol, wherein a secondary antibody, that includes the marker stain or marker signal, follows the application of a primary specific antibody.

In some embodiments, the methods as described herein can be performed, for example, by utilizing pre-packaged diagnostic kits, such as those described above, comprising at least one probe which can be conveniently used, e.g., to determine whether a subject has iPD or is at risk of developing iPD or PD.

The term "protein-binding molecule" or "antibody-based binding moiety" or "antibody" includes immunoglobulin molecules and immunologically active determinants of immunoglobulin molecules, e.g., molecules that contain an antigen binding site which specifically binds (i.e. immunoreacts with) to PLA2g6(L) proteins. The term "antibody-based binding moiety" is intended to include whole antibodies, e.g., of any isotype (IgG, IgA, IgM, IgE, etc), and includes fragments thereof which are also specifically reactive with PLA2g6(L) proteins. Antibodies can be fragmented using conventional techniques. Thus, the term includes segments of proteolytically-cleaved or recombinantly-prepared portions of an antibody molecule that are capable of selectively reacting with a certain protein. Non limiting examples of such proteolytic and/or recombinant fragments include Fab, F(ab')2, Fab', Fv, dAbs and single chain antibodies (scFv) containing a VL and VH domain joined by a peptide linker.

The scFv's can be covalently or non-covalently linked to form antibodies having two or more binding sites. Thus, "antibody-base binding moiety" includes polyclonal, monoclonal, or other purified preparations of antibodies and recombinant antibodies. The term "antibody-base binding moiety" is further intended to include humanized antibodies, bispecific antibodies, and chimeric molecules having at least one antigen binding determinant derived from an antibody molecule. In a preferred embodiment, the antibody-based binding moiety detectably labeled.

The term "labeled antibody", as used herein, includes antibodies that are labeled by a detectable means and include, but are not limited to, antibodies that are enzymatically, radioactively, fluorescently, and chemiluminescently labeled. Antibodies can also be labeled with a detectable tag, such as c-Myc, HA, VSV-G, HSV, FLAG, V5, or HIS. The detection and quantification of PLA2g6(L) present in the tissue samples correlate to the intensity of the signal emitted from the detectably labeled antibody.

In one embodiment, the antibody-based binding moiety is detectably labeled by linking the antibody to an enzyme. The enzyme, in turn, when exposed to it's substrate, will react with the substrate in such a manner as to produce a chemical moiety which can be detected, for example, by spectrophotometric, fluorometric or by visual means. Enzymes which can be used to detectably label the antibodies of the present invention include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase.

Detection can also be accomplished using any of a variety of other immunoassays. For example, by radioactively labeling an antibody, it is possible to detect the antibody through the use of radioimmune assays. The radioactive isotope can be detected by such means as the use of a gamma counter or a scintillation counter or by audioradiography. Isotopes which are particularly useful for the purpose of the present invention are $^{3}H$, $^{131}I$, $^{35}S$, $^{14}C$, and preferably $^{125}I$.

It is also possible to label an antibody with a fluorescent compound. When the fluorescently labeled antibody is exposed to light of the proper wavelength, its presence can then be detected due to fluorescence. Among the most commonly used fluorescent labeling compounds are CYE dyes, fluorescein isothiocyanate, rhodamine, phycoerytherin, phycocyanin, allophycocyanin, o-phthaldehyde and fluorescamine.

An antibody can also be detectably labeled using fluorescence emitting metals such as 152Eu, or others of the lanthanide series. These metals can be attached to the antibody using such metal chelating groups as diethylenetriaminepentaacetic acid (DTPA) or ethylenediaminetetraacetic acid (EDTA).

An antibody also can be detectably labeled by coupling it to a chemiluminescent compound. The presence of the chemiluminescent-antibody is then determined by detecting the presence of luminescence that arises during the course of a chemical reaction. Examples of particularly useful chemiluminescent labeling compounds are luminol, luciferin, isoluminol, theromatic acridinium ester, imidazole, acridinium salt and oxalate ester.

As mentioned above, levels of enzyme protein can be detected by immunoassays, such as enzyme linked immunoabsorbant assay (ELISA), radioimmunoassay (RIA), Immunoradiometric assay (IRMA), Western blotting, immunocytochemistry or immunohistochemistry, each of which are described in more detail below. Immunoassays such as ELISA or RIA, which can be extremely rapid, are more generally preferred. Antibody arrays or protein chips can also be employed, see for example U.S. Pat. Application Nos: 20030013208A1; 20020155493A1; 20030017515 and U.S. Pat. Nos. 6,329,209; 6,365,418, which are herein incorporated by reference in their entirety.

Immunoassays

The most common enzyme immunoassay is the "Enzyme-Linked Immunosorbent Assay (ELISA)." ELISA is a technique for detecting and measuring the concentration of an antigen using a labeled (e.g. enzyme linked) form of the antibody. There are different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. 1984, J. Clin. Chem. Clin. Biochem., 22:895-904.

In a "sandwich ELISA", an antibody (e.g. anti-enzyme) is linked to a solid phase (i.e. a microtiter plate) and exposed to a biological sample containing antigen (e.g. enzyme). The solid phase is then washed to remove unbound antigen. A labeled antibody (e.g. enzyme linked) is then bound to the bound-antigen (if present) forming an antibody-antigen-antibody sandwich. Examples of enzymes that can be linked to the antibody are alkaline phosphatase, horseradish peroxidase, luciferase, urease, and B-galactosidase. The enzyme linked antibody reacts with a substrate to generate a colored reaction product that can be measured.

In a "competitive ELISA", antibody is incubated with a sample containing antigen (i.e. enzyme). The antigen-antibody mixture is then contacted with a solid phase (e.g. a microtiter plate) that is coated with antigen (i.e., enzyme). The more antigen present in the sample, the less free antibody that will be available to bind to the solid phase. A labeled (e.g., enzyme linked) secondary antibody is then added to the solid phase to determine the amount of primary antibody bound to the solid phase.

In an "immunohistochemistry assay" a section of tissue is tested for specific proteins by exposing the tissue to antibodies that are specific for the protein that is being assayed. The antibodies are then visualized by any of a number of methods to determine the presence and amount of the protein present. Examples of methods used to visualize antibodies are, for example, through enzymes linked to the antibodies (e.g., luciferase, alkaline phosphatase, horseradish peroxidase, or beta-galactosidase), or chemical methods (e.g., DAB/Substrate chromagen). The sample is then analysed microscopically, most preferably by light microscopy of a sample stained with a stain that is detected in the visible spectrum, using any of a variety of such staining methods and reagents known to those skilled in the art.

Alternatively, "Radioimmunoassays" can be employed. A radioimmunoassay is a technique for detecting and measuring the concentration of an antigen using a labeled (e.g. radioactively or fluorescently labeled) form of the antigen. Examples of radioactive labels for antigens include 3H, 14C, and 125I. The concentration of antigen enzyme in a biological sample is measured by having the antigen in the biological sample compete with the labeled (e.g. radioactively) antigen for binding to an antibody to the antigen. To ensure competitive binding between the labeled antigen and the unlabeled antigen, the labeled antigen is present in a concentration sufficient to saturate the binding sites of the antibody. The higher the concentration of antigen in the sample, the lower the concentration of labeled antigen that will bind to the antibody.

In a radioimmunoassay, to determine the concentration of labeled antigen bound to antibody, the antigen-antibody complex must be separated from the free antigen. One method for separating the antigen-antibody complex from the free antigen is by precipitating the antigen-antibody complex with an anti-isotype antiserum. Another method for separating the antigen-antibody complex from the free antigen is by precipitating the antigen-antibody complex with formalin-killed S. aureus. Yet another method for separating the antigen-antibody complex from the free antigen is by performing a "solid-phase radioimmunoassay" where the antibody is linked (e.g., covalently) to Sepharose beads, polystyrene wells, polyvinylchloride wells, or microtiter wells. By comparing the concentration of labeled antigen bound to antibody to a standard curve based on samples having a known concentration of antigen, the concentration of antigen in the biological sample can be determined.

An "immunoradiometric assay" (IRMA) is an immunoassay in which the antibody reagent is radioactively labeled. An IRMA requires the production of a multivalent antigen conjugate, by techniques such as conjugation to a protein e.g., rabbit serum albumin (RSA). The multivalent antigen conjugate must have at least 2 antigen residues per molecule and the antigen residues must be of sufficient distance apart to allow binding by at least two antibodies to the antigen. For example, in an IRMA the multivalent antigen conjugate can be attached to a solid surface such as a plastic sphere. Unlabeled "sample" antigen and antibody to antigen which is radioactively labeled are added to a test tube containing the multivalent antigen conjugate coated sphere. The antigen in the sample competes with the multivalent antigen conjugate for antigen antibody binding sites. After an appropriate incubation period, the unbound reactants are removed by washing and the amount of radioactivity on the solid phase is determined. The amount of bound radioactive antibody is inversely proportional to the concentration of antigen in the sample.

Other techniques can be used to detect the PLA2g6(L) polypeptide in a non-neuronal sample, e.g., blood sample according to a practitioner's preference, and based upon the present disclosure and the type of biological sample (i.e. plasma, urine, tissue sample etc). One such technique is Western blotting (Towbin et al., Proc. Nat. Acad. Sci. 76:4350 (1979)), wherein a suitably treated sample is run on an SDS-PAGE gel before being transferred to a solid support, such as a nitrocellulose filter. Detectably labeled anti-enzyme antibodies can then be used to assess enzyme levels, where the intensity of the signal from the detectable label corresponds to the amount of enzyme present. Levels can be quantified, for example by densitometry.

In other embodiments, the levels of PLA2g6(L) polypeptide present in a non-neuronal sample, e.g., blood sample (e.g., whole blood, plasma or serum etc) can be determined by mass spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.). See for example, U.S. Pat. Application Nos: 20030199001, 20030134304, 20030077616, which are herein incorporated by reference in their entirety.

The terms "mass spectrometry" or "MS" as used herein refer to methods of filtering, detecting, and measuring ions based on their mass-to-charge ratio, or "m/z." In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., "Proteinchip surface enhanced laser desorption/ionization (SELDI) mass spectrometry: a novel protein biochip technology for detection of prostate cancer biomarkers in complex protein mixtures," Prostate Cancer and Prostatic Diseases 2: 264-76 (1999); and Merchant and Weinberger, "Recent advancements in surface-enhanced laser desorption/ionization-time of flight-mass spectrometry," Electrophoresis 21: 1164-67 (2000), each of which is hereby incorporated by reference in its entirety, including all tables, figures, and claims. Mass spectrometry methods are well known in the art and have been used to quantify and/or identify biomolecules, such as proteins and hormones (see, e.g., Li et al., (2000), Tibtech. 18:151-160; Starcevic et. al., (2003), J. Chromatography B, 792: 197-204; Kushnir M M et. al. (2006), Clin. Chem. 52:120-128; Rowley et al. (2000), Methods 20: 383-397; and Kuster and Mann (1998), Curr. Opin. Structural Biol. 8: 393-400). Further, mass spectrometric techniques have been developed that permit at least partial de novo sequencing of isolated proteins. Chait et al., (1993), Science, 262:89-92; Keough et al., (1999), Proc. Natl. Acad. Sci. USA. 96:7131-6; reviewed in Bergman (2000), EXS 88:133-44. Various methods of ionization are known in the art. For examples, Atmospheric Pressure Chemical Ionisation (APCI) Chemical Ionisation (CI) Electron Impact (EI) Electrospray Ionisation (ESI) Fast Atom Bombardment (FAB) Field Desorption/Field Ionisation (FD/FI) Matrix Assisted Laser Desorption Ionisation (MALDI) and Thermospray Ionisation (TSP) In certain embodiments, a gas phase ion spectrophotometer is used. In other embodiments, laser-desorption/ionization mass spectrometry is used to analyze the sample. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. See, e.g., U.S. Pat. No. 5,118,937 (Hillenkamp et al.), and U.S. Pat. No. 5,045,694 (Beavis & Chait). In SELDI, the substrate surface is modified so that it is an active participant in the desorption process. In one variant, the surface is derivatized with adsorbent and/or capture reagents that selectively bind the biomarker of interest. In another variant, the surface is derivatized with energy absorbing molecules that are not desorbed when struck with the laser. In another variant, the surface is derivatized with molecules that bind the protein of interest and that contain a photolytic bond that is broken upon application of the laser. In each of these methods, the derivatizing agent generally is localized to a specific location on the substrate surface where the sample is applied. See, e.g., U.S. Pat. No. 5,719,060 and WO 98/59361. The two methods can be combined by, for example, using a SELDI affinity surface to capture an analyte and adding matrix-containing liquid to the captured analyte to provide the energy absorbing material. For additional information regarding mass spectrometers, see, e.g., Principles of Instrumental Analysis, 3rd edition., Skoog, Saunders College Publishing, Philadelphia, 1985; and Kirk-Othmer Encyclopedia of Chemical Technology, 4.sup.th ed. Vol. 15 (John Wiley & Sons, New York 1995), pp. 1071-1094. Detection and quantification of the biomarker will typically depend on the detection of signal intensity. For example, in certain embodiments, the signal strength of peak values from spectra of a first sample and a second sample can be compared (e.g., visually, by computer analysis etc.), to determine the relative amounts of particular biomarker. Software programs such as the Biomarker Wizard program (Ciphergen Biosystems, Inc., Fremont, Calif.) can be used to aid in analyzing mass spectra. The mass spectrometers and their techniques are well known to those of skill in the art. The various assays are described herein in terms of the detection of PLA2g6(L) polypeptide levels in a non-neuronal sample. It is understood that the assays can be readily adapted to detect other analytes as needed e.g., for various other embodiments and or to detect protein levels and depending on the sample type, such as whole blood, plasma or serum.

Mass spectrometry methods are well known in the art and have been used to quantify and/or identify biomolecules, such as proteins (see, e.g., Li et al. (2000) Tibtech 18:151-160; Rowley et al. (2000) Methods 20: 383-397; and Kuster and Mann (1998) Curr. Opin. Structural Biol. 8: 393-400). Further, mass spectrometric techniques have been developed that permit at least partial de novo sequencing of isolated proteins. Chait et al., Science 262:89-92 (1993); Keough et al., Proc. Natl. Acad. Sci. USA. 96:7131-6 (1999); reviewed in Bergman, EXS 88:133-44 (2000).

In certain embodiments, a gas phase ion spectrophotometer is used. In other embodiments, laser-desorption/ionization mass spectrometry is used to analyze the sample. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. See, e.g., U.S. Pat. No. 5,118,937 (Hillenkamp et al.), and U.S. Pat. No. 5,045,694 (Beavis & Chait).

In SELDI, the substrate surface is modified so that it is an active participant in the desorption process. In one variant, the surface is derivatized with adsorbent and/or capture reagents that selectively bind the protein of interest. In another variant, the surface is derivatized with energy absorbing molecules that are not desorbed when struck with the laser. In another variant, the surface is derivatized with molecules that bind the protein of interest and that contain a photolytic bond that is broken upon application of the laser. In each of these methods, the derivatizing agent generally is localized to a specific location on the substrate surface where the sample is applied. See, e.g., U.S. Pat. No. 5,719,060 and WO 98/59361. The two methods can be combined by, for example, using a SELDI affinity surface to capture an analyte and adding matrix-containing liquid to the captured analyte to provide the energy absorbing material.

For additional information regarding mass spectrometers, see, e.g., Principles of Instrumental Analysis, 3rd edition., Skoog, Saunders College Publishing, Philadelphia, 1985; and Kirk-Othmer Encyclopedia of Chemical Technology, 4.sup.th ed. Vol. 15 (John Wiley & Sons, New York 1995), pp. 1071-1094.

Detection of the presence of the PLA2g6(L) polypeptide in a blood sample will typically depend on the detection of signal intensity. This, in turn, can reflect the quantity and character of a polypeptide bound to the substrate. For example, in certain embodiments, the signal strength of peak values from spectra of a first sample and a second sample can be compared (e.g., visually, by computer analysis etc.), to determine the relative amounts of particular biomolecules. Software programs such as the Biomarker Wizard program (Ciphergen Biosystems, Inc., Fremont, Calif.) can be used to aid in analyzing mass spectra. The mass spectrometers and their techniques are well known to those of skill in the art.

Arrays

In some embodiments of the disclosure, the present invention provides an array comprising a solid support and attached to the solid support probes for detection of the level of mRNA of PLA2g6(L). In some embodiments, the array also comprises probes for the detection of total PLA2g6 mRNA levels, e.g., to detect PLA2g6(L) of SEQ ID NO: 1 and PLA2g6(S) mRNA of SEQ ID NO: 3 and SEQ ID NO: 5. In some embodiments, the array also comprises probes for the detection of total PLA2g6(S) mRNA levels, e.g., to PLA2g6(S) mRNA of SEQ ID NO: 3 and SEQ ID NO: 5. Such arrays can be used for high-throughput analysis of multiple samples at the same time, e.g., for high throughput methods to identify subjects at risk of developing iPD, as well as in drug screening assays to identify agents which can decrease the progression of PD. In some embodiments, the arrays comprise can RT-PCR primers, and/or optionally probes, including e.g., TaqMan probes to detect SEQ ID NO: 1 of PLA2g6(L) mRNA and PLA2g6(S) mRNA of SEQ ID NO: 3 and SEQ ID NO: 5 accordingly.

In some embodiments of the disclosure, the present invention provides an array comprising protein-binding agents, e.g., antibodies to detect the level of PLA2g6(L) protein. In some embodiments, the array also comprises protein-binding agents, e.g., antibodies to detect total PLA2g6 protein levels, e.g., to detect PLA2g6(L) protein of SEQ ID NO: 2 and PLA2g6(S) protein of SEQ ID NO: 4 and SEQ ID NO: 6. In some embodiments, the array also comprises protein-binding agents, e.g., antibodies that specifically bind to all PLA2g6 variants (e.g. PLA2g6(L) and PLA2g6(S) variants of SEQ ID NO: 3 and SEQ ID NO: 5). Such arrays can be used for high-throughput analysis to identify multiple samples at the same time to identify subjects at risk of developing iPD, as well as in drug screening assays to identify agents which can decrease the progression of PD. In some embodiments, the arrays comprise an anti-PLA2g6(L) antibody, e.g., an antibody which binds to an epitope at least partially encoded by exon 8b of PLA2g6(L) or binds to an epitope at least partially located in any of SEQ ID NO: 16, SEQ ID NO: 17 or SEQ ID NO: 18 disclosed herein.

Kits

The present invention is also directed to commercial kits for the detection and prognostic evaluation of iPD. The kit can be in any configuration well known to those skilled in the art and is useful for performing one or more of the methods described herein for the detection of PLA2g6(L) mRNA or polypeptide in a non-neuronal sample, e.g., blood sample obtained from the subject. The kits are convenient in that they supply many, if not all, of the essential reagents for conducting an assay for the detection of PLA2g6(L) mRNA or polypeptide, and optionally PLA2g6(S) mRNA or protein, and/or optionally a normalizing protein in a non-neuronal test sample, such as described herein. In addition, the assay may be performed simultaneously with a standard or multiple standards included in the kit, such as a predetermined amount of a PLA2g6(L) polypeptide or mRNA, so that the results of the test can be quantified or validated.

In one embodiment, the kit comprises a means for detecting levels of a PLA2g6(L) mRNA or polypeptide in a non-neuronal sample, e.g., blood, or sample of plasma or sample of serum obtained from the subject. The kit may comprise a solid support, e.g., a "dipstick" with at least one PLA2g6(L) polypeptide binding agent immobilized thereon, which specifically binds to PLA2g6(L) protein. The dipstick may also comprise a PLA2g6(S) binding agent immobilized thereon, which specifically binds to PLA2g6(S) protein. In some embodiments, the dipstick or other solid support has an anti-PLA2g6(L) antibody immobilized on the solid support. In some embodiments, the kit comprises an anti-PLA2g6(L) antibody that binds to an epitope at least partially encoded by exon 8b of PLA2g6(L) or binds to an epitope at least partially located in any of SEQ ID NO: 16, SEQ ID NO: 17 or SEQ ID NO: 18 disclosed herein. Specifically bound PLA2g6(L) protein can then be detected using, for example, a second antibody that is detectably labeled with a calorimetric agent or radioisotope.

In some embodiments, a kit comprises a paper-based assay to determine levels of the PLA2g6(L) protein, and optionally PLA2g6(S) polypeptide in a non-neuronal sample, e.g., blood sample. Such paper-based assays are well known in the art, e.g., as disclosed in International Application WO 2011097412 and U.S. Pat. No. 8,821,810 and US application US 2014/0193840 and published documents by Martinez et al., (2007), Patterned Paper as a Platform for Inexpensive, Low-Volume, Portable Bioassays. Angewandte Chemie International Edition. 2007; 46(8): 1318-1320, and Chung et al., (2010) Paper-Based ELISA. Angewandte Chemie International Edition; 2010; 49(28): 4771-4774, which are all incorporated herein in their entireties by reference.

In other embodiments, the assay kits may contain components for competitive and non-competitive assays, radioimmunoassay (RIA), multiplex bead assays, bioluminescence and chemiluminescence assays, fluorometric assays, sandwich assays, immunoradiometric assays, dot blots, enzyme linked assays including ELISA, microtiter plates, or immunocytochemistry. For each kit the range, sensitivity, precision, reliability, specificity, and reproducibility of the assay are established by means well known to those skilled in the art.

In some embodiments, a kit is any manufacture (e.g., a package or container) comprising at least one reagent, e.g., a primer or probe, the manufacture being promoted, distributed, or sold as a unit for performing the methods described herein.

Figure 15A:
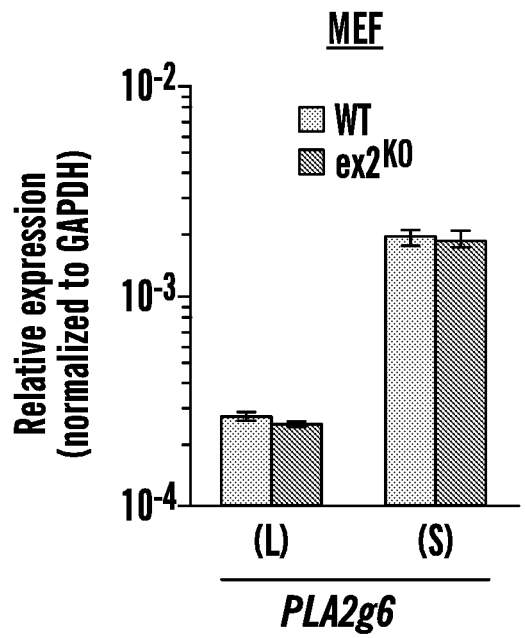
FIG. 15A-15C shows that Knock out of Exon 2 of Pla2g6 gene did not affect the level of transcripts of the (L) and (S) splice variants of PLA2g6 in different tissues. Quantitative Real Time PCR analysis of expression levels of (L) and (S) splice variants of PLA2g6 in the brains (FIG. 15A), testis (FIG. 15C) and MEF cells (FIG. 15B) from WT and $ex2^{KO}$ mice. There is significantly higher expression of PLA2g6(L) in testis. Data are normalized to GAPDH in each sample, and shown as average±SE from 2-3 experiments.
Figure 15B:
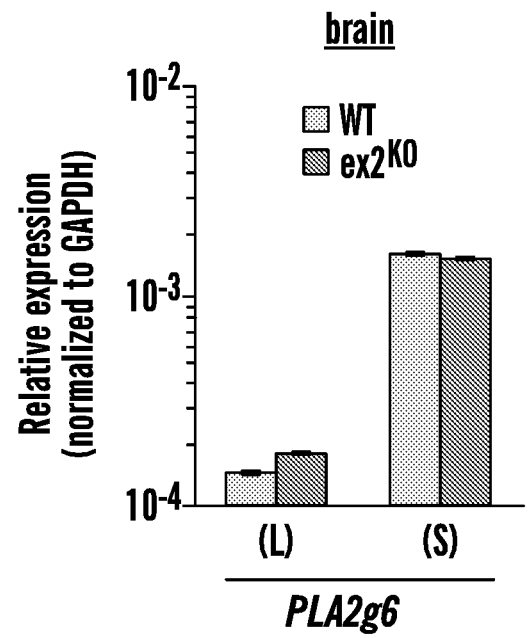
Figure 15C:
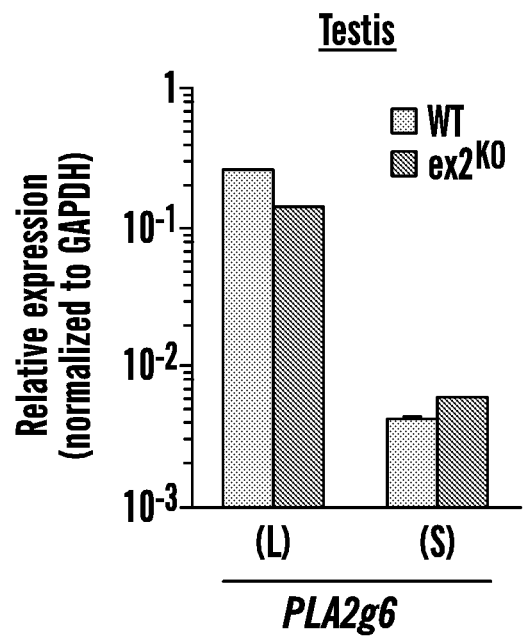
Figure 16:
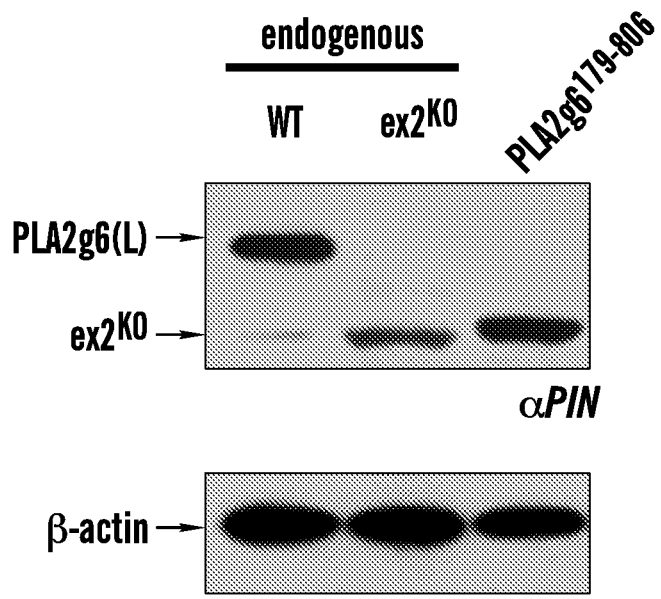
FIG. 16 shows full length PLA2g6(L) is present in WT, while only truncated protein is present in $ex2^{KO}$ mice. Representative Western blot probed with custom-made PIN antibody (mPIN or anti-PLA2g6(L) antibody) that specifically targets PIN domain encoded by exon 8b that is present only in (L) splice variant of PLA2g6, and β-actin staining of the same samples. Specificity of the anti-PIN antibody is shown in FIG. 17. Images have been cropped for presentation. Full size images are presented in FIG. 27. WT: endogenous protein from testis of WT mouse; $ex2^{KO}$: endogenous protein from testis of $ex2^{KO}$ mouse; PLA2g6$^{179-806}$: recombinant N terminally truncated myc/his-tagged PLA2g6(L)$^{179-806}$ protein expressed in FreeStyle™ 293-F cells. The recombinant protein contains myc and his tags on its N and C termini, respectively, which slightly increase its MW in comparison with equivalent endogenous protein in $ex2^{KO}$ mice.

The kits described herein can optionally comprise additional components useful for performing the methods described herein. By way of example, the kit can comprise fluids (e.g., buffers) suitable for composition comprising primer or probe as described herein, an instructional material which describes performance of a method as described herein, and the like. A kit can further comprise devices and/or reagents for use of the primers or probes as described herein. Additionally, the kit may comprise an instruction leaflet and/or may provide information as to the relevance of the obtained results Assays to Detect N-Terminal Truncated Fragments of the PLA2g6 Protein Deletion of the translation initiation $ATG_1$ (coded by exon 2), did not affect the level of expression of (L) and (S) splice variants of PLA2g6 (FIG. 15), and did not lead to the loss of PLA2g6 protein, whereas the presence of a cryptic $ATG_2$ in Exon 4 initiated translation, and resulted in expression of the truncated $ex2^{KO}$ PLA2g6 protein that lacks the first 178 amino acids in the N terminus (FIG. 16).

Accordingly, in some embodiments, the disclosure herein refers compositions assays, methods and kits to measure the cleavage of the N-terminus of the PLA2g6 protein (e.g., a deletion of at least 50, or at least 100, or at least 150, or at least 178 N-terminal amino acids of PLA2g6 protein) in non-neuronal cells obtained from the subject. In particular, the inventors demonstrate that a cryptic ATG2 in Exon 4 initiated translation and resulted in a PLA2g6 protein that lacks the first 178 N-terminal amino acids, which while it retained PARK14 catalytic activity, resulted in a loss of Ca2+ store-dependent activation of PLA2g6. In some embodiments, a subject identified with iPD according to methods and assays disclosed herein can be treated for PD or iPD, for example, administration of a treatment for PD known by one of ordinary skill in the art, or in some instances, by administering PARK14 or an agonist of PARK14.

Detecting cleavage of the N-terminus of the PLA2g6 protein can also be done by persons of ordinary skill in the art, e.g., using QRT-PCR or protein detection methods, such as antibody or western blot analysis.

Assays to Measure SOCE:

In some embodiments, the disclosure herein refers compositions assays, methods and kits to measure SOCE (endogenous Store-Operated $Ca^{2+}$ Entry) and/or $Ca^{2+}$ store levels in non-neuronal cells (e.g., blood and/or skin cells) obtained from the subject, where a lower SOCE and/or $Ca^{2+}$ store level measured as compared to a reference threshold level indicates that the subject has or is at risk of developing PD, including iPD.

In some embodiments, intracellular $Ca^{2+}$ measurements can be performed using the assays as disclosed herein, e.g., using standard Fura-2 imaging techniques or by any other method commonly known by persons of ordinary skill in the art. In some embodiments, $Ca^{2+}$ measurements are performed on live cells obtained from the subject, e.g., using standard Fura-2 imaging and measuring Fura-2/AM and cytosolic $Ca^{2+}$ simultaneously as described herein in the Examples. For SOCE recording, cells can be placed in $Ca^{2+}$-free extracellular solution and acute thapsigargin used to irreversibly inhibit SERCA activity, and allow $Ca^{2+}$ to leak out from the stores, thus causing ER store depletion. SOCE can be measured in response to extracellular application of 2-2.5 mM $Ca^{2+}$ in the presence of TG. Concentration and time of acute TG treatment can be titrated for each cell type to ensure >90% loss of $Ca^{2+}$ from TG-sensitive stores at the time of $Ca^{2+}$ addition. As an alternative to TG, SOCE can be evoked by acute 5 minute treatment with 400 μMTPEN (N,N,N',N'-Tetrakis(2-pyridylmethyl) ethylenediamine, Sigma, USA).

In some embodiments, release of $Ca^{2+}$ from intracellular stores can be measured in $Ca^{2+}$-free extracellular solution in response to acute application of ionomycin (IM, Sigma) at concentration enough to release >90% of Ca$^{2+}$ from TG-sensitive stores.

Fura-2 recordings can be done according to methods commonly known in the art.

On other embodiment, SOCE can be performed as outlined in Smani, Tarik, et al. "Ca2+-independent phospholipase A2 is a novel determinant of store-operated Ca2+ entry." Journal of Biological Chemistry 278.14 (2003): 11909-11915; Singaravelu, K., et al., Cerebellum (2008) 7: 467; and Smani et al., Nature Cell Biology, 2004; 6(2); 113-121, Boittin, François-Xavier, et al. "Ca2+-independent phospholipase A2 enhances store-operated Ca2+ entry in dystrophic skeletal muscle fibers." Journal of cell science 119.18 (2006): 3733-3742, each of which are incorporated herein in their entirety by reference.

In alternative embodiments, Store operated Ca(2+) entry (SOCE), also known as termed capacitative Ca(2+) entry can be measured using the methods and assays as disclosed herein, or as disclosed in Trepakova, et al., "Nitric oxide inhibits capacitative cation influx in human platelets by promoting sarcoplasmic/endoplasmic reticulum Ca2+-ATPase-dependent refilling of Ca2+ stores." Circulation Research 84.2 (1999): 201-209, which is incorporated herein in its entirety by reference. In all embodiments, the threshold level of SOCE or Ca2+ store levels is the level of SOCE or Ca2+ store level from healthy or control non-neuronal cells of the same type (e.g, blood, skin, PRP, etc.).

Assays to Detect Autophagic Function in Non-Neuronal Cells

In some embodiments, the disclosure herein refers compositions assays, methods and kits to measure autophagic function of non-neuronal cells (e.g., blood and/or skin cells) obtained from the subject, and an autophagic dysfunction measured as compared to a threshold level of autophagic function indicates that the subject has or is at risk of developing PD, including iPD.

In some embodiments, autophagy function of non-neuronal cell obtained from the subject can be measured using the methods and assays as disclosed herein, e.g., using quantitative immunofluorescence (e.g., see FIG. 7). For example, using fluorescent markers, e.g., tandem tagged LC3$^{mCherry-eGFP}$ as a marker of autophagic flow (see e.g., Klionsky, D. J. et al. Guidelines for the use and interpretation of assays for monitoring autophagy. Autophagy 8, 445-544 (2012)), one of ordinary skill in the art can assess autophagic dysfunction in the cells by image analysis of cells expressing LC3$^{mCherry-eGFP}$ (FIG. 5d). Other methods can be used, e.g., as disclosed in Shvets, Elena, Ephraim Fass, and Zvulun Elazar. "Utilizing flow cytometry to monitor autophagy in living mammalian cells." Autophagy 4.5 (2008): 621-628, and Mizushima et al., "Methods in mammalian autophagy research." Cell 140.3 (2010): 313-326, and Kepp, Oliver, et al. "Cell death assays for drug discovery." Nature reviews Drug discovery 10.3 (2011): 221-237, which are each incorporated herein in their entirety by reference.

In alternative embodiments, autophagy function can be measured using other methods commonly known by one of ordinary skill in the art, e.g., as disclosed in US20120178119, US2012/0042398, U.S. Pat. No. 7,139,415 and EP patent application EP 2466294, as well as by Barmada et al., *Autophagy induction enhances TDP43 turnover and survival in neuronal ALS models*. Nat Chem Biol. 2014 August; 10(8):677-85, and Degtyarev M., et al., (2014) *Novel Quantitative Autophagy Analysis by Organelle Flow Cytometry after Cell Sonication*. PLoS ONE 9(1): e87707, which are incorporated herein in its entirety by reference. In some embodiments, autophagy function can be measured by detecting levels or sub-cellular location of markers of autophagic flux (e.g., LC3 (microtubule-associated protein A1/1B-light chain 3), and where there is an accumulation of such a marker of autophagic flux (e.g., an accumulation of LC3), it indicates that there is an increase in autophagy dysfunction and/or a decrease in autophagy function. In some embodiments, the methods and assays to measure autophagy function can include measuring the ratio of LC3-II to actin ratio (LC3-II/actin), where an increase in the LC3-II/actin ratio as compared to a threshold level indicates that there is a decrease in autophagy function and/or an increase in autophagy dysfunction. In all embodiments, the threshold level of autophagy function is the autophagy function from healthy or control non-neuronal cells of the same type (e.g, blood, skin).

In some embodiments, the autophagy and/or Ca$^{2+}$ SOCE can be performed using live cell imaging, for example, using fluorescently tagged LC3 (or other marker of autophagic flux), where if there is detected a decrease in the ability of LC3 to reach the lysosomes as compared to a normal (e.g., healthy) or non-PD cell, it indicates that there is an increase in autophagy dysfunction (and/or a decrease in autophagy function or flux). In some embodiments, the detection of spatially localized fluorescently tagged LC3 in autophagosomes (as compared to no or little spatial localization of the tagged LC3 in healthy or control cells) indicates that there is an increase in autophagy dysfunction (and/or a decrease in autophagy function or flux), and the subject can be administered an appropriate treatment for PD.

Methods of Optimizing Treatments for Subjects Identified to have iPD

Other aspects of the present invention relate to a method of monitoring the progression of iPD in a subject, and/or alternatively, monitoring the progress of a treatment (e.g., treatment for PD) in a subject, by determining PLA2g6(L) mRNA or protein levels in a subject at multiple timepoints, e.g., a first time point and a second, and/or 3$^{rd}$, and/or 4$^{th}$, and/or 5$^{th}$ or more timepoints.

Other aspects of the invention provide methods for improving the efficacy of treatment for PD, by determining the levels or concentrations of PLA2g6(L) mRNA polypeptide.

One aspect of the present invention provides for a method for monitoring progression of PD or iPD in a subject with a level of PLA2g6(L) mRNA or protein at least 50% lower or decreased than a reference PLA2g6(L) level, or total PLA2g6(S) mRNA or protein levels, comprising: (a) measuring, at a first timepoint, a first level of PLA2g6(L) polypeptide or mRNA in a first sample obtained from the subject; (b) measuring, at a second timepoint, a second level of PLA2g6(L) mRNA or polypeptide in a second blood sample obtained from the subject; wherein the second timepoint is later than the first timepoint; (c) comparing the mRNA or protein level of PLA2g6(L) in the first sample with the mRNA or protein level of PLA2g6(L) in the first blood sample; and (d) identifying the subject as (a) having a more severe iPD at the second timepoint as compared to the first timepoint, where the level of mRNA or protein level of PLA2g6(L) in the sample obtained at the second timepoint is lower than the mRNA or protein level of PLA2g6(L) in the sample obtained at the first timepoint; or (b) having a less severe iPD at the second timepoint as compared to the first timepoint where the mRNA or protein level of PLA2g6(L) in the sample obtained at the second timepoint is higher than the level of mRNA or protein level of PLA2g6(L) in the sample obtained at the first timepoint. In some embodiments, the subject can be administered an appropriate treatment for PD where the subject is identified to have a more severe PD at the second or subsequent timepoint.

In some embodiments, aspects of the invention relate to a method for monitoring effective treatment for PD, or treatment progress in a subject with iPD, the method comprising: (a) measuring, at a first timepoint, a first level of PLA2g6(L) mRNA or protein in a first blood sample obtained from the subject; (b) administering to the subject an appropriate therapeutic agent for treating PD; and (c) measuring, at a second timepoint, a second level of PLA2g6(L) mRNA or protein in a second blood sample obtained from the subject; wherein the second timepoint is later than the first timepoint and after said administering; and wherein if the second level of PLA2g6(L) mRNA or protein is significantly higher than the first level, then the treatment is considered effective.

Another aspect of the present invention relates to a method for treating a subject with iPD comprising administering an appropriate therapy for PD to the subject determined to have a level of PLA2g6(L) mRNA or protein in the non-neuronal sample, e.g., blood sample, at least one, or at least 2v standard deviation σ (sigma), or at least 50% lower than a reference level of PLA2g6(L) mRNA or protein, and/or PLA2g6(S) mRNA or protein level.

In another embodiment of this aspect, the method comprises contacting a non-neuronal sample (e.g., whole blood sample, plasma sample, serum sample etc.) obtained from a subject with at least one agent that specifically binds to PLA2g6(L) mRNA or protein; (b) measuring the level or concentration of the PLA2g6(L) mRNA or protein using an assay specific for the at least one agent; and (c) comparing the level or concentration of the PLA2g6(L) mRNA or protein with a reference level or concentration of PLA2g6(L) mRNA or protein an/or PLA2g6(S) mRNA or protein, wherein if the level of PLA2g6(L) mRNA or protein in the sample is at least 50% decreased than the reference level or concentration of PLA2g6(L) mRNA or protein or th level of PLA2g6(S) mRNA or protein in the same sample, it indicates a need to administer to the subject a therapeutic treatment for PD.

In another embodiment of this aspect, a method for monitoring treatment efficacy of a subject with iPD is provided, the method comprising: (a) determining, from a non-neuronal sample obtained from a subject at a first time point, a level or concentration of PLA2g6(L) mRNA or protein; (b) determining a level or concentration of PLA2g6(L) mRNA or protein in the sample obtained from said subject at a second time point; and (c) comparing the level or concentration of the PLA2g6(L) mRNA or protein obtained at the second time point to the level or concentration of the PLA2g6(L) mRNA or protein at the first time point, wherein an increase by a statistically significant amount, e.g., by at least 1 standard deviation a, in the level or concentration of the PLA2g6(L) mRNA or protein at the second time point indicates the treatment is efficacious for said subject, and wherein the level of PLA2g6(L) mRNA or protein has stayed the same, or a decrease by a statistically significant amount, e.g., by at least 1 standard deviation a in the level or concentration of PLA2g6(L) mRNA or protein at the second time point indicates the treatment is not efficacious for said subject.

In some embodiments, a method for monitoring treatment efficacy of a subject is performed on a sample which is obtained from a subject who has a PLA2g6(L) mRNA or protein level of at least 50% lower than a reference PLA2g6(L) mRNA or protein level, or PLA2g6(S) mRNA or protein level in the same sample.

Automated Systems

The biomarkers described herein, due to their correlation with striatal degradation and/or age of onset of symptoms, can also permit determinations of the effectiveness of treatments, e.g. candidate agents for the treatment of PD or iPD. In some embodiments, the foregoing methods can be performed in vitro, e.g. the assay can comprise measuring, in a sample obtained from cultured cells and/or tissues (e.g. a sample of cells, e.g. a sample of cultured neurons and/or neural progenitors), the level of a biomarker described herein.

As used herein, the terms "candidate compound" or "candidate agent" refer to a compound or agent and/or compositions thereof that are to be screened for their ability to treat PD or iPD. The compounds/agents can include, but are not limited to, chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; nucleic acids; nucleic acid analogs and derivatives; extracts made from biological materials such as bacteria, plants, fungi, or animal cells or tissues; naturally occurring or synthetic compositions; peptides; aptamers; and antibodies and intrabodies, or fragments thereof.

Generally, compounds can be tested at any concentration that can modulate expert activity of the target biomolecule relative to a control over an appropriate time period. In some embodiments, compounds are tested at concentration in the range of about 0.1 nM to about 1000 mM. Depending upon the particular embodiment being practiced, the test compounds can be provided free in solution, or may be attached to a carrier, or a solid support, e.g., beads. A number of suitable solid supports may be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc. Additionally, for the methods described herein, test compounds may be screened individually, or in groups. Group screening is particularly useful where hit rates for effective test compounds are expected to be low such that one would not expect more than one positive result for a given group.

In one aspect, described herein is a computer system comprising a measuring module configured to measure, in a sample obtained from a subject, the level of a biomarker as described herein; a storage module configured to store data output from the measuring module; a comparison module adapted to compare the data stored on the storage module with a reference level, and to provide a retrieved content, and a display module for displaying whether the level of the biomarker in the sample obtained from the subject varies, by a statistically significant amount, from the reference level and/or displaying the relative levels of the biomarker; wherein a level of biomarker in the sample of the subject which is statistically significantly different than the reference level indicates that the subject is at increased risk of developing PD.

In one embodiment, provided herein is a system comprising: (a) at least one memory containing at least one computer program adapted to control the operation of the computer system to implement a method that includes 1) a measuring module configured to measure the level of, e.g. PLA2g6(L) mRNA or protein in a test sample obtained from a subject, 2) a storage module configured to store output data from the measuring module, 3) a computing module adapted to identify from the output data whether the level of PLA2g6 (L) mRNA or protein in a sample obtained from a subject is statistically significantly different from a reference level of PLA2g6(L) mRNA or protein or the level of PLA2g6(S) mRNA or protein and 4) a display module for displaying a content based in part on the data output from the measuring module, wherein the content comprises a signal indicative of the level of PLA2g6(L) mRNA or protein and (b) at least one processor for executing the computer program.

In some embodiments, the measuring module can measure the presence and/or intensity of a detectable signal from an assay indicating the level of the PLA2g6(L) mRNA or protein in the test sample. Exemplary embodiments of a measuring module can include an automated Chip assay, real-time PCR machine, etc.

The measuring module can comprise any system for detecting a signal elicited from an assay to determine the level of, e.g. PLA2g6(L) mRNA or protein as described above herein. In some embodiments, such systems can include an instrument, e.g., a real time PCR machine (e.g. a LIGHTCYCLER™ (Roche). In one embodiment, the measuring module can be configured to perform the methods described elsewhere herein, e.g. or detection of any detectable label or signal generated by the detection of a biomolecule described herein.

The term "computer" can refer to any non-human apparatus that is capable of accepting a structured input, processing the structured input according to prescribed rules, and producing results of the processing as output. Examples of a computer include: a computer; a general purpose computer; a supercomputer; a mainframe; a super mini-computer; a mini-computer; a workstation; a micro-computer; a server; an interactive television; a hybrid combination of a computer and an interactive television; and application-specific hardware to emulate a computer and/or software. A computer can have a single processor or multiple processors, which can operate in parallel and/or not in parallel. A computer also refers to two or more computers connected together via a network for transmitting or receiving information between the computers. An example of such a computer includes a distributed computer system for processing information via computers linked by a network.

The term "computer-readable medium" may refer to any storage device used for storing data accessible by a computer, as well as any other means for providing access to data by a computer. Examples of a storage-device-type computer-readable medium include: a magnetic hard disk; a floppy disk; an optical disk, such as a CD-ROM and a DVD; a magnetic tape; a memory chip. The term a "computer system" may refer to a system having a computer, where the computer comprises a computer-readable medium embodying software to operate the computer. The term "software" is used interchangeably herein with "program" and refers to prescribed rules to operate a computer. Examples of software include: software; code segments; instructions; computer programs; and programmed logic.

The computer readable storage media can be any available tangible media that can be accessed by a computer. Computer readable storage media includes volatile and nonvolatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

Computer-readable data embodied on one or more computer-readable media may define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied may reside on one or more of the components of either of a system, or a computer readable storage medium described herein, may be distributed across one or more of such components.

The computer-readable media may be transportable such that the instructions stored thereon can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a computer to implement aspects of the present invention. The computer executable instructions may be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

Embodiments of the invention can be described through functional modules, which are defined by computer executable instructions recorded on computer readable media and which cause a computer to perform method steps when executed. The modules are segregated by function for the sake of clarity. However, it should be understood that the modules/systems need not correspond to discreet blocks of code and the described functions can be carried out by the execution of various code portions stored on various media and executed at various times. Furthermore, it should be appreciated that the modules can perform other functions, thus the modules are not limited to having any particular functions or set of functions.

The functional modules of certain embodiments of the invention include at minimum a measuring module, a storage module, a computing module, and a display module. The functional modules can be executed on one, or multiple, computers, or by using one, or multiple, computer networks. The measuring module has computer executable instructions to provide e.g., levels of a miRNA, etc., in computer readable form.

The information determined in the measuring system can be read by the storage module. As used herein the "storage module" is intended to include any suitable computing or processing apparatus or other device configured or adapted for storing data or information. Examples of electronic apparatus suitable for use with the present invention include stand-alone computing apparatus, data telecommunications networks, including local area networks (LAN), wide area networks (WAN), Internet, Intranet, and Extranet, and local and distributed computer processing systems. Storage modules also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage module is adapted or configured for having recorded thereon, for example, sample name, biomolecule assayed and the level of said biomolecule. Such information may be provided in digital form that can be transmitted and read electronically, e.g., via the Internet, on diskette, via USB (universal serial bus) or via any other suitable mode of communication.

As used herein, "stored" refers to a process for encoding information on the storage module. Those skilled in the art can readily adopt any of the presently known methods for recording information on known media to generate manufactures comprising expression level information.

In some embodiments of any of the systems described herein, the storage module stores the output data from the measuring module. In additional embodiments, the storage module stores reference information such as levels of, e.g. PLA2g6(L) mRNA or protein in healthy subjects, subjects not having PD, and/or subject demonstrated to not to have iPD.

The "computing module" can use a variety of available software programs and formats for computing the level of, e.g. PLA2g6(L) mRNA or protein. Such algorithms are well established in the art. A skilled artisan is readily able to determine the appropriate algorithms based on the size and quality of the sample and type of data. The data analysis tools and equations described herein can be implemented in the computing module of the invention. In some embodiments, the computing module can comprise a computer and/or a computer system. In one embodiment, the computing module further comprises a comparison module, which compares the level of, e.g., PLA2g6(L) mRNA or protein in a sample obtained from a subject as described herein with a reference level as described herein (see, e.g. FIG. 1F). By way of an example, when the level of a PLA2g6(L) mRNA or protein in a sample obtained from a subject is measured, a comparison module can compare or match the output data with the mean level of the PLA2g6(L) mRNA or protein in a population of subjects not having signs or symptoms of a PD or a population of subjects not having iPD (i.e. a reference level). In certain embodiments, the mean level of, e.g. PLA2g6(L) mRNA or protein in a population of subjects not having signs or symptoms of PD, or not having iPD can be pre-stored in the storage module. During the comparison or matching process, the comparison module can determine whether the level of, e.g. PLA2g6(L) mRNA or protein in a sample obtained from a subject is statistically significantly different from the reference level. In various embodiments, the comparison module can be configured using existing commercially-available or freely-available software for comparison purpose, and may be optimized for particular data comparisons that are conducted.

The computing and/or comparison module, or any other module of the invention, can include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). In some embodiments users can directly access data (via Hypertext links for example) residing on Internet databases using a HTML interface provided by Web browsers and Web servers (FIG. 7).

The computing and/or comparison module provides a computer readable comparison result that can be processed in computer readable form by predefined criteria, or criteria defined by a user, to provide content based in part on the comparison result that may be stored and output as requested by a user using an output module, e.g., a display module.

In some embodiments, the content displayed on the display module can be a report, e.g. the level of a PLA2g6(L) mRNA or protein in the sample obtained from a subject. In some embodiments, a report can denote the ratio of PLA2g6 (L) mRNA or protein to either the total PLA2g6 protein (e.g., PLA2g(L) and (S) mRNA and protein) and/or the total PLA2g6(S) mRNA or protein level. In some embodiments, the report can denote raw values of the level of PLA2g6(L) and/or PLA2g6(S) mRNA or protein in the test sample or it indicates a percentage or fold decrease in the level of PLA2g6(L) mRNA or protein as compared to a reference level of PLA2g6(L) mRNA or protein, and/or level of PLA2g6(S) mRNA or protein, and/or total PLA2g6(L/S) mRNA or protein levels, and/or provides a signal that the subject is at risk of developing or not developing iPD.

In some embodiments, if the computing module determines that the level of, e.g. PLA2g6(L) mRNA or protein in the sample obtained from a subject is different by a statistically significant amount from the reference level, the display module provides a report displaying a signal indicating that the level in the sample obtained from a subject is different than that of the reference level. In some embodiments, the content displayed on the display module or report can be the relative level PLA2g6(L) mRNA or protein in the sample obtained from a subject as compared to the reference level. In some embodiments, the signal can indicate the degree to which the level of PLA2g6(L) mRNA or protein in the sample obtained from the subject varies from the reference level. In some embodiments, the signal can indicate that the subject is at increased risk of developing iPD. In some embodiments, the signal can indicate the subject can benefit from treatment with a therapy for PD. In some embodiments, the content displayed on the display module or report can be a numerical value indicating one of these risks or probabilities. In such embodiments, the probability can be expressed in percentages or a fraction. For example, higher percentage or a fraction closer to 1 indicates a higher likelihood of a subject developing iPD. In some embodiments, the content displayed on the display module or report can be single word or phrases to qualitatively indicate a risk or probability. For example, a word "unlikely" can be used to indicate a lower risk for developing iPD, while "likely" can be used to indicate a high risk for developing iPD.

In one embodiment of the invention, the content based on the computing and/or comparison result is displayed on a computer monitor. In one embodiment of the invention, the content based on the computing and/or comparison result is displayed through printable media. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content based on the computing/comparison result. It should be understood that other modules of the invention can be adapted to have a web browser interface. Through the Web browser, a user can construct requests for retrieving data from the computing/comparison module. Thus, the user will typically point and click to user interface elements such as buttons, pull down menus, scroll bars and the like conventionally employed in graphical user interfaces.

Systems and computer readable media described herein are merely illustrative embodiments of the invention for determining the level of, e.g. PLA2g6(L) mRNA or protein in a sample obtained from a subject, and therefore are not intended to limit the scope of the invention. Variations of the systems and computer readable media described herein are possible and are intended to fall within the scope of the invention. The modules of the machine, or those used in the computer readable medium, may assume numerous configurations. For example, function may be provided on a single machine or distributed over multiple machines.

Cell Samples

The term "sample" or "test sample" as used herein denotes a sample taken or isolated from a biological organism, e.g., a blood sample from a subject. Exemplary biological samples include, but are not limited to, a biofluid sample; serum; plasma; urine; saliva; and/or biopsy etc. The term also includes a mixture of the above-mentioned samples. The term "test sample" also includes untreated or pretreated (or pre-processed) biological samples. In some embodiments, a test sample can comprise cells from subject. In some embodiments, a test sample can be a blood sample. The test sample can be obtained by removing a sample of cells from a subject, but can also be accomplished by using previously isolated cells (e.g. isolated at a prior timepoint and isolated by the same or another person). In addition, the test sample can be freshly collected or a previously collected sample.

In some embodiments, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments, the test sample is a clarified test sample, for example, by centrifugation and collection of a supernatant comprising the clarified test sample. In some embodiments, a test sample can be a pre-processed test sample, for example, supernatant or filtrate resulting from a treatment selected from the group consisting of centrifugation, filtration, thawing, purification, and any combinations thereof. In some embodiments, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of an expression product as described herein.

Appropriate Treatments for Parkinson's Disease:

In some embodiments, administering a treatment appropriate for subjects with Parkinson's disease to the subject having Parkinson's disease identified by the methods, compositions, kits and assays disclosed herein can be any appropriate PD treatment, including, but not limited to L-dopa, selegiline, apomorphine and anticholinergics. In some embodiments, an appropriate treatment is administration of exogenous PLA2g6 protein or exogenous PLD2g6 mRNA (or a modified mRNA thereof) or other agonist of the PLA2g6 protein or gene. In some embodiments, the appropriate treatment is overexpression of the PLA2g6(L) protein, or a fragment thereof. In some embodiments, an appropriate treatment for PD is well known by one of ordinary skill in the art, or in some instances, administration of an antibody, such as PRX002, against the protein alpha-synuclein, or an anti-alpha-synuclein antibody vaccine such as disclosed in US application 2005/0196818 or 2013/0108546. In some embodiments, exogenous PLA2g6(L) nucleic acid (e.g., mRNA or modified RNA encoding PLA2g6(L) protein), or PLA2g6(L) protein or other PLA2g6(L) agonist is administered to the subject identified to have PD or iPD according to the methods, assays and screens disclosed herein.

In some embodiments, treatment for PD is administration of DHA and/or ARA, as disclosed in US patent application, US2009/0099259, which is incorporated herein in its entirety by reference. Other appropriate treatments for PD that can be administered to the subjects according to the methods in the present invention include a optically pure (−)-isomer of bupropion, (e.g. as disclosed in U.S. Pat. No. 6,277,887), as well as RNAi and shRNA oligonucleotides, as disclosed in U.S. Pat. Nos. 7,414,034, 6,551,993, and 7,160,913; U.S. patent application Ser. Nos. 11/565,831 and 11/565,847; Levodopa which functions as a partial antagonist of NMDA receptors.

Drugs commonly used to treat Parkinson's disease include, but are not limited to, L-dopa, selegiline, apomorphine and anticholinergics, Carbidopa-levodopa, Carbidopa-levodopa infusion, Dopamine agonists, MAO-B inhibitors, Catechol-O-methyltransferase (COMT) inhibitors, Anticholinergics, and Amantadine.

L-dopa (levo-dihydroxy-phenylalanine) (sinemet) is a dopamine precursor which can cross the blood-brain barrier and be converted to dopamine in the brain. Unfortunately, L-dopa has a short half life in the body and it is typical after long use (i.e. after about 4-5 years) for the effect of L-dopa to become sporadic and unpredictable, resulting in fluctuations in motor function, dyskinesias and psychiatric side effects. Additionally, L-dopa can cause B vitamin deficiencies to arise.

Selegiline (Deprenyl, Eldepryl) has been used as an alternative to L-dopa, and acts by reducing the breakdown of dopamine in the brain. Unfortunately, Selegiline becomes ineffective after about nine months of use. Apomorphine, a dopamine receptor agonist, has been used to treat Parkinson's disease, although is causes severe vomiting when used on its own, as well as skin reactions, infection, drowsiness and some psychiatric side effects.

Alternative approaches for treatment of PD include vaccination against alpha-synuclein and the like, such as those disclosed in U.S. Pat. Nos. 8,673,593, 9,034,337 and US Application 2009/0208487 and US2013/0108546, each incorporated herein in their entirety by reference, and are encompassed for use in the methods of treatment as disclosed herein.

Systemically administered anticholinergic drugs (such as benzhexol and orphenedrine) have also been used to treat Parkinson's disease and act by reducing the amount of acetylcholine produced in the brain and thereby redress the dopamine/acetylcholine imbalance present in Parkinson's disease. Unfortunately, about 70% of patients taking systemically administered anticholinergics develop serious neuropsychiatric side effects, including hallucinations, as well as dyskinetic movements, and other effects resulting from wide anticholinergic distribution, including vision effects, difficulty swallowing, dry mouth and urine retention. See e.g. Playfer, J. R., Parkinson's Disease, Postgrad Med J, 73; 257-264:1997 and Nadeau, S. E., Parkinson's Disease, J Am Ger Soc, 45; 233-240:1997.

Before the introduction of L-dopa in 1969, stereotactic surgery offered one of the few effective treatments for Parkinson's disease. The significant known deficiencies and drawbacks associated with therapeutic drugs to treat Parkinson's disease, including the long term limitations of L-dopa therapy have led to renewed interest in neurosurgical intervention. Unilateral stereotactic thalamotomy has proven to be effective for controlling contralateral tremor and rigidity, but carries a risk of hemiparesis. Bilateral thalamotomy carries an increased risk of speech and swallowing disorders resulting. Stereotactic pallidotomy, surgical ablation of part of the globus pallidus (a basal ganglia), has also be used with some success. Aside from surgical resection, high frequency stimulating electrodes placed in the ventral intermedialis nucleus has been found to suppress abnormal movements in some cases. A variety of techniques exist to permit precise location of a probe, including computed tomography and magnetic resonance imaging. Unfortunately, the akinesia, speech and gait disorder symptoms of Parkinson's disease are little helped by these surgical procedures, all of which result in destructive brain lesions.

The compositions and methods described herein can be administered to a subject having or diagnosed as having, iPD. In some embodiments, the methods described herein comprise administering an effective amount of compositions described herein, e.g. an agonist of PLA2g6(L) mRNA or protein to a subject in order to alleviate a symptom of iPD. As used herein, "alleviating a symptom of Parkinson's Disease" is ameliorating any condition or symptom associated with the disease. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, injection, or topical, administration. Administration can be local or systemic.

The term "effective amount" as used herein refers to the amount of a composition (e.g. an agonist of PLA2g6(L)) needed to alleviate at least one or more symptom of the disease or disorder, and relates to a sufficient amount of pharmacological composition to provide the desired effect. The term "therapeutically effective amount" therefore refers to an amount of a compound that is sufficient to provide a particular effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of a composition which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for neuronal degradation and/or growth, among others. The dosage can be determined by a physician and adjusted, as necessary, to suit observed effects of the treatment.

In some embodiments, the technology described herein relates to a pharmaceutical composition as described herein, and optionally a pharmaceutically acceptable carrier. Pharmaceutically acceptable carriers and diluents include saline, aqueous buffer solutions, solvents and/or dispersion media.

The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent as described herein.

In some embodiments, the pharmaceutical composition as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of a composition as disclosed herein can also be incorporated into the parenteral dosage forms of the disclosure, including conventional and controlled-release parenteral dosage forms.

Pharmaceutical compositions can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the composition can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008, 719; 5,674,533; 5,059,595; 5,591,767; 5,120,548; 5,073, 543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

The methods described herein can further comprise administering a second agent and/or treatment to the subject, e.g. as part of a combinatorial therapy.

In certain embodiments, an effective dose of a composition as described herein can be administered to a patient once. In certain embodiments, an effective dose of a composition can be administered to a patient repeatedly. For systemic administration, subjects can be administered a therapeutic amount of a composition such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the active ingredient(s). The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition can be administered over a period of time, such as over a 5 minute, 10 minute, 15 minute, 20 minute, or 25 minute period.

The dosage ranges for the administration of a composition, according to the methods described herein depend upon, for example, the form of the active ingredient, its potency, and the extent to which symptoms, markers, or indicators of a condition described herein are desired to be reduced, for example the percentage reduction desired for neural degeneration or the extent to which, for example, neuron projection growth are desired to be induced. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of a composition in, e.g. the treatment of a condition described herein, or to induce a response as described herein can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. a reduction of neuronal degeneration). It is well within the ability of one skilled in the art to monitor efficacy of administration and/or treatment by measuring any one of such parameters, or any combination of parameters. Efficacy can be assessed in animal models of a condition described herein, for example treatment of PD. When using an experimental animal model, efficacy of treatment is evidenced when a statistically significant change in a marker is observed, e.g. the growth and/or survival of axonal projections.

In vitro and animal model assays are provided herein which allow the assessment of a given dose of, e.g., an agonist of PLA2g6(L) expression. By way of non-limiting example, the effects of a dose of an agonist of PLA2g6(L) expression can be assessed by administering the composition to a mouse model of Parkinson's Disease, or the PLA2g6 ex2$^{KO}$ transgenic mouse model as disclosed herein, in which exon 2 of Pla2g6 gene was constitutively deleted, and/or monitoring the growth and/or survival of neurons in an in vitro assay, or assessing increase in SOCE and/or a decrease in Ca2+ store deficiency according to the methods as disclosed in the Examples.

The present invention can further be defined in any of the following numbered paragraphs:
1. An assay for detecting Parkinson's disease (PD) in a subject, or detecting a subject at risk of developing PD, the assay comprising;
   a. performing quantitative RT-PCR on a sample obtained from the subject to measure the expression levels of (i) PLA2g6(L), any one or more of PLA2g6 (S), total PLA2g6, and/or a normalizing control gene; and
   b. calculating the ratios of any one or more of:
      i. PLA2g6(L) to the normalizing control gene
      ii. PLA2g6(L) to PLA2g6(S)
      iii. PLA2g6(L) to total PLA2g6

2. The assay of paragraph 1, further comprising step (iv) of detecting PD in the subject where there is a statistically significant decrease in the expression of PLA2g6 (L) identified by decrease in any one of the ratios (i), (ii) or (iii), or a statistically significant decrease in the level of PLA2g6(L) as compared to a reference PLA2g6(L) level.

3. An assay for detecting Parkinson's disease (PD) in a subject, or detecting a subject at risk of developing PD, the assay comprising;
   a. contacting a sample obtained from the subject with an antibody that specifically binds to PLA2g6(L) (i.e., anti-PLA2g6(L) antibody), and at least one of; (i) a pan specific anti-PLA2g6 antibody that binds to PLA2g6(L) and PLA2g6(S) proteins, (ii) an anti-PLA2g6(S) antibody, (iii) an anti-normalizing protein antibody
   b. detecting and quantification of binding between the anti-PLA2g6(L) antibody and PLA2g6(L) protein, and detecting and quantification at least one of: the binding between the anti-PLA2g6 antibody and the PLA2g6(L) and PLA2g6(S) proteins, the binding between anti-PLA2g6(S) antibody and PLA2g6(S) protein, and the binding between anti-normalizing protein antibody and normalizing protein; and
   c. calculating the ratios of any one or more of:
      i. the amount of PLA2g6(L) protein to PLA2g6(S) protein
      ii. the amount of PLA2g6(L) protein to total PLA2g6 protein
      iii. the amount of PLA2g6(L) protein to normalizing protein 4. The assay of paragraph 3, further comprising step (iv) of detecting PD in the subject where there is a statistically significant decrease in the level of PLA2g6(L) protein revealed by changes in any one of the ratios (i), (ii) or (iii), or a statistically significant decrease in the level of PLA2g6(L) protein as compared to a reference PLA2g6(L) protein level.

5. The assay of paragraphs 1-4, wherein the statistically significant decrease is a decrease of at least one standard deviation σ (sigma) as compared to a reference standard level from healthy individuals known not to have PD.

6. The assay of any of paragraphs 1-5, wherein the sample is selected from the group of: whole blood, plasma, specific blood cells, skin fibroblasts, CSF or any non-neuronal cells collected from the subject.

7. The assay of paragraph 6, wherein the blood sample is a total plasma sample or a platelet rich plasma (PRP) sample.

8. The assay of paragraph 1, further comprising a step of reverse transcribing mRNA isolated from sample prior to performing PCR.

9. The assay of any of paragraphs 3 to 8, wherein anti-PLA2g6(L) antibody binds to an epitope at least partially encoded by exon 8b of PLA2g6(L), but is spliced out in PLA2g6(S).

10. The assay of paragraph 9, wherein the anti-PLA2g6 (L) antibody binds to an epitope at least partially located in any one of SEQ ID NO: 16, SEQ ID NO: 17 or SEQ ID NO:18.

11. The assay of any of paragraphs 1 to 10, wherein the reference PLA2g6(L) mRNA or protein level is the level of PLA2g6(L) mRNA or protein in at least one healthy individual known not to have PD, or the level of PLA2g6(L) mRNA or protein measured from a sample obtained from the same subject from at least one earlier timepoint or earlier age.

12. The assay of any of paragraphs 1 to 11, wherein the Parkinson's Disease (PD) is idiopathic PD (iPD).

13. A method for identifying a human subject having, or at risk of, developing Parkinson's Disease (PD) comprising:
    a. contacting a sample obtained from the subject with primer pairs that specifically amplify the mRNA encoding PLA2g6(L), PLA2g6(S), total PLA2g6 and/or a normalizing control gene;
    b. performing quantitative RT-PCR to produce amplified nucleic acids encoding PLA2g6(L), PLA2g6(S), total PLA2g6 and/or the normalizing control gene;
    c. detecting the presence of the amplified nucleic acids encoding PLA2g6(L), PLA2g6(S), total PLA2g6 and/or the normalizing control gene;
    d. calculating the ratios of any one or more of:
       i. PLA2g6(L) to the normalizing control gene
       ii. PLA2g6(L) to PLA2g6(S)
       iii. PLA2g6(L) to total PLA2g6

14. The method of paragraph 13, further comprising diagnosing the subject as having, or at risk of developing Parkinson's Disease (PD) when the level of PLA2g6(L) mRNA, or ratios (i) to (iii) is detected to be statistically significantly lower by at least 1, or 2, or 3, or 4 standard deviation σ (sigma) than a reference standard.

15. The method of paragraph 14, wherein the reference standard is the corresponding level from the same subject from at least one earlier timepoint or earlier age.

16. The method of paragraph 14, wherein the reference standard is the level from a control population of individuals identified not to have PD.

17. A method for identifying a human subject having, or at risk of, developing Parkinson's Disease (PD) comprising:
    a. contacting a sample obtained from the subject with a pan specific anti-PLA2g6 antibody and an antibody that specifically binds to PLA2g6(L) (anti-PLA2g6 (L) antibody), and
    b. detecting binding between the anti-PLA2g6 antibody and the total PLA2g6 protein, and detecting the binding between the anti-PLA2g6(L) antibody and PLA2g6(L) protein.
    c. quantification of the changes in the amount of PLA2g6(L) protein by changes in the ratios of any one or more of:
       i. PLA2g6(L) to the normalizing protein
       ii. PLA2g6(L) to PLA2g6(S)
       iii. PLA2g6(L) to total PLA2g6.

18. The method of paragraph 17, further comprising diagnosing the subject as having or at risk of developing Parkinson's Disease (PD) when any of the (i) to (iii) ratio level of PLA2g6(L) protein is detected to be significantly lower by at least one standard deviation σ (sigma) than a reference standard.

19. The method of paragraph 18, wherein the reference standard is the corresponding level of PLA2g6(L) protein from the same subject assayed at least at one earlier timepoint.

20. The method of paragraph 19, wherein the reference standard is the level of PLA2g6(L) protein from a control population of individuals identified not to have PD.

21. A method for identifying a human subject at risk of developing Parkinson's Disease or idiopathic Parkinson's disease comprising:
   a. contacting a sample obtained from the subject with an antibody that specifically binds to PLA2g6(L) (anti-PLA2g6(L) antibody) and does not specifically bind to PLA2g6(S),
   b. detecting binding between PLA2g6(L) protein and the anti-PLA2g6(L) antibody;
   c. diagnosing the subject as having or at risk of developing Parkinson's Disease (PD) when the protein level of PLA2g6(L) in the sample obtained from the subject is detected to be significantly decreased by at least 1, or 2, or 3, or 4 standard deviation $\sigma$ (sigma) as compared to a reference control level for PLA2g6 (L) protein.

22. The method of paragraph 21, wherein the reference standard is the corresponding level of PLA2g6(L) protein from the same subject assayed at least at an earlier timepoint.

23. The method of paragraph 21, wherein the reference standard is the level of PLA2g6(L) protein from a control population of individuals identified not to have PD.

24. The method of any of paragraph 17 to 23, wherein anti-PLA2g6(L) antibody binds to an epitope at least partially encoded by exon 8b of PLA2g6(L), which is spliced out in PLA2g6(S).

25. The method of paragraph 24, wherein the anti-PLA2g6(L) antibody binds to an epitope at least partially located in any one of SEQ ID NO: 16, SEQ ID NO: 17 or SEQ ID NO:18.

26. The method of any of paragraphs 17 to 25, wherein the sample is selected from the group of: whole blood, plasma, specific blood cells, skin fibroblasts, CSF or non-neuronal cells collected from the subject.

27. The method of any of paragraphs 17 to 26, wherein Parkinson's Disease is idiopathic Parkinson's disease (iPD).

28. A kit comprising:
   a. a set of primers and probes specific for PLA2g6(L) mRNA; and
   b. at least one of: a set of primers and probes specific for PLA2g6(S) mRNA, a set of primers and probes specific for a total PLA2g6 mRNA, a set of primers and probes for normalization control mRNA.

29. A kit comprising:
   a. an anti-PLA2g6(L) antibody;
   b. at least one of:
      i. a pan-specific PLA2g6 antibody that binds to PLA2g6(L) and PLA2g6(S)
      ii. an anti-PLA2g6(S) antibody;
      iii. an anti-normalizing protein antibody.

30. A method for identifying a human subject having, or at risk of, developing Parkinson's Disease (PD) comprising:
   a. measuring Store operated $Ca^{2+}$ Entry (SOCE) in response to experimental (artificial) depletion of Ca in the stores in a sample comprising live cells from the subject,
   b. detecting a decrease in SOCE response, by at least 1, or 2, or 3, or 4 standard deviation $\sigma$ (sigma) in the cells obtained as compared to a reference standard.

31. A method for identifying a human subject having, or at risk of, developing Parkinson's Disease (PD) comprising:
   a. measuring ER $Ca^{2+}$ store levels in a sample comprising live cells from the subject,
   b. detecting a decrease in ER $Ca^{2+}$ store levels, by at least 1, or 2, or 3, or 4 standard deviation $\sigma$ (sigma) in the cells obtained as compared to a reference standard.

32. A method for identifying a human subject having, or at risk of, developing Parkinson's Disease (PD) comprising:
   a. measuring autophagy function in a sample comprising live cells from the subject
   b. detecting a decrease in autophagy function, by at least 1, or 2, or 3, or 4 standard deviation $\sigma$ (sigma) in the cells obtained as compared to a reference standard.

33. The method of any of paragraphs 30 to 32, wherein the reference standard is the corresponding level from the same subject assayed at least at an earlier timepoint.

34. The method of any of paragraphs 30 to 32, wherein the reference standard is the corresponding level from a control population of individuals identified not to have PD.

35. The assay of any of paragraph 1 to 12, further comprising second assay to measure $Ca^{2+}$ levels, by measuring any one of:
   a. Store operated $Ca^{2+}$ Entry (SOCE) in response to experimental (artificial) depletion of Ca2+ in stores in a sample comprising live cells from the subject, and detecting a decrease in SOCE response, by at least 1, or 2, or 3, or 4 standard deviation $\sigma$ (sigma) in the cells obtained as compared to a reference standard; or
   b. measuring ER $Ca^{2+}$ store levels in a sample comprising live cells from the subject, and detecting a decrease in ER $Ca^{2+}$ store levels, by at least 1, or 2, or 3, or 4 standard deviation $\sigma$ (sigma) in the cells obtained as compared to a reference standard.

36. The assay of any of paragraph 1 to 12 or 35 further comprising second assay to measure autophagy function in a sample comprising live cells from the subject, and detecting a decrease in autophagy function, by at least 1, or 2, or 3, or 4 standard deviation $\sigma$ (sigma) in the cells obtained as compared to a reference standard.

37. The method of any of paragraph 13 to 27 further comprising measuring any one of:
   a. Store operated $Ca^{2+}$ Entry (SOCE) in response to experimental (artificial) depletion of Ca2+ in stores in a sample comprising live cells from the subject, and detecting a decrease in SOCE response, by at least 1, or 2, or 3, or 4 standard deviation $\sigma$ (sigma) in the cells obtained as compared to a reference standard; or
   b. measuring ER $Ca^{2+}$ store levels in a sample comprising live cells from the subject, and detecting a decrease in ER $Ca^{2+}$ store levels, by at least 1, or 2, or 3, or 4 standard deviation $\sigma$ (sigma) in the cells obtained as compared to a reference standard.

38. The method of any of paragraph 13 to 27 or 37 further comprising measuring autophagy function in a sample comprising live cells from the subject, and detecting a decrease in autophagy function, by at least 1, or 2, or 3, or 4 standard deviation $\sigma$ (sigma) in the cells obtained as compared to a reference standard.

39. A method for treating idiopathic Parkinson's Disease (iPD) comprising identifying a subject as having or at risk of idiopathic Parkinson's Disease (iPD) according to the assays of any of the paragraphs above, or any of the methods in the paragraphs above, and administering preventive or restorative therapy to delay, or reverse progression of the disease.

40. The method of paragraph 39, wherein the effective therapy for PD is administering an agonist of PLA2g6 (L) or a nucleic acid expressing human PLA2g6(L) or a functional fragment thereof 41. A method for treating idiopathic Parkinson's disease (iPD), or a subject at risk of developing Parkinson's Disease (PD) or comprising:
    a. performing quantitative duplex RT-PCR on a non-neuronal sample obtained from the subject to measure the expression levels of (i) PLA2g6(L) and (ii) PLA2g6(S) or a normalizing gene; and
    b. calculating the ratios of any one or more of:
        i. PLA2g6(L): PLA2g6(S),
        ii. PLA2g6(L): total PLA2g6,
        iii. PLA2g6(L): normalizing gene,
        wherein iPD, or a risk of developing iPD in the subject is detected when there is a statistically significant decrease in any of the ratios of: PLA2g6(L): PLA2g6(S), or PLA2g6(L): total PLA2g6, or a statistically significant decrease in the level of PLA2g6(L) as compared to a reference PLA2g6(L) level,
    c. administering a therapy for PD to the subject when iPD or a risk of developing iPD in the subject is detected.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology disclosed herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are disclosed herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments disclosed herein can be combined to provide further embodiments. Aspects of the disclosure can be modified, if necessary, to employ the compositions, functions and concepts of the above references and application to provide yet further embodiments of the disclosure.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The present invention is further illustrated by the following Examples. These Examples are provided to aid in the understanding of the invention and are not construed as a limitation thereof.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

The technology disclosed herein is further illustrated by the following examples which in no way should be construed as being further limiting.

Material and Methods

Animals.

Figure 12:
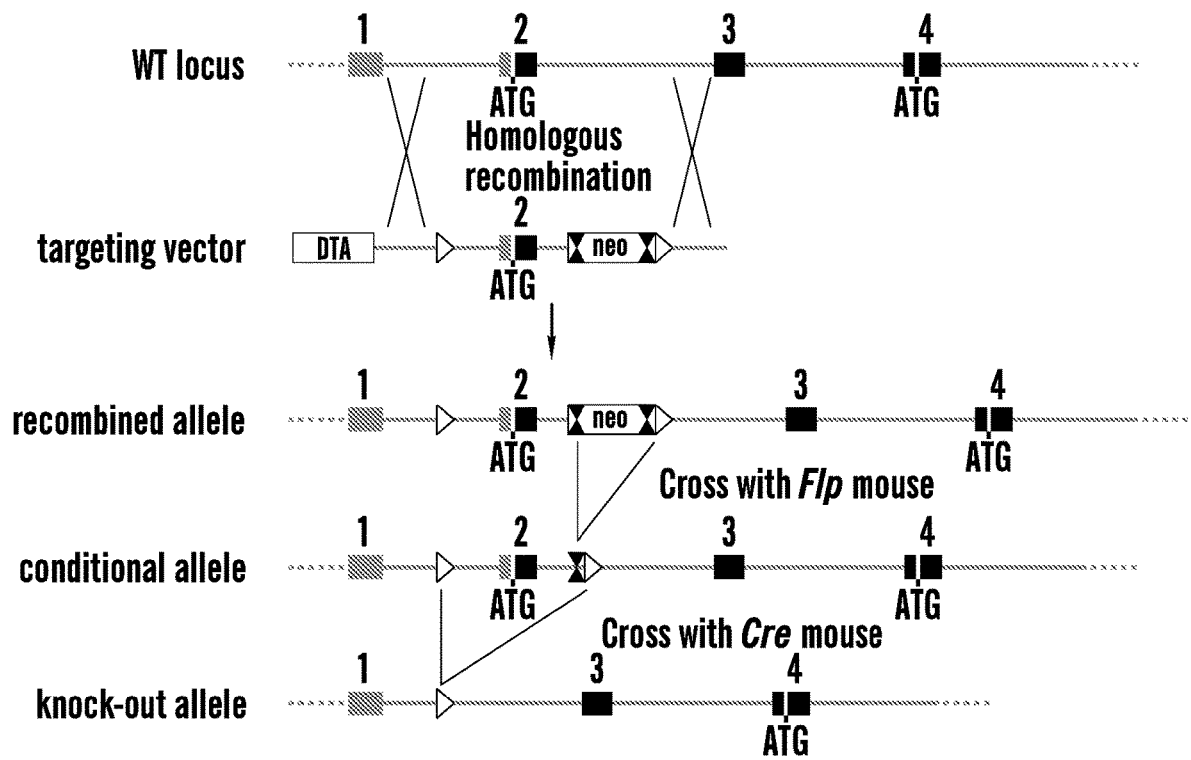
FIG. 12 shows the generation of constitutive PARK14 (PLA2g6) $ex2^{KO}$ mouse model (B6.129S-$Pla2g6^{\Delta Ex2-VB}$/J). WT Pla2g6 locus and the targeting vector are schematically represented at the top of the panel. Exon 2 of Pla2g6, containing the translation initiation codon, is flanked by two loxP sites (open triangles), whereas the neomycin cassette (Neo) is immediately flanked by two FRT sites (double filled triangles). As depicted, the expected homologous recombination event creates the recombined (floxed) locus and removes Diphtheria Toxin A (DTA) negative selection marker. Crossing a recombined Pla2g6 locus mouse with a ubiquitous Flp recombinase C57BL/6 animal allowed for excision of the FRT-flanked region, creating an animal carrying conditional $Pla2g6^{Ex2}$ allele without neomycin selection cassette. Breeding the heterozygous recombined F1 mouse with a ubiquitous Cre recombinase C57BL/6 animal resulted in the Cre-mediated excision of the floxed exon 2 region, creating a total exon 2 knockout ($ex2^{KO}$) mouse. For other details, see Methods section herein.

A novel PLA2g6 ex2$^{KO}$ transgenic mouse model, in which exon 2 of Pla2g6 gene was constitutively deleted, was custom created by GenOway (www.genoway.com, France). The strategy for creation and results of model validation are presented herein and in FIGS. 12-14. Heterozygote ex2$^{KO}$ males were backcrossed to C57BL/6 females for 9 generations, and congenic B6.Cg-Pla2g6$^{\Delta Ex2-VB}$/J line was established. Due to infertility of homozygous ex2$^{KO}$ males, and the inability of homozygous females to sustain neonatal pups, cross-breeding of heterozygous mice was employed to obtain homozygous ex2$^{KO}$ animals used in this study. Ageing male mice were used for in vivo studies, while female mice were used for preparation of mouse embryonic fibroblasts (MEFs). Experimental sets of homozygous ex2$^{KO}$ and wild type (WT) littermate males were housed and aged together. Animal number for each study group was determined for the experimental results to reach statistical significance with a power of 90% at p<0.05, or to demonstrate that there is no difference between the groups. Animals were maintained in an advanced pathogen-free facility with veterinary service and unlimited access to food and water. All experimental procedures were compliant with ethical regulations and approved by the Institutional Animal Care and Use Committee of Boston University.

Animal Models.

Figure 13:
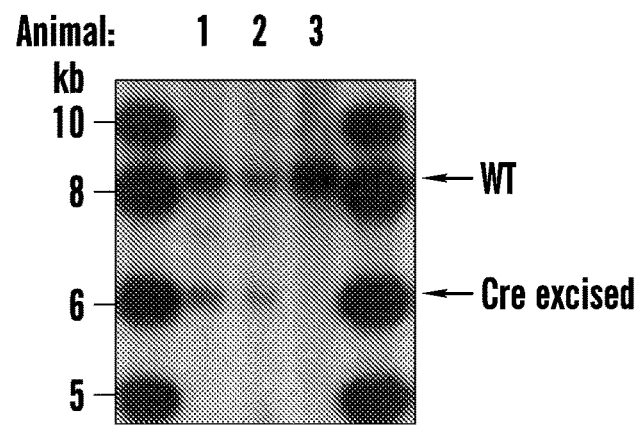
FIG. 13 shows Southern blot confirmation of the constitutive Pla2g6(ex2) knockout. The genomic DNA of the 2 tested F1 mice (lanes 1 and 2) were compared with wild-type DNA (lane 3). The HpaI/NheI digested DNAs were blotted on nylon membrane and hybridized with the probe expected to anneal to the 3' end of homology arm of the targeting vector to validate the zygocity of the Pla2g6(ex2) constitutive knock-out gene mutation in these animals. The expected fragments are: 8.2, 9, and 6.1 kb for WT allele, recombined/floxed allele, and constitutive knock-out allele (floxed region deleted), respectively.
Figure 14A:
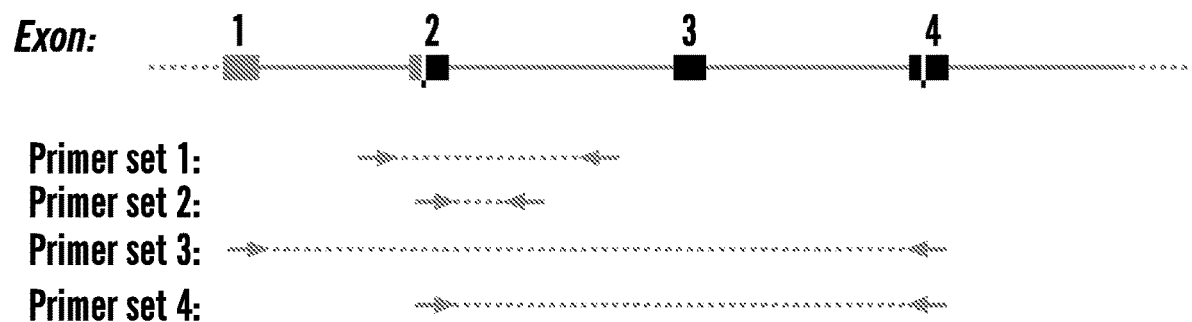
FIG. 14A-14E shows PCR-based genotyping and confirmation of the constitutive Exon 2 knockout at the genome and transcript level.
Figure 14D:
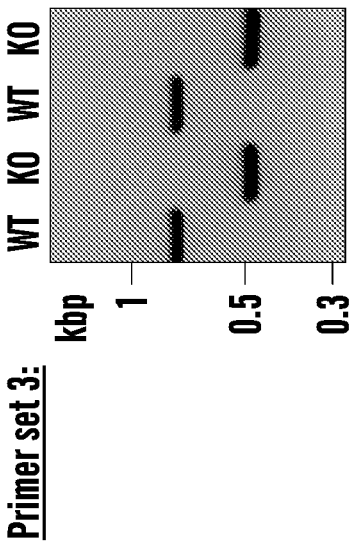
Figure 14E:
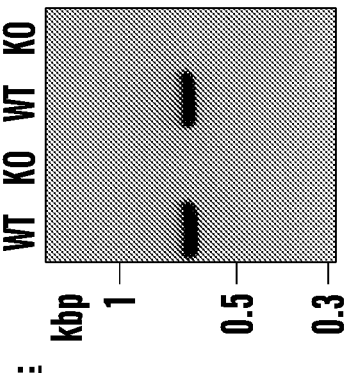
Figure 14B:
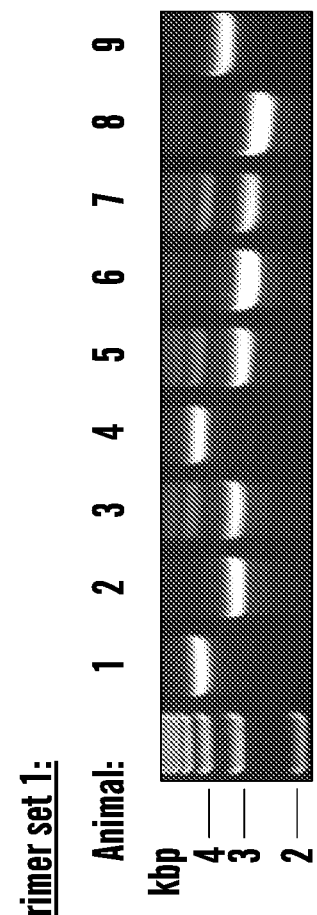
Figure 14C:
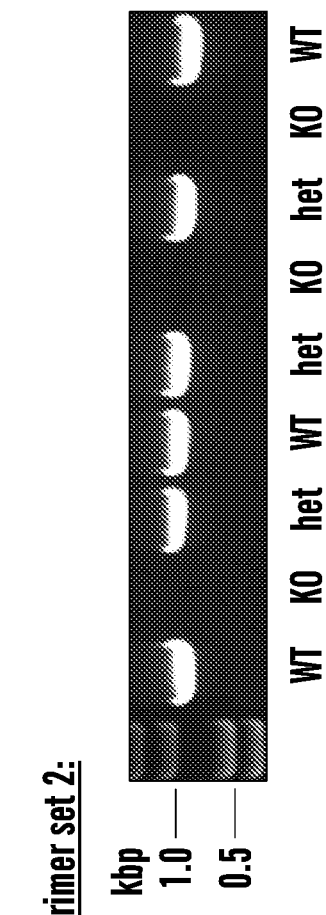
Figure 20A:
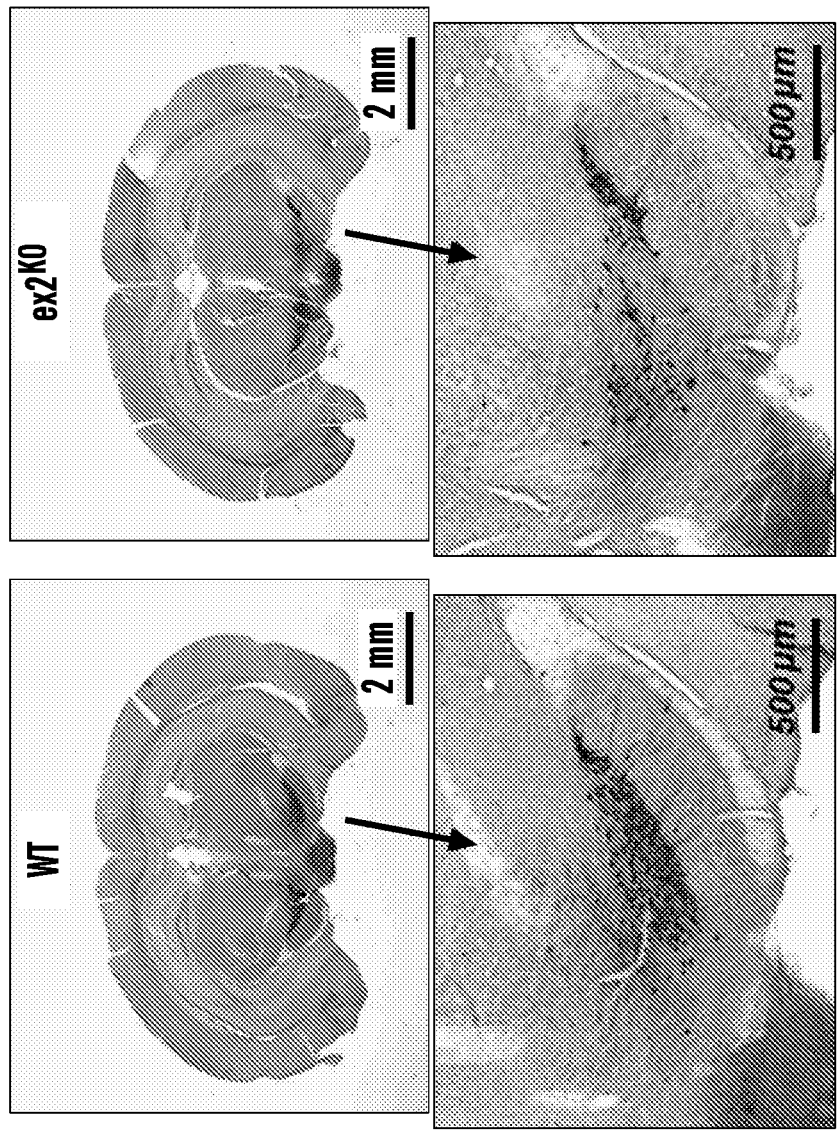
FIGS. 20A-20C show the results of blinded stereological analysis of TH+ neurons in SN of 8, 16 and 24-month old WT and $ex2^{KO}$ littermates.
Figure 20B:
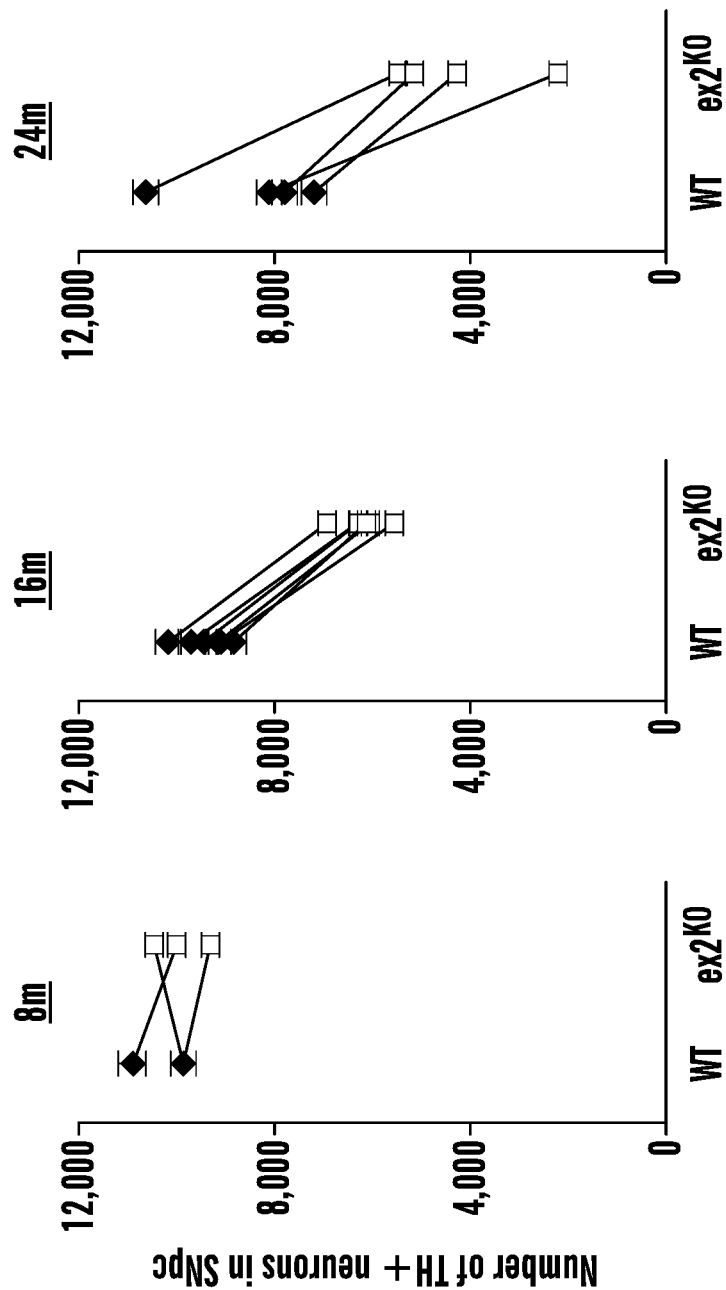
Figure 20C:
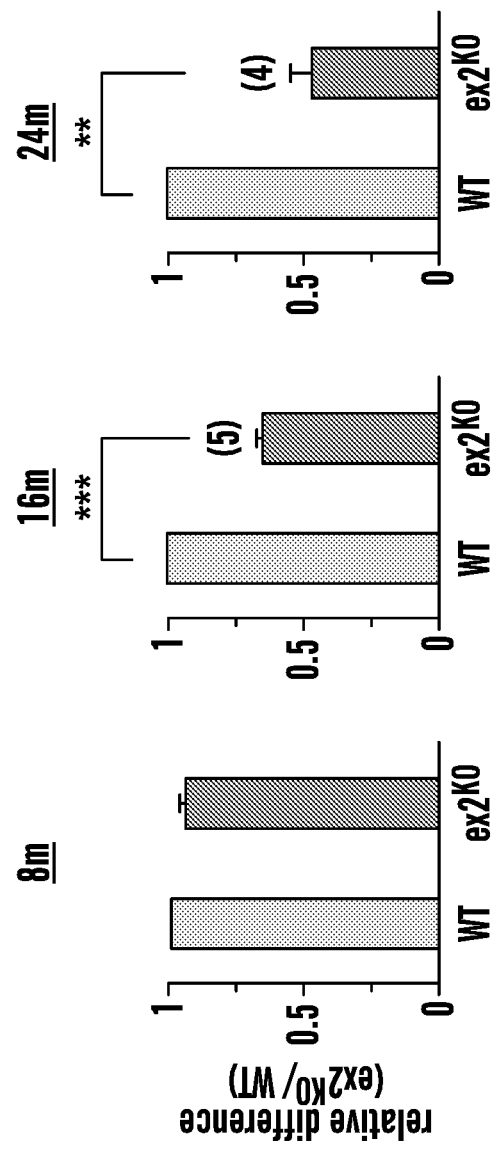

A novel PARK14 (Pla2g6) ex2$^{KO}$ transgenic mouse model (B6.Cg-Pla2g6$^{\Delta Ex2-VB}$/J), in which ex2 of Pla2g6 gene was constitutively deleted, was custom created by GenOway (France). The strategy is outlined in FIG. 12. Briefly, the DNA fragment containing exon 2 and adjacent intron regions of the Pla2g6 gene was isolated by PCR from the 129Sv/Pas genetic background mouse, and subcloned into the pCR4-TOPO vector (Invitrogen). To construct a targeting vector, a fragment including exon 2 (containing ATG$_1$ codon) and a fragment located in the third intron of the Pla2g6 gene were used to flank a neomycin selection cassette (FRT site-MCl-Neo-FRT site-loxPsite), and a distal loxP site in intron 1. The 129Sv ES cells (GenOway, France) were electroporated with the linearized targeting construct and homologous recombination was assessed in 1408 selected ES cell clones via PCR and Southern blot (FIG. 13). One of the Pla2g6 recombined ES cell clones was microinjected into C57BL/6 blastocysts, and gave rise to male chimeras with significant ES cell contribution as determined by an agouti coat color ≥50%. After mating the chimeras with C57BL/6 female, the agouti colored F1 offspring were genotyped for germ line transmission of the Pla2g6 recombined allele. Floxed heterozygous Pla2g6 conditional knockout animals were generated by Flp-mediated excision of the neomycin resistance gene. The heterozygous constitutive ex2 knockout mice were generated by breeding of floxed conditional heterozygous mice with ubiquitous Cre recombinase C57BL/6 mice, and Cre-mediated excision of targeted exon 2 was verified by genotyping of tail DNA via PCR (FIG. 20). Oligonucleotides used as PCR genotyping primers were as follows: set 1: GTGAACACACAGGCTAAGGCTCCAATCTA (SEQ ID NO: 7) AND TCAACAAGCAAAGGACAGACATCCCAC (SEQ ID NO: 8); SET 2: AGCAGAGGGGCAGGCTGGGTCTCTC (SEQ ID NO: 9) AND AGGAACACAGTTGTTGGGCTGGGGTTGTC (SEQ ID NO: 10); SET 3: TATCTTCTCGAGTTCTCTAGCCTCCAATCCTGGG (SEQ ID NO: 11) AND CACATAGAAT-TCGTCCCCTTGCACAGCGTAATGG (SEQ ID NO: 12); AND SET 4: AGCAGAGGGGCAGGCTGGGTCTCTC (SEQ ID NO: 13) AND CACATAGAAT-TCGTCCCCTTGCACAGCGTAATGG (SEQ ID NO: 14).

Heterozygote ex2$^{KO}$ males were backcrossed to C57BL/6 females for 9 generations, and congenic B6.Cg-Pla2g6$^{\Delta Ex2-VB}$/J line was established. Due to infertility of homozygous ex2 knockout males, and the inability of homozygous females to produce/sustain live pups, cross-breeding of heterozygous mice was used to produce homozygous constitutive ex2 knockout (ex2$^{KO}$) animals that were used in this study. Ageing male mice were used for all live animal studies, while female mice were used for MEF cell preparation. Experimental sets of homozygous ex2 KO)(ex2$^{KO}$ and wild type (WT) littermate males were housed and aged together.

Constitutive Orai1 knockout)(Orai1$^{KO}$) mice (ref.[71]) were kindly provided by Dr. Monica Vig. Because homozygous Orai1$^{KO}$ mice have a very limited life span (up to 4-6 weeks), cross-breeding of heterozygous mice was used to produce embryos for Orai1$^{KO}$ MEF cell isolation.

Animal number for each study group was determined for the experimental results to reach statistical significance with a power of 90% at $p<0.05$, or to demonstrate that there is no difference between the groups. Animals were maintained in an advanced pathogen-free facility with veterinary service and unlimited access to food and water. All experimental procedures were compliant with ethical regulations and approved by the Institutional Animal Care and Use Committee of Boston University.

Motor Coordination Tests.

Aging PLA2g6 ex2$^{KO}$ and WT mice were monitored for the signs and severity of clinical symptoms, and motor deficit was initially assessed in arbitrary units (AU) using the following scale: 0=No abnormalities; 1=subtle signs of motor dysfunction; 2=clear signs of movement impairment, but sustained postural stability; 3=impairment in movement and occasional postural instability; 4=strong ataxia and instability, but no difficulty with eating, drinking and grooming; 5=very strong ataxia resulting in difficulty with keeping sternal/upright position, and frequently falls when walking, but still able to eat, drink and groom, although with some difficulty.

Analysis of motor function was performed in age-matched ex2$^{KO}$ and WT animals using standard behavior tests, as described herein. Balance beam test assessed the ability of ageing mice to maintain balance while walking along a narrow beam (the number of missteps/meter was counted). The pole test assessed the time that is needed for balance and orientation on the top of the pole. The rotarod test determined how long the mouse can maintain its balance and stay on a rotating rod. The grip test was used to objectively quantify the muscular strength of the forelimbs and hind limbs. L-DOPA challenge test was performed on ex2$^{KO}$ mice with motor deficits to determine the ability of L-DOPA to temporarily improve motor function, which was assessed using balance beam test. The data were summarized for each group as mean±SE. The number of animals used for each study is identified on the graphs.

Motor Coordination Tests.

Figure 3D:
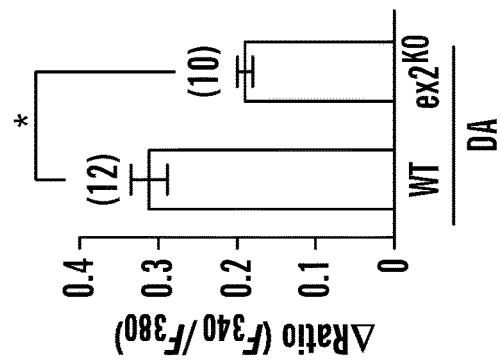
Figure 3F:
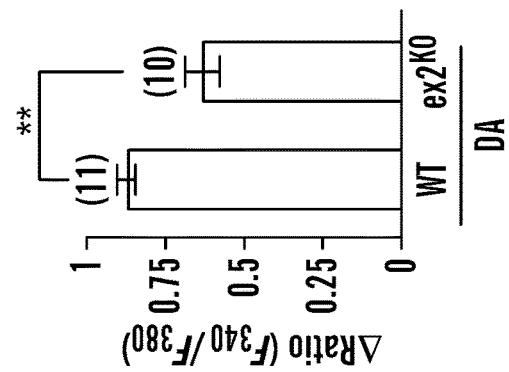

Age-dependent progression of the overall motor deficit was determined during monthly evaluation of ex2$^{KO}$ and WT mice for the signs and severity of clinical symptoms. Motor deficit was assessed in arbitrary units (AU) using the following scale: 0=No abnormalities noted; 1=first subtle signs of motor dysfunction; 2=clear signs of movement impairment, but sustained postural stability; 3=obvious signs of impairment in movement and occasional postural instability; 4=strong ataxia and instability, but no difficulty with eating, drinking and grooming; 5=very strong ataxia resulting in difficulty with keeping sternal/upright position, and frequently falls when walking, but still able to eat, drink and groom, although with some difficulty. FIG. 3a present the time course of motor deficit development in age matched groups of WT and ex2$^{KO}$ mice, and each point indicates median severity±SE of the symptoms in multiple animals. The number of animals tested at different time points is identified on the graph.

The balance beam test (ref 72, 73) was used to assess the ability of ageing ex2$^{KO}$ and WT mice to maintain balance while walking along a narrow (2 cm) beam placed 20 cm above a soft mattress. Each mouse was placed on a beam for 2 minutes, and its movement was recorded by video camera. The total travel distance, the number of missteps (paw faults, or slips) during travel, and the number of falls off the beam were analyzed for each mouse, and data summarized for each group as mean±SE. The numbers of animals used for each group are identified on the graphs.

L-DOPA challenge test (ref 3) was performed on three age groups (12, 16 and 20 months old) ex2$^{KO}$ male mice with motor deficits. Control balance beam test was performed in the morning a day before L-3,4-dihydroxyphenylalanine (L-DOPA) challenge. In the morning of the following day, all mice received a single dose of L-DOPA (5, 10 or 25 mg/kg, Sigma) via peritoneal injection. Twenty minutes before L-DOPA administration, mice were given 6 mg/kg of benserazide (Sigma) to inhibit peripheral DOPA decarboxylase. The balance beam test was done 1 h after L-DOPA injection, as described above. Video-recorded data for each mouse were analyzed later, and summarized for each group as mean±SE. The numbers of animals used for each age group are identified next to the graph.

The pole test was performed using the standard approach (Ref.[73]). Briefly, animals were placed head-up on top of a vertical wooden pole (50 cm in length, 1 cm in diameter). The base of the pole was placed in a cage filled with bedding material. When placed on the pole, the animals need to balance on the tip of the pole to orient downward, before they can descend back into the cage. Balance time that is needed to orient downward was analyzed. After 5 training runs, and 1 day resting, each animal received 5 test trials and average of 5 measurements was determined. Summary data show results (mean±SE). The numbers of animals used for these studies is identified on the graphs.

The rotarod test was performed using the standard approach (Ref.[72]). Age-matched ex2$^{KO}$ and WT males (16-18 months of age) were tested for the length of time each mouse can maintain its balance and stay on a rotating rod (3 cm diameter). After 4 training sessions and one day resting, the mouse was placed on the rod, and then the rod started to rotate at 5 rpm with acceleration to 40 rpm within 5 minutes until the animal fell from the rod. Average of 4 measurements of the latency to fall (in seconds) was determined for each mouse and data summarized for each group as mean±SE. The numbers of animals used for these studies is identified on the graphs.

The grip test was performed using the standard approach (Ref.[72]). Grip Strength Meter (GSM) (Columbus Instruments, Columbus, Ohio) was used to objectively quantify the muscular strength of the forelimbs and hind limbs of age-matched ex2$^{KO}$ and WT animals (16-18 months of age). All tests (4 repetitions) were performed at the same time in the morning. Strength force was normalized to body weight, which was measured each time after the test. The data were summarized for each group as mean±SE. The numbers of animals used for these studies is identified on the graphs.

Brain Slices: Preparation, Immunostaining and Analysis.

The brains were extracted following paraformaldehyde (PFA, 4%) perfusion, and cryopreserved in 15% and 30% (w/v) sucrose solutions at 4° C. Brain sections were prepared using standard methods, as described herein. Briefly, coronal 30 μm thick free-floating sections containing the substantia nigra pars compacta (SNc) were collected using a staggering method, and sets of six brain sections were collated: each set contained similar sections from the rostral, middle, and caudal parts of the SNc region. Investigators were blinded during sectioning, tyrosine hydroxylase (TH) staining, unbiased stereology and analysis of PAS staining; mouse phenotypes were revealed/confirmed only after data was generated. No samples were excluded from analysis in targeted age groups.

Blinded unbiased stereological analysis of DA neurons in SNc of age-matched pairs of ex2$^{KO}$ and WT littermates was performed using standard methodology described in herein. Briefly, the matching sets of brain slices were stained with TH rabbit polyclonal antibody (Calbiochem) and 3,3'-Diaminobenzidine (DAB) HRP substrate (Vector Laboratories). To estimate the number of TH positive (TH+) neurons, matching sets of 6 sections from SNc area of the brain of each experimental animal were analyzed using a Nikon Eclipse E600 microscope and the Stereo-Investigator v11.01.2 software. The total number of TH+ cells in the SN was estimated using the optical fractionator technique, as described in herein. The data were summarized for each group as average±SE. Paired t test was used for statistical analysis of the differences within the matching pairs of WT and ex2$^{KO}$ littermates. The numbers of littermate pairs used for these studies is identified on the graphs.

Periodic acid-Schiff (PAS) staining and analysis was performed using Sigma kit (#395B) and standard procedures, as described in herein. PAS positive cells (stained rose to magenta with blue to black nuclei) were counted in SNc, hippocampus (Hp) and M1/M2 motor cortex regions. Summary data show average number of PAS+ neurons per mm$^2$ (±SE) from 3 pairs of age-matched WT and ex2$^{KO}$ 16 months old animals. Periodic acid-Schiff (PAS) staining was performed using the standard procedure and kit available from Sigma (#395B). Briefly, the tissue sections were rehydrated in deionized water and placed in periodic acid solution for 5 minutes. After washing with deionized water, the sections were immersed in Schiff's reagent for 15 minutes. The slides were washed under running tap water for 5 minutes and then counterstained in Gill's Hematoxylin No. 3 for 90 seconds. After a final wash under running tap water, the tissue was dehydrated in alcohol and xylene and mounted. PAS positive cells (stained rose to magenta with blue to black nuclei) were counted in SNc, hippocampus (Hp) and M1/M2 motor cortex regions. Summary data show average number of PAS+ neurons per mm$^2$ (±SE) from 3 pairs of age-matched WT and ex2$^{KO}$ 16 months old animals. Immunostaining for TH and LC3 was done using primary chicken polyclonal anti-TH antibody (Abcam ab76442), primary rabbit polyclonal anti-LC3 antibody (Cell Signaling #2775), secondary goat anti-rabbit Alexa488 (Invitrogen A11034), and goat anti-chicken Alexa594 (Abcam AB150172) antibodies, as described in herein.

Nissl staining (cresyl violet staining) was performed using the standard procedure. Briefly, the tissue was de-fatted for 10 minutes in xylene, followed by 10 minutes in 100% ethanol. The sections were stained with 0.1% cresyl violet acetate (Sigma C5042) solution for 10 minutes and rinsed in tap water to remove the excess stain. After a final 5 minute wash with 80% ethanol, the tissue was cleared in xylene for 5 minutes and mounted with Permount. The Nissl substance in the cytoplasm of neurons stains dark blue and confirms the reduction of TH+ neurons in the substantia nigra. For Nissl staining, the brains were extracted following paraformaldehyde (PFA, 4% in standard PBS) perfusion, and stored in 4% PFA at 4° C. for 24 hours. The brains were then cryopreserved in PBS containing 15% and 30% (w/v) sucrose and stored at 4° C. Brain sections were prepared and stained using standard protocols (Ref 74). Briefly, each brain was embedded and frozen in OCT Tissue-Tek, and a small cut was placed on the right side of the frozen OCT block near the right cortex for side identification. WT and ex2$^{KO}$ brains were sectioned coronal (30 μm thickness) with a cryostat microtome and collected as free-floating sections in a 24-well plate and stored at 4° C. The sections containing the substantia nigra pars compacta (SNc) were collected using a staggering method, and six sets of six brain sections were collated: each set contained similar sections from the rostral, middle, and caudal parts of the SNc region. Investigators were blinded during sectioning, TH staining, unbiased stereology and analysis of PAS staining; mouse phenotypes were revealed/confirmed only after all data was generated. No samples were excluded from analysis in targeted age groups.

Blinded Unbiased Stereological Analysis:

For stereological analysis (described below) one set of slices from each brain was immunostained with tyrosine hydroxylase (TH) rabbit polyclonal antibody (Calbiochem) and 3,3'-Diaminobenzidine (DAB) HRP substrate (Vector Laboratories) using the standard techniques. Briefly, the endogenous peroxidase activity was blocked by 3% hydrogen peroxide in PBS. The sections were washed with PBS, permeabilized in 0.1% Triton X-100/PBS and blocked with 10% normal goat serum in 0.1% Triton/PBS. The TH antibody was diluted 1:1000 in blocking buffer and incubated overnight at 4° C. The next day, the sections were washed with 0.1% Triton/PBS and incubated in Envision™+ Rabbit (Dako) solution at room temperature for 1 hour. After washing with 0.1% Triton/PBS, DAB (Vector Laboratories) staining was developed. The stained sections were mounted on slides, counterstained with Harris-modified hematoxylin and sealed with Permount. To estimate the number of TH positive (TH+) neurons in SNc of age-matched pairs of ex2$^{KO}$ and WT littermates, matching sets of 6 sections from SNc area of the brain of each experimental animal were analyzed using a Nikon Eclipse E600 microscope and the Stereo-Investigator v11.01.2 software. The total number of TH+ cells in the substantia nigra was estimated using the optical fractionator technique (Ref.[75]). Briefly, both sides (left/right) of the substantia nigra regions were outlined separately using a 4×/0.1 air objective (Nikon). Then the TH+ cells were manually counted with a 10×/0.25 air objective (Nikon) using a 60×60 µm counting frame within a 180×180 µm grid with a 18 µm optical dissector height. 100-200 total cells were counted per section to ensure that the coefficient of error (CE) was less than 0.1. The data were summarized for each group as average±SE. Paired t test was used for statistical analysis of the differences within the matching pairs of WT and ex2$^{KO}$ littermates. The numbers of littermate pairs used for these studies is identified on the graphs.

Immunostaining for TH and LC3 was done using the chicken polyclonal anti-TH antibody (Abcam ab76442), and rabbit polyclonal anti-LC3 antibody (Cell Signaling #2775). Briefly, the free-floating sections were washed with PBS and incubated in 0.1M glycine/PBS for 30 minutes. After additional washing, the sections were transferred to the antigen-retrieval buffer solution (10 mM citric acid, 0.05% Tween-20, pH 6.0) and incubated in the steam phase of a 85° C. water bath. The sections were then blocked with 10% goat serum/0.1% Triton X-100 for 60 minutes at room temperature. The TH and LC3 antibodies were diluted 1:250 and 1:20 respectively and applied to the sections overnight at 4° C. The following day, the sections were washed and the secondary antibodies goat anti-rabbit Alexa488 (Invitrogen A11034), and goat anti-chicken Alexa594 (Abcam AB150172) were diluted 1:1000 and applied for 60 minutes at room temperature. The nuclei were stained blue with 1 ug/ml DAPI (Sigma D9542). Sections were mounted with Vectashield (H-1000) and sealed with nail polish.

Primary Mouse Embryonic Fibroblasts (MEF).

Mouse embryonic fibroblasts (MEFs) were isolated from WT, ex2$^{KO}$ and Orai1$^{KO}$ embryos (14.5 days old). Ex2$^{KO}$ embryos were obtained from homozygote ex2$^{KO}$ females mated with heterozygote ex2$^{KO}$ males. Orai1$^{KO}$ embryos were obtained by cross-breeding of heterozygous Orai1$^{KO}$ mice. Each embryo was genotyped. Head, vertebral column, dorsal root ganglia and all internal organs were removed and discarded; the remaining embryonic tissue was manually dissociated and incubated in 0.25% trypsin (Gibco) for 15-30 min. Cells from each embryo were plated onto a 10 cm tissue culture dish in MEF media (Dulbecco's modified Eagle medium, DMEM; Mediatech Inc.) containing 10% fetal bovine serum (FBS; Hyclone), non-essential amino acids, sodium pyruvate and penicillin/streptomycin (Invitrogen). After reaching confluence, primary MEFs from WT and ex2$^{KO}$ embryos were tested (and confirmed to be negative) for mycoplasma contamination, collected and stored in liquid nitrogen for future use. Only MEFs from passages 2-3 were used for experiments, and studied after 24-48 hours in culture. For each experimental condition, independent experiments were performed on the cells from 3 different MEF preparations; the number of cells (or samples) for each condition is shown in the figures, and/or stated in Figure Legends.

Transfection of MEFs was performed using the Amaxa Nucleofector™ system (Lonza, Allendale, N.J., USA). Briefly, the cells were plated in a 6-well plate at a density of 200,000/well. After 24h the cells from each well were collected, centrifuged, re-suspended in 100 µl of electroporation solution (Mirus Bio, Madison, Wis., USA), mixed with 2 µg of the recombinant plasmid DNA and transfected using the T020 program. After electroporation, the cells were plated in 2 ml of warm DMEM containing 10% FBS and 1% penicillin/streptomycin, and grown for 24-48 hours, as specified. Transfection efficiency (verified by expression of GFP or LC3$^{mCherry/eGFP}$) was >70%.

iPSC-derived A9 midbrain dopaminergic neurons. Derivation of iPSC from MEFs was performed using STEMCCA approach. In brief, derivation of iPSC from MEFs was performed as previously described (Ref[76,77]). Briefly, ~100,000 MEFs were plated in MEF media and transduced with the constitutive STEMCCA vector at an MOI of 2.5 for 24 hr. Media was then changed to ESC media (DMEM supplemented with 15% FBS, 1× GlutaMAX, 350 k units of ESGRO leukemia inhibitory factor, and 0.1 mM 2-Mercaptoethanol), with media changes every second day until appearance of colonies. Putative iPSC colonies were picked and expanded for STEMCCA excision and characterization. Excision was done as described (Ref[78]) using Adeno-Cre infection and confirmed by PCR. Colonies positive for Alkaline Phosphatase, Oct3/4, Zfp96, Nanog and ERas were expanded and banked for neural differentiation. The cultures were routinely checked and confirmed to be negative for mycoplasma.

Differentiation of iPSC into DA neurons was done using standard protocol (Ref[79]) by first inducing formation of embryoid bodies in non-adherent conditions for 4 days in knockout serum replacement (KSR) media. Cells were then transferred to adherent plates and incubated in ITS media (DMEM/F12 (Gibco)+1×ITS Supplement (Sigma I13146)+1 µg/ml Bovine fibronectin (Sigma F1141)) for 6 to 10 days to induce ectoderm formation. Cells were then expanded onto polyornithine/fibronectin coated coverslips in media containing N2 Max supplement, FGF2, FGF-8b, Shh-N and Ascorbic Acid for 5-7 days until cells reach confluency. Neural identity was confirmed by staining against αIII tubulin and nestin. Final differentiation into dopaminergic neurons was done by incubating the cells for 10 more days in minimal media (DMEM/F12 (Gibco)+1× N2 Max+200 µM Ascorbic Acid (Sigma A4403)). Confirmation of DA neuron identity was done by staining the cells for TH (Abcam ab76442), Dopamine transporter (DAT, Abcam ab5990) and Vesicular monoamine transporter 2 (VMAT2, Abcam 70808).

Colonies positive for Alkaline Phosphatase, Oct3/4, Zfp96, Nanog and ERas were expanded and banked for neural differentiation. The cultures were routinely checked and confirmed to be negative for mycoplasma.

Differentiation of iPSC into DA neurons was done using standard protocol[42] by first inducing formation of embryoid bodies in non-adherent conditions for 4 days in KSR media. Cells were then transferred to adherent plates and incubated in ITS media (DMEM/F12 (Gibco)+1×ITS Supplement (Sigma I13146)+1 µg/ml Bovine fibronectin (Sigma F1141)) for 6 to 10 days to induce ectoderm formation. Cells were then expanded onto polyornithine/fibronectin coated coverslips in media containing N2 Max supplement, FGF2, FGF-8b, Shh-N and Ascorbic Acid for 5-7 days until cells reach confluency. Neural identity was confirmed by staining against βIII tubulin and nestin. Final differentiation into dopaminergic neurons was done by incubating the cells for 10 more days in minimal media (DMEM/F12 (Gibco)+1× N2 Max+200 µM Ascorbic Acid (Sigma A4403)). Confirmation of DA neuron identity was done by staining the cells for TH (Abcam ab76442), Dopamine transporter (DAT, Abcam ab5990) and Vesicular monoamine transporter 2 (VMAT2, Abcam 70808).

Human Primary Skin Fibroblasts (hPSF).

The samples of hPSF (see Table 1A-1C for all details) were obtained from the NINDS Cell Line Repository (http://ccr.coriell.org/ninds). Each sample was verified to be mycoplasma-free by PCR. The hPSFs from individual donors were cultured as recommended. Briefly, hPSF cells were grown in Eagle's Minimum Essential Medium (EMEM; Gibco) supplemented with 15% FBS (Atlanta Biologicals, Ga., USA), 2 mM L-glutamine (Gibco), and 1% penicillin/streptomycin (Gibco), and passaged 1:4 every 7 days. Only hPSF from early passages (3 to 5) were used in these studies. For each experimental condition, at least 3 independent experiments were performed; the numbers of cells (or samples) for each condition is shown in the figures, and/or stated in Figure Legends.

Transfection of hPSFs was performed using the Amaxa Nucleofector system. The cells were plated at a density of 300,000/well in a 6-well plate. After 24h the cells from individual wells were collected, centrifuged, resuspended in 100 µl of electroporation solution, mixed with 2 µg of total plasmid DNA, and transfected using the U023 program. After electroporation, the cells were plated in fibronectin-coated (2.5 µg/cm$^2$, Sigma, St. Louis, Mo., USA) 35 mm glass bottom dishes. Live cell imaging was performed 48 hours after transfection. Transfection efficiency (verified by expression of GFP, or LC3$^{mCherry/eGFP}$) was about 50%.

Tables 1A-1C: A list of human primary skin fibroblasts (hPSF) used in this study:

TABLE 1A human primary skin fibroblasts (hPSF)
from 5 control individuals (control)

| Sample | Catalogue ID | Passage | Onset Age | Collection Age | Duration |
|---|---|---|---|---|---|
| Control 1 | ND34770 | P2 | — | 72 | — |
| Control 2 | ND29179 | P3 | — | 68 | — |
| Control 3 | ND35044 | P2 | — | 77 | — |
| Control 4 | ND29178 | P3 | — | 66 | — |
| Control 5 | ND38530 | P5 | — | 55 | — |
| Average ± SD | | | | 68 ± 8 | |

TABLE 1B human primary skin fibroblasts (hPSF)
from 10 idiopathic PD (idPD) patients

| Sample | Catalogue ID | Passage | Onset Age | Collection Age | Duration |
|---|---|---|---|---|---|
| idPD1 | ND32697 | P2 | 55 | 58 | 3 |
| idPD2 | ND34265 | P2 | 55 | 62 | 7 |
| idPD3 | ND39510 | P2 | 50 | 69 | 19 |
| idPD4 | ND39955 | P2 | 50 | 55 | 5 |
| idPD5 | ND35976 | P2 | 59 | 63 | 4 |
| idPD6 | ND33424 | P2 | 47 | 57 | 10 |
| idPD7 | ND37132 | P2 | 60 | 66 | 6 |
| idPD8 | ND35320 | P1 | 59 | 64 | 5 |
| idPD9 | ND37609 | P3 | 62 | 68 | 6 |
| idPD10 | ND35322 | P3 | 49 | 61 | 12 |
| average ± SD | | | 55 ± 5 | 62 ± 5 | 7 ± 5 |

TABLE 1C human primary skin fibroblasts (hPSF) from a patient with familial PD caused by PD-associated R747W mutation in PLA2g6 (fPD PLA2g6R747W) Basic information provided by NINDS Repository (Coriell Institute for Medical Research).

| Sample | Catalogue ID | Passage | Onset Age | Collection Age | Duration |
|---|---|---|---|---|---|
| PLA2g6-m1 | ND32974 | P6 | 18 | 24 | 6 |

$Ca^{2+}$ Imaging.

Intracellular $Ca^{2+}$ studies were performed using standard Fura-2 imaging technique. Briefly, the cells were loaded with Fura-2/AM (5 µM) (Invitrogen) and cytosolic $Ca^{2+}$ (using $F_{340}/F_{380}$ ratio) was recorded simultaneously in individual cells. Representative traces in the figures show average (±SD) responses from up to 20 cells recorded simultaneously. $Ca^{2+}$ changes are shown by ΔRatio ($\Delta F_{340}/F_{380}$), which is the difference between the basal and peak values of $Ca^{2+}$ responses. Summary bar graphs show the average (±SE) from 3 independent experiments for each condition; the total number of cells in each experimental group is identified on the graphs.

For SOCE recording, the cells were placed in $Ca^{2+}$-free extracellular solution (130 mM NaCl, 4.6 mM KCl, 2 mM $MgCl_2$, 10 mM Hepes/Na, 5 mM Glucose, 100 µM EGTA, pH 7.4), and acute (5-20 min) application of 5 µM thapsigargin (TG, Sigma) was used to irreversibly inhibit SERCA activity, and allow $Ca^{2+}$ to leak out from the stores, thus causing ER store depletion. Acute treatment with TG did not cause unfolded protein response (data not shown). SOCE was measured in response to extracellular application of 2-2.5 mM $Ca^{2+}$ in the presence of TG. Concentration and time of acute TG treatment was titrated for each cell type to ensure >90% loss of $Ca^{2+}$ from TG-sensitive stores at the time of $Ca^{2+}$ addition. As an alternative to TG, in some experiments SOCE was evoked by acute 5 minute treatment with 400 µM TPEN (N,N,N',N'-Tetrakis(2-pyridylmethyl) ethylenediamine, Sigma, USA). To inhibit PLA2g6 activity, (S)-BEL (S-bromoenol lactone, Cayman, USA) was applied (10-50 µM for 20 min in serum-free medium at 37° C.) to the cells after their loading with Fura-2/AM, and was washed away before the start of experiment.

Release of $Ca^{2+}$ from intracellular stores was measured in $Ca^{2+}$-free extracellular solution in response to acute application of ionomycin (IM, Sigma) at concentration enough to release >90% of $Ca^{2+}$ from TG-sensitive stores (titrated for each cell type): 1 µM for MEFs, 0.1 µM for hPSF, and 0.1 µM for iPSC-derived DA neurons.

Fura-2 recordings in MEFs were done at 20-22° C. using dual-excitation Intracellular Imaging system (Intracellular Imaging Inc, Cincinnati, Ohio), unless specified differently. Fura-2 fluorescence in hPSF and iPSC-derived DA neurons was recorded using Nikon Eclipse Ti (Nikon, Melville, N.Y.)/Lambda DG-4 system (Sutter Instrument, Novato, Calif.) equipped with Fura-2 cube (FURA2-C-NTE-ZERO, Semrock, Rochester, N.Y.), CFI S Plan Fluor 20×/0.45 objective (Nikon), perfect focus, X/Y positioning, and multiple fields stitching. Fura-2 recordings in iPSC-derived neurons were done at 37° C. and the data from the whole field, which was labeled with a scratch for later identification, was stored. The cells were then immediately fixed, stained for TH, and imaged. The paired images (Fura2 recordings and ICC stainings) were superimposed and $Ca^{2+}$ responses were analyzed in TH+ iPSC-derived A9 midbrain DA neurons.

For comparison of $Ca^{2+}$ responses in iPSC-derived DA neurons and MEFs, a separate set of experiments was performed with both cell types treated and studied at exactly the same experimental conditions (37° C.) using the same settings on Nikon Eclipse Ti/Lambda DG-4 system.

Live Cell Imaging and Co-Localization Analysis:

Live cell imaging was done using Nikon Ti inverted fluorescence microscope equipped with a Perfect Focus system and environmental chamber (InVivo Scientific). Live cells transfected with $LC3^{mCherry/eGFP}$ (alone, or in combination with PLA2g6, or its mutants) were imaged in glass-bottom dishes in culture medium at 37° C. and 5% $CO_2$. Images of individual cells were taken using a 60×/1.4 Plan-Apochromat oil immersion objective (Nikon) and filter sets for GFP (ex: 465-496, em: 515-555) and Texas Red (ex: 540-580, em: 600-660). Images of representative cells were analyzed using ImageJ (Wayne Rasband, NIH) software. For increased accuracy and better visualization, the background was subtracted (rolling ball radius: 5.35 µm), and the unsharp mask filter (radius: 0.428 um, mask weight: 0.6) was identically applied to both green and red channels for all images. Analysis of mCherry and eGFP colocalization was done using Pearson's correlation coefficient[70]. Briefly, the normalized covariance image of each cell was computed using ImageJ and the equation:

$$g_{ij} = \frac{e_{ij}f_{ij} - \overline{EF}}{\sqrt{[\overline{E^2} - (\overline{E})^2][\overline{F^2} - (\overline{F})^2]}}$$

where $e_{ij}$ and $f_{ij}$ are the pixels in the respective panels, $\overline{E}$ and $\overline{F}$ are the mean values of the pixels and $\overline{E^2}$ and $\overline{F^2}$ are the means of the squared pixel values. The average of the values of all pixels $g_{ij}$ was equal to Pearson's correlation coefficient. A correlation map was generated using the Interactive 3D surface plot plugin in ImageJ, and the positive contribution at each pixel to the correlation coefficient is displayed. Summary data show the average±SE of correlation coefficients and sizes of fluorescent particles in a total of 15 cells from 3 independent experiments (5 representative cells per experiment).

Confocal and TIRF Imaging.

Confocal imaging of brain slices was done using LSM710 Duo imaging system (Zeiss, Thornwood, N.Y., USA) with either a 20× non immersion, or 63×/1.4 Plan-Apochromat oil immersion objectives. Total Internal Reflection Fluorescence (TIRF) imaging of the bottom plane of MEFs was done using a Nikon Ti inverted fluorescence microscope with a 60×/1.49 Apo-TIRF oil objective (Nikon) and a filter set for GFP illumination.

Confocal imaging of brain slices was done using LSM710 Duo imaging system (Zeiss, Thornwood, N.Y., USA) with either a 20× non immersion, or 63×/1.4 Plan-Apochromat oil immersion objectives, as previously described (Ref.[81]). Briefly, the 488 nm argon laser was used for imaging Alexa 488 and emitted fluorescence was collected in the range of 492-586 nm. The 594 nm HeNe laser was used to excite Alexa594 and emitted fluorescence was collected in the range of 604-698 nm. The 2-photon laser was set to 750 nm to visualize DAPI staining and fluorescence was collected in the range of 415-492 nm. For better visualization of individual cells, ImageJ was used for background fluorescence subtraction using rolling ball radius of 13.3 µm (100 pixels).

Total Internal Reflection Fluorescence (TIRF) imaging of the bottom plane of cells was done using a Nikon Ti inverted fluorescence microscope with a 60×/1.49 Apo-TIRF oil objective (Nikon) and a filter set for GFP illumination.

PLA2g6 Activity.

A modified PLA2 assay kit (Cayman for MEFs, and AbCam for hPSF) was used as previously described[21,26]. Briefly, each sample of live hPSF or MEF cells was homogenized using a cold lysis buffer (10 mM Tris-HCl, pH 7.0, 300 mM sucrose, 0.5% Triton X-100). To identify specific activity of $Ca^{2+}$-independent PLA2g6, the assay buffers were modified to contain no $Ca^{2+}$. To assess catalytic activity of PLA2g6, the cells were homogenized and treated with 10 mM EGTA for 10 min, which is known to directly displace inhibitory calmodulin, and fully activate PLA2g6. For analysis of PLA2g6 activation by store depletion, live cells were pretreated with TG (5 µM for 10 min) before homogenization, and homogenates were not treated with 10 mM EGTA. The specificity of PLA2g6 activity in both cases was confirmed by its inhibition with S-BEL (25 µM for 10 min), a chiral-specific suicidal substrate[38] that discriminates PLA2g6 from all other phospholipases. PLA2g6 activity in each sample was assayed (in triplicates) by incubating the samples with the substrate, 1-hexadecyl-2-arachidonoylthio-2-deoxy-sn-glycero-3-phosphorylcholine for 1 h at room temperature in a modified $Ca^{2+}$-free assay buffer (10 mM HEPES, pH 7.4, 300 mM NaCl, 60% glycerol, 8 mM Triton X-100, 4 mM EGTA, and 2 mg/ml bovine serum albumin). The reaction was stopped and the generation of free thiols was visualized by addition of DTNB for 5 min: the absorbance was determined at 405 nm using a standard microplate reader. In calculations of specific PLA2g6 activity a value of 10 $mM^{-1}$ was used as extinction coefficient for DTNB at 405 nm. The activity of PLA2g6 was expressed in nM/min/mg of protein.

Western Blot.

Tissue preparation and Western blot analysis was done using standard approaches Tissue or cell lysates were prepared with RIPA buffer (50 mM Tris-HCl (pH 7.4), 150 mM NaCl, 1% NP-40, 0.5% sodium deoxycholate, 0.1% SDS, 5 mM EDTA, 5 mM DTT, 1 mM PMSF and protease inhibitor cocktail (Roche)). Protein concentrations were determined using a Bio-Rad Bradford protein assay. Proteins (10 µg) were electrophoresed through an 7.5% SDS-polyacrylamide gel for detecting PLA2g6(L) using rabbit polyclonal PIN antibody (1:1000). Proteins (20 µg) were electrophoresed through an 4-20% gradient SDS-polyacrylamide gel for detecting the microtubule-associated protein 1 light chain 3 (LC3) using rabbit polyclonal anti-LC3 antibody (1:1000). Proteins separated by SDS-PAGE were transferred to a Supported Nitrocellulose membrane (Bio-Rad) by electroblotting. The membranes were incubated in blocking buffer (5% nonfat dried milk, 10 mM Tris (pH 7.5), 100 mM NaCl, and 0.1% Tween 20) before immunoblotting was performed with primary Abs. HRP-conjugated anti-mouse or anti-rabbit IgG were used as secondary Ab. The blots were developed with SuperSignal Western Dura Extended Duration Substrate (Thermo Scientific). Western blotting was repeated at least three times.

Antibodies.

The following primary antibodies were used in this study: rabbit polyclonal anti-tyrosine hydroxylase (TH) antibody (Calbiochem, #657012); chicken polyclonal anti-tyrosine hydroxylase (TH) antibody (Abcam, ab76442); rabbit polyclonal anti-LC3B antibody (Cell Signaling, #2775); rabbit polyclonal anti-VMAT2 antibody (Abcam, ab70808); rat monoclonal anti-DAT antibody (Abcam, ab5990); rabbit polyclonal anti-PIN antibody targeting mouse PLA2g6 PIN domain (encoded by exon 8b, which is present in (L), but spliced out in (S) variant) were custom made by Yenzym Antibodies, LLC (San Francisco, Calif.), rabbit polyclonal anti-LC3B antibody (MBL, PD014); monoclonal anti-β-actin antibody (Sigma, A1978). Secondary antibodies: goat anti-rabbit Alexa488 (Invitrogen A11034), goat anti-chicken Alexa594 (Abcam ab150172), goat anti-rat Alexa647 (Abcam ab150167) were used for imaging; HRP-conjugated anti-rabbit (Dako, K4002) was used for DAB staining; HRP-conjugated anti-mouse (Cell Signaling, #7076) or anti-rabbit IgG (Cell Signaling, 7074) were used as secondary Ab for WBs.

Quantitative RT-PCR.

Total RNA was isolated from hPSF of each individual donor, and from primary MEFs from $ex2^{KO}$ and WT mice using High Pure RNA isolation kit (Roche Applied Science). Concentration and quality of samples was confirmed spectrophotometrically. RNA was reverse-transcribed using High Capacity RNA-to-cDNA Kit (Life Technologies), and cDNA (equivalent of 200 ng RNA) was analyzed per each reaction (in duplicates for technical control) in quantitative PCR on StepOnePlus™ Real Time PCR System (Applied Biosystems). For the full list of TaqMan® gene expression assays. The relative expression level for each gene was normalized to the level of GAPDH in the same sample.

In brief, for quantitative RT-PCR, Total RNA was isolated from hPSF of each individual donor, and from primary MEFs from $ex2^{KO}$ and WT mice using High Pure RNA isolation kit (Roche Applied Science). Concentration and quality of samples was confirmed spectrophotometrically. RNA was reverse-transcribed using High Capacity RNA-to-cDNA Kit (Life Technologies), and cDNA (equivalent of 200 ng RNA) was analyzed per each reaction (in duplicates for technical control) in quantitative PCR on StepOnePlus™ Real Time PCR System (Applied Biosystems).

The following TaqMan® gene expression assays were used for hPSF: Hs00385627_m1 for Orai1, Hs00963373_m1 for STIM1, Hs00957788_m1 for STIM2, Hs00608195_m1 for TRPC1, Hs00899715_m1 for PLA2g6(L), Hs00895670_m1 for PLA2g6(S), and 4333764F for glyceraldehyde-3-phosphate dehydrogenase (GAPDH).

The following TaqMan® gene expression assays were used for mouse cells and tissue: Mm03929082 ml for PLA2g6(L), Mm03010833_m1 for PLA2g6(S), and 4352932 for mouse glyceraldehyde-3-phosphate dehydrogenase (GAPDH). The relative expression level for each gene to the level of GAPDH in the same sample was analyzed using the comparative $C_T$ method[12]

DNA Constructs.

Tandem $LC3^{mCherry/cGFP}$ construct was obtained from Addgene. cDNA for human PLA2g6(L) variant[39] (Genbank #AF064594) was a kind gift from Dr. Brian P. Kennedy (Karolinska Institute, Stockholm, Sweden) and MERCK FROSST CANADA Inc. His-tagged and/or myc-tagged expression constructs of PLA2g6(L) were created by PCR-subcloning of the full-length long variant of human PLA2g6 (L) into pcDNA3.1 plasmid. F72L and A80T mutants of $^{myc}$PLA2g6 (L)$^{his}$ were created by Mutagenex (USA), and confirmed by sequencing. Tandem $LC3^{mCherry/cGFP}$ construct was from Addgene. cDNA for human PLA2g6(L) variant (Ref[83,84]) (Genbank #AF064594) was a kind gift from Dr. Brian P. Kennedy (Karolinska Institute, Stockholm, Sweden) and MERCK FROSST CANADA Inc., and was used for creation of all other constructs. His-tagged and/or myc-tagged expression constructs of PLA2g6(L) were created by PCR-subcloning of the full-length long variant of human PLA2g6(L) into pcDNA3.1 plasmid with polylinker between restriction sites NheI and PmeI exchanged for the following sequence: GCT AGC GTT AAC ACC GGT ATG GAA TTC GAA CAA AAA CTC ATC TCA GAA GAG GAT CTG GAT ATC CCT GCA GGC TAA GGA TCC CAC GTG CTC GAG CGT CTC CAA TTG GCG GCC GCA AGA GGA TCG CAT CAC CAT CAC CAT CAC TAG AGT GAA GCT TAA GTT TAA AC (SEQ ID NO: 15), allowing for expression of various double- and single-tagged fusions with myc and/or his tags. F72L and A80T mutants of $^{myc}$PLA2g6(L)$^{his}$ were created by Mutagenex (USA), and confirmed by sequencing.

Statistical Analysis.

A two-sided un-paired t test was used for comparison among different data sets, unless stated differently. Normal distribution was confirmed using D'Agostino-Pearson omnibus normality test ($\alpha<0.05$). A two-sided paired t test was used for stereological analysis. One-way analysis of variance (ANOVA) was used for analysis of the data from L-DOPA challenge test. The difference between data sets was considered significant at $p<0.05$; p values are identified in the figures and legends as *($p<0.05$), ($p<0.01$), * ($p<0.001$). Summary data represent average±standard error (SE), or standard deviation (SD), as specified in the figure legends.

Example 1

The etiology of idiopathic Parkinson's disease (PD) remains enigmatic despite recent successes in identification of numerous genes (PARKs) that underlie familial PD. To find new keys to this still incurable neurodegenerative disorder, the inventors focused on the poorly understood PARK14 disease locus (identified as the Pla2g6 gene) and the store-operated Ca2+ signaling pathway. Analysis of the cells from idiopathic PD (idPD) patients revealed a significant deficiency in store-operated PLA2g6(L)-dependent Ca2+ signaling, which we could mimic in a new B6.Cg-Pla2g6ΔEx2-VB (PLA2g6 ex2KO) mouse model. Here, the inventors demonstrate that genetic or molecular impairment of PLA2g6(L)-dependent Ca2+ signaling is a trigger for autophagic dysfunction, progressive loss of dopaminergic (DA) neurons in substantia nigra pars compacta (SNc) and age-dependent L-DOPA-sensitive motor dysfunction. Discovery of this previously unknown sequence of pathological events contributes to iPD, and the ability to mimic this pathology in a novel genetic mouse model opens new opportunities for finding a cure for this devastating neurodegenerative disease that increasingly affects ageing populations.

To find new triggers and signaling pathways that can lead to age-dependent idPD, the inventors focused on the store-operated $Ca^{2+}$ signaling and the poorly understood disease locus, PARK14 (which is also referred to as the Pla2g6 gene[5]) and encodes the $Ca^{2+}$-independent phospholipase A2 group 6 (PLA2g6, or iPLA$_2$β). Although distinct mutations in Pla2g6 gene (PARK14) have been reported to be associated with familial Parkinsonism[6-11], the underlying mechanism and the role of PLA2g6 in idPD remain unclear.

PLA2g6 is a multifaceted enzyme that is best known for its catalytic function, which was linked to phospholipid remodeling in cells (for review see[12]). The loss of the catalytic activity of PLA2g6 was reported to be associated with infantile neuroaxonal dystrophy (INAD) and results in early death in humans, and in mouse models[13-19]. In contrast to INAD mutations, PD-associated mutations in PLA2g6 were reported not to affect its catalytic activity[20]. The question remains open as to which cellular function of PLA2g6 could be involved in human PD, and may be responsible for a PD-like phenotype that would appear later with ageing.

The inventors previously discovered[21;22-26] and others confirmed[27-31] that PLA2g6 plays an important role in activation of endogenous store-operated $Ca^{2+}$ entry (SOCE). Notably, besides Orai1 (store-operated plasma membrane $Ca^{2+}$ channel) and STIM1 ($Ca^{2+}$ sensor in endoplasmic reticulum (ER)), PLA2g6 was identified in an RNAi screen as one of the essential components of endogenous SOCE (see, e.g., supplemental material in ref.[32]). It is well established that SOCE is activated upon depletion of ER $Ca^{2+}$ stores (for review see Refs.[33-35]), and is crucial for their timely refilling in a wide variety of cell types. However, the role of store-operated $Ca^{2+}$ signaling in dopaminergic (DA) neurons and PD remains largely unknown.

SOCE and PLA2g6 are Impaired in idPD and fPD$^{R747W}$ Patients

One of the requirements for $Ca^{2+}$ signaling studies is the live cell preparation. Because live DA neurons cannot be extracted from the midbrain of PD patients, primary skin fibroblasts (hPSF) or other non-neuronal cells, such as blood provide an alternative cellular model representing PD and control patients, which proved to be instrumental for the studies of human neurodegeneration. To determine if idiopathic PD (idPD) may be associated with changes in store-operated $Ca^{2+}$ signaling, primary skin fibroblasts from control donors and idPD patients were obtained from the NINDS Cell Line Repository (http://ccr.coriell.org/ninds) (see Table 1), and used in the experiments presented herein. The idPD group was represented by aged (62±5 years old) male Caucasian idPD patients with no documented mutations in the PARK genes and no family history of PD. The group of neurological control donors was represented by aged (68±8 years old) Caucasian males with no symptoms, or family history of PD.

Analysis of live primary skin fibroblasts (P3-5) from idPD and control donors revealed a significant deficit in endogenous SOCE in the cells from all idPD patients tested (FIG. 1A, 1C and FIG. 8): on average, there was more than 40% reduction in thapsigargin (TG)-induced $Ca^{2+}$ influx in idPD patients compared to the control group. SOCE in both groups was highly sensitive to diethylstilbestrol (DES, inhibitor of PLA2g6(L)-dependent Orai1-mediated SOCE[36,37]): 10 μM of DES produced 80±1% and 82±4% inhibition of TG-induced $Ca^{2+}$ influx in control and idPD groups, respectively.

Figure 8C:
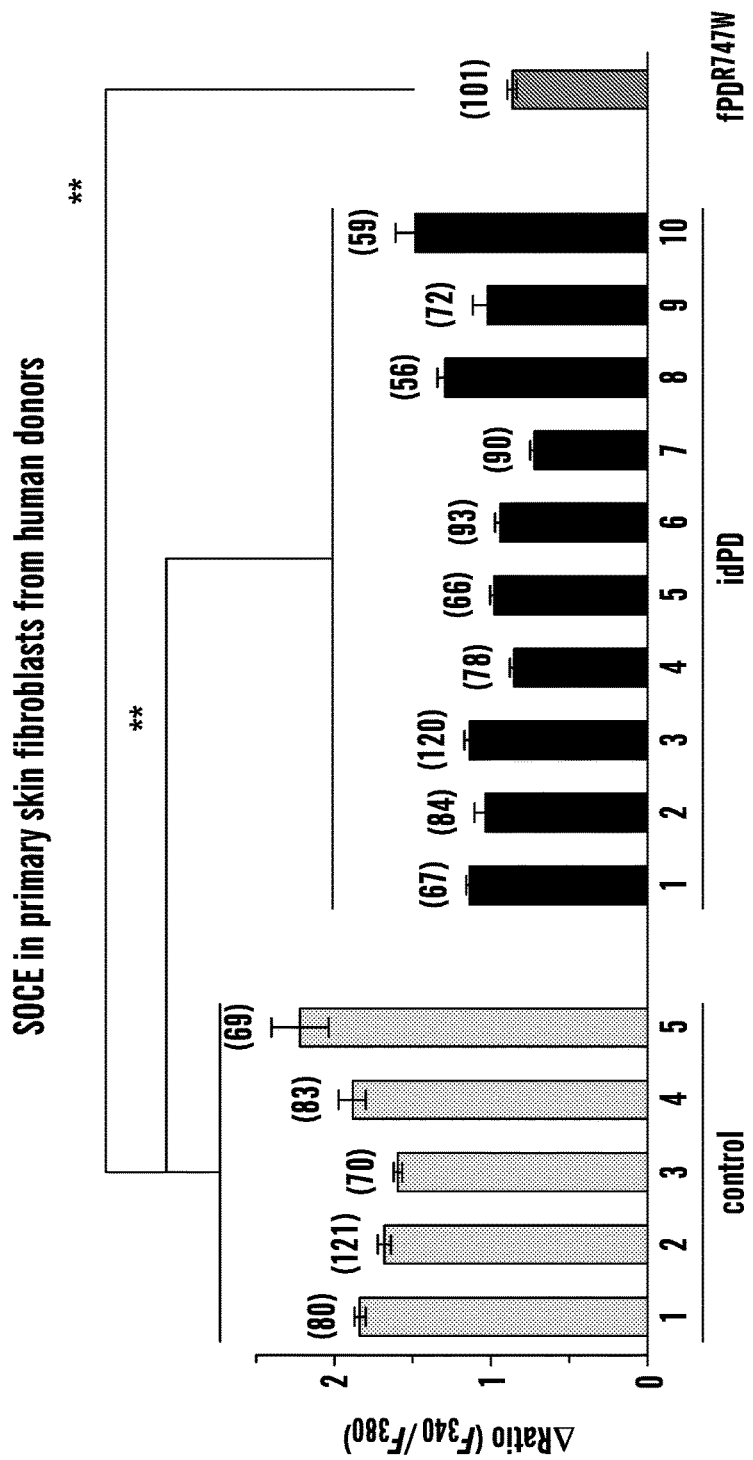
Figure 9A:
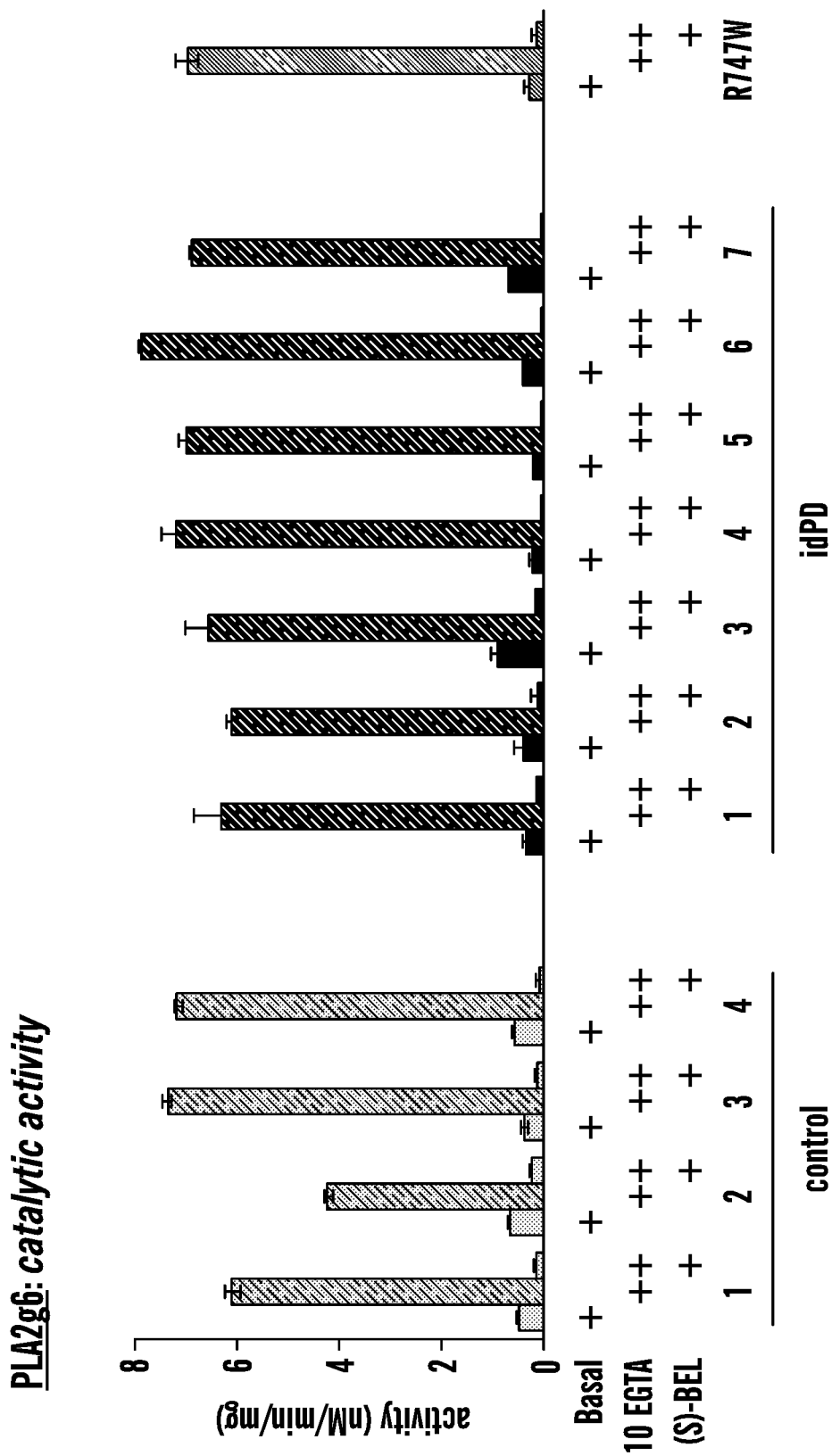
FIGS. 9A-9B shows the catalytic activity and TG-induced activation of PLA2g6 in primary skin fibroblasts (hPSF) from idiopathic PD (idPD) patients, familial PD patient with R747W mutation in PLA2g6, and control individuals. For analysis of the catalytic activity of PLA2g6, the cells were homogenized and treated with 10 mM EGTA, which is known to directly displace inhibitory calmodulin and fully activate PLA2g6. To assess store depletion-induced activation of PLA2g6, live cells were pretreated with TG before homogenization, and homogenates were not treated with 10 mM EGTA. The specificity of PLA2g6 activity in both cases was confirmed by its inhibition with S-BEL, a chiral-specific suicidal substrate that discriminates PLA2g6 from all other phospholipases.
Figure 9B:
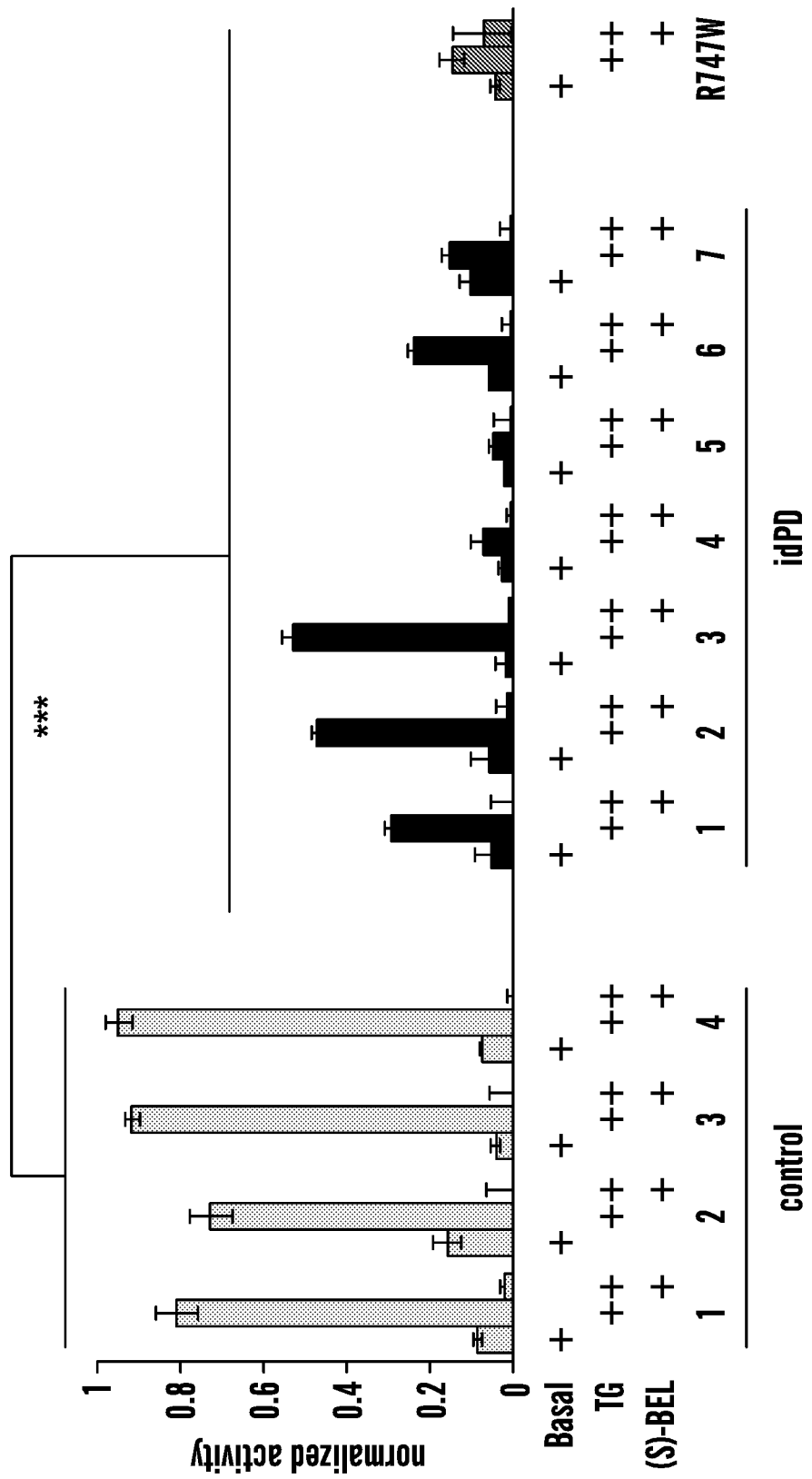

Importantly, the inventors discovered that the cells from a patient with familial PD associated with R747W mutation in PARK14/PLA2g6 (fPD$^{R747W}$) have a similar deficit in SOCE (FIG. 1B, 1C and FIG. 8). To understand which PLA2g6 function may be associated with human PD, catalytic activity and store-dependent activation of PLA2g6 was analyzed and compared in the cells from control, idPD and fPD$^{R747W}$ patients. The inventors discovered that activation of PLA2g6 by TG-induced $Ca^{2+}$ store depletion[26] seen in control donors is significantly impaired in the cells from idPD and fPD$^{R747W}$ patients, while the catalytic activity of PLA2g6 is the same (FIGS. 1E-1D and FIGS. 9A-9B). The specificity of PLA2g6 activity in both cases was confirmed by its inhibition with S-BEL, a chiral-specific suicidal substrate that discriminates PLA2g6 from all other phospholipases[38].

Figure 1F:
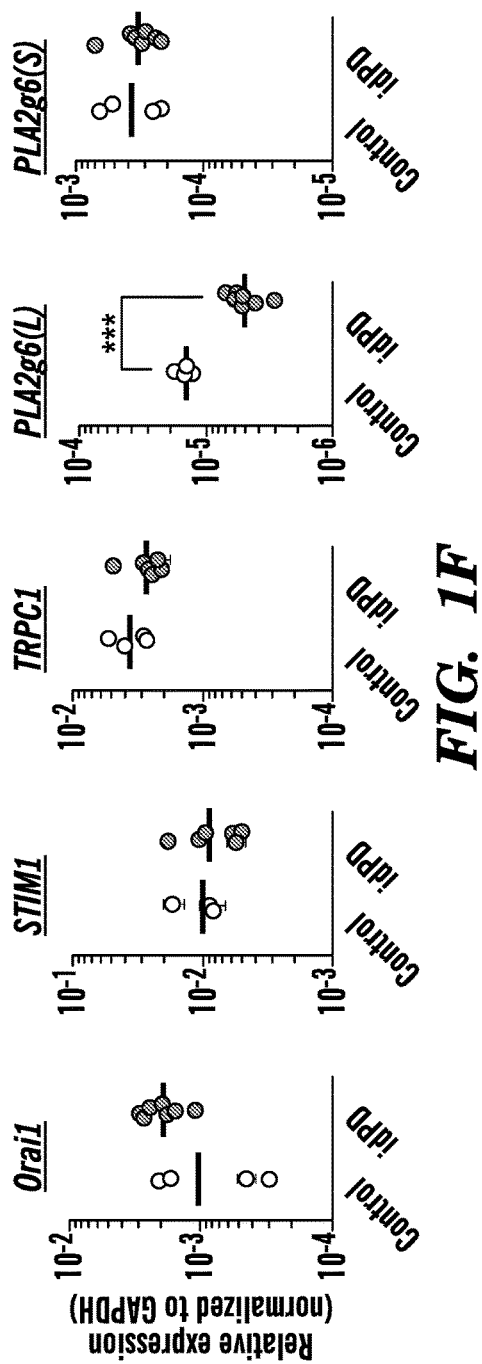
Figure 1G:
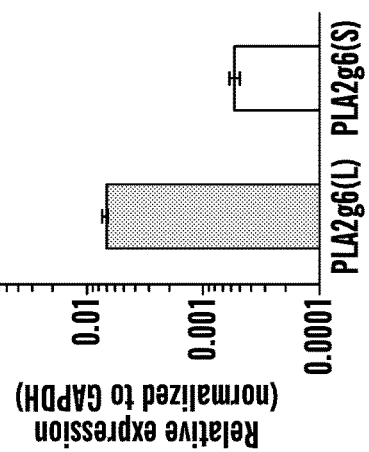
Figure 10A:
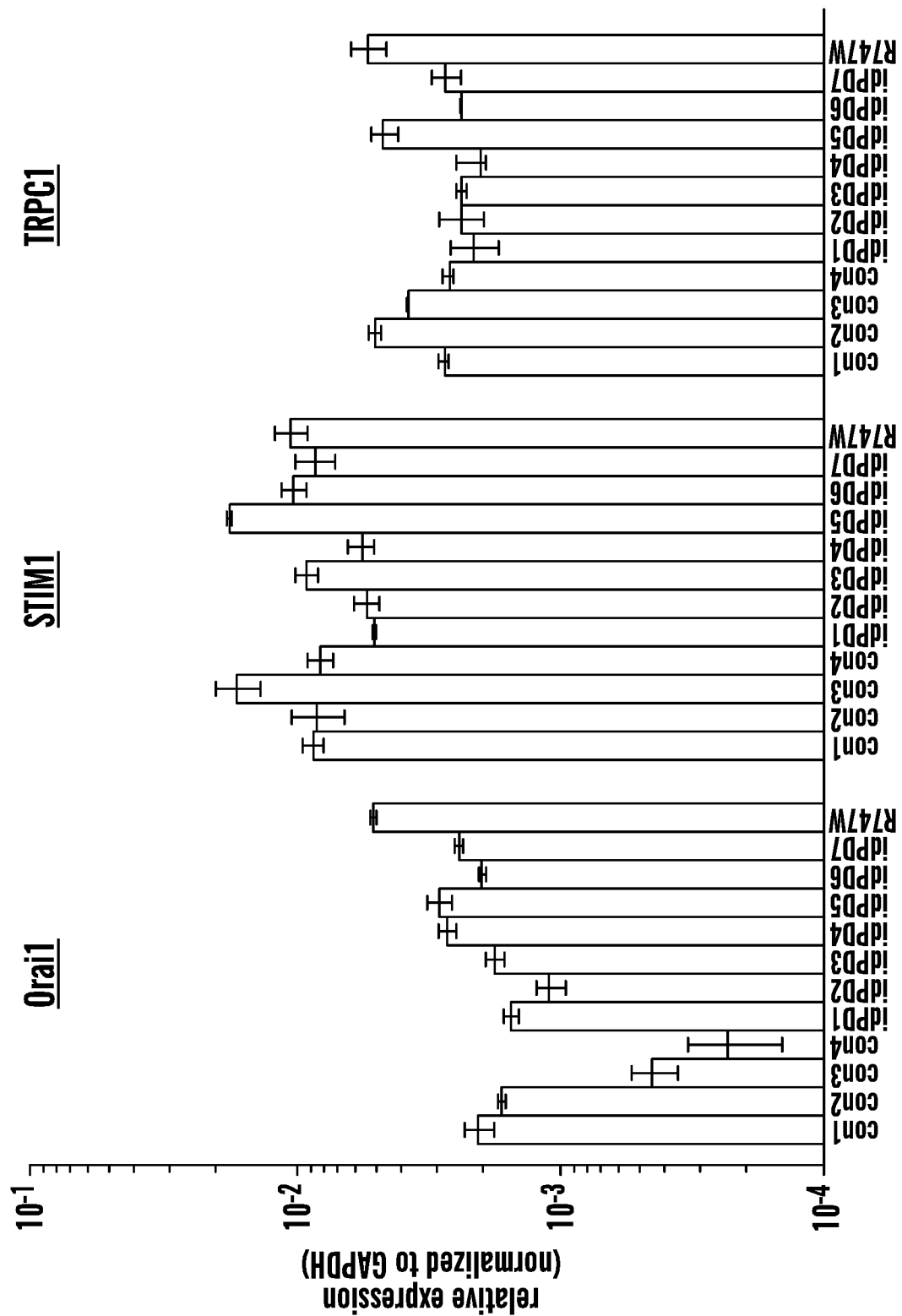
FIG. 10A-10B shows the expression levels of Orai1, STIM1, TRPC1, and PLA2g6 in human primary skin fibroblasts (hPSF) from control individuals (con1-4), idiopathic PD (idPD) patients (idPD1-7), and familial PD patient with R747W mutation in PLA2g6 ($PLA2g6^{R747W}$).
Figure 10B:
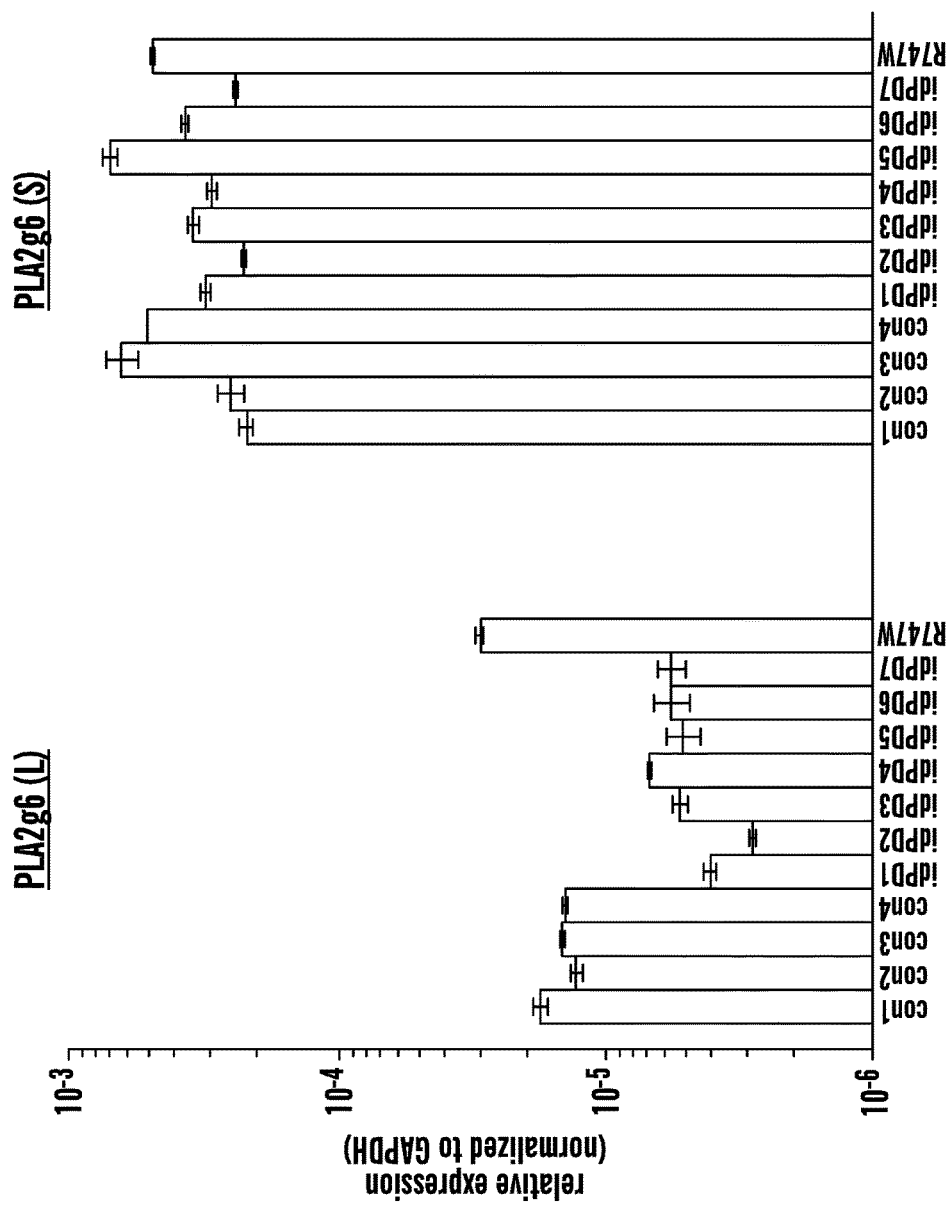

Notably, the analysis of the expression of several major components of SOCE revealed that SOCE deficiency in the cells from idPD patients was not associated with reduction in Orai1, TRPC1, STIM1, or STIM2 expression: FIG. 1F and FIGS. 10-11 demonstrate no difference in mRNA levels for these genes in control and PD patients. In contrast, the inventors surprisingly discovered that the expression of PLA2g6(L) (a specific plasma membrane-associated splice variant of PLA2g6[39]) is significantly reduced in idPD patients (FIG. 1F and FIG. 10B), while expression of the PLA2g6(S) splice variant (which lacks exon 8b and encodes a cytosolic enzyme that was shown to be involved in lipid remodeling[12]) is the same, as in control donors. Thus, primary skin fibroblasts from idPD and fPD$^{R747W}$ patients share a striking deficiency in store-dependent activation of PLA2g6, as well as significant impairment in endogenous SOCE.

Example 2

PLA2g6 Ex2$^{KO}$ Mice Mimics SOCE Deficiency in idPD Patients

To determine if and how the defects in the store-dependent activation of PLA2g6 and impaired SOCE could be translated into the age-dependent PD, the inventors used a mouse model with targeted impairment of these specific cellular functions. Currently existing transgenic PLA2g6 mouse models[13-18] appear to be unsuitable for PD studies, as they have impaired catalytic activity of PLA2g6, which the inventors discovered was unaffected in idPD patients. Moreover, PD pathology develops later in life, while the loss of catalytic activity of PLA2g6 is associated with infantile neuroaxonal dystrophy (INAD) and early death in mice and humans.

Figure 2A:
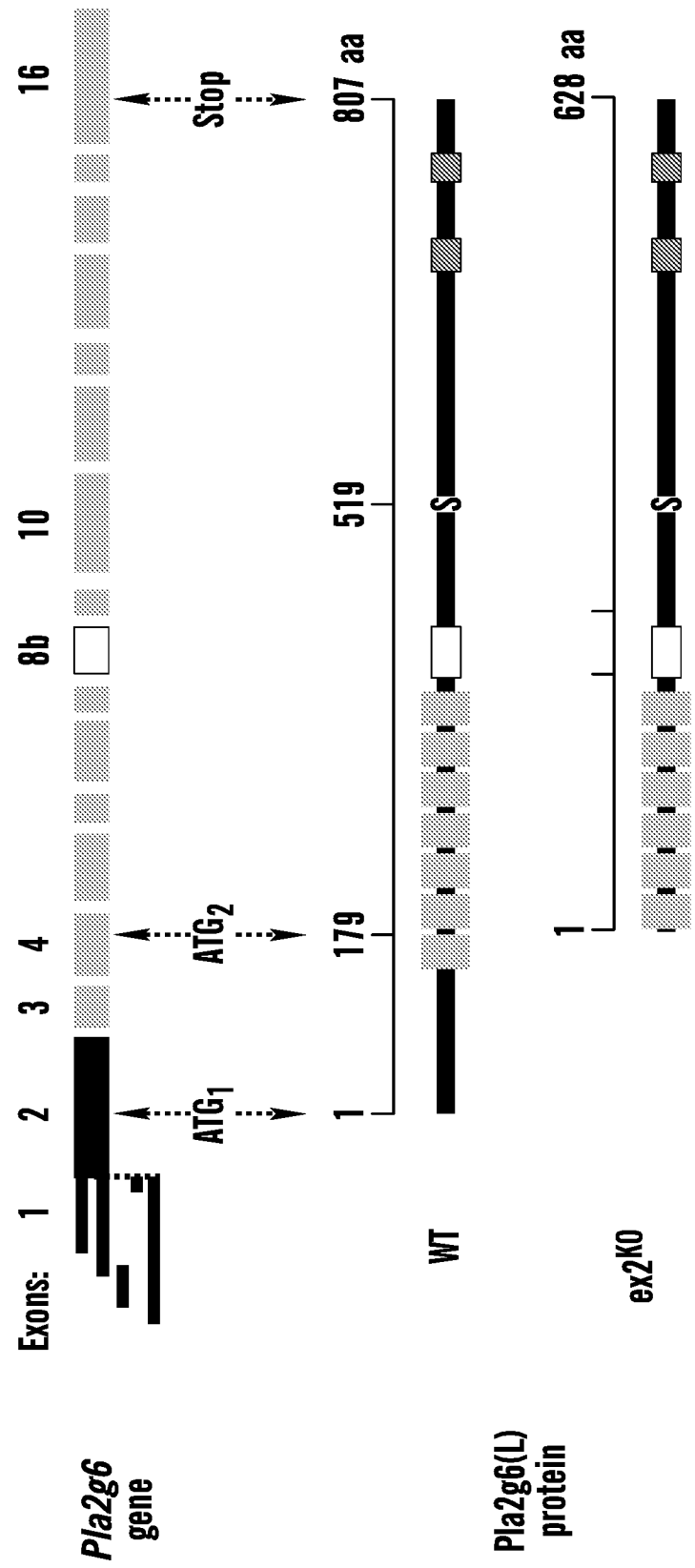

To create a new model suitable for PD studies, the inventors targeted PLA2g6 in a different manner. The inventors tested the hypothesis that if a genetic deletion of the N terminus of PLA2g6 (FIG. 2A) does not affect its catalytic activity (encoded by $S^{519}$-containing catalytic domain in C terminus), it may impair PLA2g6 activation by depleted stores, thus reproducing the specific deficiency that we found in idPD patients. To test this approach, a novel PLA2g6 ex2$^{KO}$ mouse model was created (B6.Cg-Pla2g6$^{\Delta Ex2-VB}$/J), in which exon 2 of Pla2g6 gene was constitutively deleted (see FIG. 2A, FIGS. 12-14, and Methods for details on generation and validation of this model). Deletion of the translation initiation ATG$_1$ (coded by exon 2), did not affect expression of (L) and (S) splice variants of PLA2g6 (FIG. 15), and did not lead to the loss of PLA2g6 protein: the presence of a cryptic ATG$_2$ in Exon 4 initiated translation, and resulted in expression of the truncated ex2$^{KO}$ PLA2g6 protein that lacks the first 178 amino acids in the N terminus (FIG. 16), while the rest of the molecule remained intact.

Analysis of the PLA2g6 activity in mouse embryonic fibroblasts (MEFs) from WT and ex2$^{KO}$ animals revealed that genetic truncation of the N terminus did not affect its catalytic activity (FIG. 2B), but resulted in the loss of PLA2g6 activation by TG-induced depletion of the stores (FIG. 2C). Thus, similar to the cells from idPD and fPD$^{R747W}$ patients, ex2$^{KO}$ mice appear to have deficiency in the store-dependent activation of PLA2g6. It is important to emphasize that preserved catalytic activity of PLA2g6 clearly discriminates this new ex2$^{KO}$ mouse model from other PLA2g6 models[13-18], in which catalytic activity of this enzyme was genetically impaired.

Figure 2D:
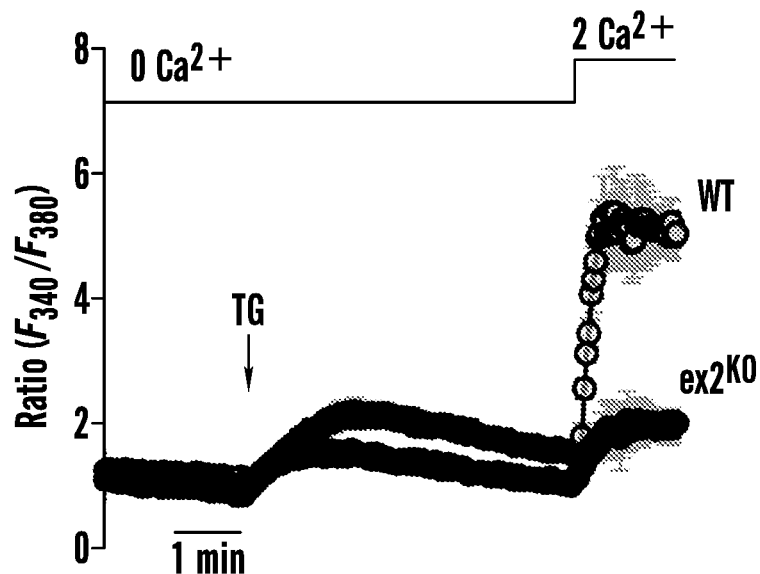
Figure 2E:
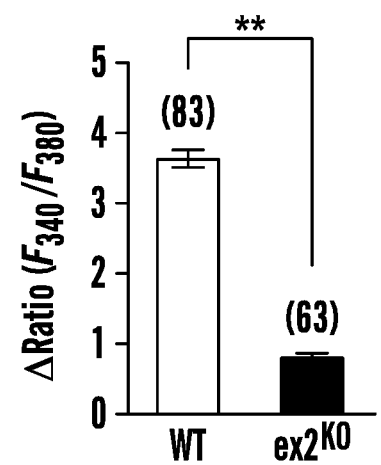
Figure 2F:
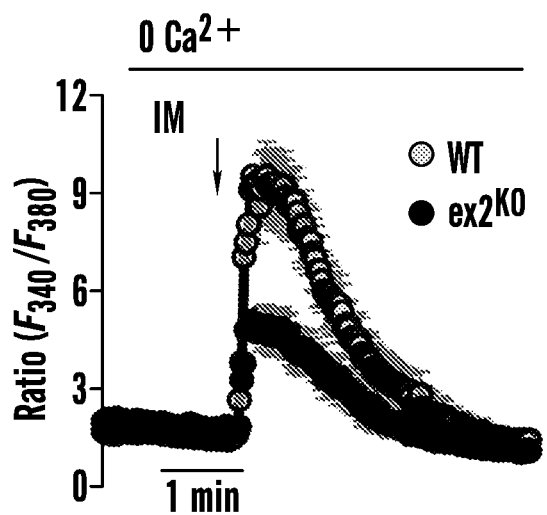
Figure 2G:
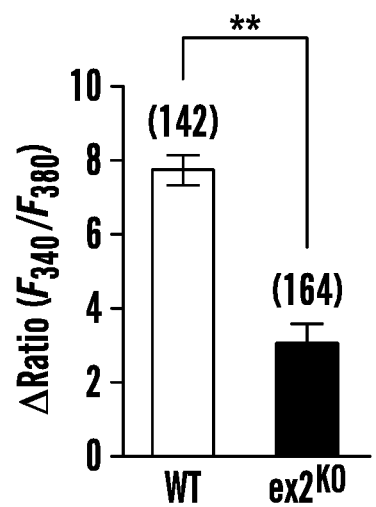
Figures 18A, 18B:
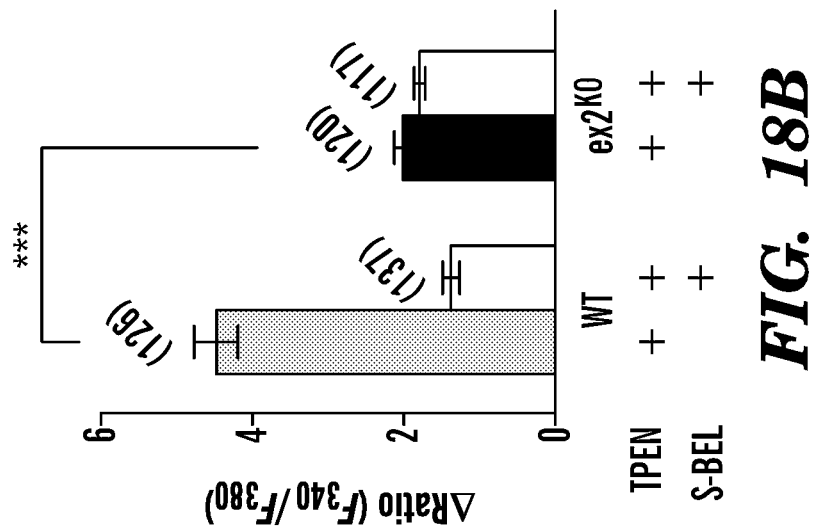
FIGS. 18A-18B show that Impairment of TPEN-induced PLA2g6(L)-dependent store-operated $Ca^{2+}$ entry (SOCE) in primary mouse embryonic fibroblasts (MEFs) from PLA2g6 $ex2^{KO}$ mice.

To test if PLA2g6 ex2$^{KO}$ mice could also mimic the defect of the store-operated $Ca^{2+}$ signaling that the inventors discovered that in fibroblasts from idPD patients, endogenous SOCE was analyzed and compared in MEFs from WT and ex2$^{KO}$ animals. The results of these studies indicated that TG-induced SOCE is significantly impaired in MEFs from ex2$^{KO}$ mice (FIG. 2D, 2E). Similarly, the inventors found that TPEN (a low affinity Ca$^{2+}$ chelator that is known to mimic depletion of Ca$^{2+}$ in ER stores[40,41]) activates PLA2g6 (L)-dependent (BEL-sensitive) SOCE in the cells from WT, but not ex2$^{KO}$ mice (FIG. 18). Consistent with the physiological role of SOCE in refilling of ER Ca$^{2+}$ stores, significant impairment of endogenous SOCE resulted in constitutive depletion of intracellular Ca$^{2+}$ stores in ex2$^{KO}$ cells, as indicated by more than 50% decrease in intracellular Ca$^{2+}$ release caused by ionomycin (IM) (FIG. 2F, 2G). Passive Ca$^{2+}$ release in response to TG application in the absence of extracellular Ca$^{2+}$ (FIG. 2d) was also significantly decreased in ex2$^{KO}$ cells (by 56±5%, p<0.01).

Importantly, primary skin fibroblasts from idPD patients also appear to have significant reduction in IM-induced Ca$^{2+}$ release: the A Ratio ($F_{340}/F_{380}$) was 5.9±0.5 (n=7) in idPD and 8.5±0.9 (n=4) in control patients, respectively (p<0.05).

Therefore, PLA2g6 ex2$^{KO}$ mice where discovered to exhibit major functional deficiencies in store-operated PLA2g6(L)-dependent Ca$^{2+}$ signaling that mirrors the pathological cellular phenotype found in idPD and fPD$^{R747W}$ patients (FIG. 1): MEFs from ex2$^{KO}$ mice (i) retain normal catalytic activity of PLA2g6 (FIG. 2B), (ii) have a major defect in PLA2g6 activation by depleted stores (FIG. 2C, (iii) have a significant impairment of endogenous SOCE, and (iv) show a significant depletion of intracellular Ca$^{2+}$ stores (FIG. 2F, 2G). The PLA2g6 ex2$^{KO}$ mouse model offers a unique tool to determine if and how such cellular deficiencies could lead to PD pathology.

Example 3 iPSC-Derived DA Neurons from PLA2g6 Ex2$^{KO}$ and WT Mice

The role of SOCE in live dopaminergic (DA) neurons is obscure, so the inventor addressed two additional questions: (i) whether SOCE is present in DA neurons, and (ii) if DA neurons from PLA2g6 ex2$^{KO}$ mice had similar defects in SOCE and ER Ca$^{2+}$, as the inventors had discovered in human fibroblasts. To assess the role of PLA2g6 and SOCE in live DA neurons, an iPSC (induced pluripotent stem cell) approach was used to create iPSC-derived A9 midbrain DA neurons[42] from WT and PLA2g6 ex2$^{KO}$ mouse embryonic fibroblasts (see Methods and Data not shown, which showed co-localization of TH with other dopaminergic neuronal proteins (DAT and VMAT2) typical for mature DA neurons.).

Figure 3C:
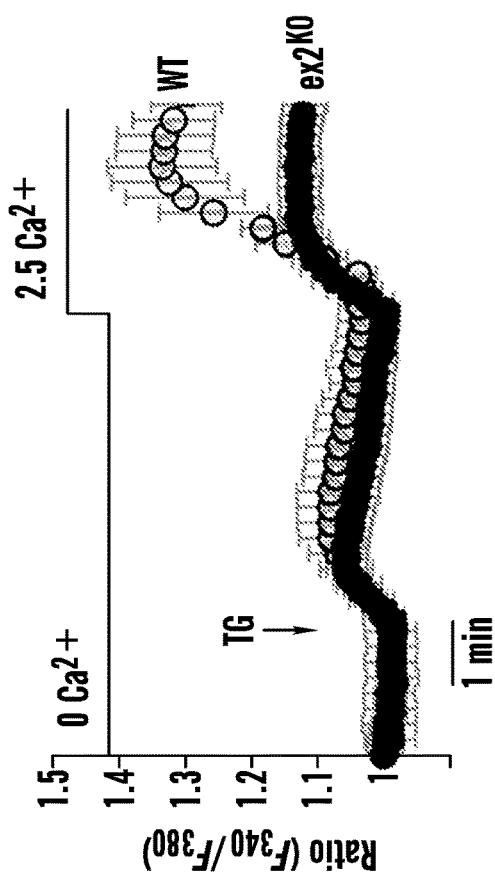
Figure 3E:
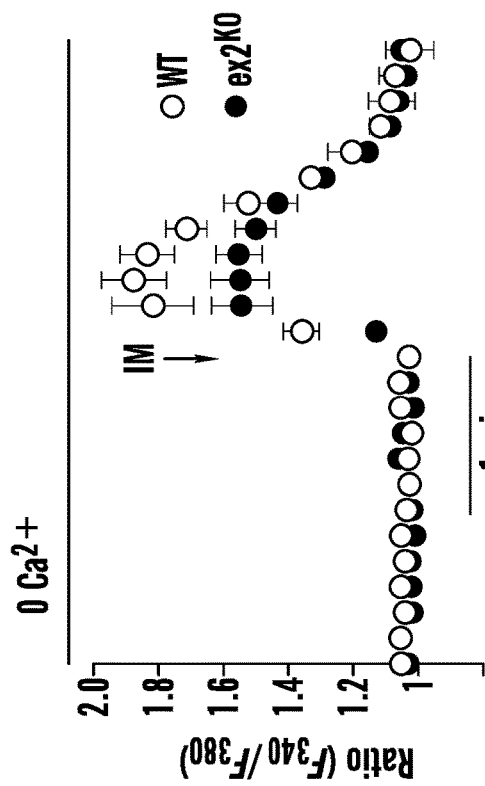

Live cell Ca$^{2+}$ imaging (FIG. 3A, 3B) revealed that iPSC-derived TH-positive (TH+) DA neurons indeed have classical TG-induced Ca$^{2+}$ responses (FIG. 3C), including passive release of Ca$^{2+}$ from the stores and SOCE that could be detected upon Ca$^{2+}$ re-addition. These data present first evidence for SOCE in iPSC-derived DA neurons. Notably, the amplitude of SOCE in DA neurons appeared to be very small compared to SOCE in MEFs under the same experimental conditions: upon Ca$^{2+}$ addition to TG-treated cells ΔRatio was 0.31±0.18 in DA neurons (n=12) vs 2.39±0.16 (n=31) in MEFs. Similarly, IM-induced Ca$^{2+}$ release in DA neurons (FIG. 3e,f) also appeared to be significantly smaller than in MEFs: ΔRatio=0.87±0.03 (n=11) in DA neurons, vs 2.66±0.21 (n=26) in MEFs. Small Ca$^{2+}$ release was consistent with previously acknowledged low Ca$^{2+}$ buffering capacity of intracellular Ca$^{2+}$ stores in DA neurons of SNc[43].

Further, the inventors discovered that SOCE and IM-induced Ca$^{2+}$ store release are significantly impaired in DA neurons from PLA2g6 ex2$^{KO}$ mice (FIG. 3C-3F), emulating the results obtained in MEF cells. Thus, impairment of PLA2g6 translates into significant loss of apparently limited store-operated Ca$^{2+}$ signaling in DA neurons, which could make these cells particularly vulnerable to PLA2g6 and SOCE dysfunction.

PLA2g6 Ex2$^{KO}$ Mice Develops Age-Dependent PD-Like Phenotype

Figure 4B:
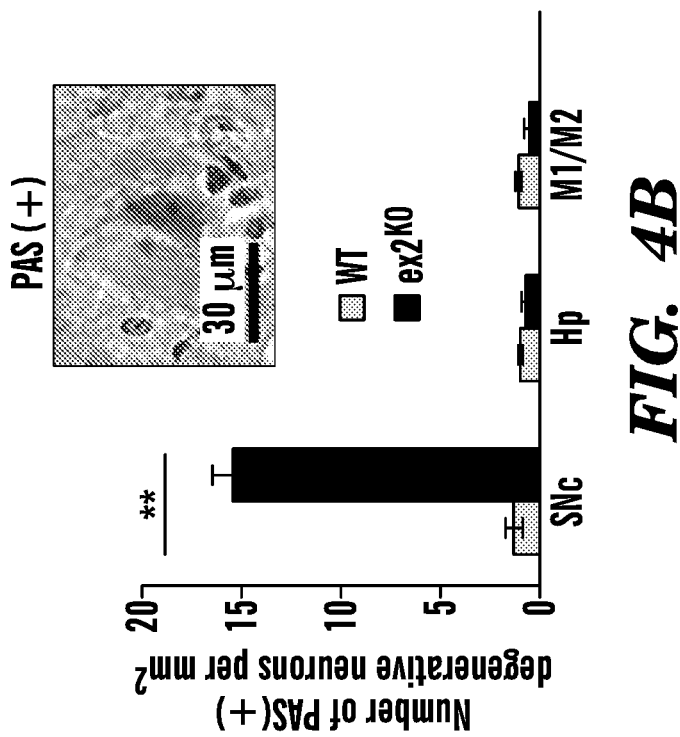
FIGS. 4A-4I shows the progressive loss of dopaminergic neurons and age-dependent Parkinson's disease-like motor dysfunction in $ex2^{KO}$ mice.
Figure 4A:
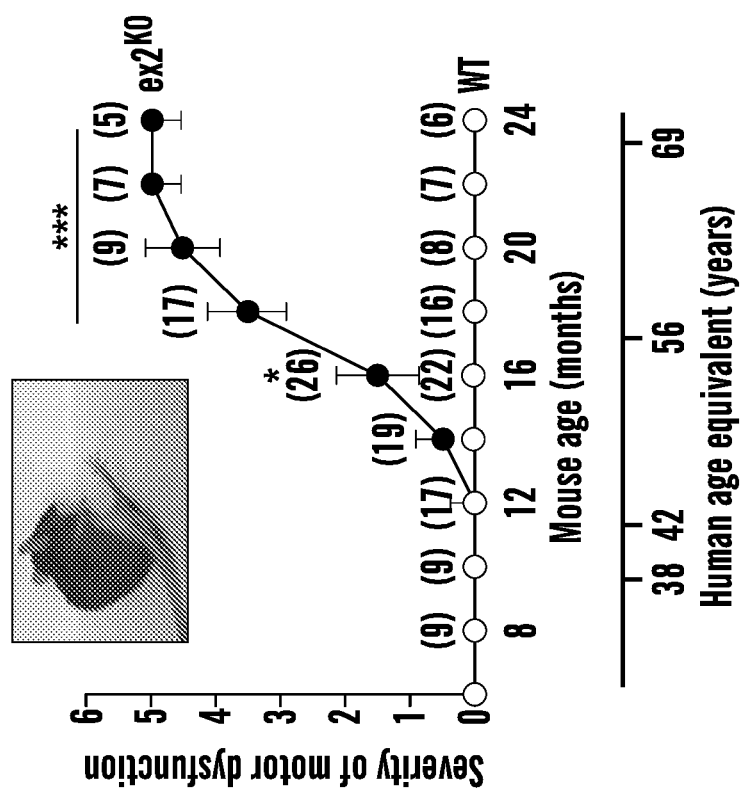
Figure 4C:
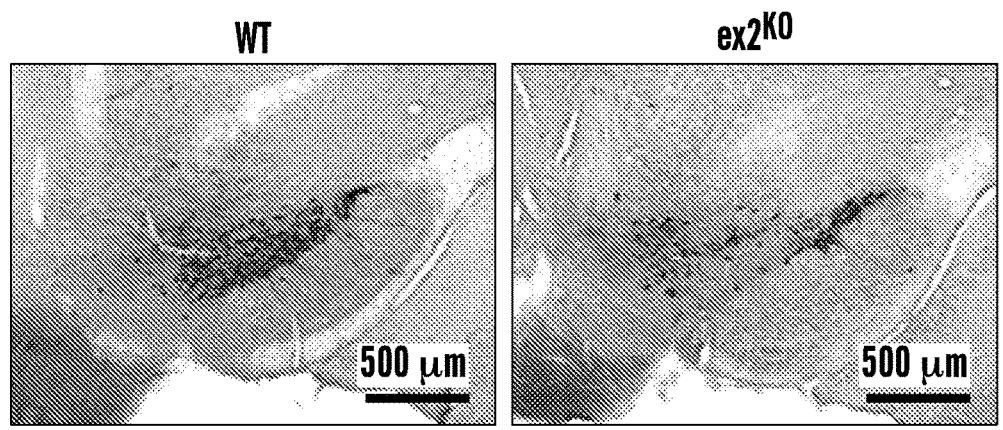
Figure 4D:
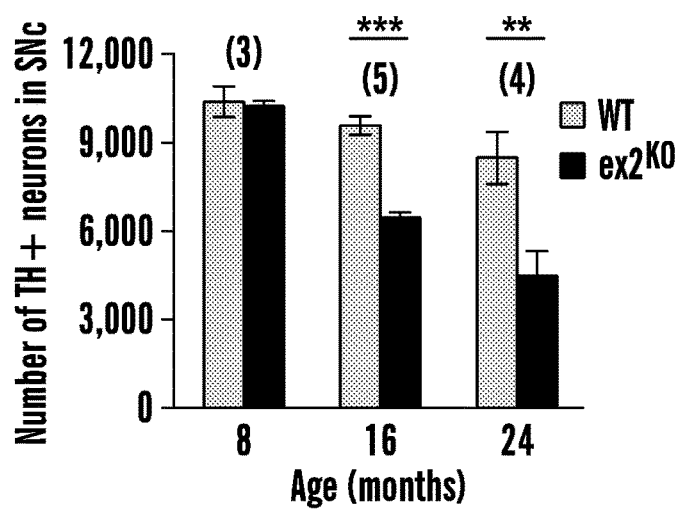
Figure 4E:
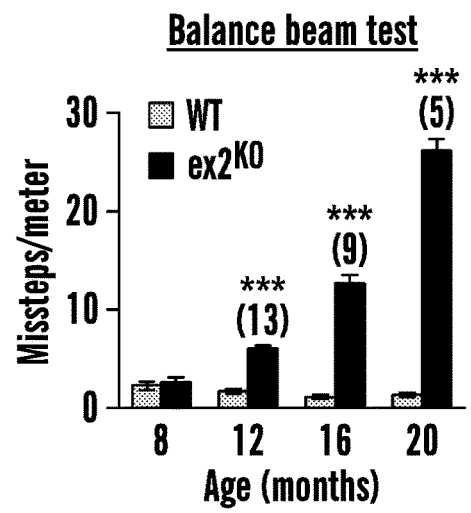
Figure 19A:
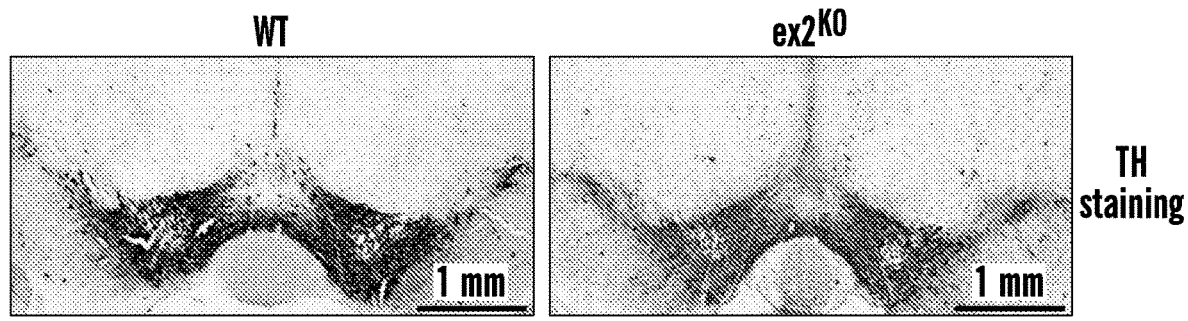
FIGS. 19A-19B show representative images of VTA and SNc areas of the brain of WT and $ex2^{KO}$ littermates (24 months old).
Figure 19B:
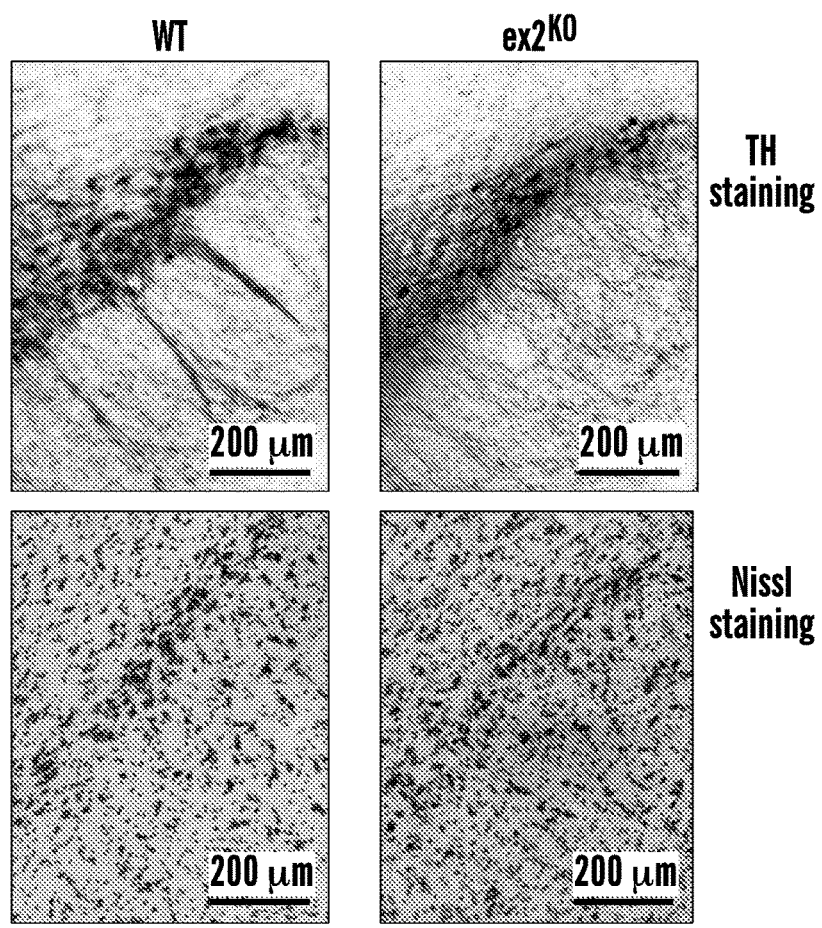

Ageing is a primary risk factor for idiopathic PD[44], and strikingly, all homozygous PLA2g6 ex2$^{KO}$ mice (males and females) developed progressive age-dependent motor dysfunction (FIG. 4A) at an age range that aligns with that typical of idiopathic PD in humans. WT and heterozygous littermates remained normal throughout the same observation period, consistent with autosomal recessive inheritance of PARK14 (PLA2g6)-associated familial PD in humans. Analysis of the SNc area of the brain from aged animals revealed a significant increase in the number of degenerative (periodic acid-Schiff, PAS)-positive neurons (FIG. 4b) in the ex2$^{KO}$ animals, and Nissl staining suggested potential loss of DA neurons (FIG. 19). The results of the blinded stereological analysis of SNc confirmed progressive age-dependent loss of tyrosine hydroxylase (TH)-positive DA neurons (FIG. 4c,d and FIG. 19-20): while the number of TH+ neurons was the same in 8-month old ex2$^{KO}$ and WT animals (consistent with no motor dysfunction in this preclinical stage), over 30% of DA neurons in SNc of Ex2$^{KO}$ mice was lost by 16 months (early clinical), and over 50% was lost by 24 months of age (late clinical stage). Notably, analysis of the hippocampus and M1/M2 areas of the temporal cortices revealed no signs of neurodegeneration in ex2$^{KO}$ animals (FIG. 4b), demonstrating that motor dysfunction and DA neuronal loss in SNc was not the result of a widespread nonspecific neurodegeneration.

Figure 4F:
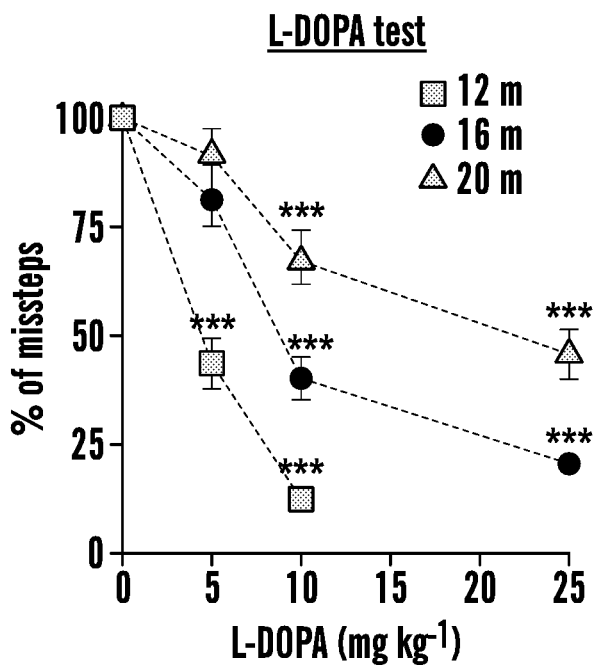
Figure 4G:
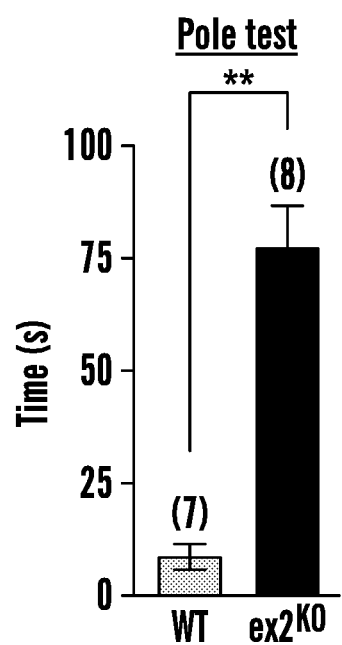
Figure 4H:
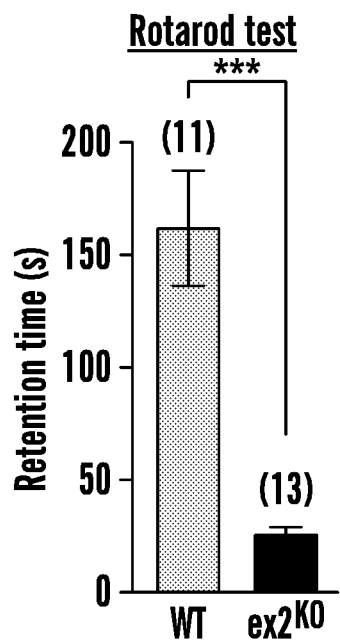
Figure 4I:
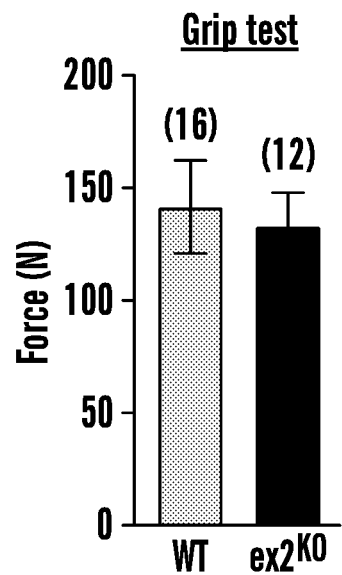

Progressive loss of DA neurons in SNc is known to be a major factor in motor dysfunction in human PD[45]. Similarly, ex2$^{KO}$ animals developed a strong age-dependent PD-like motor dysfunction, which was validated using an array of the standard behavioral tests (FIG. 4e-i). The balance beam test (FIG. 4e) showed impairment of motor coordination and progressive age-dependent increase in the number of missteps made by ex2$^{KO}$ mice, with no change in performance of ageing WT animals. Importantly, the dopaminergic nature of motor dysfunction was confirmed by the L-DOPA test (FIG. 4f): administration of L-DOPA dramatically improved motor coordination of ex2$^{KO}$ animals in age and dose dependent manner, which was similar to L-DOPA effects in humans[46]. FIG. 4F shows that while the lowest dose of L-DOPA (5 mg/kg body weight) produced a dramatic improvement in the balance beam performance (60% reduction in the number of missteps) of the 12-month old ex2$^{KO}$ animals (early clinical stage), significantly higher doses were required to produce similar effects at more advanced clinical stages in 16- and 20-months old animals. The pole (FIG. 4g) and rotarod tests (FIG. 4h) further confirmed significant PD-like motor dysfunction in ex2$^{KO}$ animals. Grip test (FIG. 4i) showed no difference between WT and ex2$^{KO}$ animals, thus demonstrating that motor dysfunction in ex2$^{KO}$ animals is not caused by the loss of the strength in their limbs. Thus, the inventors have developed a PLA2g6 ex2$^{KO}$ mouse model which demonstrates progressive loss of DA neurons in SNc and age-dependent L-DOPA-sensitive PD-like motor dysfunction, which mimics iPD in ageing humans.

Example 4

Autophagic Dysfunction in DA Neurons of PLA2g6 $ex2^{KO}$ Mice

Figure 5B:
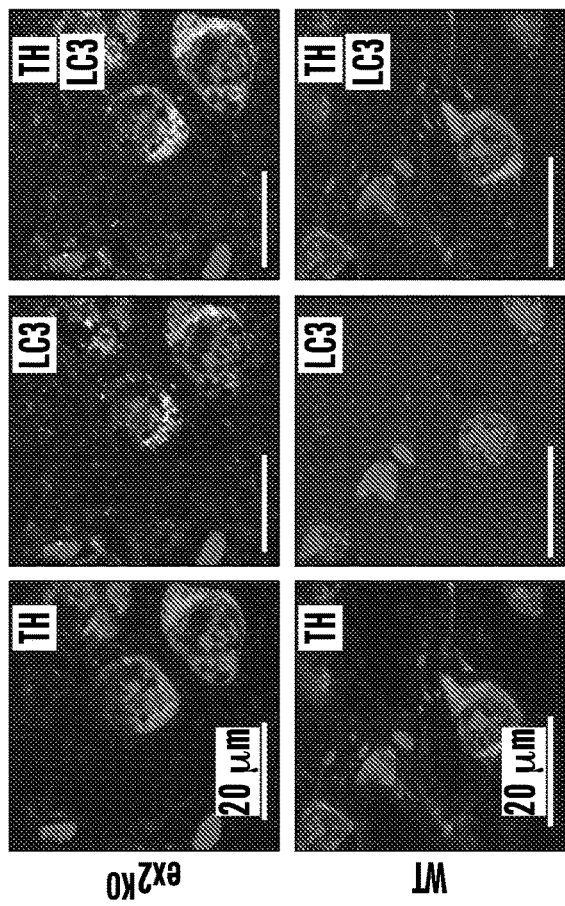
Figure 5A:
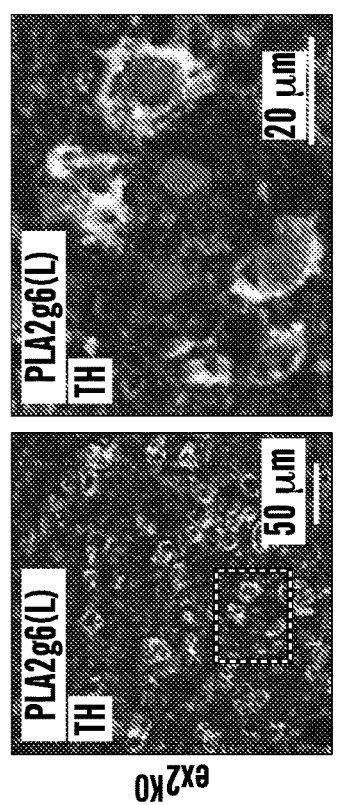
Figure 5C:
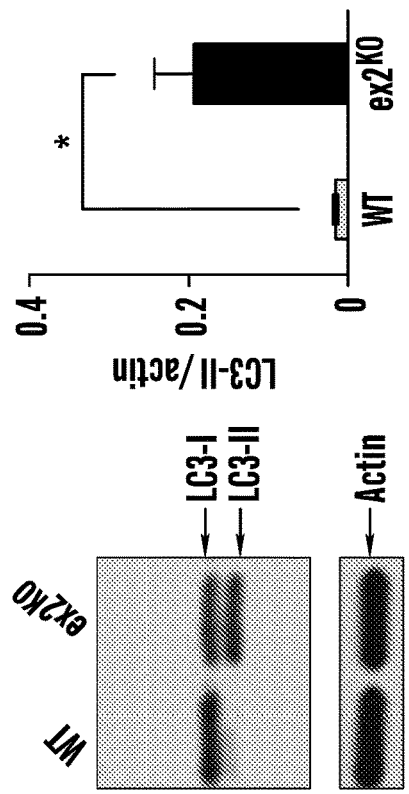
Figure 21A:
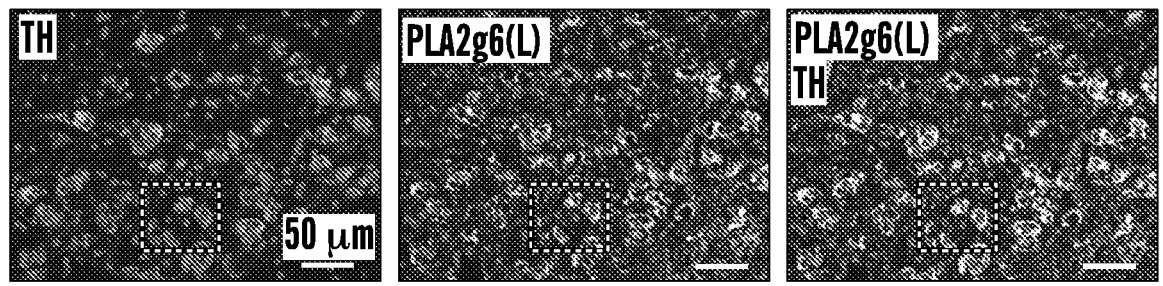
FIGS. 21A-21C show high level of PLA2g6(L) protein in dopaminergic TH+ neurons in SNpc of $ex2^{KO}$ mice.
Figure 21B:
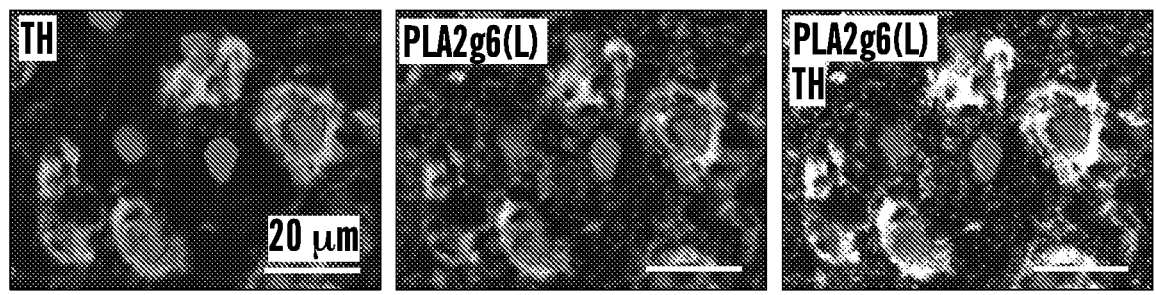
Figure 21C:
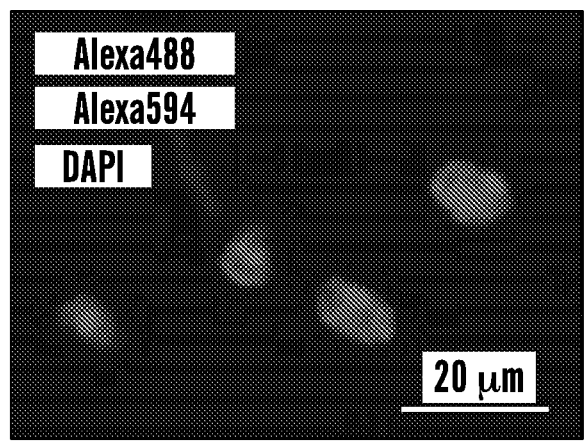

The inventors next assessed the question of how does impairment of store-operated $Ca^{2+}$ signaling lead to demise of DA neurons in SNc? More specifically, the inventors assessed if a disruption in store-operated $Ca^{2+}$ signaling trigger a cellular pathology that is already established as a hallmark of human PD? Analysis of the SNc area of the brain in $ex2^{KO}$ mice revealed that PLA2g6(L) protein is highly expressed in specific TH+DA neurons (FIG. 5a and FIG. 21), demonstrating that DA neurons in SNc may have a particularly high demand for PLA2g6(L), and impairment of the PLA2g6(L)-dependent SOCE function (FIG. 3) is particularly stressful for these neurons. Closer analysis of TH+ neurons in SNc of PLA2g6 $ex2^{KO}$ mice revealed that DA neurons experience significant autophagic dysfunction, as shown in FIG. 5b. The inventors also demonstrated the accumulation of endogenous LC3 in tyrosine hydroxylase (TH+) neurons in SNpc of ex2KO, but not WT 16-month old mice. (data not shown), demonstrating that TH positive neurons in SNc in $ex2^{KO}$ have significant accumulation of LC3 (microtubule-associated protein 1A/1B-light chain 3, established marker of autophagic flux), which is not found in WT animals. The increased autophagosome numbers in $ex2^{KO}$ mice, which can result from impaired autophagic flux, was also manifested by a significant increase in the ratio of LC3-II/actin (FIG. 5c). Thus, in vivo DA neurons in the SNc of PLA2g6-deficient $ex2^{KO}$ mice experience marked autophagic dysfunction, which is one of the major hallmarks of human PD[47-51].

Causal Link Between PLA2g6, SOCE, ER $Ca^{2+}$ and Autophagy

Figure 22A:
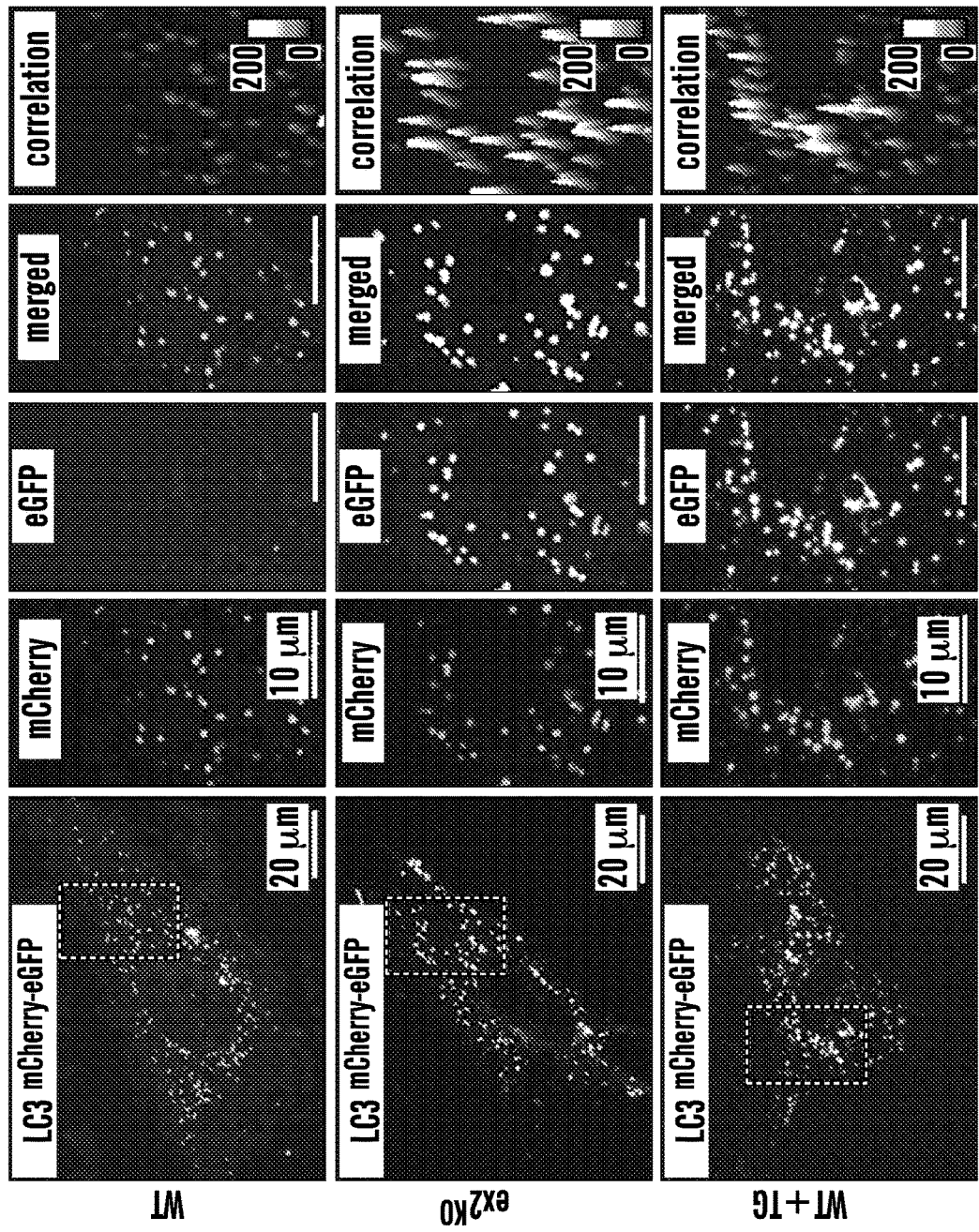
FIG. 22A-22C shows the analysis of LC3$^{mCherry/eGFP}$ autophagic flow in WT and $ex2^{KO}$ MEFs, and WT MEFs treated with thapsigargin.
Figure 22B:
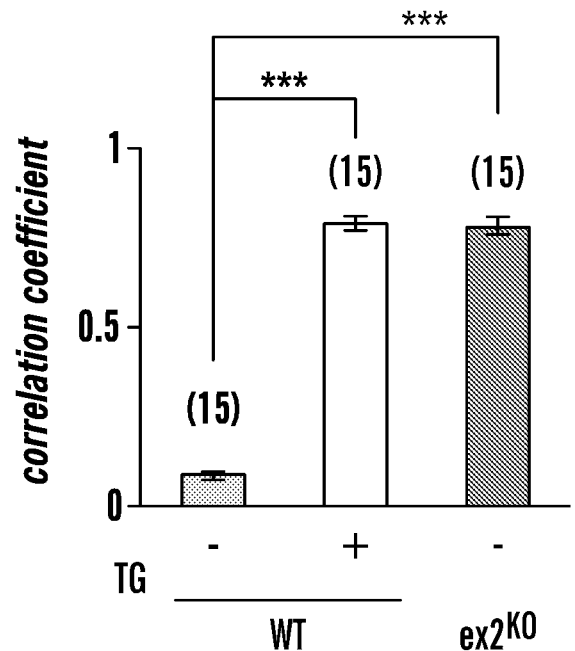
Figure 22C:
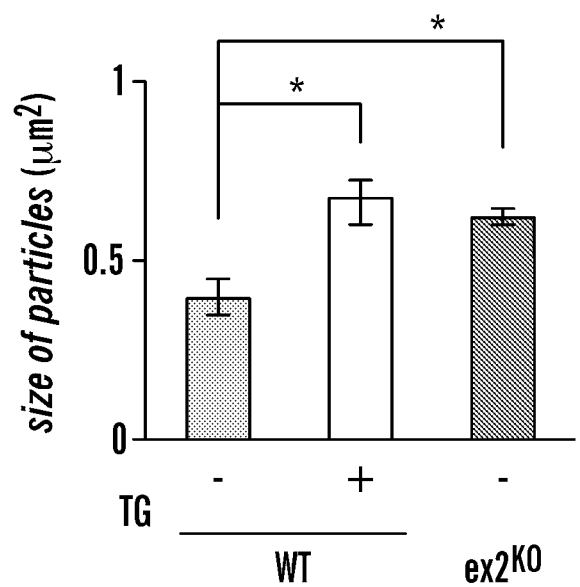
Figure 23A:
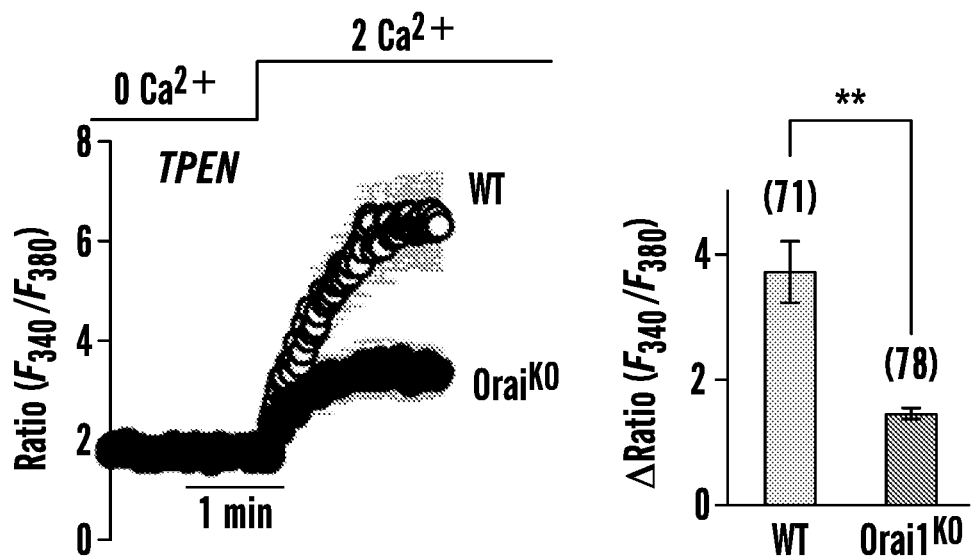
FIG. 23A-23E shows that primary MEFs from Orai1 knockout (Orai1$^{KO}$) mice have impaired SOCE, depleted ER Ca$^{2+}$ stores and significant autophagic dysfunction, which mimic deficiencies found in MEFs from PLA2g6 ex2$^{KO}$ mice.
Figure 23B:
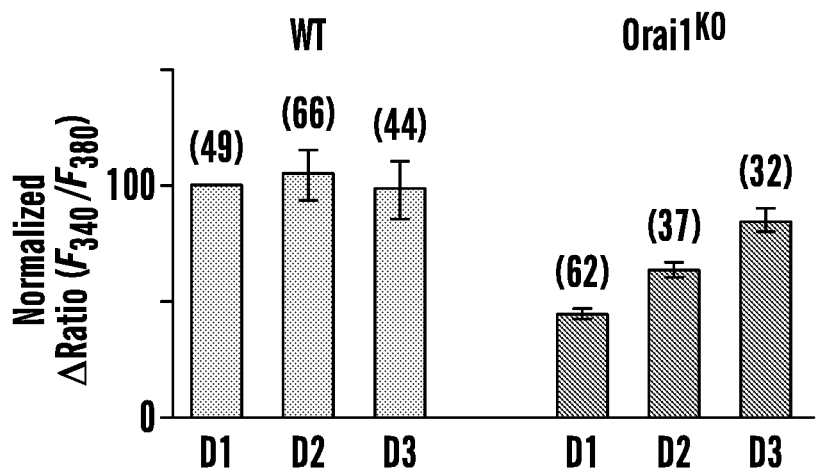
Figure 23C:
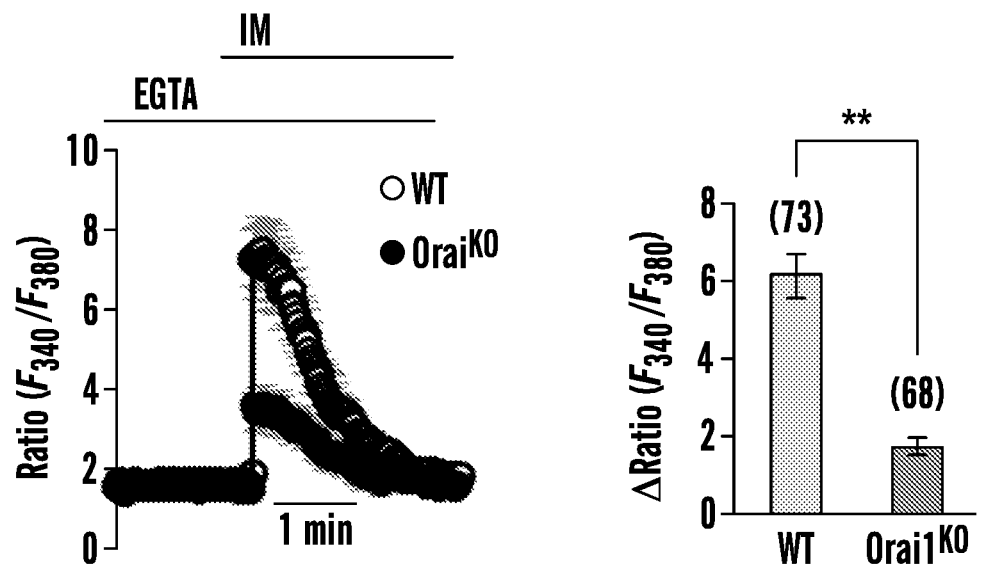
Figure 23D:
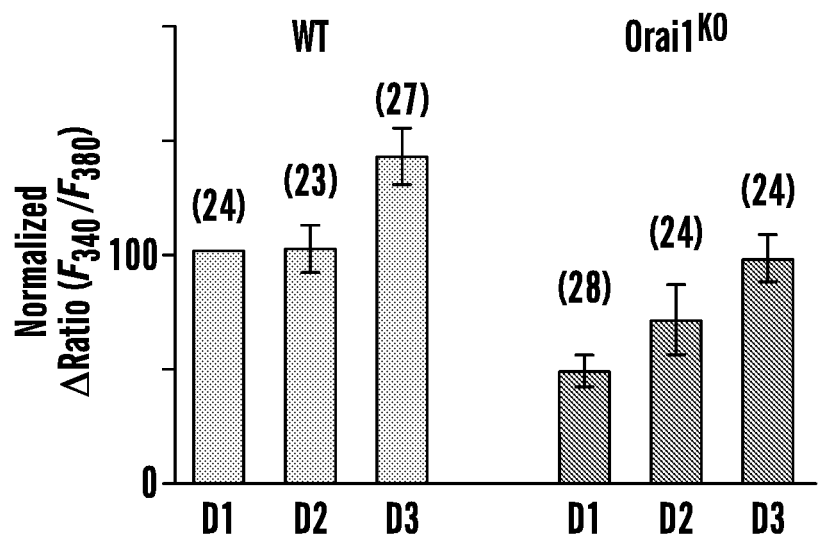
Figure 23E:
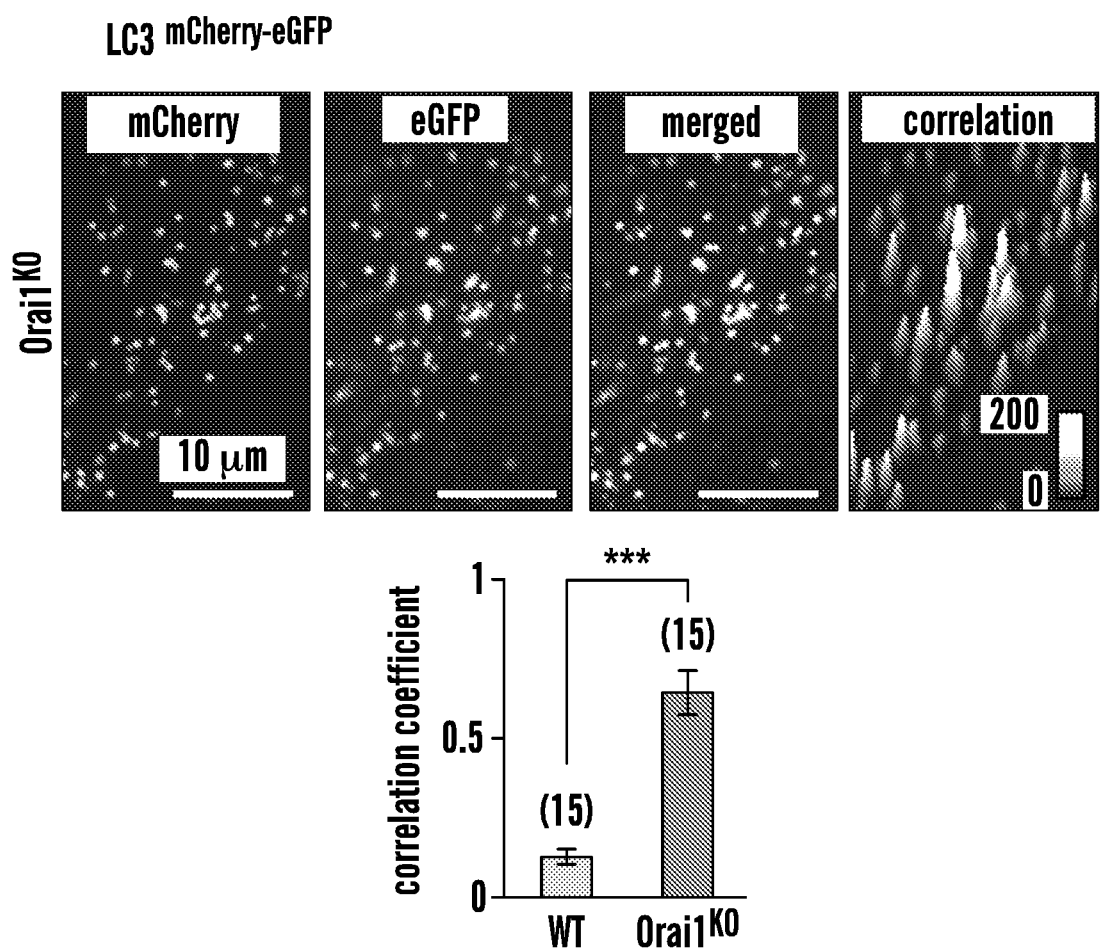

To better understand a previously unknown association of PLA2g6(L)-dependent $Ca^{2+}$ signaling with autophagy, primary MEFs from WT and $ex2^{KO}$ mice were used as a model for live cell imaging and molecular rescue studies. Using a tandem tagged $LC3^{mCherry-eGFP}$ as a marker of autophagic flow[52], the inventors confirmed significant autophagic dysfunction in the cells from $ex2^{KO}$ animals. Image analysis of MEFs expressing $LC3^{mCherry-eGFP}$ (FIG. 5d) revealed that in WT cells this marker successfully reaches lysosomes, where the eGFP (but not mCherry) signal is quenched by the high acidic environment, resulting in a loss of GFP fluorescence. In contrast, the eGFP signal remained very prominent and spatially colocalized with mCherry in autophagosomes of $ex2^{KO}$ cells. Correlation analysis of mCherry and eGFP fluorescence confirmed very significant differences between $ex2^{KO}$ and WT cells: in $ex2^{KO}$ cells, the fluorescent signals were strongly correlated (FIG. 5e) and the size of LC3-containing particles was larger (FIG. 22) than in WT cells. Autophagic arrest in $ex2^{KO}$ cells resembled the effects of prolonged TG treatment in WT MEFs (FIG. 22), which was consistent with recent report[53] of TG-induced autophagic arrest due to impairment of autophagosome fusion with lysosomes. There is also a possibility that fusion may occur, but lysosomal acidification may be defective.

Interestingly, a similar autophagic dysfunction was also produced by the targeted deletion of the Orai1 channel (FIG. 5f), which is a critical component of SOCE machinery located downstream from PLA2g6[25,26]. FIG. 23 demonstrate that MEF cells from $Orai1^{KO}$ mice[32,54] have significant impairment of SOCE, depletion of ER $Ca^{2+}$ stores and autophagic dysfunction, which closely mimic deficiencies in PLA2g6 $ex2^{KO}$ cells. Thus, similar autophagic arrest can be produced by genetic deletion of Orai1, or impairing PLA2g6 activation, or inhibiting SERCA-dependent refilling of the stores with TG. Remarkably, while all these interventions cause depletion of ER $Ca^{2+}$ stores, only $Orai1^{KO}$ and $ex2^{KO}$ inhibit SOCE, while TG activates it. Thus, depletion of $Ca^{2+}$ stores (rather than simple loss of SOCE) seems to be the trigger for autophagic dysfunction.

Example 5

To verify a causative role of PLA2g6 in impairment of the store-operated $Ca^{2+}$ signaling and autophagic dysfunction, and to further link it to human PD, two molecular approaches were used. First, molecular rescue experiments were performed in $ex2^{KO}$ MEFs (FIG. 6a-g) to determine if expression of WT PLA2g6 could recover normal store-operated $Ca^{2+}$ signaling and autophagic function. Second, the inventor tested if expression of a PLA2g6 mutant that is associated with human familial PD could impair normal function of WT cells (FIG. 6h-n).

Figure 6A:
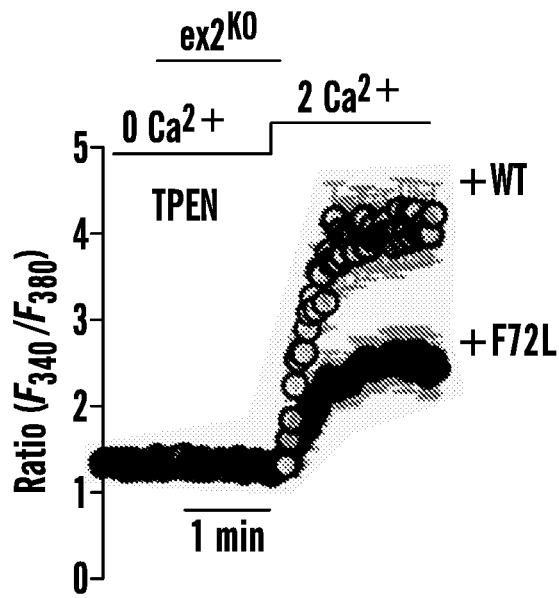
FIGS. 6A-6N show the relationship between PLA2g6(L)-dependent $Ca^{2+}$ signaling and autophagic dysfunction, and its relevance to human PD.
Figure 6B:
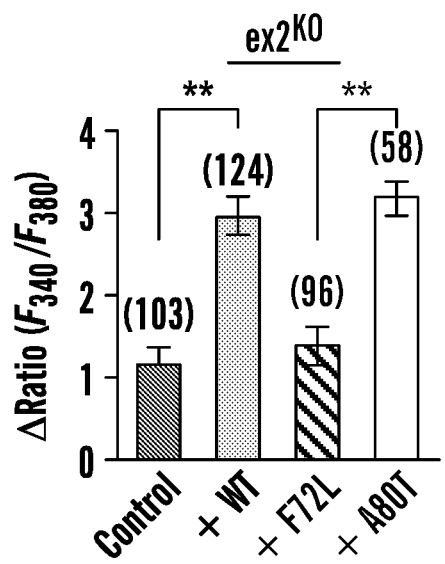
Figure 6C:
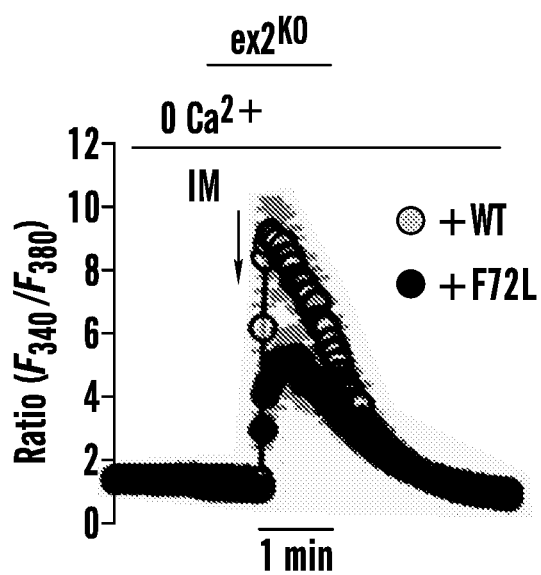
Figure 6D:
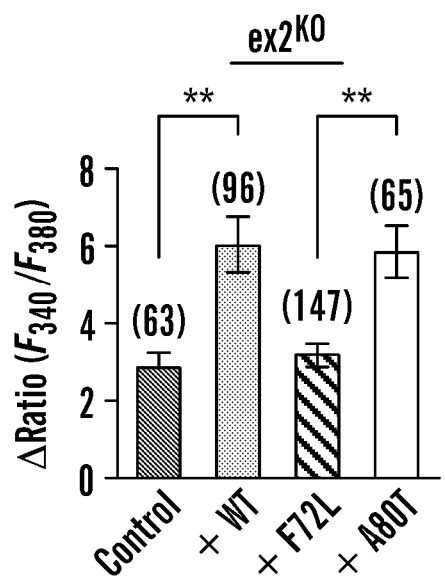
Figure 6E:
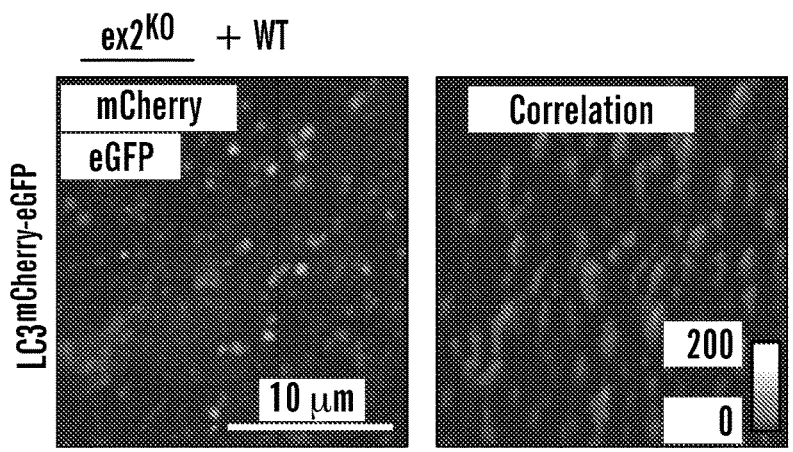
Figure 6F:
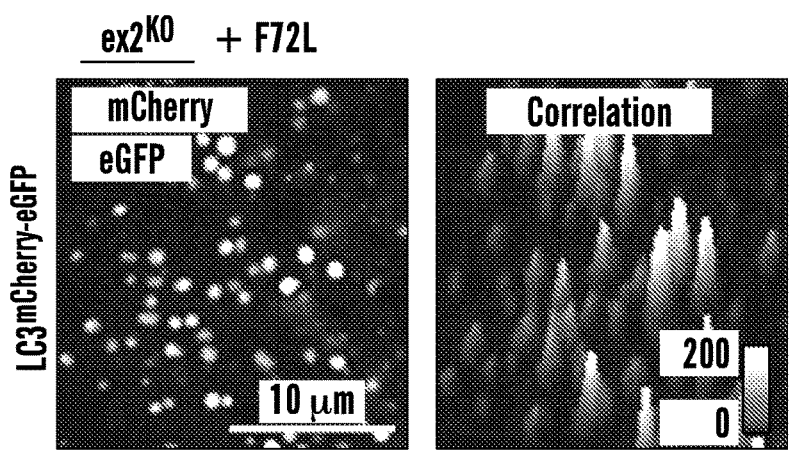
Figure 6G:
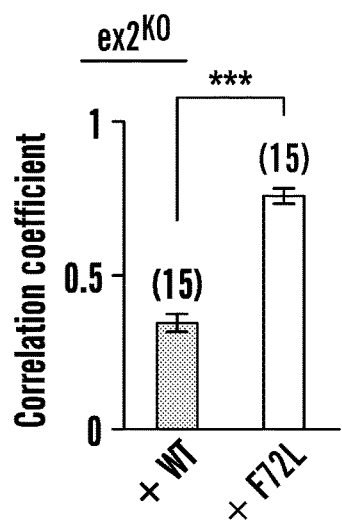
Figure 24A:
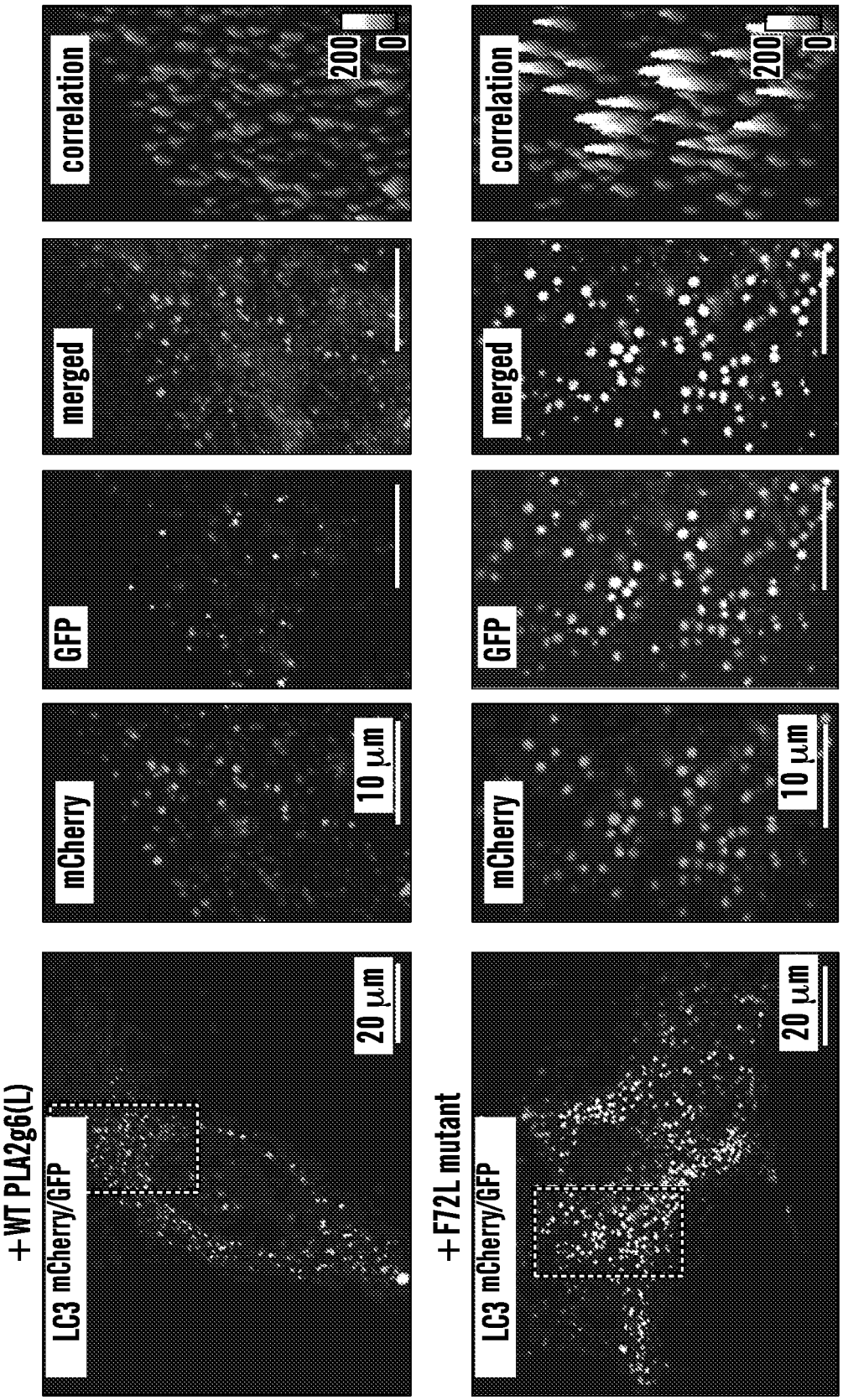
FIGS. 24A-24C show the rescue of LC3$^{mCherry/eGFP}$ autophagic flow in ex2$^{KO}$ MEFs by WT PLA2g6(L), but not F72L mutant.
Figure 24B:
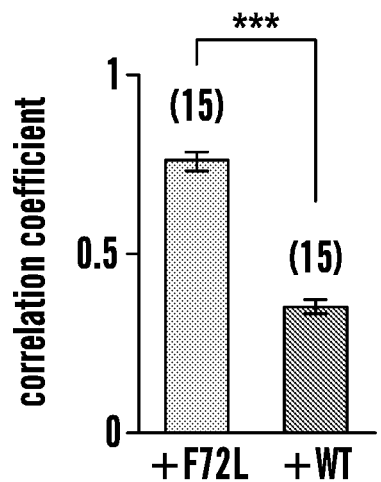
Figure 24C:
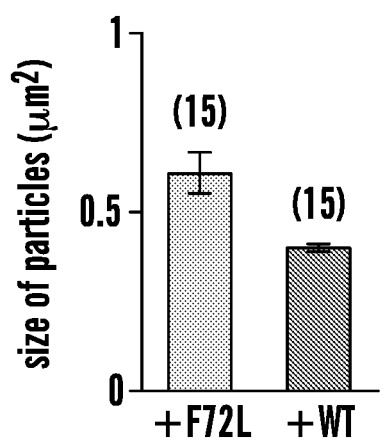

It was discovered that deficient SOCE and depleted $Ca^{2+}$ stores in $ex2^{KO}$ cells can be effectively rescued by simple expression of the functional PLA2g6(L) (FIG. 6a,d). Remarkably, restoration of SOCE and $Ca^{2+}$ stores by WT PLA2g(L) was also sufficient to rescue autophagic flow and restore processing of $LC3^{mCherry-eGFP}$ (FIG. 6e,g and FIG. 24). Remarkably, expression of PLA2g6(L) that carries human familial PD mutation[6] (F72L, located in N terminus of PLA2g6) failed to recover SOCE, or refill $Ca^{2+}$ in the stores, and did not restore autophagic function (FIG. 6a-g and FIG. 24). In contrast, the A80T mutant, which is not associated with human PD was able to fully restore normal $Ca^{2+}$ signaling function (FIG. 6b,d).

Figure 6H:
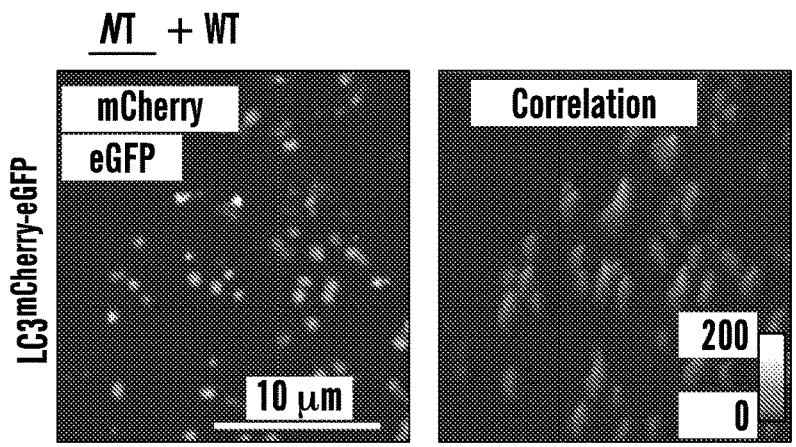
Figure 6I:
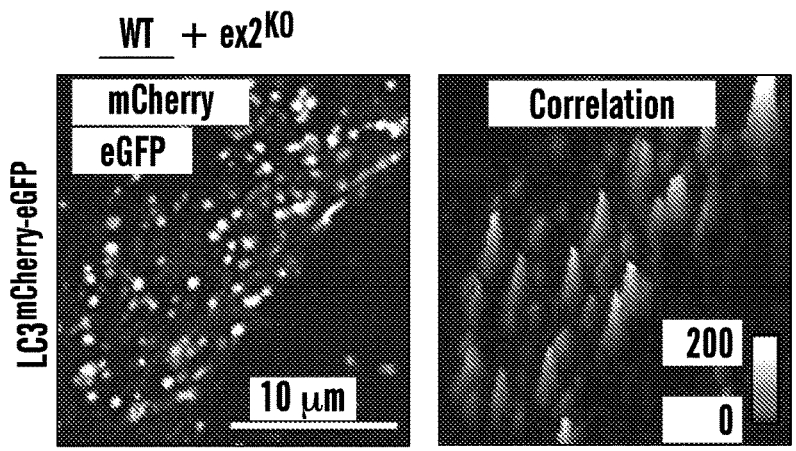
Figure 6J:
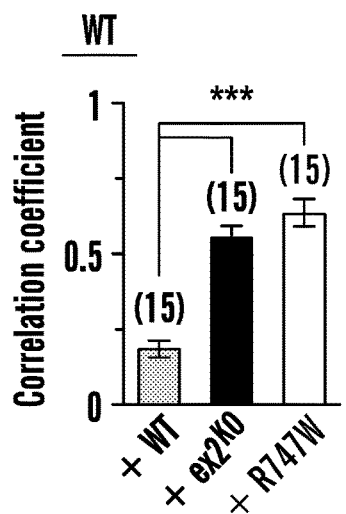
Figure 6K:
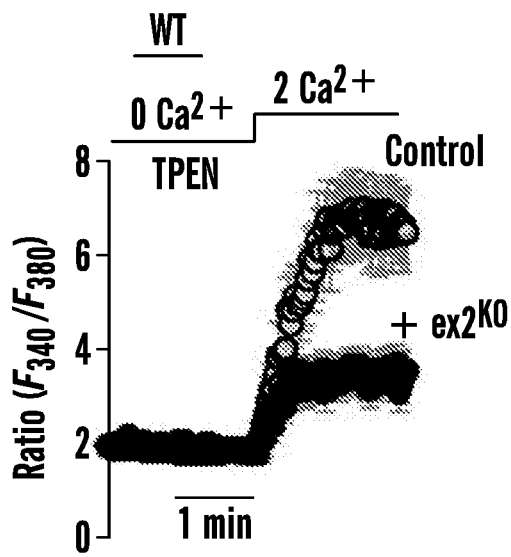
Figure 6L:
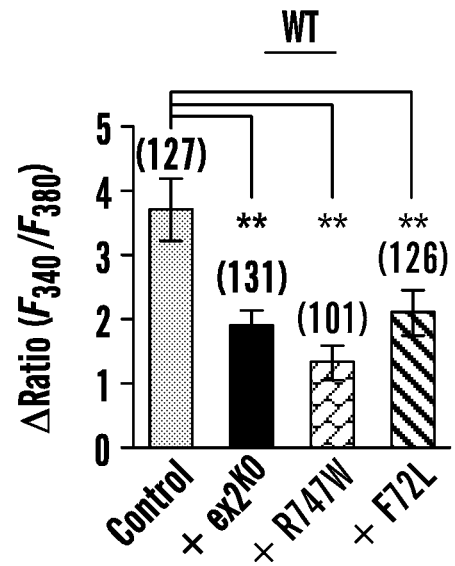
Figure 6M:
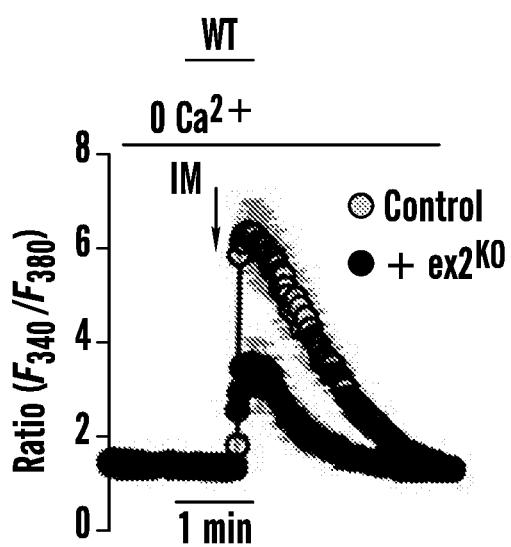
Figure 6N:
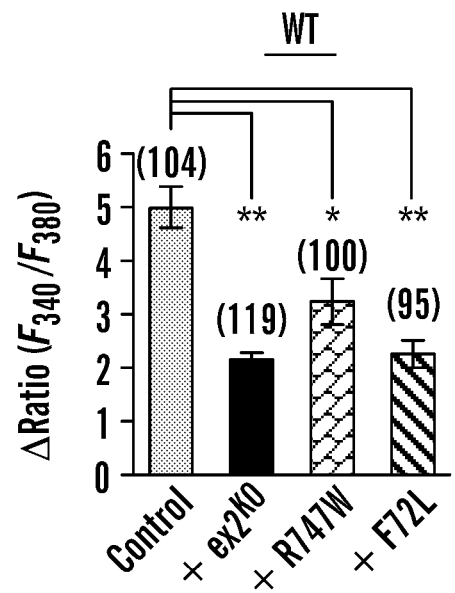
Figure 25B:
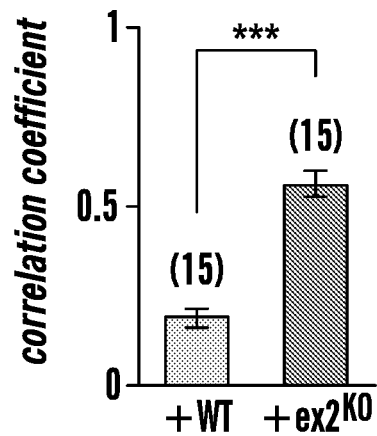
Figure 25C:
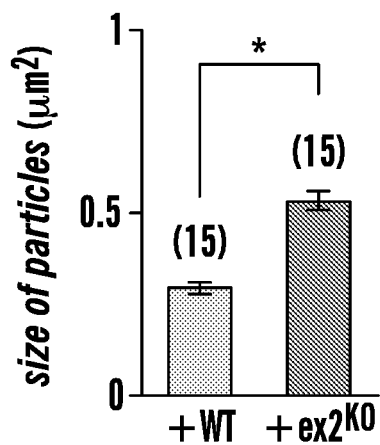

To test if human PD-associated mutations in PLA2g6/PARK14 indeed may cause targeted impairment of the store-operated $Ca^{2+}$ signaling leading to autophagic dysfunction, the effects of acute expression of F72L and R747W mutants of PLA2g6(L) were tested in WT MEFs. FIGS. 6K-6 N demonstrate that these PD-associated mutants can indeed cause impairment of SOCE, depletion of the stores and impairment of autophagic flux. Importantly, the pathological effects of human PD-associated mutants were identical to those produced by expression of the N-terminally truncated PLA2g6(L) that mimics $ex2^{KO}$ deficiency in our mouse model: expression of $ex2^{KO}$ protein effectively impaired SOCE (FIG. 6k,l), depleted $Ca^{2+}$ stores (FIG. 6m,n), and lead to significant autophagic dysfunction (FIG. 6h,i,j, and FIG. 25). The effects caused by overexpression of these mutants were similar to what we found in MEFs from $ex2^{KO}$ mice (FIG. 2d-g and FIG. 4d-e), and in fibroblasts from the $fPD^{R747W}$ patient. Thus, targeted impairment or restoration of PLA2g6 protein indeed can respectively impair, or rescue store-operated $Ca^{2+}$ signaling and autophagic function, further demonstrating direct association and leading role of PLA2g6 in these cellular events.

PLA2g6(L) can Rescue SOCE and Autophagy in idPD Cells

The results of the genetic and molecular manipulations with PLA2g6 validated a link between PLA2g6 deficiency, store-operated $Ca^{2+}$ signaling and autophagy, and demonstrated that two PLA2g6(L) mutations associated with human familial PD can cause impairment in SOCE, depletion of the stores and autophagic dysfunction. To determine if a similar sequence of pathological events could be associated with idiopathic PD, live cell imaging and molecular rescue experiments were performed in primary human skin fibroblasts from idPD and control patients.

Figure 7A:
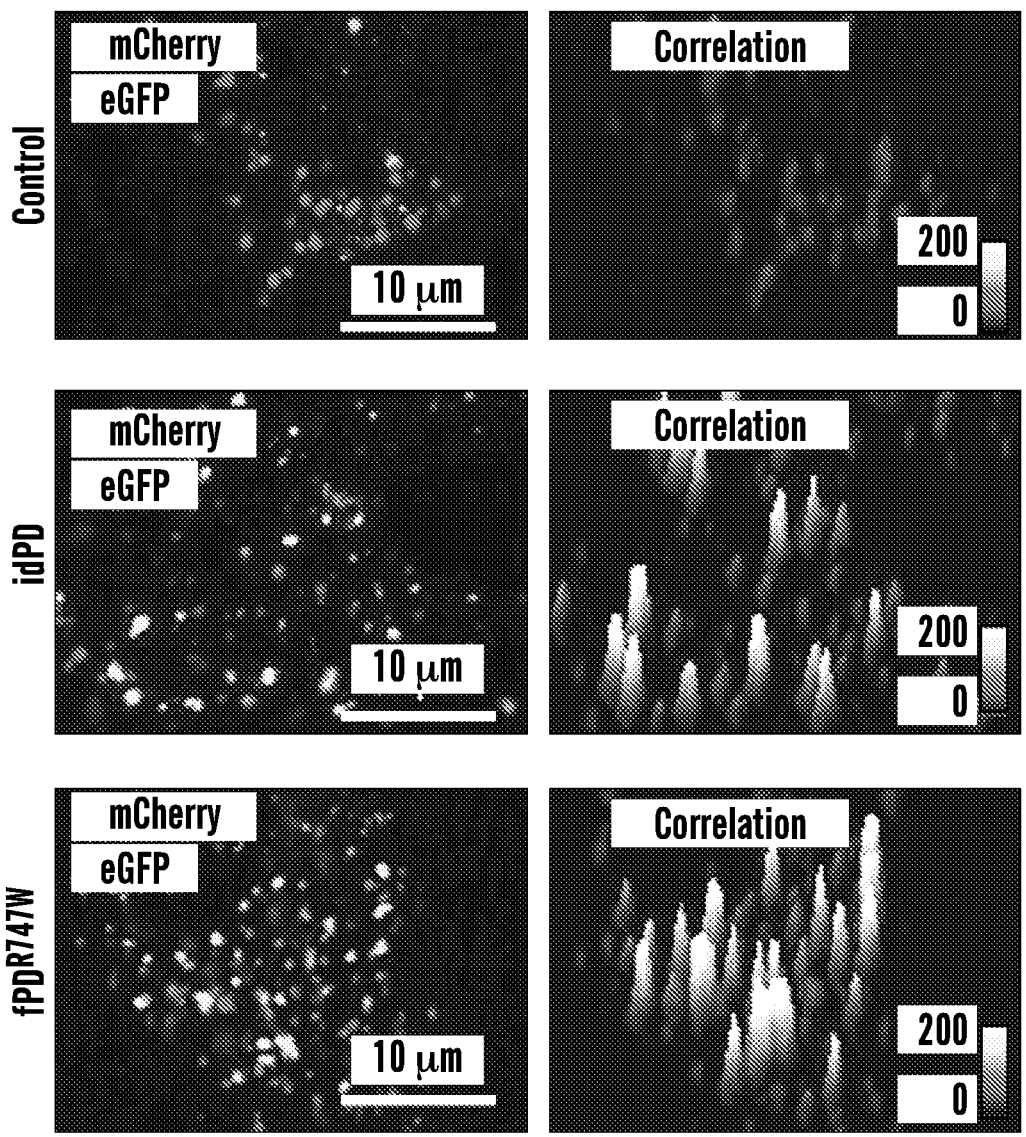
FIGS. 7A-7E show that PARK14 (PLA2g6)-dependent $Ca^{2+}$ signaling as a novel determinant of Parkinson's disease.
Figure 7B:
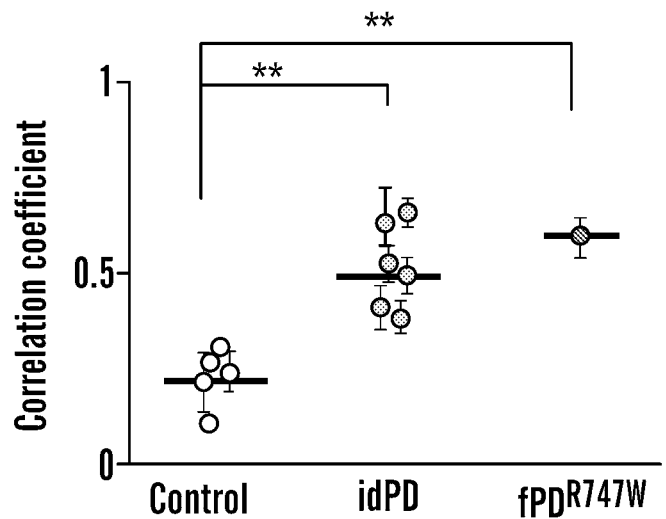
Figure 26A:
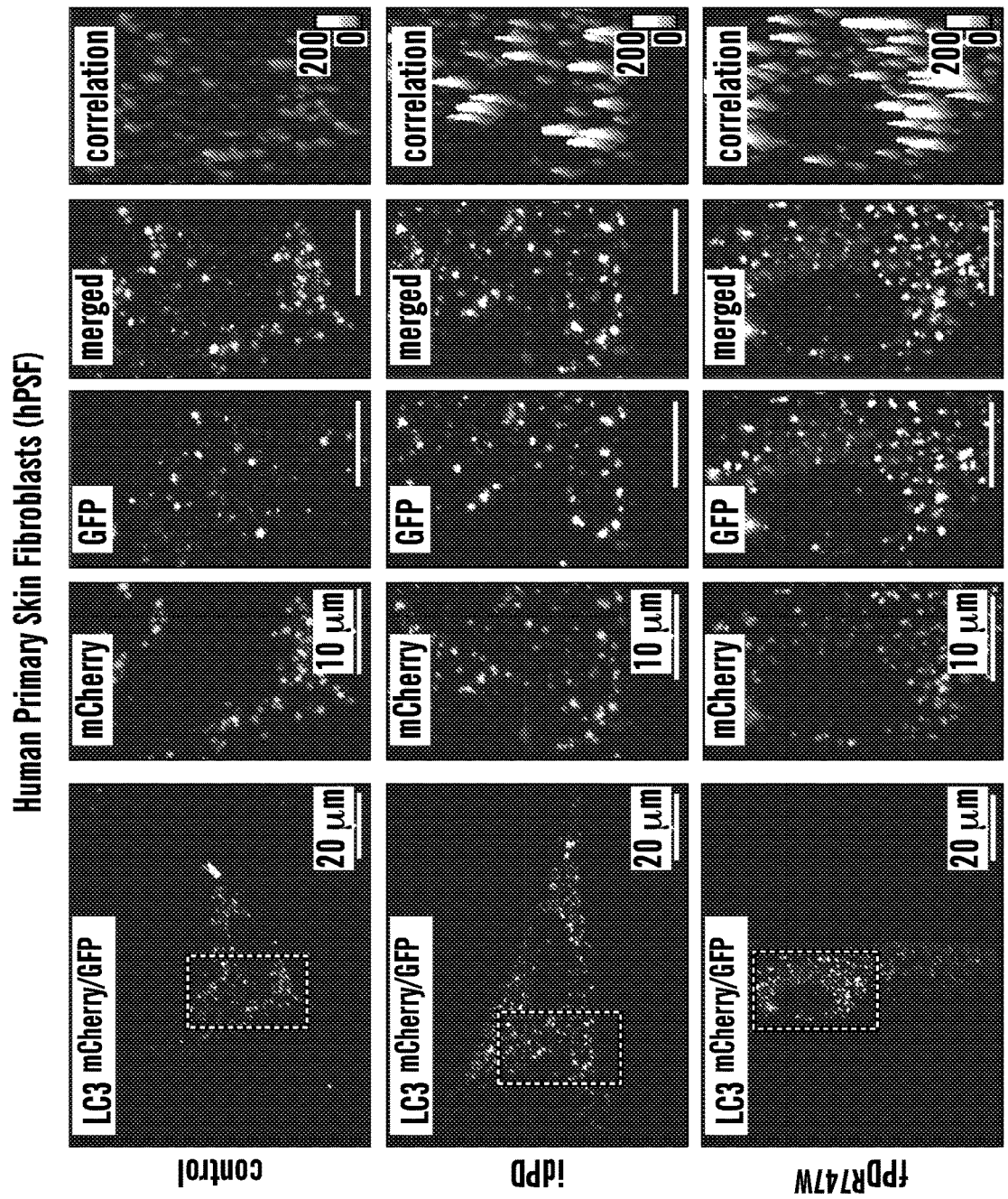
FIGS. 26A-26C shows LC3$^{mCherry/eGFP}$ autophagic flow in hPSF from control, idPD and fPD$^{R747W}$ patients.
Figure 26B:
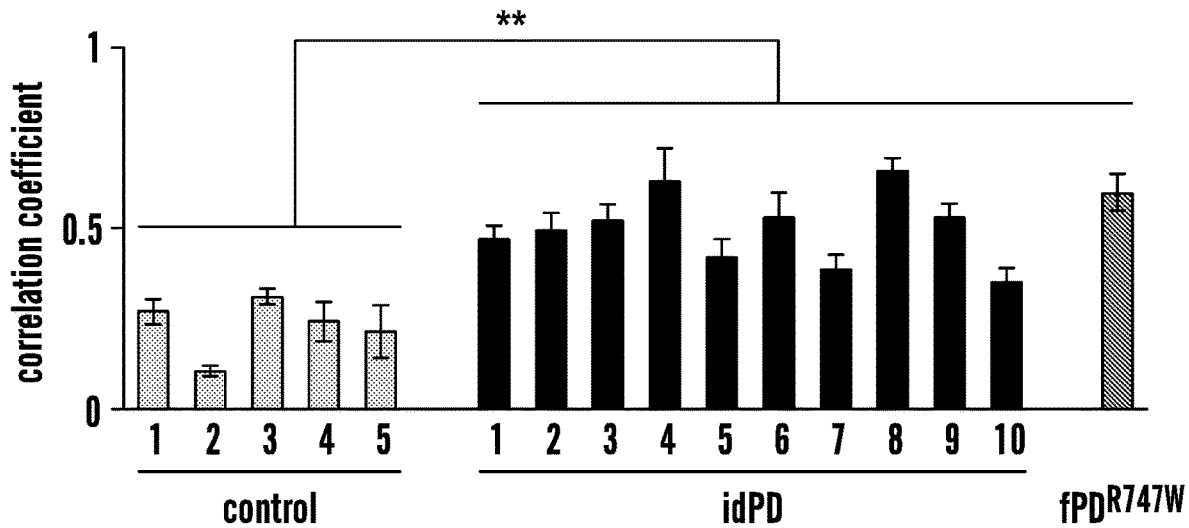
Figure 26C:
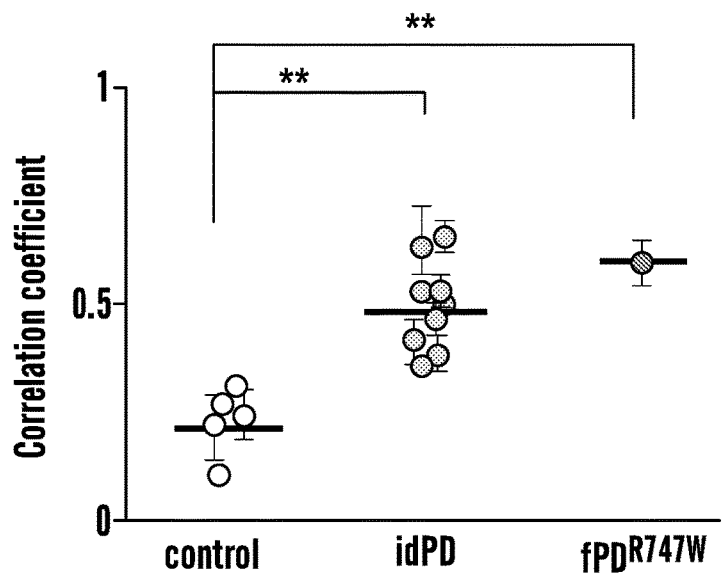
Figure 27A:
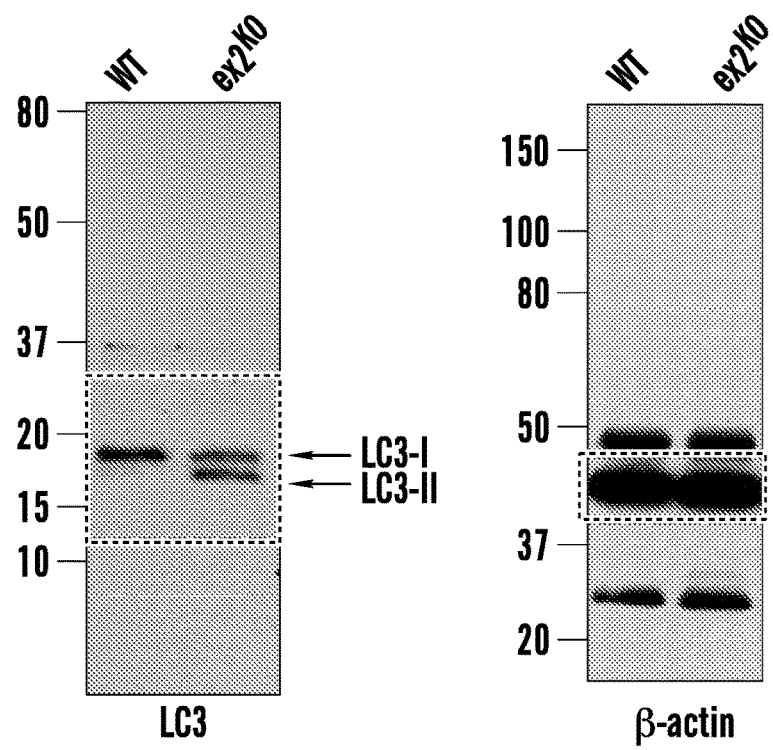
FIGS. 27A-27D show the full images of the western blots used FIG. 5C (FIG. 27A), FIG. 16 (FIG. 27B), FIGS. 17A (FIG. 27C), and 17B (FIG. 27D). Orange rectangles show the parts of the blots that have been cropped for presentation.
Figure 27B:
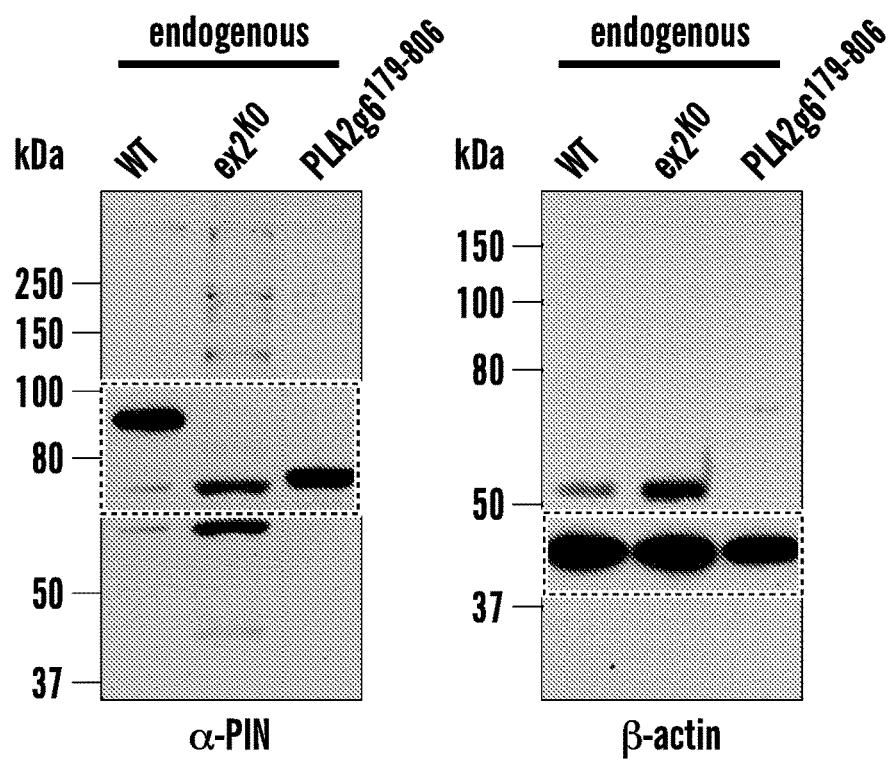
Figure 27C:
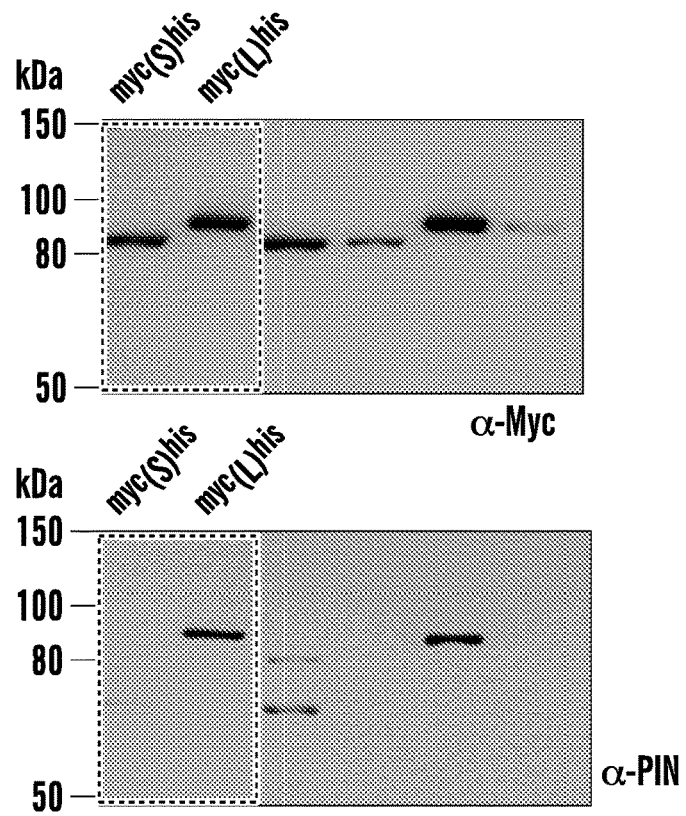
Figure 27D:
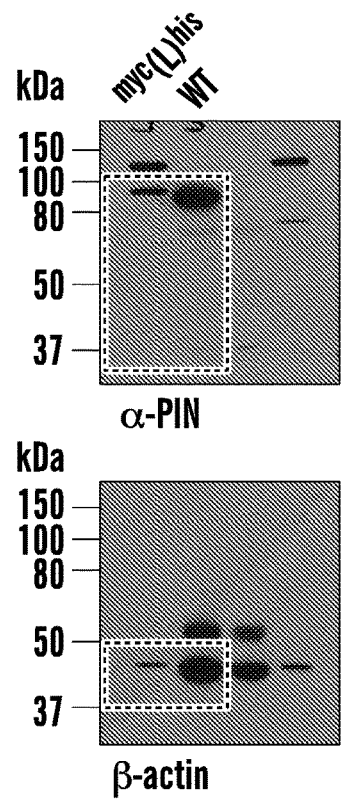

Analysis of primary skin fibroblasts from idPD and fPD$^{R747W}$ patients revealed that in addition to reduced SOCE and depleted stores (FIG. 1), they all have significant autophagic dysfunction, as demonstrated by significant impairment of LC3$^{mCherry-eGFP}$ flow (FIG. 7a,b and FIG. 26). Thus, impairment of SOCE, depletion of ER Ca$^{2+}$ stores, and autophagic dysfunction (FIG. 7a,b) represent a new distinct sequence of pathological cellular events that could be found not only in DA neurons and MEFs from PLA2g6ex2$^{KO}$ mice, but also in primary skin fibroblasts from idPD and fPD(PARK14) patients.

If specific defects in PLA2g6(L) expression (FIG. 1f) and/or store-dependent activation (FIG. 1e) could indeed be a major cause of SOCE deficiency and autophagic dysfunction in idPD cells, one would expect that overexpression of functional WT PLA2g6(L) should rescue SOCE and improve autophagic flux in iPD cells. Remarkably, the results of rescue experiments presented in FIG. 7c,d demonstrate that this prediction is correct, and PLA2g6(L) expression can indeed significantly improve SOCE and autophagic flux in iPD cells.

Altogether, the results in primary cells from idPD and fPD$^{R747W}$ patients confirmed the critical role of PLA2g6(L) in impaired SOCE and autophagic dysfunction, and validated previously unknown association of these events with human idiopathic and PARK14 familial Parkinson's disease.

Example 6

Figure 7C:
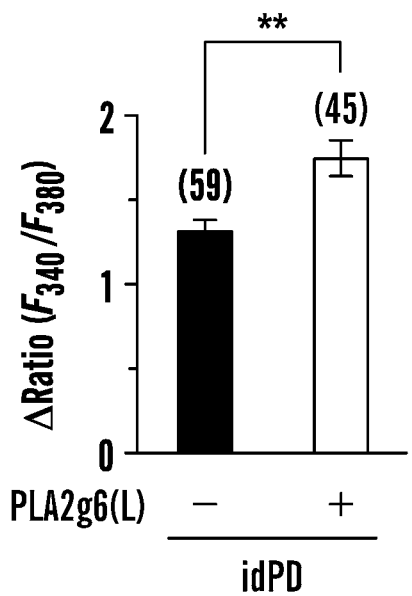
Figure 7D:
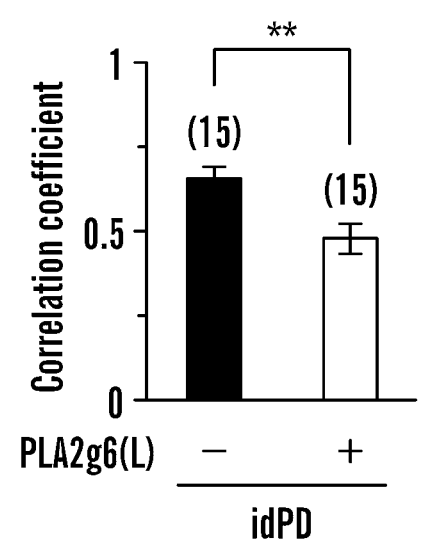
Figure 7E:
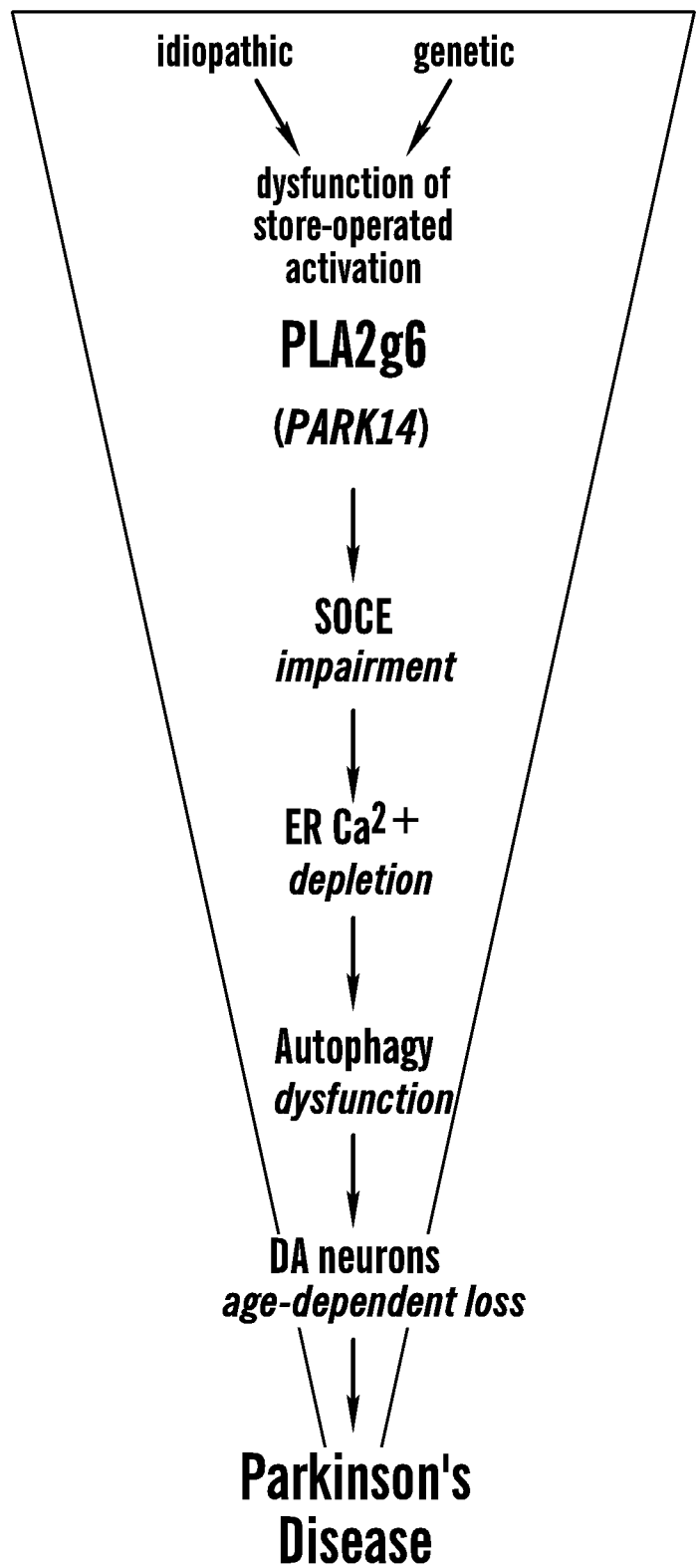

Based on the findings disclosed herein, the inventor has demonstrated that dysfunction of PLA2g6(L)-dependent Ca$^{2+}$ signaling contributes to the pathophysiology of human PD. FIG. 7e illustrates a sequence of pathological events that could be initiated by dysfunction of the store-dependent activation of PLA2g6, which we found in idiopathic and genetically-induced forms of PD. Defects in PLA2g6(L) activation by depleted stores can be due to PD-associated mutations (like in fPD$^{R747W}$ patient), or reduced expression (like in idPD patients), or cleavage of N terminus (mimicked in ex2$^{KO}$ mice), all of which were found to cause impairment of SOCE and depletion of ER Ca$^{2+}$. The limited SOCE and low capacity of Ca$^{2+}$ stores (FIG. 3) likely make DA neurons particularly vulnerable to additional loss of SOCE found in idPD humans and PLA2g6 ex2$^{KO}$ mice, thus setting the stage for their premature demise, which could be aggravated and accelerated by other factors that will be discussed below. Further, the studies present herein are based on the unexpected discovery of a previously unknown ability of the defects in PLA2g6(L)-dependent store-operated Ca$^{2+}$ signaling to trigger autophagic dysfunction, premature loss of DA neurons in SNc, and age-dependent Parkinsonism. This sequence of pathological events was validated in a novel PLA2g6 ex2$^{KO}$ mouse model, which mimics deficient PLA2g6(L)-dependent Ca$^{2+}$ signaling and autophagic dysfunction found in idPD and fPD$^{R747W}$ patients. Importantly, such defects in ex2$^{KO}$ mice were directly associated with a marked age-dependent phenotype, which exhibits selective loss of DA neurons in the SNc and L-DOPA-sensitive motor dysfunction resembling human PD. The anatomic selectivity of age-dependent neurodegeneration in this model appears to be the best yet observed for PD-associated genetic defects in murine models[55,56].

Discovery of a novel relationship between impaired SOCE, depleted stores, autophagic dysfunction and PD-like pathology illuminates complex role of Ca$^{2+}$ signaling in PD. It creates an interesting paradigm: insufficient Ca$^{2+}$ entry through SOCE mechanism can be as detrimental to DA neurons as excessive Ca$^{2+}$ entry through voltage-gated Ca$_V$1.3 channels. This apparent duality has a simple explanation: distinct Ca$^{2+}$ entry pathways regulate different cellular processes[57], and apparently can be linked to different pathological hallmarks of PD. Pioneering studies from Surmeier's laboratory showed that excessive Ca$^{2+}$ entry through Ca$_V$1.3 channels is linked to mitochondrial oxidant stress[58,59], so that the physiological pacemaker activity of this Ca$^{2+}$ channel increases pathological vulnerability of DA neurons. In contrast, Ca$^{2+}$ entry through PLA2g6-independent[36] TRPC1 channels was recently shown[60] to be protective in a MPP+(1-methyl-4-phenylpyridinium) model of dopaminergic neuronal cell death. Our current findings demonstrate that impairment of Ca$^{2+}$ influx through the PLA2g6(L)-dependent SOCE mechanism leads to depletion of ER Ca$^{2+}$ stores, autophagic dysfunction and premature death of DA neurons, suggesting that preservation of SOCE and refilling of ER Ca$^{2+}$ stores is essential for DA neuronal health and survival.

There are several reasons why deficiency in SOCE, depleted ER Ca$^{2+}$ stores and autophagic dysfunction is particularly detrimental to DA neurons. Several reasons can be of particular importance, starting with the new empirical data demonstrating rather limited SOCE and low capacity of ER Ca stores in live iPSC-derived A9 midbrain DA neurons. Poor store-dependent Ca$^{2+}$ signaling can increase vulnerability of DA neurons to mitochondrial stress imposed by constant pacemaker activity of CaV1.3 channels (highlighted by the work of Surmeier's group[58,59]). This stress can be further exacerbated by idiopathic or genetic defect in PLA2g6(L)-dependent Ca$^{2+}$ signaling and autophagic dysfunction (found in idPD and fPD$^{R747W}$ patients, and demonstrated in DA neurons from PLA2g6-deficient mice), which can push DA neurons over the threshold. Moreover, high demand for dopamine production makes DA neurons especially vulnerable to ER Ca$^{2+}$ store depletion and autophagic dysfunction, which altogether may explain premature age-dependent demise of the nigral DA neurons in idPD patients and PLA2g6 ex2$^{KO}$ mice.

Interestingly, distinct defects in Ca$^{2+}$ signaling were recently associated with Alzheimer's (AD) and Huntington's (HD) diseases: in contrast to Parkinson's disease, ER Ca$^{2+}$ stores in AD and HD were found to be overfilled[61,62]. Moreover, Bezprozvany and colleagues reported that HD can be associated with TRPC1 overexpression and upregulation of TRPC1-dependent Ca$^{2+}$ entry[62]. In contrast, AD can be associated with a significant reduction in synaptic expression of STIM2 leading to impairment of highly localized STIM2-dependent Ca$^{2+}$ entry in mushroom spines, and resulting in their loss[61]. Altogether, these findings identify a rather high specificity of distinct Ca$^{2+}$ signaling pathways for specific forms of neurodegeneration: pathological changes in expression or function of PLA2g6, Orai1, TRPC1, STIM1, STIM2, or other molecules can affect distinct mechanisms of Ca$^{2+}$ entry and/or storage, and lead to pathological changes in neurons (or distinct neuronal structures) that are most vulnerable to each specific defect.

The results of genetic and molecular manipulations with distinct molecules involved in SOCE presented new clues for the link between PLA2g6(L)-dependent Ca$^{2+}$ signaling events leading to autophagic dysfunction. The genetic ablation of Orai1 (in MEFs from Orai1$^{KO}$ mice) mimics impairment of SOCE, ER store depletion and autophagic dysfunction found in PLA2g6 ex2$^{KO}$ MEFs. Similar autophagic dysfunction can be also produced by thapsigargin, which inhibits SERCA and depletes ER Ca$^{2+}$ stores. However, in contrast to thapsigargin, which activates SOCE, there is a significant loss of SOCE in Orai1$^{KO}$ and PLA2g6 ex2$^{KO}$ cells that have normal cytosolic Ca$^{2+}$. Thus, PLA2g6(L)-dependent depletion of Ca$^{2+}$ stores (rather than actual reduction in SOCE) is most likely to be responsible for autophagic dysfunction, and loss of DA neurons in SNc leading to PD, as illustrated by the sequence of pathological processes proposed in FIG. 7e.

Impairment of the store-operated Ca$^{2+}$ signaling can trigger or accelerate other pathological processes that are detrimental to DA neurons beyond the impairment of autophagy. For example, significant depletion of ER Ca$^{2+}$ stores can also cause ER stress[63] and unfolded protein response that plays important role in neurodegeneration[64-66]. It is important to emphasize that, since PLA2g6(L)-dependent Ca$^{2+}$ signaling appears to be upstream of both autophagy and the unfolded protein response, its deficiency in DA neurons can contribute to (or set the stage for) aggregation to human α-synuclein and Lewy body formation, which is a diagnostic hallmark of PD[47,50,51,64,67,68], and can be found in patients with familial PARK14 mutations[7]. The late life onset of idiopathic PD and the late onset of PD-like phenotype in PLA2g6 ex2$^{KO}$ mouse model indicate that additional age-dependent processes participate in the final demise of DA neurons that are put at risk by insufficient store-operated Ca$^{2+}$ signaling (FIG. 3). Oxidative stress, mitochondrial dysfunction, and/or protein misfolding are the hallmarks of a normal ageing process[44], and while they do not by themselves cause PD in ageing WT mice, they may become lethal for DA neurons weakened by PLA2g6 deficiency, sustained Ca$^{2+}$ store depletion and autophagic dysfunction. It is appealing to speculate that idiopathic or genetic loss of PLA2g6(L)-dependent SOCE function could be especially detrimental to DA neurons, which are physiologically weakened by excessive mitochondrial oxidant stress due to the life-long pacemaker activity of Ca$_V$1.3 channels. Our study supports the idea of nigrostriatal degenerative processes as a complex phenomenon[43,56,69] that goes beyond mitochondrial dysfunction, oxidative damage and/or defects in protein degradation. The impairment of PLA2g6(L)-dependent store-operated Ca$^{2+}$ signaling can initiate, or in tandem with other age-related processes exacerbate a sequence of pathological events leading to demise of specific DA neurons in SNc, and resulting in PD.

Altogether, the disclosure herein provides evidence of the link between PARK14/PLA2g6, SOCE and human PD. First, primary skin fibroblasts from idPD patients have a characteristic cellular phenotype with pronounced deficiency in SOCE and significant autophagic dysfunction (FIG. 1,7). Importantly, the inventor demonstrated that such idPD phenotype (impaired SOCE and autophagic dysfunction) can be rescued by simple overexpression of the functional PLA2g6(L) (FIG. 7c,d). Second, the cells from familial PD patient carrying PLA2g6$^{R747W}$ mutation have the same cellular phenotype (loss of PLA2g6 activation by the stores, deficient SOCE, depleted stores and autophagic dysfunction) as were also found in idPD patients (FIG. 1,7). Third, human PD-associated mutations in PARK14 (F72L and R747W) appeared to be sufficient to impair SOCE, deplete the stores and cause autophagic dysfunction (FIG. 6). Fourth, cellular phenotype of human idPD and PARK14 fPD patients can be mimicked by targeted impairment of PLA2g6 function in a new transgenic mouse model (FIG. 1,2, 6). Importantly, impairment of SOCE and depletion of Ca$^{2+}$ stores was found not only in fibroblasts, but also in iPSC-derived A9 midbrain DA neurons from PLA2g6 ex2$^{KO}$ mice. Fifth, genetic impairment of Ca$^{2+}$ signaling function of PLA2g6 in a new ex2$^{KO}$ mouse model resulted in pronounced age-dependent PD-like phenotype that mimics idPD in humans.

The PLA2g6 ex2$^{KO}$ mouse model exhibits not only PD-like motor dysfunction, but also an anatomically selective depletion of nigral DA neurons resulting from an endogenous pan-neuronal deficit, and provides an important addition to existing mouse models of PD[55,56]. PLA2g6 ex2$^{KO}$ mouse reproduces several major parameters of human sporadic PD, and combines autophagic dysfunction, progressive loss of DA neurons in SNc and age-dependent L-DOPA-sensitive PD-like motor dysfunction. This new mammalian model of iPD opens unique opportunities to investigate mechanisms contributing to the etiology of sporadic PD, and provides a powerful tool for developing novel strategies for prevention and treatment of this devastating neurodegenerative disease.

REFERENCES

All references cited herein are incorporated in their entireties by reference.

1. Trinh, J. & Farrer, M. Advances in the genetics of Parkinson disease. *Nat Rev Neurol* 9, 445-454 (2013).
2. Antony, P. M. A., Diederich, N. J., Kruger, R., & Balling, R. The hallmarks of Parkinson's disease. *FEBS J* 280, 5981-5993 (2013).
3. Dexter, D. T. & Jenner, P. Parkinson disease: from pathology to molecular disease mechanisms. *Free Radic. Biol. Med.* 62, 132-144 (2013).
4. Obeso, J. A. et al. Missing pieces in the Parkinson's disease puzzle. *Nat Med* 16, 653-661 (2010).
5. Paisan-Ruiz, C. et al. Characterization of PLA2G6 as a locus for dystonia-parkinsonism. *Ann. Neurol.* 65, 19-23 (2009).
6. Yoshino, H. et al. Phenotypic spectrum of patients with PLA2G6 mutation and PARK14-linked parkinsonism. *Neurology* 75, 1356-1361 (2010).
7. Paisan-Ruiz, C. et al. Widespread Lewy body and tau accumulation in childhood and adult onset dystonia-parkinsonism cases with PLA2G6 mutations. *Neurobiol Aging* 33, 814-823 (2010).
8. Tomiyama, H. et al. PLA2G6 variant in Parkinson's disease. *J Hum Genet* 56, 401-403 (2011).
9. Kauther, K. M., Hoft, C., Rissling, I., Oertel, W. H., & Moller, J. C. The PLA2G6 gene in early-onset Parkinson's disease. *Mov. Disord.* 26, 2415-2417 (2011).
10. Sina, F., Shojaee, S., Elahi, E., & Paisan-Ruiz, C. R632W mutation in PLA2G6 segregates with dystonia-parkinsonism in a consanguineous Iranian family. *Eur. J Neurol.* 16, 101-104 (2009).
11. Lu, C. S. et al. PLA2G6 mutations in PARK14-linked young-onset parkinsonism and sporadic Parkinson's disease. *Am. J. Med. Genet.* 159B, 183-191 (2012).
12. Dennis, E. A., Cao, J., Hsu, Y. H., Magrioti, V., & Kokotos, G. Phospholipase A2 enzymes: physical structure, biological function, disease implication, chemical inhibition, and therapeutic intervention. *Chem Rev* 111, 6130-6185 (2011).
13. Bao, S. et al. Male mice that do not express group VIA phospholipase A2 produce spermatozoa with impaired motility and have greatly reduced fertility. *J Biol Chem.* 279, 38194-38200 (2004).
14. Malik, I. et al. Disrupted membrane homeostasis and accumulation of ubiquitinated proteins in a mouse model of infantile neuroaxonal dystrophy caused by PLA2G6 mutations. *Am J Pathol* 172, 406-416 (2008).

15. Shinzawa, K. et al. Neuroaxonal dystrophy caused by group VIA phospholipase A2 deficiency in mice: a model of human neurodegenerative disease. *J. Neurosci.* 28, 2212-2220 (2008).
16. Wada, H. et al. Establishment of an improved mouse model for infantile neuroaxonal dystrophy that shows early disease onset and bears a point mutation in Pla2g6. *Am J Pathol* 175, 2257-2263 (2009).
17. Beck, G. et al. Neuroaxonal dystrophy in calcium-independent phospholipase A2beta deficiency results from insufficient remodeling and degeneration of mitochondrial and presynaptic membranes. *J Neurosci* 31, 11411-11420 (2011).
18. Zhao, Z. et al. Genetic Ablation of PLA2G6 in Mice Leads to Cerebellar Atrophy Characterized by Purkinje Cell Loss and Glial Cell Activation. *PLoS ONE* 6, e26991 (2011).
19. Strokin, M., Seburn, K. L., Cox, G. A., Martens, K. A., & Reiser, G. Severe disturbance in the Ca2+ signaling in astrocytes from mouse models of human infantile neuroaxonal dystrophy with mutated Pla2g6. *Human Molecular Genetics* 21, 2807-2814 (2012).
20. Engel, L. A., Jing, Z., O'Brien, D. E., Sun, M., & Kotzbauer, P. T. Catalytic function of PLA2G6 is impaired by mutations associated with infantile neuroaxonal dystrophy but not dystonia-parkinsonism. *PLoS. One.* 5, e12897 (2010).
21. Smani, T. et al. A novel mechanism for the store-operated calcium influx pathway. *Nature Cell Biology* 6, 113-120 (2004).
22. Bolotina, V. M. Orai, STIM1 and iPLA2beta: a view from a different perspective. *J Physiol (Lond)* 586, 3035-3042 (2008).
23. Bolotina, V. M. Microdomain Organization and the Role of Second Messengers. Store-Operated Ca Entry: Endogenous Messengers and Mediators in *Store-Operated Calcium Entry (SOCE) Pathways* (ed. Groschner, K.) 115-130 (Springer-Verlag/Wien, 2012).
24. Gwozdz, T., Dutko-Gwozdz, J., Schafer, C., & Bolotina, V. M. Overexpression of Orai1 and STIM1 Proteins Alters Regulation of Store-operated Ca2+ Entry by Endogenous Mediators. *J Biol Chem.* 287, 22865-22872 (2012).
25. Gwozdz, T., Dutko-Gwozdz, J., Zarayskiy, V., Peter, K., & Bolotina, V. M. How strict is the correlation between STIM1 and Orai1 expression, puncta formation, and ICRAC activation? *Am J Physiol Cell Physiol* 295, C1133-C1140 (2008).
26. Csutora, P. et al. Activation mechanism for CRAC current and store-operated $Ca^{2+}$ entry: calcium influx factor and $Ca^{2+}$-independent phospholipase $A_2$b-mediated pathway. *J Biol. Chem.* 281, 34926-34935 (2006).
27. Martinez, J. & Moreno, J. J. Role of Ca2+-independent phospholipase A2 and cytochrome P-450 in store-operated calcium entry in 3T6 fibroblasts. *Biochem. Pharmacol.* 70, 733-739 (2005).
28. Singaravelu, K., Lohr, C., & Deitmer, J. W. Regulation of store-operated calcium entry by calcium-independent phospholipase A2 in rat cerebellar astrocytes. *J Neurosci* 26, 9579-9592 (2006).
29. Boittin, F. X. et al. Ca2+-independent phospholipase A2 enhances store-operated Ca2+ entry in dystrophic skeletal muscle fibers. *J Cell Sci.* 119, 3733-3742 (2006).
30. Boittin, F. X., Gribi, F., Serir, K., & Beny, J. L. Ca2+-independent PLA2 controls endothelial store-operated Ca2+ entry and vascular tone in intact aorta. *Am J Physiol Heart Circ Physiol* 295, H2466-H2474 (2008).
31. Ross, K., Whitaker, M., & Reynolds, N. J. Agonist-induced calcium entry correlates with STIM1 translocation. *Journal of Cellular Physiology* 211, 569-576 (2007).
32. Vig, M. et al. CRACM1 is a plasma membrane protein essential for store-operated Ca2+ entry. *Science* 312, 1220-1223 (2006).
33. Putney, J. W. The physiological function of store-operated calcium entry. *Neurochem. Res* 36, 1157-1165 (2011).
34. Parekh, A. B. Store-operated CRAC channels: function in health and disease. *Nat. Rev. Drug Discov.* 9, 399-410 (2010).
35. Lewis, R. S. Store-operated calcium channels: new perspectives on mechanism and function. *Cold Spring Harb. Perspect. Biol* 3, 1-24 (2011).
36. Zarayskiy, V. et al. Store-operated Orai1 and IP3 receptor-operated TRPC1 channel. *Channels (Austin.)* 1, 246-252 (2007).
37. Zakharov, S. I. et al. Diethylstilbestrol Is a Potent Inhibitor of Store-Operated Channels and Capacitative Ca2+ Influx. *Molecular Pharmacol* 66, 702-707 (2004).
38. Jenkins, C. M., Han, X., Mancuso, D. J., & Gross, R. W. Identification of Calcium-independent Phospholipase A2 (iPLA2) beta, and Not iPLA2gamma, as the Mediator of Arginine Vasopressin-induced Arachidonic Acid Release in A-10 Smooth Muscle Cells. Enantioselective mechanism-based discrimination of mammalian iPLA2s. *J Biol Chem* 277, 32807-32814 (2002).
39. Larsson, P. K., Claesson, H. E., & Kennedy, B. P. Multiple splice variants of the human calcium-independent phospholipase A2 and their effect on enzyme activity. *J Biol. Chem.* 273, 207-214 (1998).
40. Hofer, A. M., Fasolato, C., & Pozzan, T. Capacitative $Ca^{2+}$ entry is closely linked to the filling state of internal $Ca^{2+}$ stores: A study using simultaneous measurements of $I_{crac}$ and intraluminal $[Ca^{2+}]$. *J. Cell Biol.* 140, 325-334 (1998).
41. Csutora, P. et al. Novel Role for STIM1 as a Trigger for Calcium Influx Factor Production. *J Biol Chem* 283, 14524-14531 (2008).
42. Lee, S. H., Lumelsky, N., Studer, L., Auerbach, J. M., & McKay, R. D. Efficient generation of midbrain and hindbrain neurons from mouse embryonic stem cells. *Nat Biotechnol.* 18, 675-679 (2000).
43. Surmeier, D. J., Guzman, J. N., Sanchez, J., & Schumacker, P. T. Physiological phenotype and vulnerability in Parkinson's disease. *Cold Spring Harb. Perspect. Med* 2, a009290 (2012).
44. Collier, T. J., Kanaan, N. M., & Kordower, J. H. Ageing as a primary risk factor for Parkinson's disease: evidence from studies of non-human primates. *Nat Rev Neurosci* 12, 359-366 (2011).
45. Albin, R. L., Young, A. B., & Penney, J. B. The functional anatomy of disorders of the basal ganglia. *Trends in Neurosciences* 18, 63-64 (1995).
46. Savitt, J. M., Dawson, V. L., & Dawson, T. M. Diagnosis and treatment of Parkinson disease: molecules to medicine. *The Journal of Clinical Investigation* 116, 1744-1754 (2006).
47. Lynch-Day, M. A., Mao, K., Wang, K., Zhao, M., & Klionsky, D. J. The role of autophagy in Parkinson's disease. *Cold Spring Harb. Perspect. Med* 2, a009357 (2012).
48. Dehay, B. et al. Lysosomal impairment in Parkinson's disease. *Mov Disord.* 28, 725-732 (2013).

49. Orenstein, S. J. et al. Interplay of LRRK2 with chaperone-mediated autophagy. *Nat Neurosci* 16, 394-406 (2013).
50. Cuervo, A. M., Stefanis, L., Fredenburg, R., Lansbury, P. T., & Sulzer, D. Impaired Degradation of Mutant +|-Synuclein by Chaperone-Mediated Autophagy. *Science* 305, 1292-1295 (2004).
51. Tong, Y. et al. Loss of leucine-rich repeat kinase 2 causes impairment of protein degradation pathways, accumulation of alpha-synuclein, and apoptotic cell death in aged mice. *Proc. Natl. Acad. Sci. U.S.A* 107, 9879-9884 (2010).
52. Klionsky, D. J. et al. Guidelines for the use and interpretation of assays for monitoring autophagy. *Autophagy* 8, 445-544 (2012).
53. Ganley, I., Wong, P. M., Gammoh, N., & Jiang, X. Distinct Autophagosomal-Lysosomal Fusion Mechanism Revealed by Thapsigargin-Induced Autophagy Arrest. *Molecular Cell* 42, 731-743 (2011).
54. Vig, M. et al. Defective mast cell effector functions in mice lacking the CRACM1 pore subunit of store-operated calcium release-activated calcium channels. *Nat. Immunol.* 9, 89-96 (2008).
55. Lee, Y., Dawson, V. L., & Dawson, T. M. Animal models of Parkinson's disease: vertebrate genetics. *Cold Spring Harb. Perspect. Med* 2, (2012).
56. Chesselet, M. F. & Richter, F. Modelling of Parkinson's disease in mice. *The Lancet Neurology* 10, 1108-1118 (2011).
57. Berridge, M. J., Bootman, M. D., & Roderick, H. L. Calcium signalling: dynamics, homeostasis and remodelling. *Nat. Rev. Mol. Cell Biol.* 4, 517-529 (2003).
58. Goldberg, J. A. et al. Calcium entry induces mitochondrial oxidant stress in vagal neurons at risk in Parkinson's disease. *Nat Neurosci* 15, 1414-1421 (2012).
59. Surmeier, D. J., Guzman, J. N., Sanchez-Padilla, J., & Schumacker, P. T. The role of calcium and mitochondrial oxidant stress in the loss of substantia nigra pars compacta dopaminergic neurons in Parkinson's disease. *Neuroscience* 198, 221-231 (2011).
60. Selvaraj, S. et al. Neurotoxin-induced ER stress in mouse dopaminergic neurons involves downregulation of TRPC1 and inhibition of AKT/mTOR signaling. *J Clin. Invest* 122, 1354-1367 (2012).
61. Sun, S. et al. Reduced synaptic STIM2 expression and impaired store-operated calcium entry cause destabilization of mature spines in mutant presenilin mice. *Neuron* 82, 79-93 (2014).
62. Wu, J. et al. Neuronal Store-Operated Calcium Entry Pathway asáaáNovel Therapeutic Target foráHuntington'sáDisease Treatment. *Chemistry & Biology* 18, 777-793 (2011).
63. Sammels, E., Parys, J. B., Missiaen, L., De Smedt, H., & Bultynck, G. Intracellular Ca2+ storage in health and disease: A dynamic equilibrium. *Cell Calcium* 47, 297-314 (2010).
64. Mercado, G., Valdes, P., & Hetz, C. An ERcentric view of Parkinson's disease. *Trends Mol. Med.* 19, 165-175 (2013).
65. Roussel, B. D. et al. Endoplasmic reticulum dysfunction in neurological disease. *Lancet Neurol.* 12, 105-118 (2013).
66. Hoozemans, J. J., van Haastert, E. S., Nijholt, D. A., Rozemuller, A. J., & Scheper, W. Activation of the unfolded protein response is an early event in Alzheimer's and Parkinson's disease. *Neurodegener. Dis* 10, 212-215 (2012).
67. Colla, E. et al. Endoplasmic reticulum stress is important for the manifestations of alpha-synucleinopathy in vivo. *J Neurosci* 32, 3306-3320 (2012).
68. Luk, K. C. et al. Pathological alpha-synuclein transmission initiates Parkinson-like neurodegeneration in non-transgenic mice. *Science* 338, 949-953 (2012).
69. Dehay, B. & Bezard, E. New animal models of Parkinson's disease. *Mov Disord.* 26, 1198-1205 (2011).
70. Kirber, M. T., Chen, K., & Keaney, J. F., Jr. YFP photoconversion revisited: confirmation of the CFP-like species. *Nat. Methods* 4, 767-768 (2007).
71. Vig, M. et al. Defective mast cell effector functions in mice lacking the CRACM1 pore subunit of store-operated calcium release-activated calcium channels. *Nat. Immunol.* 9, 89-96 (2008).
72. Brooks, S. P. & Dunnett, S. B. Tests to assess motor phenotype in mice: a user's guide. *Nat Rev Neurosci* 10, 519-529 (2009).
73. Fleming, S. M. et al. Behavioral effects of dopaminergic agonists in transgenic mice overexpressing human wild-type alpha-synuclein. *Neuroscience* 142, 1245-1253 (2006).
74. Jackson-Lewis, V. & Przedborski, S. Protocol for the MPTP mouse model of Parkinson's disease. *Nat. Protocols* 2, 141-151 (2007).
75. Giannaris, E. L. & Rosene, D. L. A stereological study of the numbers of neurons and glia in the primary visual cortex across the lifespan of male and female rhesus monkeys. *J. Comp Neurol.* 520, 3492-3508 (2012).
76. Sommer, C. A. & Mostoslaysky, G. Experimental approaches for the generation of induced pluripotent stem cells. *Stem Cell Res Ther* 1, 26 (2010).
77. Sommer, C. A. et al. Induced pluripotent stem cell generation using a single lentiviral stem cell cassette. *Stem Cells* 27, 543-549 (2009).
78. Sommer, C. A. et al. Excision of reprogramming transgenes improves the differentiation potential of iPS cells generated with a single excisable vector. *Stem Cells* 28, 64-74 (2010).
79. Lee, S. H., Lumelsky, N., Studer, L., Auerbach, J. M., & McKay, R. D. Efficient generation of midbrain and hindbrain neurons from mouse embryonic stem cells. *Nat Biotechnol.* 18, 675-679 (2000).
80. Kirber, M. T., Chen, K., & Keaney, J. F., Jr. YFP photoconversion revisited: confirmation of the CFP-like species. *Nat. Methods* 4, 767-768 (2007).
81. Schafer, C., Rymarczyk, G., Ding, L., Kirber, M. T., & Bolotina, V. M. Role of molecular determinants of store-operated Ca(2+) entry (Orai1, phospholipase A2 group 6, and STIM1) in focal adhesion formation and cell migration. *J. Biol. Chem.* 287, 40745-40757 (2012).
82. Schmittgen, T. D. & Livak, K. J. Analyzing real-time PCR data by the comparative C(T) method. *Nat Protoc.* 3, 1101-1108 (2008).
83. Larsson Forsell, P. K. A., Kennedy, B. P., & Claesson, H. E. The human calcium-independent phospholipase A2 gene: Multiple enzymes with distinct properties from a single gene. *Eur J Biochem* 262, 575-585 (1999).
84. Larsson, P. K., Claesson, H. E., & Kennedy, B. P. Multiple splice variants of the human calcium-independent phospholipase A2 and their effect on enzyme activity. *J Biol. Chem.* 273, 207-214 (1998).

SEQ ID NO: 1 (mRNA nucleic acid of PLA2g6(L); PLA2g6 variant 1)
>gi|3142699|gb|AF064594.1| Homo sapiens calcium-independent phospholipase A2
mRNA, complete cds
CTGGGGGTCCGTTCCCCAACTTCCTCGGCGCTCCGGACTCCCAAGTCTCCGCCGGACCCTCCTTTGGATA

TTCCTCGTGTCTCCGATTCTGAGAGAGGGGGAAGACGGTGGGGCCTCCCCACCTGCCCCGCAGAAGATGC

AGTTCTTTGGCCGCCTGGTCAATACCTTCAGTGGCGTCACCAACTTGTTCTCTAACCCATTCCGGGTGAA

GGAGGTGGCTGTGGCCGACTACACCTCGAGTGACCGAGTTCGGGAGGAAGGGCAGCTGATTCTGTTCCAG

AACACTCCCAACCGCACCTGGGACTGCGTCCTGGTCAACCCCAGGAACTCACAGAGTGGATTCCGACTCT

TCCAGCTGGAGTTGGAGGCTGACGCCCTAGTGAATTTCCATCAGTATTCTTCCCAGCTGCTACCCTTCTA

TGAGAGCTCCCCTCAGGTCCTGCACACTGAGGTCCTGCAGCACCTGACCGACCTCATCCGTAACCACCCC

AGCTGGTCAGTGGCCCACCTGGCTGTGGAGCTAGGGATCCGCGAGTGCTTCCATCACAGCCGTATCATCA

GCTGTGCCAATTGCGCGGAGAACGAGGAGGGCTGCACACCCCTGCACCTGGCCTGCCGCAAGGGTGATGG

GGAGATCCTGGTGGAGCTGGTGCAGTACTGCCACACTCAGATGGATGTCACCGACTACAAGGGAGAGACC

GTCTTCCATTATGCTGTCCAGGGTGACAATTCTCAGGTGCTGCAGCTCCTTGGAAGGAACGCAGTGGCTG

GCCTGAACCAGGTGAATAACCAAGGGCTGACCCCGCTGCACCTGGCCTGCCAGCTGGGGAAGCAGGAGAT

GGTCCGCGTGCTGCTGCTGTGCAATGCTCGGTGCAACATCATGGGCCCCAACGGCTACCCCATCCACTCG

GCCATGAAGTTCTCTCAGAAGGGGTGTGCGGAGATGATCATCAGCATGGACAGCAGCCAGATCCACAGCA

AAGACCCCCGTTACGGAGCCAGCCCCCTCCACTGGGCCAAGAACGCAGAGATGGCCCGCATGCTGCTGAA

ACGGGGCTGCAACGTGAACAGCACCAGCTCCGCGGGGAACACGGCCCTGCACGTGGCGGTGATGCGCAAC

CGCTTCGACTGTGCCATAGTGCTGCTGACCCACGGGGCCAACGCGGATGCCCGCGGAGAGCACGGCAACA

CCCCGCTGCACCTGGCCATGTCGAAAGACAACGTGGAGATGATCAAGGCCCTCATCGTGTTCGGAGCAGA

AGTGGACACCCCGAATGACTTTGGGGAGACTCCTACATTCCTAGCCTCCAAAATCGGCAGACTTGTCACC

AGGAAGGCGATCTTGACTCTGCTGAGAACCGTGGGGGCCGAATACTGCTTCCCACCCATCCACGGGGTCC

CCGCGGAGCAGGGCTCTGCAGCGCCACATCATCCCTTCTCCCTGGAAAGAGCTCAGCCCCCACCGATCAG

CCTAAACAACCTAGAACTACAGGATCTCATGCACATCTCACGGGCCCGGAAGCCAGCGTTCATCCTGGGC

TCCATGAGGGACGAGAAGCGGACCCACGACCACCTGCTGTGCCTGGATGGAGGAGGAGTGAAAGGCCTCA

TCATCATCCAGCTCCTCATCGCCATCGAGAAGGCCTCGGGTGTGGCCACCAAGGACCTGTTTGACTGGGT

GGCGGGCACCAGCACTGGAGGCATCCTGGCCCTGGCCATTCTGCACAGTAAGTCCATGGCCTACATGCGC

GGCATGTACTTTCGCATGAAGGATGAGGTGTTCCGGGGCTCCAGGCCCTACGAGTCGGGGCCCCTGGAGG

AGTTCCTGAAGCGGGAGTTTGGGGAGCACACCAAGATGACGGACGTCAGGAAACCCAAGGTGATGCTGAC

AGGGACACTGTCTGACCGGCAGCCGGCTGAACTCCACCTCTTCCGGAACTACGATGCTCCAGAAACTGTC

CGGGAGCCTCGTTTCAACCAGAACGTTAACCTCAGGCCTCCAGCTCAGCCCTCAGACCAGCTGGTGTGGC

GGGCGGCCCGAAGCAGCGGGGCAGCTCCTACTTACTTCCGACCCAATGGGCGCTTCCTGGACGGTGGGCT

GCTGGCCAACAACCCCACGCTGGATGCCATGACCGAGATCCATGAGTACAATCAGGACCTGATCCGCAAG

GGTCAGGCCAACAAGGTGAAGAAACTCTCCATCGTTGTCTCCCTGGGACAGGGAGGTCCCCACAAGTGC

CTGTGACCTGTGTGGATGTCTTCCGTCCCAGCAACCCCTGGGAGCTGGCCAAGACTGTTTTTGGGGCCAA

GGAACTGGGCAAGATGGTGGTGGACTGTTGCACGGATCCAGACGGGCGGGCTGTGGACCGGGCACGGGCC

TGGTGCGAGATGGTCGGCATCCAGTACTTCAGATTGAACCCCAGCTGGGGACGGACATCATGCTGGATG

AGGTCAGTGACACAGTGCTGGTCAACGCCCTCTGGGAGACCGAGGTCTACATCTATGAGCACCGCGAGGA

GTTCCAGAAGCTCATCCACCTGCTGCTCTCACCCTGAGGGTCCCCAGCCTCTCACCGGCCCAGCTGACC

TCGTCCATTCAGCCCCTGCCAGGCCAAGCCCAGCCACTGCCCTCCCGGGCAGATCTGGGCCCAGGCACCT

CTGAGTCCATAGACCAGGCCTGGGAGAATGCCAAGCTGCCTGCCCGAGGCTGGTCCTGAAGGCCTGTCTC

```
CCACTAACCCCCCCTTCCATCACTTTCTGTCATGCCAGGNTGGGAAAGTCTAGAGCCCCTTTGGCCCCT

TTCCCTGACTGTCAAGGACAACTGACTCCCCCATCAGCTCAAACATTAAGGGTACCCGGGCACAACCGTA

CCCGTGCCCCCAGCCCCAGCCTACCCTGAGGGCCTGCCGGGCTGCCTTTGCCCCAGCCCCCAGCAAGGGC

ATTCCCAGGCTTCCTGGTGGGTGCAGCCCAATCCCTCTGCCCTCTGCTCCGTTCCCTGGGGGCTGGGACT

AAAGAAATGGGTGTCCCCCACCCCATCAGCTGGGAAAGCCCAGGCCGCAGGAGTGGGATGCCCGTTGGAC

TTTGCCCCTCACACTGGCCCAGCCCCTCACACTGCCCCACCCCGAGAACCCTCAGCTCTCAAAGGTCACT

CCTGGGAGTTTCTTCTTCCCAATGGAAGTGGCTTAAGAGCCAAAACTGAAATAAATCATTTGGATTCAAG

TTCAAAAAAAAAAAAAAAAA
```

SEQ ID NO: 2 (aa of PLA2g6(L); encoded by PLA2g6 variant 1)
>gi|3142700|gb|AAC97486.1| calcium-independent phospholipase A2 [Homo sapiens]
```
MQFFGRLVNTFSGVTNLFSNPFRVKEVAVADYTSSDRVREEGQLILFQNTPNRTWDCVLVNPRNSQSGFR

LFQLELEADALVNFHQYSSQLLPFYESSPQVLHTEVLQHLTDLIRNHPSWSVAHLAVELGIRECFHHSRI

ISCANCANCAENEEGCTPLHLACRKGDGEILVELVQYCHTQMDVTDYKGETVFHYAVQGDNSQVLQLLGRNAV

AGLNQVNNQGLTPLHLACQLGKQEMVRVLLLCNARCNIMGPNGYPIHSAMKESQKGCAEMIISMDSSQIH

SKDPRYGASPLHWAKNAEMARMLLKRGCNVNSTSSAGNTALHVAVMRNRFDCAIVLLTHGANADARGEHG

NTPLHLAMSKDNVEMIKALIVFGAEVDTPNDFGETPTFLASKIGRLVTRKAILTLLRTVGAEYCFPPIHG

VPAEQGSAAPHHPFSLERAQPPPISLNNLELQDLMHISRARKPAFILGSMRDEKRTHDHLLCLDGGGVKG

LIIIQLLIAIEKASGVATKDLFDWVAGTSTGGILALAILHSKSMAYMRGMYFRMKDEVFRGSRPYESGPL

EEFLKREFGEHTKMTDVRKPKVMLTGTLSDRQPAELHLFRNYDAPETVREPRFNQNVNLRPPAQPSDQLV

WRAARSSGAAPTYFRPNGRFLDGGLLANNPTLDAMTEIHEYNQDLIRKGQANKVKKLSIVVSLGTGRSPQ

VPVTCVDVFRPSNPWELAKTVFGAKELGKMVVDCCTDPDGRAVDRARAWCEMVGIQYFRLNPQLGTDIML

DEVSDTVLVNALWETEVYIYEHREEFQKLIHLLLSP
```

SEQ ID NO: 3 (mRNA nucleic acid of PLA2g6(S); PLA2g6 variant 2)
>gi|52486250|ref|NM_001004426.1| Homo sapiens phospholipase A2 group VI
(PLA2G6), transcript variant 2, mRNA
```
GGGGGTCCGTTCCCCAACTTCCTCGGCGCTCCGGACTCCCAAGTCTCCGCCGGACCCTCCTTTGGATATT

CCTCGTGTCTCCGATTCTGAGACAGAGGGGGAAGACGGTGGGGCCTCCCCACCTGCCCCGCAGAAGATGC

AGTTCTTTGGCCGCCTGGTCAATACCTTCAGTGGCGTCACCAACTTGTTCTCTAACCCATTCCGGGTGAA

GGAGGTGGCTGTGGCCGACTACACCTCGAGTGACCGAGTTCGGGAGGAAGGGCAGCTGATTCTGTTCCAG

AACACTCCCAACCGCACCTGGGACTGCGTCCTGGTCAACCCCAGGAACTCACAGAGTGGATTCCGACTCT

TCCAGCTGGAGTTGGAGGCTGACGCCCTAGTGAATTTCCATCAGTATTCTTCCCAGCTGCTACCCTTCTA

TGAGAGCTCCCCTCAGGTCCTGCACACTGAGGTCCTGCAGCACCTGACCGACCTCATCCGTAACCACCCC

AGCTGGTCAGTGGCCCACCTGGCTGTGGAGCTAGGGATCCGCGAGTGCTTCCATCACAGCCGTATCATCA

GCTGTGCCAATTGCGCGGAGAACGAGGAGGGCTGCACACCCCTGCACCTGGCCTGCCGCAAGGGTGATGG

GGAGATCCTGGTGGAGCTGGTGCAGTACTGCCACACTCAGATGGATGTCACCGACTACAAGGGAGAGACC

GTCTTCCATTATGCTGTCCAGGGTGACAATTCTCAGGTGCTGCAGCTCCTTGGAAGGAACGCAGTGGCTG

GCCTGAACCAGGTGAATAACCAAGGGCTGACCCCGCTGCACCTGGCCTGCCAGCTGGGGAAGCAGGAGAT

GGTCCGCGTGCTGCTGCTGTGCAATGCTCGGTGCAACATCATGGGCCCCAACGGCTACCCCATCCACTCG

GCCATGAAGTTCTCTCAGAAGGGGTGTGCGGAGATGATCATCAGCATGGACAGCAGCCAGATCCACAGCA

AAGACCCCCGTTACGGAGCCAGCCCCCTCCACTGGGCCAAGAACGCAGAGATGGCCCGCATGCTGCTGAA

ACGGGGCTGCAACGTGAACAGCACCAGCTCCGCGGGGAACACGGCCCTGCACGTGGCGGTGATGCGCAAC

CGCTTCGACTGTGCCATAGTGCTGCTGACCCACGGGGCCAACGCGGATGCCCGCGGAGAGCACGGCAACA

CCCCGCTGCACCTGGCCATGTCGAAAGACAACGTGGAGATGATCAAGGCCCTCATCGTGTTCGGAGCAGA
```

-continued
```
AGTGGACACCCCGAATGACTTTGGGGAGACTCCTACATTCCTAGCCTCCAAAATCGGCAGACAACTACAG

GATCTCATGCACATCTCACGGGCCCGGAAGCCAGCGTTCATCCTGGGCTCCATGAGGGACGAGAAGCGGA

CCCACGACCACCTGCTGTGCCTGGATGGAGGAGGAGTGAAAGGCCTCATCATCATCCAGCTCCTCATCGC

CATCGAGAAGGCCTCGGGTGTGGCCACCAAGGACCTGTTTGACTGGGTGGCGGGCACCAGCACTGGAGGC

ATCCTGGCCCTGGCCATTCTGCACAGTAAGTCCATGGCCTACATGCGCGGCATGTACTTTCGCATGAAGG

ATGAGGTGTTCCGGGGCTCCAGGCCCTACGAGTCGGGGCCCCTGGAGGAGTTCCTGAAGCGGGAGTTTGG

GGAGCACACCAAGATGACGGACGTCAGGAAACCCAAGGTGATGCTGACAGGGACACTGTCTGACCGGCAG

CCCGGCTGAACTCCACCTCTTCCGGAACTACGATGCTCCAGAAACTGTCCGGGAGCCTCGTTTCAACCAGA

ACGTTAACCTCAGGCCTCCAGCTCAGCCCTCAGACCAGCTGGTGTGGCGGGCGGCCCGAAGCAGCGGGGC

AGCTCCTACTTACTTCCGACCCAATGGGCGCTTCCTGGACGGTGGGCTGCTGGCCAACAACCCCACGCTG

GATGCCATGACCGAGATCCATGAGTACAATCAGGACCTGATCCGCAAGGGTCAGGCCAACAAGGTGAAGA

AACTCTCCATCGTTGTCTCCCTGGGGACAGGGAGGTCCCCACAAGTGCCTGTGACCTGTGTGGATGTCTT

CCGTCCCAGCAACCCCTGGGAGCTGGCCAAGACTGTTTTTGGGGCCAAGGAACTGGGCAAGATGGTGGTG

GACTGTTGCACGGATCCAGACGGGCGGGCTGTGGACCGGGCACGGGCCTGGTGCGAGATGGTCGGCATCC

AGTACTTCAGATTGAACCCCCAGCTGGGGACGGACATCATGCTGGATGAGGTCAGTGACACAGTGCTGGT

CAACGCCCTCTGGGAGACCGAGGTCTACATCTATGAGCACCGCGAGGAGTTCCAGAAGCTCATCCAGCTG

CTGCTCTCACCCTGAGGGTCCCCAGCCTCTCACCGGCCCCAGCTGACCTCGTCCATTCAGCCCCTGCCAG

GCCAAGCCCAGCCACTGCCCTCCCGGGCAGATCTGGGCCCAGGCACCTCTGAGTCCATAGACCAGGCCTG

GGAGAATGCCAAGCTGCCTGCCCGAGGCTGGTCCTGAAGGCCTGTCTCCCACTAACCCCGCCTTCCAGCA

CTTTCTGTCATTCCAGGCTGGGAAAGTCTAGAGCCCCCTTTGGCCCCTTTCCCTGACTGTCAAGGACAAC

TGACTCCCCCATCAGCTCAAACATTAAGGGTACCCGGGCACAACCGTACCCCTGCCCCCAGCCCCAGCCT

CCCTGAGGGCCTGCCGGGCTGCCTCTGCCCCAGCCCCAGCAAGGGCACTCCCAGGCTTCCTGGTGGGTG

CAGCCCACTCCCTCTGCCCTCTGCTCCGTTCCCTGGGGGCTGGGACTAAAGAAATGGGTGTCCCCCACCC

CATCAGCTGGGAAAGCCCAGGCCGCAGGAGTGGGATGCCCGTTGGACTTTGCCCCTCACACTGGCCCAGC

CCCTCACACTGCCCCACCCCGAGAACCCTCAGCTCTCAAAGGTCACTCCTGGGAGTTTCTTCTTCCCAAT

GGAAGTGGCTTAAGAGCCAAAACTGAAATAAATCATTTGGATTCAAGTTCAAAAAAAAAAAAAAAAAAAA
```

SEQ ID NO: 4 (aa of PLA2g6(S); PLA2g6 variant 2)
>gi|52486251|ref|NP_001004426.1| 85/88 kDa calcium-independent phospholipase A2
isoform b [Homo sapiens]
```
MQFFGRLVNTFSGVTNLFSNPFRVKEVAVADYTSSDRVREEGQLILFQNTPNRTWDCVLVNPRNSQSGFR

LFQLELEADALVNFHQYSSQLLPEYESSPQVLHTEVQHLTDLIRNHPSWSVAHLAVELGIRECFHHSRI

ISCANCAENEEGCTPLHLACRKGDGEILVELVQYCHTQMDVTDYKGETVFHYAVQGDNSQVLQLLGRNAV

AGLNQVNNQGLTPLHLACQLGKQEMVRVLLLCNARCNIMGPNGYPIHSAMKFSQKGCAEMIISMDSSQIH

SKDPRYGASPLHWAKNAEMARMLLKRGCNVNSTSSAGNTALHVAVMRNRFDCAIVLLTHGANADARGEHG

NTPLHLAMSKDNVEMIKALIVFGAEVDTPNDFGETPTFLASKIGRQLQDLMHISRARKPAFILGSMRDEK

RTHDHLLCLDGGGVKGLIIQLLIAIEKASGVATKDLFDWVAGTSTGGILALAILHSKSMAYMRGMYFRM

KDEVFRGSRPYESGPLEEFLKREFGEHTKMTDVRKPKVMLTGTLSDRQPAELHLFRNYDAPETVREPRFN

QNVNLRPPAQPSDQLVWRAARSSGAAPTYFRPNGRFLDGGLLANNPTLDAMTEIHEYNQDLIRKGQANKV

KKLSIVVSLGTGRSPQVPVTCVDVFRPSNPWELAKTVFGAKELGKMVVDCCTDPDGRAVDRARAWCEMVG

IQYFRLNPQLGTDIMLDEVSDTVLVNALWETEVYIYEHREEFQKLIQLLLSP
```

SEQ ID NO: 5 (mRNA nucleic acid sequence of PLA2g6(S) encoded by PLA2g6 variant 3)
>gi|313760591|ref|NM_001199562.1| Homo sapiens phospholipase A2 group VI (PLA2G6), transcript variant 3, mRNA
TTTGTTTGCGGAAGTAGGAGGAAGTAGAAGTGCTGAGTAAGCCGAGACAGAGGGGGAAGACGGTGGGGCC

TCCCCACCTGCCCCGCAGAAGATGCAGTTCTTTGGCCGCCTGGTCAATACCTTCAGTGGCGTCACCAACT

TGTTCTCTAACCCATTCCGGGTGAAGGAGGTGGCTGTGGCCGACTACACCTCGAGTGACCGAGTTCGGGA

GGAAGGGCAGCTGATTCTGTTCCAGAACACTCCCAACCGCACCTGGGACTGCGTCCTGGTCAACCCCAGG

AACTCACAGAGTGGATTCCGACTCTTCCAGCTGGAGTTGGAGGCTGACGCCCTAGTGAATTTCCATCAGT

ATTCTTCCCAGCTGCTACCCTTCTATGAGAGCTCCCCTCAGGTCCTGCACACTGAGGTCCTGCAGCACCT

GACCGACCTCATCCGTAACCACCCCAGCTGGTCAGTGGCCCACCTGGCTGTGGAGCTAGGGATCCGCGAG

TGCTTCCATCACAGCCGTATCATCAGCTGTGCCAATTGCGCGGAGAACGAGGAGGGCTGCACACCCCTGC

ACCTGGCCTGCCGCAAGGGTGATGGGAGATCCTGGTGGAGCTGGTGCAGTACTGCCACACTCAGATGGA

TGTCACCGACTACAAGGGAGAGACCGTCTTCCATTATGCTGTCCAGGGTGACAATTCTCAGGTGCTGCAG

CTCCTTGGAAGGAACGCAGTGGCTGGCCTGAACCAGGTGAATAACCAAGGGCTGACCCCGCTGCACCTGG

CCTGCCAGCTGGGGAAGCAGGAGATGGTCCGCGTGCTGCTGCTGTGCAATGCTCGGTGCAACATCATGGG

CCCCAACGGCTACCCCATCCACTCGGCCATGAAGTTCTCTCAGAAGGGGTGTGCGGAGATGATCATCAGC

ATGGACAGCAGCCAGATCCACAGCAAAGACCCCCGTTACGGAGCCAGCCCCCTCCACTGGGCCAAGAACG

CAGAGATGGCCCGCATGCTGCTGAAACGGGGCTGCAACGTGAACAGCACCAGCTCCGCGGGGAACACGGC

CCTGCACGTGGCGGTGATGCGCAACCGCTTCGACTGTGCCATAGTGCTGCTGACCCACGGGGCCAACGCG

GATGCCCGCGGAGAGCACGGCAACACCCCGCTGCACCTGGCCATGTCGAAAGACAACGTGGAGATGATCA

AGGCCCTCATCGTGTTCGGAGCAGAAGTGGACACCCCGAATGACTTTGGGGAGACTCCTACATTCCTAGC

CTCCAAAATCGGCAGACAACTACAGGATCTCATGCACATCTCACGGGCCCGGAAGCCAGCGTTCATCCTG

GGCTCCATGAGGGACGAGAAGCGGACCCACGACCACCTGCTGTGCCTGGATGGAGGAGGAGTGAAAGGCC

TCATCATCATCCAGCTCCTCATCGCCATCGAGAAGGCCTCGGGTGTGGCCACCAAGGACCTGTTTGACTG

GGTGGCGGGCACCAGCACTGGAGGCATCCTGGCCCTGGCCATTCTGCACAGTAAGTCCATGGCCTACATG

CGCGGCATGTACTTTCGCATGAAGGATGAGGTGTTCCGGGGCTCCAGGCCCTACGAGTCGGGGCCCCTGG

AGGAGTTCCTGAAGCGGGAGTTTGGGGAGCACACCAAGATGACGGACGTCAGGAAACCCAAGGTGATGCT

GACAGGGACACTGTCTGACCGGCAGCCGGCTGAACTCCACCTCTTCCGGAACTACGATGCTCCAGAAACT

GTCCGGGAGCCTCGTTTCAACCAGAACGTTAACCTCAGGCCTCCAGCTCAGCCCTCAGACCAGCTGGTGT

GGCGGGCGGCCCGAAGCAGCGGGGCAGCTCCTACTTACTTCCGACCCAATGGGCGCTTCCTGGACGGTGG

GCTGCTGGCCAACAACCCCACGCTGGATGCCATGACCGAGATCCATGAGTACAATCAGGACCTGATCCGC

AAGGGTCAGGCCAACAAGGTGAAGAAACTCTCCATCGTTGTCTCCCTGGGGACAGGGAGGTCCCCACAAG

TGCCTGTGACCTGTGTGGATGTCTTCCGTCCCAGCAACCCCTGGGAGCTGGCCAAGACTGTTTTTGGGGC

CAAGGAACTGGGCAAGATGGTGGTGGACTGTTGCACGGATCCAGACGGGCGGCTGTGGACCGGGCACGG

GCCTGGTGCGAGATGGTCGGCATCCAGTACTTCAGATTGAACCCCAGCTGGGGACGGACATCATGCTGG

ATGAGGTCAGTGACACAGTGCTGGTCAACGCCCTCTGGGAGACCGAGGTCTACATCTATGAGCACCGCGA

GGAGTTCCAGAAGCTCATCCAGCTGCTGCTCTCACCCTGAGGGTCCCCAGCCTCTCACCGGCCCCAGCTG

ACCTCGTCCATTCAGCCCTGCCAGGCCAAGCCCAGCCACTGCCCTCCCGGGCAGATCTGGGCCCAGGCA

CCTCTGAGTCCATAGACCAGGCCTGGGAGAATGCCAAGCTGCCTGCCCGAGGCTGGTCCTGAAGGCCTGT

CTCCCACTAACCCCGCCTTCCAGCACTTTCTGTCATTCCAGGCTGGGAAAGTCTAGAGCCCCCTTTGGCC

CCTTTCCCTGACTGTCAAGGACAACTGACTCCCCCATCAGCTCAAACATTAAGGGTACCCGGGCACAACC

```
GTACCCCTGCCCCCAGCCCCAGCCTCCCTGAGGGCCTGCCGGGCTGCCTCTGCCCCAGCCCCAGCAAGG

GCACTCCCAGGCTTCCTGGTGGGTGCAGCCCACTCCCTCTGCCCTCTGCTCCGTTCCCTGGGGGCTGGGA

CTAAAGAAATGGGTGTCCCCCACCCCATCAGCTGGGAAAGCCCAGGCCGCAGGAGTGGGATGCCCGTTGG

ACTTTGCCCCTCACACTGGCCCAGCCCCTCACACTGCCCCACCCCGAGAACCCTCAGCTCTCAAAGGTCA

CTCCTGGGAGTTTCTTCTTCCCAATGGAAGTGGCTTAAGAGCCAAAACTGAAATAAATCATTTGGATTCA

AGTTCAAAAAAAAAAACCCCCC

SEQ ID NO: 6 (aa of PLA2g6(S)encoded by PLA2g6 variant 3)
>gi|313760592|ref|NP_001186491.1| 85/88 kDa calcium-independent phospholipase A2
isoform b [Homo sapiens]
MQFFGRLVNTFSGVTNLFSNPFRVKEVAVADYTSSDRVREEGQLILFQNTPNRTWDCVLVNPRNSQSGFR

LFQLELEADALVNFHQYSSQLLPFYESSPQVLHTEVLQHLTDLIRNHPSWSVAHLAVELGIRECFHHSRI

ISCANCAENEEGCTPLHLACRKGDGEILVELVQYCHTQMDVTDYKGETVFHYAVQGDNSQVLQLLGRNAV

AGLNQVNNQGLTPLHLACQLGKQEMVRVLLLCNARCNIMGPNGYPIHSAMKFSQKGCAEMIISMDSSQIH

SKDPRYGASPLHWAKNAEMARMLLKRGCNVNSTSSAGNTALHVAVMRNRFDCAIVLLTHGANADARGEHG

NTPLHLAMSKDNVEMIKALIVFGAEVDTPNDFGETPTFLASKIGRQLQDLMHISRARKPAFILGSMRDEK

RTHDHLLCLDGGGVKGLIIIQLLIAIEKASGVATKDLFDWVAGTSTGGILALAILHSKSMAYMRGMYFRM

KDEVFRGSRPYESGPLEEFLKREFGEHTKMTDVRKPKVMLTGTLSDRQPAELHLFRNYDAPETVREPRFN

QNVNLRPPAQPSDQLVWRAARSSGAAPTYFRPNGRFLDGGLLANNPTLDAMTEIHEYNQDLIRKGQANKV

KKLSIVVSLGTGRSPQVPVTCVDVFRPSNPWELAKTVFGAKELGKMVVDCCTDPDGRAVDRARAWCEMVG

IQYFRLNPQLGTDIMLDEVSDTVLVNALWETEVYIYEHREEFQKLIQLLLSP

SEQ ID NO: 16:
TRKAILTLLRTVGAEYCFPPIHGVPAEQGSAAPHHPFSLERAQPPPISLNNLELQDLMHISRARKP

SEQ ID NO: 17:
TRKAILTLLRTVGAEYCFPPIHGVPAEQGSAAP

SEQ ID NO: 18:
PISLNNLELQDLMHISRARKP
```

---

The invention claimed is:

1. An assay, the assay comprising;
   (a) obtaining a biological sample from a subject at risk of having Parkinson's Disease (PD); and
   (b) measuring the mRNA expression level of the long splice variant of phospholipase A2, group VI (plasma membrane-associated calcium-independent) (PLA2g6(L)), and the mRNA expression level of any one or more of the short variant of phospholipase A2, group VI (cytosolic, calcium-independent) (PLA2g6(S)), total PLA2g6, and/or a normalizing control gene in said biological sample.

2. The assay of claim 1, wherein the biological sample is selected from the group of: whole blood, plasma, specific blood cells, skin fibroblasts, CSF or any non-neuronal cells collected from the subject.

3. The assay of claim 1, wherein the Parkinson's Disease (PD) is idiopathic PD (iPD).

4. The assay of claim 1, performed by a method comprising:
   contacting the biological sample with primer pairs that specifically amplify the mRNA encoding PLA2g6(L), PLA2g6(S), total PLA2g6 and/or a normalizing control gene;
   performing quantitative RT-PCR to produce amplified nucleic acids specifically encoding PLA2g6(L), PLA2g6(S), total PLA2g6 and/or the normalizing control gene; and
   measuring the level of the amplified nucleic acids specifically encoding PLA2g6(L), PLA2g6(S), total PLA2g6 and/or the normalizing control gene.

* * * * *

SEQUENCE LISTING

```
<160> NUMBER OF SEQ IDS: 18

<210> SEQ ID NO 1
<211> LENGTH: 3240
<212> TYPE: DNA
<213> ORGANISM: Homo sapiens
<220> FEATURE:
<221> NAME/KEY: modified_base
<222> LOCATION: (2770)..(2770)
<223> OTHER INFORMATION: a, c, t, g, unknown or other

<400> SEQUENCE: 1
ctgggggtcc gttccccaac ttcctcggcg ctccggactc ccaagtctcc gccggaccct      60
cctttggata ttcctcgtgt ctccgattct gagagagggg gaagacggtg gggcctcccc     120
acctgccccg cagaagatgc agttctttgg ccgcctggtc aataccttca gtggcgtcac     180
caacttgttc tctaacccat tccgggtgaa ggaggtggct gtggccgact acacctcgag     240
tgaccgagtt cggaggaag ggcagctgat tctgttccag aacactccca accgcacctg     300
ggactgcgtc ctggtcaacc ccaggaactc acagagtgga ttccgactct ccagctgga     360 gttggaggct gacgccctag tgaatttcca tcagtattct tcccagctgc tacccttcta     420
tgagagctcc cctcaggtcc tgcacactga ggtcctgcag cacctgaccg acctcatccg     480
```

-continued

```
taaccacccc agctggtcag tgcccacct ggctgtggag ctagggatcc gcgagtgctt    540
ccatcacagc cgtatcatca gctgtgccaa ttgcgcggag aacgaggagg gctgcacacc    600
cctgcacctg gcctgccgca agggtgatgg ggagatcctg gtggagctgg tgcagtactg    660
ccacactcag atggatgtca ccgactacaa gggagagacc gtcttccatt atgctgtcca    720
gggtgacaat tctcaggtgc tgcagctcct tggaaggaac gcagtggctg gcctgaacca    780
ggtgaataac caagggctga ccccgctgca cctggcctgc cagctgggga agcaggagat    840
ggtccgcgtg ctgctgctgt gcaatgctcg gtgcaacatc atgggcccca acggctaccc    900
catccactcg gccatgaagt tctctcagaa ggggtgtgcg gagatgatca tcagcatgga    960
cagcagccag atccacagca agaccccccg ttacggagcc agccccctcc actgggccaa   1020
gaacgcagag atggcccgca tgctgctgaa acgggctgc aacgtgaaca gcaccagctc    1080
cgcggggaac acggccctgc acgtggcggt gatgcgcaac cgcttcgact gtgccatagt   1140
gctgctgacc cacggggcca acgcggatgc ccgcggagag cacggcaaca ccccgctgca   1200
cctggccatg tcgaaagaca acgtggagat gatcaaggcc ctcatcgtgt tcggagcaga   1260
agtggacacc ccgaatgact ttggggagac tcctacattc ctagcctcca aaatcggcag   1320
acttgtcacc aggaaggcga tcttgactct gctgagaacc gtgggggccg aatactgctt   1380
cccacccatc cacggggtcc ccgcggagca gggctctgca gcgccacatc atcccttctc   1440
cctggaaaga gctcagcccc caccgatcag cctaaacaac ctagaactac aggatctcat   1500
gcacatctca cgggcccgga agccagcgtt catcctgggc tccatgaggg acgagaagcg   1560
gacccacgac cacctgctgt gcctggatgg aggaggagtg aaaggcctca tcatcatcca   1620
gctcctcatc gccatcgaga aggcctcggg tgtggccacc aaggacctgt ttgactgggt   1680
ggcgggcacc agcactggag gcatcctggc cctggccatt ctgcacagta agtccatggc   1740
ctacatgcgc ggcatgtact ttcgcatgaa ggatgaggtg ttccggggct ccaggcccta   1800
cgagtcgggg cccctggagg agttcctgaa gcggagtttt ggggagcaca ccaagatgac   1860
ggacgtcagg aaacccaagg tgatgctgac agggacactg tctgaccggc agccggctga   1920 actccaccctc ttccggaact acgatgctcc agaaactgtc cggagcctc gttccaacca   1980 gaacgttaac ctcaggcctc cagctcagcc ctcagaccag ctggtgtggc gggcggccg   2040 aagcagcggg gcagctccta cttacttccg acccaatggg gcttcctgg acggtgggct   2100 gctggccaac aaccccacgc tggatgccat gaccgagatc catgagtaca atcaggacct   2160
gatccgcaag ggtcaggcca acaaggtgaa gaaactctcc atcgttgtct ccctggggac   2220
agggaggtcc ccacaagtgc ctgtgacctg tgtggatgtc ttccgtccca gcaaccctg   2280 ggagctggcc aagactgttt ttggggccaa ggaactgggc aagatggtgg tggactgttg   2340
cacggatcca gacgggcggg ctgtggaccg ggcacgggcc tggtgcgaga tggtcggcat   2400
ccagtacttc agattgaacc cccagctggg gacggacatc atgctggatg aggtcagtga   2460
cacagtgctg gtcaacgccc tctgggagac cgaggtctac atctatgagc accgcgagga   2520
gttccagaag ctcatccacc tgctgctctc accctgaggg tccccagcct ctcaccggcc   2580
ccagctgacc tcgtccattc agccctgcc aggccaagcc cagccactgc cctcccgggc   2640
agatctgggc ccaggcacct ctgagtccat agaccaggcc tgggagaatg ccaagctgcc   2700
tgcccgagcc tggtcctgaa ggcctgtctc ccactaaccc ccccttccat cactttctgt   2760
catgccaggn tgggaaagtc tagagccccc tttggcccct ttccctgact gtcaaggaca   2820
actgactccc ccatcagctc aaacattaag ggtacccggg cacaaccgta cccgtgcccc   2880
```

```
cagccccagc ctaccctgag ggcctgccgg gctgcctttg ccccagcccc cagcaagggc    2940
attcccaggc ttcctggtgg gtgcagccca atccctctgc cctctgctcc gttccctggg    3000
ggctgggact aaagaaatgg gtgtccccca ccccatcagc tgggaaagcc caggccgcag    3060
gagtgggatg cccgttggac tttgcccctc acactggccc agcccctcac actgccccac    3120
cccgagaacc ctcagctctc aaaggtcact cctgggagtt tcttcttccc aatggaagtg    3180
gcttaagagc caaaactgaa ataaatcatt tggattcaag ttcaaaaaaa aaaaaaaaa     3240
```

<210> SEQ ID NO 2
<211> LENGTH: 806
<212> TYPE: PRT
<213> ORGANISM: Homo sapiens

<400> SEQUENCE: 2

```
Met Gln Phe Phe Gly Arg Leu Val Asn Thr Phe Ser Gly Val Thr Asn
1               5                   10                  15

Leu Phe Ser Asn Pro Phe Arg Val Lys Glu Val Ala Val Ala Asp Tyr
            20                  25                  30

Thr Ser Ser Asp Arg Val Arg Glu Glu Gly Gln Leu Ile Leu Phe Gln
        35                  40                  45

Asn Thr Pro Asn Arg Thr Trp Asp Cys Val Leu Val Asn Pro Arg Asn
    50                  55                  60

Ser Gln Ser Gly Phe Arg Leu Phe Gln Leu Glu Leu Glu Ala Asp Ala
65                  70                  75                  80

Leu Val Asn Phe His Gln Tyr Ser Ser Gln Leu Leu Pro Phe Tyr Glu
                85                  90                  95

Ser Ser Pro Gln Val Leu His Thr Glu Val Leu Gln His Leu Thr Asp
            100                 105                 110

Leu Ile Arg Asn His Pro Ser Trp Ser Val Ala His Leu Ala Val Glu
        115                 120                 125

Leu Gly Ile Arg Glu Cys Phe His His Ser Arg Ile Ile Ser Cys Ala
    130                 135                 140

Asn Cys Ala Glu Asn Glu Glu Gly Cys Thr Pro Leu His Leu Ala Cys
145                 150                 155                 160

Arg Lys Gly Asp Gly Glu Ile Leu Val Glu Leu Val Gln Tyr Cys His
                165                 170                 175

Thr Gln Met Asp Val Thr Asp Tyr Lys Gly Glu Thr Val Phe His Tyr
            180                 185                 190

Ala Val Gln Gly Asp Asn Ser Gln Val Leu Gln Leu Leu Gly Arg Asn
        195                 200                 205

Ala Val Ala Gly Leu Asn Gln Val Asn Asn Gln Gly Leu Thr Pro Leu
    210                 215                 220

His Leu Ala Cys Gln Leu Gly Lys Gln Glu Met Val Arg Val Leu Leu
225                 230                 235                 240

Leu Cys Asn Ala Arg Cys Asn Ile Met Gly Pro Asn Gly Tyr Pro Ile
                245                 250                 255

His Ser Ala Met Lys Phe Ser Gln Lys Gly Cys Ala Glu Met Ile Ile
            260                 265                 270

Ser Met Asp Ser Ser Gln Ile His Ser Lys Asp Pro Arg Tyr Gly Ala
        275                 280                 285

Ser Pro Leu His Trp Ala Lys Asn Ala Glu Met Ala Arg Met Leu Leu
    290                 295                 300

Lys Arg Gly Cys Asn Val Asn Ser Thr Ser Ser Ala Gly Asn Thr Ala
```

-continued

```
                305                 310                 315                 320
            Leu His Val Ala Val Met Arg Asn Arg Phe Asp Cys Ala Ile Val Leu
                            325                 330                 335
            Leu Thr His Gly Ala Asn Ala Asp Ala Arg Gly Glu His Gly Asn Thr
                            340                 345                 350
            Pro Leu His Leu Ala Met Ser Lys Asp Asn Val Glu Met Ile Lys Ala
                            355                 360                 365
            Leu Ile Val Phe Gly Ala Glu Val Asp Thr Pro Asn Asp Phe Gly Glu
                            370                 375                 380
            Thr Pro Thr Phe Leu Ala Ser Lys Ile Gly Arg Leu Val Thr Arg Lys
            385                 390                 395                 400
            Ala Ile Leu Thr Leu Leu Arg Thr Val Gly Ala Glu Tyr Cys Phe Pro
                            405                 410                 415
            Pro Ile His Gly Val Pro Ala Glu Gln Gly Ser Ala Ala Pro His His
                            420                 425                 430
            Pro Phe Ser Leu Glu Arg Ala Gln Pro Pro Ile Ser Leu Asn Asn
                            435                 440                 445
            Leu Glu Leu Gln Asp Leu Met His Ile Ser Arg Ala Arg Lys Pro Ala
                            450                 455                 460
            Phe Ile Leu Gly Ser Met Arg Asp Glu Lys Arg Thr His Asp His Leu
            465                 470                 475                 480
            Leu Cys Leu Asp Gly Gly Val Lys Gly Leu Ile Ile Gln Leu
                            485                 490                 495
            Leu Ile Ala Ile Glu Lys Ala Ser Gly Val Ala Thr Lys Asp Leu Phe
                            500                 505                 510
            Asp Trp Val Ala Gly Thr Ser Thr Gly Gly Ile Leu Ala Leu Ala Ile
                            515                 520                 525
            Leu His Ser Lys Ser Met Ala Tyr Met Arg Gly Met Tyr Phe Arg Met
                            530                 535                 540
            Lys Asp Glu Val Phe Arg Gly Ser Arg Pro Tyr Glu Ser Gly Pro Leu
            545                 550                 555                 560
            Glu Glu Phe Leu Lys Arg Glu Phe Gly Glu His Thr Lys Met Thr Asp
                            565                 570                 575
            Val Arg Lys Pro Lys Val Met Leu Thr Gly Thr Leu Ser Asp Arg Gln
                            580                 585                 590
            Pro Ala Glu Leu His Leu Phe Arg Asn Tyr Asp Ala Pro Glu Thr Val
                            595                 600                 605
            Arg Glu Pro Arg Phe Asn Gln Asn Val Asn Leu Arg Pro Pro Ala Gln
                            610                 615                 620
            Pro Ser Asp Gln Leu Val Trp Arg Ala Ala Arg Ser Ser Gly Ala Ala
            625                 630                 635                 640
            Pro Thr Tyr Phe Arg Pro Asn Gly Arg Phe Leu Asp Gly Gly Leu Leu
                            645                 650                 655
            Ala Asn Asn Pro Thr Leu Asp Ala Met Thr Glu Ile His Glu Tyr Asn
                            660                 665                 670
            Gln Asp Leu Ile Arg Lys Gly Gln Ala Asn Lys Val Lys Lys Leu Ser
                            675                 680                 685
            Ile Val Val Ser Leu Gly Thr Gly Arg Ser Pro Gln Val Pro Val Thr
                            690                 695                 700
            Cys Val Asp Val Phe Arg Pro Ser Asn Pro Trp Glu Leu Ala Lys Thr
            705                 710                 715                 720
            Val Phe Gly Ala Lys Glu Leu Gly Lys Met Val Val Asp Cys Cys Thr
                            725                 730                 735
```

```
Asp Pro Asp Gly Arg Ala Val Asp Arg Ala Arg Ala Trp Cys Glu Met
            740                 745                 750

Val Gly Ile Gln Tyr Phe Arg Leu Asn Pro Gln Leu Gly Thr Asp Ile
        755                 760                 765

Met Leu Asp Glu Val Ser Asp Thr Val Leu Val Asn Ala Leu Trp Glu
770                 775                 780

Thr Glu Val Tyr Ile Tyr Glu His Arg Glu Glu Phe Gln Lys Leu Ile
785                 790                 795                 800

His Leu Leu Leu Ser Pro
            805

<210> SEQ ID NO 3
<211> LENGTH: 3077
<212> TYPE: DNA
<213> ORGANISM: Homo sapiens

<400> SEQUENCE: 3
```

| | | | | |
|---|---|---|---|---|
| gggggtccgt | tccccaactt | cctcggcgct | ccggactccc | aagtctccgc | cggaccctcc |    60
| tttggatatt | cctcgtgtct | ccgattctga | dacagagggg | gaagacggtg | gggcctcccc |   120
| acctgccccg | cagaagatgc | agttctttgg | ccgcctggtc | aataccttca | gtggcgtcac |   180
| caacttgttc | tctaacccat | tccgggtgaa | ggaggtggct | gtggccgact | acacctcgag |   240
| tgaccgagtt | cgggaggaag | ggcagctgat | tctgttccag | aacactccca | accgcacctg |   300
| ggactgcgtc | ctggtcaacc | ccaggaactc | acagagtgga | ttccgactct | tccagctgga |   360
| gttggaggct | gacgccctag | tgaatttcca | tcagtattct | tcccagctgc | tacccttcta |   420
| tgagagctcc | cctcaggtcc | tgcacactga | ggtcctgcag | cacctgaccg | acctcatccg |   480
| taaccacccc | agctggtcag | tgcccacct | ggctgtggag | ctagggatcc | gcgagtgctt |   540
| ccatcacagc | cgtatcatca | gctgtgccaa | ttgcgcggag | aacgaggagg | ctgcacacc |   600
| cctgcacctg | gcctgccgca | agggtgatgg | ggagatcctg | gtggagctgg | tgcagtactg |   660
| ccacactcag | atggatgtca | ccgactacaa | gggagagacc | gtcttccatt | atgctgtcca |   720
| gggtgacaat | tctcaggtgc | tgcagctcct | tggaaggaac | gcagtggctg | gcctgaacca |   780
| ggtgaataac | caagggctga | ccccgctgca | cctggcctgc | cagctgggga | agcaggagat |   840
| ggtccgcgtg | ctgctgctgt | gcaatgctcg | gtgcaacatc | atgggcccca | acggctaccc |   900
| catccactcg | gccatgaagt | tctctcagaa | ggggtgtgcg | gagatgatca | tcagcatgga |   960
| cagcagccag | atccacagca | aagacccccg | ttacggagcc | agccccctcc | actgggccaa |  1020
| gaacgcagag | atggcccgca | tgctgctgaa | acggggctgc | aacgtgaaca | gcaccagctc |  1080
| cgcggggaac | acggccctgc | acgtggcggt | gatgcgcaac | cgcttcgact | gtgccatagt |  1140
| gctgctgacc | cacggggcca | acgcggatgc | ccgcggagag | cacggcaaca | ccccgctgca |  1200
| cctggccatg | tcgaaagaca | acgtggagat | gatcaaggcc | ctcatcgtgt | tcggagcaga |  1260
| agtggacacc | ccgaatgact | ttgggagac | tcctacattc | ctagcctcca | aaatcggcag |  1320
| acaactacag | gatctcatgc | acatctcacg | ggcccggaag | ccagcgttca | tcctgggctc |  1380
| catgagggac | gagaagcgga | cccacgacca | cctgctgtgc | ctggatggag | aggagtgaa  |  1440
| aggcctcatc | atcatccagc | tcctcatcgc | catcgagaag | gcctcgggtg | tggccaccaa |  1500
| ggacctgttt | gactgggtgg | cgggcaccag | cactggaggc | atcctggccc | tggccattct |  1560
| gcacagtaag | tccatggcct | acatgcgcgg | catgtacttt | cgcatgaagg | atgaggtgtt |  1620
| ccggggctcc | aggccctacg | agtcggggcc | cctggaggag | ttcctgaagc | gggagtttgg |  1680

-continued

```
ggagcacacc aagatgacgg acgtcaggaa acccaaggtg atgctgacag ggacactgtc    1740
tgaccggcag ccggctgaac tccacctctt ccggaactac gatgctccag aaactgtccg    1800
ggagcctcgt ttcaaccaga acgttaacct caggcctcca gctcagccct cagaccagct    1860
ggtgtggcgg gcgccccgaa gcagcggggc agctcctact tacttccgac ccaatgggcg    1920
cttcctggac ggtgggctgc tggccaacaa ccccacgctg gatgccatga ccgagatcca    1980
tgagtacaat caggacctga tccgcaaggg tcaggccaac aaggtgaaga aactctccat    2040
cgttgtctcc ctggggacag ggaggtcccc acaagtgcct gtgacctgtg tggatgtctt    2100
ccgtcccagc aacccctggg agctggccaa gactgttttt ggggccaagg aactgggcaa    2160
gatggtggtg gactgttgca cggatccaga cgggcgggct gtggaccggg cacgggcctg    2220
gtgcgagatg gtcggcatcc agtacttcag attgaacccc cagctgggga cggacatcat    2280
gctggatgag gtcagtgaca cagtgctggt caacgccctc tgggagaccg aggtctacat    2340
ctatgagcac cgcgaggagt tccagaagct catccagctg ctgctctcac cctgagggtc    2400
cccagcctct caccggcccc agctgacctc gtccattcag cccctgccag gccaagccca    2460
gccactgccc tcccgggcag atctgggccc aggcacctct gagtccatag accaggcctg    2520
ggagaatgcc aagctgcctg cccgaggctg gtcctgaagg cctgtctccc actaaccccg    2580
ccttccagca ctttctgtca ttccaggctg ggaaagtcta gagcccccttt tggcccctttt   2640 ccctgactgt caaggacaac tgactccccc atcagctcaa acattaaggg tacccgggca    2700
caaccgtacc cctgccccca gccccagcct ccctgagggc ctgccgggct gcctctgccc    2760
cagcccccag caagggcact cccaggcttc ctggtgggtg cagcccactc cctctgccct    2820
ctgctccgtt ccctgggggc tgggactaaa gaaatgggtg tccccacccc catcagctgg    2880
gaaagcccag gccgcaggag tgggatgccc gttggacttt gcccctcaca ctggcccagc    2940
ccctcacact gccccacccc gagaaccctc agctctcaaa ggtcactcct gggagtttct    3000
tcttcccaat ggaagtggct taagagccaa aactgaaata aatcatttgg attcaagttc    3060
aaaaaaaaaa aaaaaaa                                                   3077
```

<210> SEQ ID NO 4
<211> LENGTH: 752
<212> TYPE: PRT
<213> ORGANISM: Homo sapiens

<400> SEQUENCE: 4

```
Met Gln Phe Phe Gly Arg Leu Val Asn Thr Phe Ser Gly Val Thr Asn
1               5                   10                  15

Leu Phe Ser Asn Pro Phe Arg Val Lys Glu Val Ala Val Ala Asp Tyr
            20                  25                  30

Thr Ser Ser Asp Arg Val Arg Glu Glu Gly Gln Leu Ile Leu Phe Gln
        35                  40                  45

Asn Thr Pro Asn Arg Thr Trp Asp Cys Val Leu Val Asn Pro Arg Asn
    50                  55                  60

Ser Gln Ser Gly Phe Arg Leu Phe Gln Leu Glu Leu Ala Asp Ala
65                  70                  75                  80

Leu Val Asn Phe His Gln Tyr Ser Ser Gln Leu Pro Phe Tyr Glu
                85                  90                  95

Ser Ser Pro Gln Val Leu His Thr Glu Val Leu Gln His Leu Thr Asp
            100                 105                 110

Leu Ile Arg Asn His Pro Ser Trp Ser Val Ala His Leu Ala Val Glu
```

-continued

```
            115                 120                 125
Leu Gly Ile Arg Glu Cys Phe His His Ser Arg Ile Ile Ser Cys Ala
        130                 135                 140
Asn Cys Ala Glu Asn Glu Gly Cys Thr Pro Leu His Leu Ala Cys
145                 150                 155                 160
Arg Lys Gly Asp Gly Glu Ile Leu Val Glu Leu Val Gln Tyr Cys His
                    165                 170                 175
Thr Gln Met Asp Val Thr Asp Tyr Lys Gly Glu Thr Val Phe His Tyr
                180                 185                 190
Ala Val Gln Gly Asp Asn Ser Gln Val Leu Gln Leu Leu Gly Arg Asn
                195                 200                 205
Ala Val Ala Gly Leu Asn Gln Val Asn Asn Gln Gly Leu Thr Pro Leu
        210                 215                 220
His Leu Ala Cys Gln Leu Gly Lys Gln Glu Met Val Arg Val Leu Leu
225                 230                 235                 240
Leu Cys Asn Ala Arg Cys Asn Ile Met Gly Pro Asn Gly Tyr Pro Ile
                    245                 250                 255
His Ser Ala Met Lys Phe Ser Gln Lys Gly Cys Ala Glu Met Ile Ile
                260                 265                 270
Ser Met Asp Ser Ser Gln Ile His Ser Lys Asp Pro Arg Tyr Gly Ala
                275                 280                 285
Ser Pro Leu His Trp Ala Lys Asn Ala Glu Met Ala Arg Met Leu Leu
        290                 295                 300
Lys Arg Gly Cys Asn Val Asn Ser Thr Ser Ser Ala Gly Asn Thr Ala
305                 310                 315                 320
Leu His Val Ala Val Met Arg Asn Arg Phe Asp Cys Ala Ile Val Leu
                    325                 330                 335
Leu Thr His Gly Ala Asn Ala Asp Ala Arg Gly Glu His Gly Asn Thr
                340                 345                 350
Pro Leu His Leu Ala Met Ser Lys Asp Asn Val Glu Met Ile Lys Ala
        355                 360                 365
Leu Ile Val Phe Gly Ala Glu Val Asp Thr Pro Asn Asp Phe Gly Glu
    370                 375                 380
Thr Pro Thr Phe Leu Ala Ser Lys Ile Gly Arg Gln Leu Gln Asp Leu
385                 390                 395                 400
Met His Ile Ser Arg Ala Arg Lys Pro Ala Phe Ile Leu Gly Ser Met
                405                 410                 415
Arg Asp Glu Lys Arg Thr His Asp His Leu Leu Cys Leu Asp Gly Gly
                420                 425                 430
Gly Val Lys Gly Leu Ile Ile Ile Gln Leu Leu Ile Ala Ile Glu Lys
                435                 440                 445
Ala Ser Gly Val Ala Thr Lys Asp Leu Phe Asp Trp Val Ala Gly Thr
        450                 455                 460
Ser Thr Gly Gly Ile Leu Ala Leu Ala Ile Leu His Ser Lys Ser Met
465                 470                 475                 480
Ala Tyr Met Arg Gly Met Tyr Phe Arg Met Lys Asp Glu Val Phe Arg
                    485                 490                 495
Gly Ser Arg Pro Tyr Glu Ser Gly Pro Leu Glu Phe Leu Lys Arg
                500                 505                 510
Glu Phe Gly Glu His Thr Lys Met Thr Asp Val Arg Lys Pro Lys Val
            515                 520                 525
Met Leu Thr Gly Thr Leu Ser Asp Arg Gln Pro Ala Glu Leu His Leu
        530                 535                 540
```

```
Phe Arg Asn Tyr Asp Ala Pro Glu Thr Val Arg Glu Pro Arg Phe Asn
545                 550                 555                 560

Gln Asn Val Asn Leu Arg Pro Pro Ala Gln Pro Ser Asp Gln Leu Val
            565                 570                 575

Trp Arg Ala Ala Arg Ser Ser Gly Ala Ala Pro Thr Tyr Phe Arg Pro
        580                 585                 590

Asn Gly Arg Phe Leu Asp Gly Gly Leu Leu Ala Asn Asn Pro Thr Leu
    595                 600                 605

Asp Ala Met Thr Glu Ile His Glu Tyr Asn Gln Asp Leu Ile Arg Lys
610                 615                 620

Gly Gln Ala Asn Lys Val Lys Lys Leu Ser Ile Val Val Ser Leu Gly
625                 630                 635                 640

Thr Gly Arg Ser Pro Gln Val Pro Val Thr Cys Val Asp Val Phe Arg
                645                 650                 655

Pro Ser Asn Pro Trp Glu Leu Ala Lys Thr Val Phe Gly Ala Lys Glu
            660                 665                 670

Leu Gly Lys Met Val Val Asp Cys Cys Thr Asp Pro Asp Gly Arg Ala
        675                 680                 685

Val Asp Arg Ala Arg Ala Trp Cys Glu Met Val Gly Ile Gln Tyr Phe
    690                 695                 700

Arg Leu Asn Pro Gln Leu Gly Thr Asp Ile Met Leu Asp Glu Val Ser
705                 710                 715                 720

Asp Thr Val Leu Val Asn Ala Leu Trp Glu Thr Glu Val Tyr Ile Tyr
                725                 730                 735

Glu His Arg Glu Glu Phe Gln Lys Leu Ile Gln Leu Leu Leu Ser Pro
            740                 745                 750

<210> SEQ ID NO 5
<211> LENGTH: 3032
<212> TYPE: DNA
<213> ORGANISM: Homo sapiens

<400> SEQUENCE: 5
tttgtttgcg gaagtaggag gaagtagaag tgctgagtaa gccgagacag agggggaaga      60
cggtggggcc tccccacctg ccccgcagaa gatgcagttc tttggccgcc tggtcaatac     120
cttcagtggc gtcaccaact tgttctctaa cccattccgg gtgaaggagg tggctgtggc     180
cgactacacc tcgagtgacc gagttcggga ggaagggcag ctgattctgt ccagaacac      240 tcccaaccgc acctgggact gcgtcctggt caaccccagg aactcacaga gtggattccg     300
actcttccag ctggagttgg aggctgacgc cctagtgaat tccatcagt attcttccca      360 gctgctaccc ttctatgaga gctcccctca ggtcctgcac actgaggtcc tgcagcacct     420
gaccgacctc atccgtaacc accccagctg gtcagtggcc cacctggctg tggagctagg     480
gatccgcgag tgcttccatc acagccgtat catcagctgt gccaattgcg cggagaacga     540
ggagggctgc acacccctgc acctggcctg ccgcaagggt gatggggaga tcctggtgga     600
gctggtgcag tactgccaca ctcagatgga tgtcaccgac tacaaggag agaccgtctt      660 ccattatgct gtccagggtg acaattctca ggtgctgcag ctccttggaa ggaacgcagt     720
ggctggcctg aaccaggtga ataaccaagg gctgaccccg ctgcacctgg cctgccagct     780
ggggaagcag gagatggtcc gcgtgctgct gctgtgcaat gctcggtgca acatcatggg     840
ccccaacggc tacccatcc actcggccat gaagttctct cagaagggt gtgcggagat      900 gatcatcagc atggacagca gccagatcca cagcaaagac ccccgttacg gagccagccc     960
```

```
cctccactgg gccaagaacg cagagatggc ccgcatgctg ctgaaacggg gctgcaacgt      1020
gaacagcacc agctccgcgg ggaacacggc cctgcacgtg gcggtgatgc gcaaccgctt      1080
cgactgtgcc atagtgctgc tgacccacgg ggccaacgcg gatgcccgcg gagagcacgg      1140
caacaccccg ctgcacctgg ccatgtcgaa agacaacgtg gagatgatca aggccctcat      1200
cgtgttcgga gcagaagtgg acaccccgaa tgactttggg gagactccta cattcctagc      1260
ctccaaaatc ggcagacaac tacaggatct catgcacatc tcacgggccc ggaagccagc      1320
gttcatcctg ggctccatga gggacgagaa gcggacccac gaccacctgc tgtgcctgga      1380
tggaggagga gtgaaaggcc tcatcatcat ccagctcctc atcgccatcg agaaggcctc      1440
gggtgtggcc accaaggacc tgtttgactg ggtggcgggc accagcactg gaggcatcct      1500
ggccctggcc attctgcaca gtaagtccat ggcctacatg cgcggcatgt actttcgcat      1560
gaaggatgag gtgttccggg gctccaggcc ctacgagtcg gggcccctgg aggagttcct      1620
gaagcgggag tttggggagc acaccaagat gacggacgtc aggaaaccca aggtgatgct      1680
gacagggaca ctgtctgacc ggcagccggc tgaactccac ctcttccgga actacgatgc      1740
tccagaaact gtccgggagc tcgtttcaa ccagaacgtt aacctcaggc ctccagctca      1800
gccctcagac cagctggtgt ggcgggcggc ccgaagcagc ggggcagctc ctacttactt      1860
ccgacccaat gggcgcttcc tggacggtgg gctgctggcc aacaacccca cgctggatgc      1920
catgaccgag atccatgagt acaatcagga cctgatccgc aagggtcagg ccaacaaggt      1980
gaagaaactc tccatcgttg tctccctggg gacaggagg tccccacaag tgcctgtgac      2040
ctgtgtggat gtcttccgtc ccagcaaccc ctgggagctg gccaagactg tttttggggc      2100
caaggaactg ggcaagatgg tggtggactg ttgcacggat ccagacgggc gggctgtgga      2160
ccgggcacgg gcctggtgcg agatggtcgg catccagtac ttcagattga accccagct      2220 ggggacggac atcatgctgg atgaggtcag tgacacagtg ctggtcaacg ccctctggga      2280
gaccgaggtc tacatctatg agcaccgcga ggagttccag aagctcatcc agctgctgct      2340
ctcaccctga gggtccccag cctctcaccg gccccagctg acctcgtcca ttcagcccct      2400
gccaggccaa gcccagccac tgccctcccg ggcagatctg ggcccaggca cctctgagtc      2460
catagaccag gctgggagaa atgccaagct gcctgcccga ggctggtcct gaaggcctgt      2520
ctcccactaa ccccgccttc cagcactttc tgtcattcca ggctgggaaa gtctagagcc      2580 cccctttggcc cctttccctg actgtcaagg acaactgact cccccatcag ctcaaacatt      2640
aagggtaccc gggcacaacc gtaccctgc ccccagcccc agcctccctg agggcctgcc      2700
gggctgcctc tgccccagcc cccagcaagg gcactcccag gcttcctggt gggtgcagcc      2760
cactccctct gccctctgct ccgttccctg ggggctggga ctaaagaaat gggtgtcccc      2820 cacccccatca gctgggaaag cccaggccgc aggagtggga tgcccgttgg actttgcccc      2880
tcacactggc ccagcccctc acactgcccc accccgagaa ccctcagctc tcaaaggtca      2940
ctcctgggag tttcttcttc ccaatggaag tggcttaaga gccaaaactg aaataaatca      3000
tttggattca agttcaaaaa aaaaaaaaaa aa                                    3032
```

<210> SEQ ID NO 6
<211> LENGTH: 752
<212> TYPE: PRT
<213> ORGANISM: Homo sapiens

<400> SEQUENCE: 6

-continued

```
Met Gln Phe Phe Gly Arg Leu Val Asn Thr Phe Ser Gly Val Thr Asn
1               5                   10                  15
Leu Phe Ser Asn Pro Phe Arg Val Lys Glu Val Ala Val Ala Asp Tyr
            20                  25                  30
Thr Ser Ser Asp Arg Val Arg Glu Glu Gly Gln Leu Ile Leu Phe Gln
        35                  40                  45
Asn Thr Pro Asn Arg Thr Trp Asp Cys Val Leu Val Asn Pro Arg Asn
    50                  55                  60
Ser Gln Ser Gly Phe Arg Leu Phe Gln Leu Glu Leu Ala Asp Ala
65                  70                  75                  80
Leu Val Asn Phe His Gln Tyr Ser Ser Gln Leu Leu Pro Phe Tyr Glu
                85                  90                  95
Ser Ser Pro Gln Val Leu His Thr Glu Val Leu Gln His Leu Thr Asp
            100                 105                 110
Leu Ile Arg Asn His Pro Ser Trp Ser Val Ala His Leu Ala Val Glu
            115                 120                 125
Leu Gly Ile Arg Glu Cys Phe His His Ser Arg Ile Ile Ser Cys Ala
        130                 135                 140
Asn Cys Ala Glu Asn Glu Glu Gly Cys Thr Pro Leu His Leu Ala Cys
145                 150                 155                 160
Arg Lys Gly Asp Gly Glu Ile Leu Val Glu Leu Val Gln Tyr Cys His
            165                 170                 175
Thr Gln Met Asp Val Thr Asp Tyr Lys Gly Glu Thr Val Phe His Tyr
            180                 185                 190
Ala Val Gln Gly Asp Asn Ser Gln Val Leu Gln Leu Leu Gly Arg Asn
        195                 200                 205
Ala Val Ala Gly Leu Asn Gln Val Asn Asn Gln Gly Leu Thr Pro Leu
    210                 215                 220
His Leu Ala Cys Gln Leu Gly Lys Gln Glu Met Val Arg Val Leu Leu
225                 230                 235                 240
Leu Cys Asn Ala Arg Cys Asn Ile Met Gly Pro Asn Gly Tyr Pro Ile
            245                 250                 255
His Ser Ala Met Lys Phe Ser Gln Lys Gly Cys Ala Glu Met Ile Ile
            260                 265                 270
Ser Met Asp Ser Ser Gln Ile His Ser Lys Asp Pro Arg Tyr Gly Ala
        275                 280                 285
Ser Pro Leu His Trp Ala Lys Asn Ala Glu Met Ala Arg Met Leu Leu
    290                 295                 300
Lys Arg Gly Cys Asn Val Asn Ser Thr Ser Ser Ala Gly Asn Thr Ala
305                 310                 315                 320
Leu His Val Ala Val Met Arg Asn Arg Phe Asp Cys Ala Ile Val Leu
            325                 330                 335
Leu Thr His Gly Ala Asn Ala Asp Ala Arg Gly Glu His Gly Asn Thr
        340                 345                 350
Pro Leu His Leu Ala Met Ser Lys Asp Asn Val Glu Met Ile Lys Ala
    355                 360                 365
Leu Ile Val Phe Gly Ala Glu Val Asp Thr Pro Asn Asp Phe Gly Glu
370                 375                 380
Thr Pro Thr Phe Leu Ala Ser Lys Ile Gly Arg Gln Leu Gln Asp Leu
385                 390                 395                 400
Met His Ile Ser Arg Ala Arg Lys Pro Ala Phe Ile Leu Gly Ser Met
            405                 410                 415
Arg Asp Glu Lys Arg Thr His Asp His Leu Leu Cys Leu Asp Gly Gly
```

-continued

```
                420                 425                 430
        Gly Val Lys Gly Leu Ile Ile Ile Gln Leu Leu Ile Ala Ile Glu Lys
                    435                 440                 445

Ala Ser Gly Val Ala Thr Lys Asp Leu Phe Asp Trp Val Ala Gly Thr
            450                 455                 460

Ser Thr Gly Gly Ile Leu Ala Leu Ala Ile Leu His Ser Lys Ser Met
        465                 470                 475                 480

Ala Tyr Met Arg Gly Met Tyr Phe Arg Met Lys Asp Glu Val Phe Arg
                        485                 490                 495

Gly Ser Arg Pro Tyr Glu Ser Gly Pro Leu Glu Glu Phe Leu Lys Arg
                    500                 505                 510

Glu Phe Gly Glu His Thr Lys Met Thr Asp Val Arg Lys Pro Lys Val
                515                 520                 525

Met Leu Thr Gly Thr Leu Ser Asp Arg Gln Pro Ala Glu Leu His Leu
            530                 535                 540

Phe Arg Asn Tyr Asp Ala Pro Glu Thr Val Arg Glu Pro Arg Phe Asn
        545                 550                 555                 560

Gln Asn Val Asn Leu Arg Pro Pro Ala Gln Pro Ser Asp Gln Leu Val
                        565                 570                 575

Trp Arg Ala Ala Arg Ser Ser Gly Ala Ala Pro Thr Tyr Phe Arg Pro
                    580                 585                 590

Asn Gly Arg Phe Leu Asp Gly Gly Leu Leu Ala Asn Asn Pro Thr Leu
                595                 600                 605

Asp Ala Met Thr Glu Ile His Glu Tyr Asn Gln Asp Leu Ile Arg Lys
            610                 615                 620

Gly Gln Ala Asn Lys Val Lys Lys Leu Ser Ile Val Val Ser Leu Gly
        625                 630                 635                 640

Thr Gly Arg Ser Pro Gln Val Pro Val Thr Cys Val Asp Val Phe Arg
                        645                 650                 655

Pro Ser Asn Pro Trp Glu Leu Ala Lys Thr Val Phe Gly Ala Lys Glu
                    660                 665                 670

Leu Gly Lys Met Val Val Asp Cys Cys Thr Asp Pro Asp Gly Arg Ala
                675                 680                 685

Val Asp Arg Ala Arg Ala Trp Cys Glu Met Val Gly Ile Gln Tyr Phe
            690                 695                 700

Arg Leu Asn Pro Gln Leu Gly Thr Asp Ile Met Leu Asp Glu Val Ser
        705                 710                 715                 720

Asp Thr Val Leu Val Asn Ala Leu Trp Glu Thr Glu Val Tyr Ile Tyr
                        725                 730                 735

Glu His Arg Glu Glu Phe Gln Lys Leu Ile Gln Leu Leu Leu Ser Pro
                    740                 745                 750
```

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 7
gtgaacacac aggctaaggc tccaatcta                                    29

<210> SEQ ID NO 8
<211> LENGTH: 27
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 8
tcaacaagca aaggacagac atcccac                                        27

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
agcagagggg caggctgggt ctctc                                          25

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aggaacacag ttgttgggct ggggttgtc                                      29

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tatcttctcg agttctctag cctccaatcc tggg                                34

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cacatagaat tcgtcccctt gcacagcgta atgg                                34

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agcagagggg caggctgggt ctctc                                          25

<210> SEQ ID NO 14
<211> LENGTH: 34
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 14
cacatagaat tcgtcccctt gcacagcgta atgg                                      34

<210> SEQ ID NO 15
<211> LENGTH: 164
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
gctagcgtta acaccggtat ggaattcgaa caaaaactca tctcagaaga ggatctggat          60
atccctgcag gctaaggatc ccacgtgctc gagcgtctcc aattggcggc cgcaagagga         120
tcgcatcacc atcaccatca ctagagtgaa gcttaagttt aaac                          164

<210> SEQ ID NO 16
<211> LENGTH: 66
<212> TYPE: PRT
<213> ORGANISM: Homo sapiens

<400> SEQUENCE: 16

Thr Arg Lys Ala Ile Leu Thr Leu Leu Arg Thr Val Gly Ala Glu Tyr
1               5                  10                  15

Cys Phe Pro Pro Ile His Gly Val Pro Ala Glu Gln Gly Ser Ala Ala
            20                  25                  30

Pro His His Pro Phe Ser Leu Glu Arg Ala Gln Pro Pro Ile Ser
        35                  40                  45

Leu Asn Asn Leu Glu Leu Gln Asp Leu Met His Ile Ser Arg Ala Arg
    50                  55                  60

Lys Pro
65

<210> SEQ ID NO 17
<211> LENGTH: 33
<212> TYPE: PRT
<213> ORGANISM: Homo sapiens

<400> SEQUENCE: 17

Thr Arg Lys Ala Ile Leu Thr Leu Leu Arg Thr Val Gly Ala Glu Tyr
1               5                  10                  15

Cys Phe Pro Pro Ile His Gly Val Pro Ala Glu Gln Gly Ser Ala Ala
            20                  25                  30

Pro

<210> SEQ ID NO 18
<211> LENGTH: 21
<212> TYPE: PRT
<213> ORGANISM: Homo sapiens

<400> SEQUENCE: 18

Pro Ile Ser Leu Asn Asn Leu Glu Leu Gln Asp Leu Met His Ile Ser
1               5                  10                  15

Arg Ala Arg Lys Pro
            20
```